United States Patent
Guo et al.

(10) Patent No.: US 11,155,546 B2
(45) Date of Patent: Oct. 26, 2021

(54) 4,6,7-TRISUBSTITUTED 1,2-DIHYDROPYRROLO[3,4-C]PYRIDIN/PYRIMIDIN-3-ONE DERIVATIVES AND USES THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Shuchun Guo, Shanghai (CN); Fusheng Zhou, Shanghai (CN); Xiang Chen, Shanghai (CN); Jinzhu Zhao, Shanghai (CN); Dong Huang, Shanghai (CN); Jing Xie, Shanghai (CN); Changjiang Qiao, Shanghai (CN); Wan He, Shanghai (CN); Kai Zhang, Shanghai (CN); Xi Chen, Shanghai (CN); Jiong Lan, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

( * ) Notice: Subject to any disclaimer, the term of this patent is extended or adjusted under 35 U.S.C. 154(b) by 77 days.

(21) Appl. No.: 16/833,467

(22) Filed: Mar. 27, 2020

(65) Prior Publication Data
US 2020/0223846 A1 Jul. 16, 2020

Related U.S. Application Data

(63) Continuation of application No. PCT/CN2018/098481, filed on Aug. 3, 2018.

(30) Foreign Application Priority Data

Sep. 28, 2017 (CN) .......................... 201710897909.5

(51) Int. Cl.
| C07D 471/04 | (2006.01) |
| C07D 519/00 | (2006.01) |
| A61P 35/04 | (2006.01) |
| A61P 35/00 | (2006.01) |
| C07D 487/04 | (2006.01) |

(52) U.S. Cl.
CPC ............ *C07D 471/04* (2013.01); *A61P 35/00* (2018.01); *A61P 35/04* (2018.01); *C07D 487/04* (2013.01); *C07D 519/00* (2013.01)

(58) Field of Classification Search
CPC ...... C07D 471/04; C07D 519/00; A61P 35/04

USPC ..................................................... 514/210.18
See application file for complete search history.

(56) References Cited

U.S. PATENT DOCUMENTS 8,440,689 B2 * 5/2013 Arikawa ................. A61P 37/08
514/300
2016/0264548 A1 9/2016 Qiu et al.

FOREIGN PATENT DOCUMENTS

| CA | 3012882 | 8/2017 |
| CN | 102753548 | 10/2012 |
| CN | 105939998 A | 9/2016 |
| CN | 107021963 A | 8/2017 |
| WO | 2012/177714 | 12/2012 |
| WO | 2015/048662 A2 | 4/2015 |
| WO | 2015/061247 | 4/2015 |
| WO | 2015/131080 | 9/2015 |
| WO | 2017/075394 | 5/2017 |
| WO | 2017/128917 A1 | 8/2017 |

OTHER PUBLICATIONS

International Search Report for PCT/CN2018/098481, dated Oct. 25, 2018, 6 pages including its English translation.
European Search Report for Application 18862262.5, dated May 18, 2020, 8 pages.
International Search Report for PCT/CN2018/098479, dated Oct. 15, 2018, 2 pages.
Office Action issued for Australia Application 2018342342, dated Jun. 4, 2020, 3 pages.
Office Action issued for U.S. Appl. No. 16/486,110, dated Oct. 7, 2020, 34 pages.

\* cited by examiner

*Primary Examiner* — Niloofar Rahmani
(74) *Attorney, Agent, or Firm* — Adsero IP

(57) ABSTRACT

The present disclosure relates to 4,6,7-trisubstituted 1,2-dihydropyrrolo[3,4-c]pyridin/pyrimidin-3-one derivatives, and their preparations and medicinal use. Specifically, the present disclosure discloses a compound of formula (I) or a pharmaceutically acceptable salt, stereoisomer, solvate or prodrug thereof, and a preparation method and use thereof, wherein the definition of each group is as described in the specification and claims.

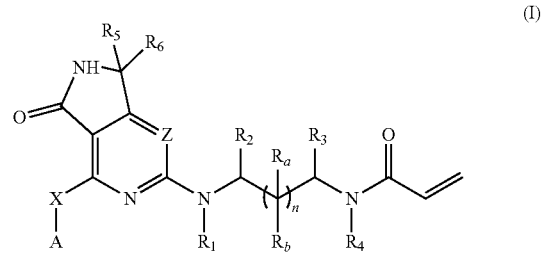

19 Claims, No Drawings

4,6,7-TRISUBSTITUTED 1,2-DIHYDROPYRROLO[3,4-C]PYRIDIN/ PYRIMIDIN-3-ONE DERIVATIVES AND USES THEREOF

CROSS REFERENCE TO RELATED APPLICATIONS

This application is a continuation application for International Application PCT/CN2018/098481, filed on Aug. 3, 2018, which claims the priority benefit of Chinese Patent Application No. 201710897909.5, titled "4,6,7-trisubstituted 1,2-dihydropyrrolo[3,4-c]pyridin/pyrimidin-3-one derivatives and uses thereof" and filed on Sep. 28, 2017. The entireties of both applications are incorporated by reference herein for all purposes.

TECHNICAL FIELD

The present disclosure belongs to the field of medical technology. In particular, the present disclosure relates to a 4,6,7-trisubstituted 1,2-dihydropyrrolo[3,4-c]pyridin/pyrimidin-3-one derivative and its preparation method and use as a BTK inhibitor, and a pharmaceutical composition prepared therefrom.

BACKGROUND

BTK kinase, a non-receptor tyrosine kinase in the TEC kinase family and a key regulator of the BCR signaling pathway, plays an important role in B cell maturation, proliferation and survival. BTK is overexpressed in a variety of B-cell lymphomas and is the only clinically proven effective target for drug development in the TEC kinase family. Inhibition of BTK can inhibit proliferation of a range of B cell lymphomas.

Activation of B cell antigen receptor (BCR) signaling pathway plays an important role in inducing and maintaining B cell malignancies and autoimmune diseases. Bruton's tyrosine kinase (Btk) plays a key role in the hematopoietic cell BCR signaling pathway and is a very good target for new lymphoma therapy. BTK inhibitors act on the BCR pathway, inhibit Btk autophosphorylation, phosphorylation of Btk's physiological substrate PLCγ and phosphorylation of the downstream kinase ERK.

BTK inhibitors act on chronic lymphocytic leukemia (CLL) cells, induce cytotoxicity, and inhibit the proliferation of CLL cells. It inhibits the proliferation of primary B cells activated by BCR and the secretion of TNFα, IL-1β and IL-6 in primary monocytes. BTK inhibitors act on collagen-induced arthritis models and significantly reduce clinical arthritis symptoms such as foot swelling and joint inflammation by inhibiting B cell activity.

Currently, only one BTK inhibitor, ibrutinib, has been approved for marketing, so it is necessary to develop more active, safer and more effective BTK inhibitors.

SUMMARY

It is an object of the present disclosure to provide a novel class of compounds which can be used as Btk inhibitors.

In the first aspect of the present disclosure there is provided a compound of formula (I), or a pharmaceutically acceptable salt, stereoisomer, solvate or prodrug thereof:

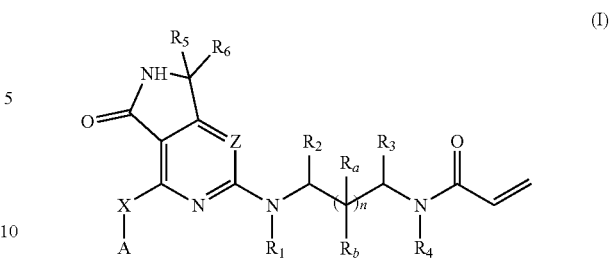

wherein X is a bond, $NR_{a1}$, S, SO, $SO_2$ or O; wherein $R_{a1}$ is hydrogen, hydroxy or $C_{1-8}$ alkyl (preferably $C_{1-6}$ alkyl, more preferably $C_{1-3}$ alkyl);

A is $C_{6-10}$ aryl (preferably phenyl), a 4- to 7-membered saturated or unsaturated monoheterocyclic ring, a 5- to 6-membered monocyclic heteroaryl ring, or an 8- to 10-membered bicyclic heteroaryl ring;

Z is N or $CR_{b1}$; wherein $R_{b1}$ is hydrogen, halogen (preferably fluoro, chloro, bromo), cyano, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) or $C_{3-8}$ cycloalkoxy (preferably $C_{3-6}$ cycloalkoxy);

$R_5$ and $R_6$ are each independently hydrogen, halogen (preferably fluoro, chloro, bromo), $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) or $C_{3-8}$ cycloalkoxy (preferably $C_{3-6}$ cycloalkoxy);

n is 0 or 1; wherein (i) when n is 0, $R_1$ and $R_3$ are each independently hydrogen, halogen, hydroxy, alkoxy, or $C_{1-8}$ alkyl (preferably $C_{1-6}$ alkyl, more preferably $C_{1-3}$ alkyl); $R_2$ and $R_4$ are bonded together to form a 4- to 7-membered saturated or unsaturated monoheterocyclic ring;

(ii) when n is 0, $R_2$ and $R_4$ are each independently hydrogen, halogen, hydroxy, alkoxy, or $C_{1-8}$ alkyl (preferably $C_{1-6}$ alkyl, more preferably $C_{1-3}$ alkyl); $R_1$ and $R_3$ are bonded together to form a 4- to 7-membered saturated or unsaturated monoheterocyclic ring;

(iii) when n is 0, $R_2$ is hydrogen, halogen, $C_{1-8}$ alkyl (preferably $C_{1-6}$ alkyl, more preferably $C_{1-3}$ alkyl); $R_3$ is bonded with $R_1$ and $R_4$ to form a bridged heterocycle; or, $R_3$ is hydrogen, halogen, or $C_{1-8}$ alkyl (preferably $C_{1-6}$ alkyl, more preferably $C_{1-3}$ alkyl); $R_2$ is bonded with $R_1$ and $R_4$ to form a bridged heterocycle;

(iv) when n is 1, $R_2$ and $R_3$ are each independently hydrogen, halogen, hydroxy, alkoxy, or $C_{1-8}$ alkyl (preferably $C_{1-6}$ alkyl, more preferably $C_{1-3}$ alkyl); $R_a$ and $R_1$ are bonded and $R_b$ and $R_4$ are bonded which together form a spiro heterocycle;

(v) when n is 1, $R_2$, $R_3$ and $R_b$ are each independently hydrogen, halogen, hydroxy, alkoxy, or $C_{1-8}$ alkyl (preferably $C_{1-6}$ alkyl, more preferably $C_{1-3}$ alkyl); $R_a$ is bonded with $R_1$ and $R_4$ respectively and together form a bridged heterocycle;

(vi) when n is 1, $R_1$, $R_3$, $R_a$ and $R_b$ are each independently hydrogen, halogen, hydroxy, alkoxy, or $C_{1-8}$ alkyl (preferably $C_{1-6}$ alkyl, more preferably $C_{1-3}$ alkyl); $R_2$ and $R_4$ are bonded together to form a 5- to 7-membered saturated or unsaturated monoheterocyclic ring;

the alkyl, cycloalkyl, alkoxy, aryl, saturated or unsaturated monoheterocyclic ring, monocyclic heteroaryl ring, bicyclic heteroaryl ring, spiro heterocyclic ring, or bridged heterocyclic ring is unsubstituted or substituted with 1, 2 or 3 substituents selected from the group consisting of: hydroxymethyl, hydroxyethyl, hydroxy, carboxy, halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, C$_{1-8}$ alkyl (preferably C$_{1-6}$ alkyl, more preferably C$_{1-3}$ alkyl), C$_{3-8}$ cycloalkyl (preferably C$_{3-6}$ cycloalkyl), halogenated C$_{1-8}$ alkyl (preferably halogenated C$_{1-6}$ alkyl, more preferably halogenated C$_{1-3}$ alkyl), halogenated C$_{3-8}$ cycloalkyl (preferably halogenated C$_{3-6}$ cycloalkyl), hydroxy-substituted C$_{1-8}$ alkyl (preferably hydroxy-substituted C$_{1-6}$ alkyl, more preferably hydroxy-substituted C$_{1-3}$ alkyl), NR$_{a0}$R$_{b0}$, —C(O)OC$_{1-6}$ alkyl, acetyl, C$_{1-8}$ alkoxy (preferably C$_{1-6}$ alkoxy, more preferably C$_{1-3}$ alkoxy), C$_{1-8}$ alkoxy-substituted C$_{1-8}$ alkyl (preferably C$_{1-6}$ alkoxy-substituted C$_{1-6}$ alkyl, more preferably C$_{1-3}$ alkoxy-substituted C$_{1-3}$ alkyl), halogenated C$_{1-8}$ alkoxy (preferably halogenated C$_{1-6}$ alkoxy, more preferably halogenated C$_{1-3}$ alkoxy), —SO$_2$C$_{1-8}$ alkyl (preferably —SO$_2$C$_{1-6}$ alkyl, more preferably —SO$_2$C$_{1-3}$ alkyl), C$_{6-10}$ aryl (preferably phenyl), 5- to 6-membered monocyclic heteroaryl or —Y-L; wherein Y is (CH$_2$)$_q$ or C(O); L is a 4- to 6-membered saturated monoheterocyclic ring or a 5- to 6-membered monocyclic heteroaryl ring; and p and q are each independently 1, 2 or 3; R$_{a0}$ and R$_{b0}$ are each independently hydrogen, acetyl, C$_{1-8}$ alkyl (preferably C$_{1-6}$ alkyl, more preferably C$_{1-3}$ alkyl).

In another preferred embodiment, the 4- to 6-membered saturated monoheterocyclic ring in the substituents is unsubstituted or substituted with 1, 2 or 3 groups selected from the group consisting of halogen, hydroxy, C$_{1-6}$ alkyl, O=, NR$_{a0}$R$_{b0}$, hydroxymethyl, hydroxyethyl, carboxyl, —C(O)OC$_{1-6}$ alkyl, acetyl, halogenated C$_{1-3}$ alkyl, C$_{1-3}$ alkoxy, C$_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein R$_{a0}$ and R$_{b0}$ are each independently hydrogen or C$_{1-3}$ alkyl.

In another preferred embodiment, the 4- to 7-membered or 5- to 7-membered saturated or unsaturated monocyclic ring is selected from the group consisting of azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide and tetrahydropyran.

In another preferred embodiment, the 5- to 6-membered monocyclic heteroaryl ring is selected from the group consisting of a thiophene ring, a N-alkylcyclopyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, and a pyrazine ring.

In another preferred embodiment, the bridged heterocyclic ring is a bicyclic bridged heterocyclic ring containing 4-, 5- or 6-membered rings.

In another preferred embodiment, the spiro heterocyclic ring is a bicyclic spiro heterocyclic ring containing 4-, 5- or 6-membered rings.

In another preferred embodiment, when n is 0, R$_2$ and R$_4$ are bonded together to form a 4- to 7-membered saturated monoheterocyclic ring containing only nitrogen heteroatom(s).

In another preferred embodiment, when n is 0, R$_1$ and R$_3$ are bonded together to form a 4- to 7-membered saturated monoheterocyclic ring containing only nitrogen heteroatom(s).

In another preferred embodiment, when n is 0, R$_3$ is bonded with R$_1$ and R$_4$ to form a double bridged heterocyclic ring containing only nitrogen heteroatom(s); or, R$_2$ is bonded with R$_1$ and R$_4$ to form a double bridged heterocyclic ring containing only nitrogen heteroatom(s).

In another preferred embodiment, when n is 1, R$_a$ and R$_1$ are bonded and R$_b$ and R$_4$ are bonded which together form a double spiro heterocycle containing only nitrogen heteroatom(s).

In another preferred embodiment, when n is 1, R$_a$ is bonded with R$_1$ and R$_4$ respectively and together form a double bridged heterocycle containing only nitrogen heteroatom(s).

In another preferred embodiment, when n is 1, R$_2$ and R$_4$ are bonded together to form a 5- to 7-membered saturated monoheterocyclic ring containing only nitrogen heteroatom(s).

In another preferred embodiment, R$_5$ and R$_6$ are hydrogen.

In another preferred embodiment, Z is N or CR$_{b1}$; wherein R$_{b1}$ is hydrogen or halogen (preferably fluoro, chloro, bromo).

In another preferred embodiment, Z is CR$_{b1}$; wherein R$_{b1}$ is halogen (preferably fluoro, chloro, bromo).

In another preferred embodiment, X is a bond or NH.

In another preferred embodiment,

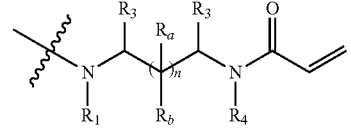

is a structure as shown in formula (A), (B) or (C):

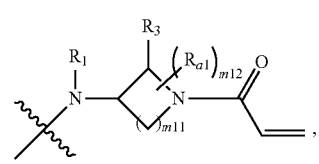

(A)

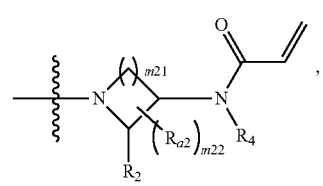

(B)

-continued

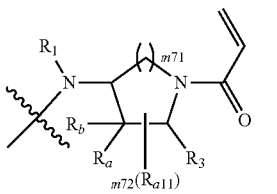
(C)

wherein, m11 and m21 are each independently 1, 2, 3 or 4; m71 is 1, 2 or 3;

m12 and m22 are each independently 0, 1, 2, 3 or 4; m72 is 0, 1, 2 or 3;

$R_{a1}$, $R_{a2}$, and $R_{a11}$ are each independently halogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), hydroxy-substituted $C_{1-8}$ alkyl (preferably hydroxy-substituted $C_{1-6}$ alkyl), $C_{1-s}$ alkoxy (preferably $C_{1-6}$ alkoxy, more preferably $C_{1-3}$ alkoxy), $C_{1-8}$ alkoxy-substituted $C_{1-8}$ alkyl (preferred $C_{1-6}$ alkoxy-substituted $C_{1-6}$ alkyl, more preferably $C_{1-3}$ alkoxy-substituted $C_{1-3}$ alkyl), $C_{3-8}$ cycloalkyl (preferably $C_{3-6}$ cycloalkyl);

$R_1$, $R_2$, $R_3$, $R_4$, $R_a$, and $R_b$ are as defined in claim 1,

In another preferred embodiment,

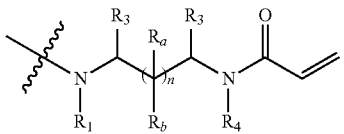

is a structure as shown in formula (D), (E) or (F):

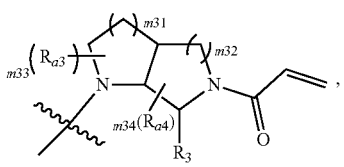
(D)

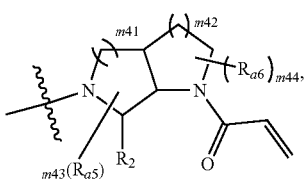
(E)

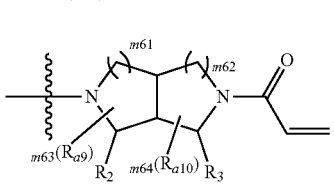
(F)

wherein, m31, m32, m41, m42, m61 and m62 are each independently 0, 1, 2, or 3;

m33, m34, m43, m44, m63 and m64 are each independently 0, 1, 2, or 3;

$R_{a3}$, $R_{a4}$, $R_{a5}$, $R_{a6}$, $R_{a9}$ and $R_{a10}$ are each independently halogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), hydroxy-substituted $C_{1-8}$ alkyl (preferably hydroxy-substituted $C_{1-6}$ alkyl), $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferred $C_{1-6}$ alkoxy-substituted $C_{1-6}$ alkyl, more preferably $C_{1-3}$ alkoxy-substituted $C_{1-3}$ alkyl), $C_{3-8}$ cycloalkyl (preferably $C_{3-6}$ cycloalkyl);

$R_2$ and $R_3$ are as defined in claim 1.

In another preferred embodiment,

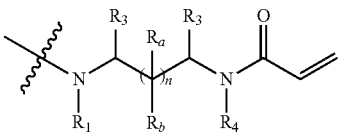

is a structure as shown in formula (G):

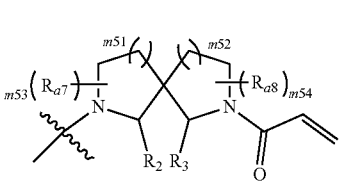
(G)

wherein, m51 and m52 are each independently 0, 1, 2, or 3;

m53 and m54 are each independently 0, 1, 2, 3 or 4;

$R_{a7}$ and $R_{a5}$ are each independently halogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), hydroxy-substituted $C_{1-8}$ alkyl (preferably hydroxy-substituted $C_{1-6}$ alkyl), $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferred $C_{1-6}$ alkoxy-substituted $C_{1-6}$ alkyl, more preferably $C_{1-3}$ alkoxy-substituted $C_{1-3}$ alkyl), $C_{3-8}$ cycloalkyl (preferably $C_{3-6}$ cycloalkyl);

$R_2$ and $R_3$ are as defined in claim 1.

In another preferred embodiment, m11 is 1, 2, 3 or 4; $R_3$ is hydrogen, halogen or $C_{1-8}$ alkyl (preferably $C_{1-6}$ alkyl, more preferably $C_{1-3}$ alkyl); m12 is 0.

In another preferred embodiment, m11 is 1, 2, 3 or 4; $R_3$ is hydrogen; m12 is 1, 2, 3 or 4; $R_{a1}$ is halogen or $C_{1-8}$ alkyl (preferably $C_{1-6}$ alkyl, more preferably $C_{1-3}$ alkyl).

In another preferred embodiment, m21 is 1, 2, 3 or 4; $R_2$ is hydrogen; $R_4$ is hydrogen or $C_{1-8}$ alkyl (preferably $C_{1-6}$ alkyl, more preferably $C_{1-3}$ alkyl); m22 is 0, 1, 2, 3 or 4; $R_{a2}$ is halogen or $C_{1-8}$ alkyl (preferably $C_{1-6}$ alkyl, more preferably $C_{1-3}$ alkyl).

In another preferred embodiment, m21 is 1, 2, 3 or 4; $R_2$ and $R_4$ are hydrogen; m22 is 0.

In another preferred embodiment, m71 is 1, 2, or 3; $R_a$ and $R_b$ are hydrogen; m72 is 0.

In another preferred embodiment, m31 and m32 are each independently 0, 1, 2, or 3; m33 and m34 are 0; $R_3$ is hydrogen, halogen or $C_{1-8}$ alkyl (preferably $C_{1-6}$ alkyl, more preferably $C_{1-3}$ alkyl).

In another preferred embodiment, m31 and m32 are each independently 1, or 2; m33 and m34 are 0; $R_3$ is hydrogen.

In another preferred embodiment, m31 is 1; m32 is 1 or 2; m33 and m34 are 0; $R_3$ is hydrogen.

In another preferred embodiment, m41 and m42 are each independently 0, 1, 2, or 3; m43 and m44 are 0; $R_2$ is hydrogen, halogen or $C_{1-8}$ alkyl (preferably $C_{1-6}$ alkyl, more preferably $C_{1-3}$ alkyl).

In another preferred embodiment, m41 and m42 are 1; m43 and m44 are 0; $R_2$ is hydrogen.

In another preferred embodiment, m61 and m62 are each independently 0, 1, 2, or 3; m63 and m64 are 0; $R_2$ and $R_3$ are each independently hydrogen, halogen or $C_{1-8}$ alkyl (preferably $C_{1-6}$ alkyl, more preferably $C_{1-3}$ alkyl).

In another preferred embodiment, m61 and m62 are 1; m63 and m64 are 0; $R_2$ and $R_3$ are hydrogen.

In another preferred embodiment, m51 and m52 are each independently 1 or 2; m53 and m54 are 0; $R_2$ and $R_3$ are hydrogen.

In another preferred embodiment, X is a bond or $NR_{a1}$; wherein $R_{a1}$ is hydrogen or $C_{1-3}$ alkyl.

In another preferred embodiment, A is $C_{6-10}$ aryl (preferably phenyl), or a 5- to 6-membered monocyclic heteroaryl ring; A is optionally substituted with 1, 2 or 3 substituents selected from the group A1, the optional substitution means that the hydrogen on the ring atoms (including carbon atoms and N atoms) is replaced by a substituent.

In another preferred embodiment, X is NH; A is $C_{6-10}$ aryl (preferably phenyl), or a 5- to 6-membered monocyclic heteroaryl ring; A is optionally substituted with 1, 2 or 3 substituents selected from the group A1, the optional substitution means that the hydrogen on the ring atoms (including carbon atoms and N atoms) is replaced by a substituent.

In another preferred embodiment, X is a bond; A is a 5- to 6-membered monocyclic heteroaryl ring; A is optionally substituted with 1, 2 or 3 substituents selected from the group A1, the optional substitution means that the hydrogen on the ring atoms (including carbon atoms and N atoms) is replaced by a substituent.

In another preferred embodiment, the 5- to 6-membered monocyclic heteroaryl ring is selected from the group consisting of a thiophene ring, a N-alkylcyclopyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, and a pyrazine ring.

In another preferred embodiment, the 5- to 6-membered monocyclic heteroaryl ring is selected from the group consisting of

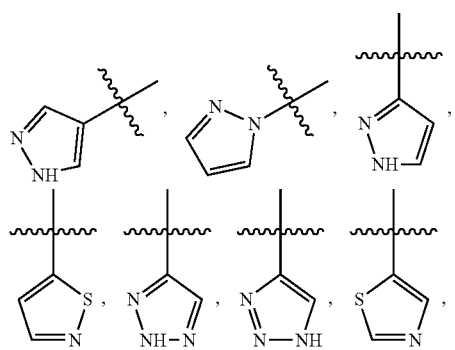

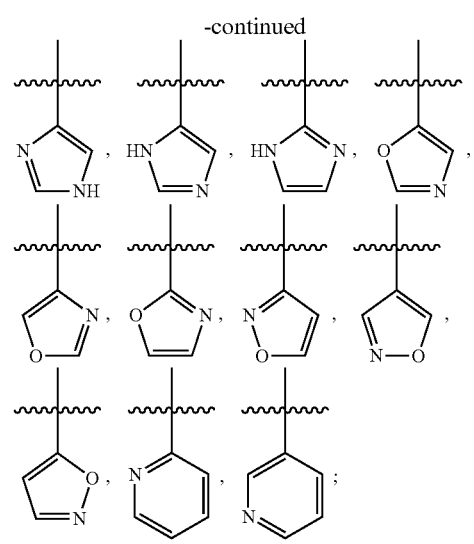

the 5- to 6-membered monocyclic heteroaryl ring is optionally substituted by 1, 2 or 3 substituents selected from the group A1, the optional substitution means that the hydrogen on the ring atoms (including carbon atoms and N atoms) is replaced by a substituent.

In another preferred embodiment, X is NH; A is a structure selected from the group B1.

In another preferred embodiment, X is a bond; A is a structure selected from the group B1 or B2.

In another preferred embodiment, X is NH; A is $C_{6-10}$ aryl (preferably phenyl), or a 5- to 6-membered monocyclic heteroaryl ring; A is optionally substituted by 1, 2 or 3 substituents selected from the group A1, the optional substitution means that the hydrogen on the ring atoms (including carbon atoms and N atoms) is replaced by a substituent;

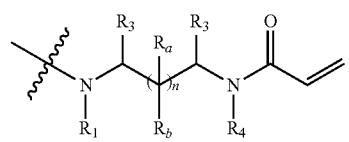

is a structure of formula (A); wherein the groups in formula (A) are defined as in claim 1;

$R_1$ is hydrogen or $C_{1-8}$ alkyl (preferably $C_{1-6}$ alkyl, more preferably $C_{1-3}$ alkyl).

In another preferred embodiment, X is NH; A is a structure selected from the group B1;

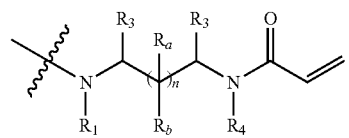

is a structure of formula (A); wherein the groups in formula (A) are defined as in claim 1;

$R_1$ is hydrogen or $C_{1-8}$ alkyl (preferably $C_{1-6}$ alkyl, more preferably $C_{1-3}$ alkyl).

In another preferred embodiment, X is a bond; A is a 5- to 6-membered monocyclic heteroaryl ring; A is optionally substituted with 1, 2 or 3 substituents selected from the group A1, the optional substitution means that the hydrogen on the ring atoms (including carbon atoms and N atoms) is replaced by a substituent;

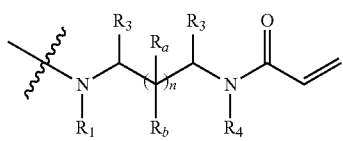

is a structure of formula (A); wherein the groups in formula (A) are defined as in claim 1;

$R_1$ is hydrogen or $C_{1-8}$ alkyl (preferably $C_{1-6}$ alkyl, more preferably $C_{1-3}$ alkyl).

In another preferred embodiment, X is a bond; A is a structure selected from the group B1 or B2;

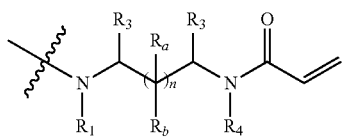

is a structure of formula (A); wherein the groups in formula (A) are defined as in claim 1;

$R_1$ is hydrogen or $C_{1-8}$ alkyl, preferably $R_1$ is $C_{1-8}$ alkyl (preferably $C_{1-6}$ alkyl, more preferably $C_{1-3}$ alkyl).

In another preferred embodiment, m11 is 3.

In another preferred embodiment, the formula (D), (E), (F) or (G) is selected from:

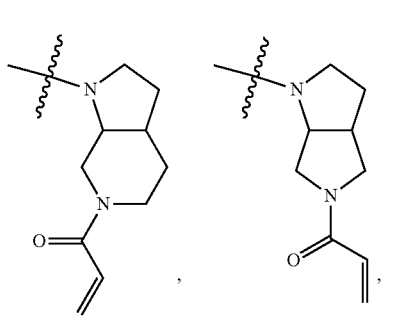

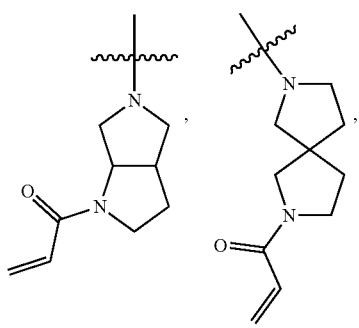

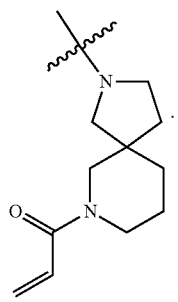

In another preferred embodiment, the formula (A) is selected from structures of a group C1.

In another preferred embodiment, the structure of the group C1 is:

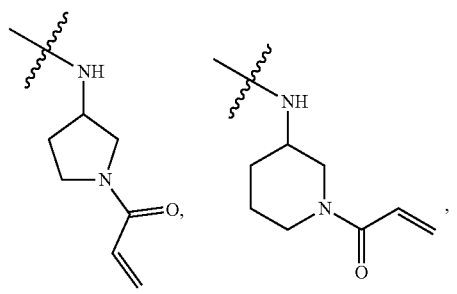

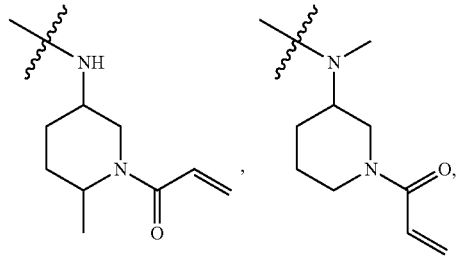

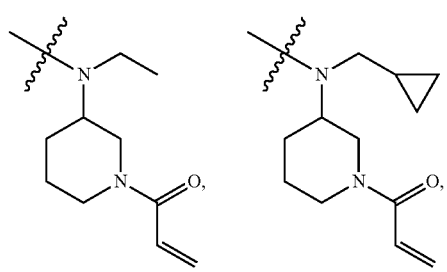

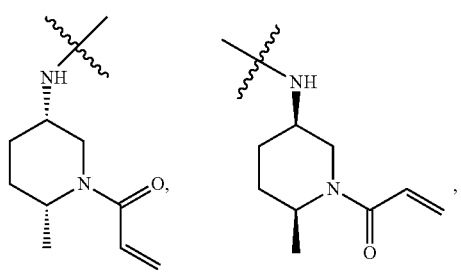

-continued
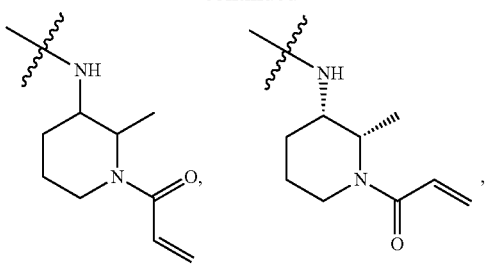
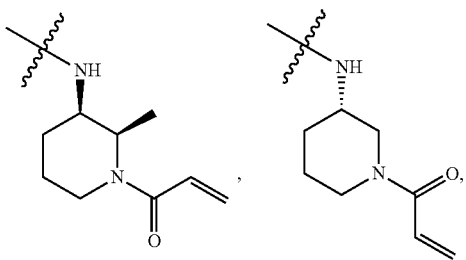
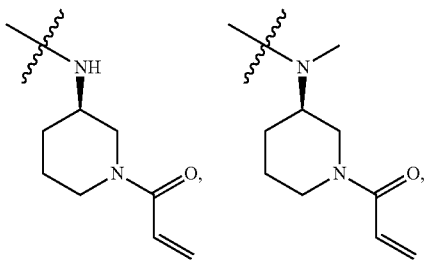
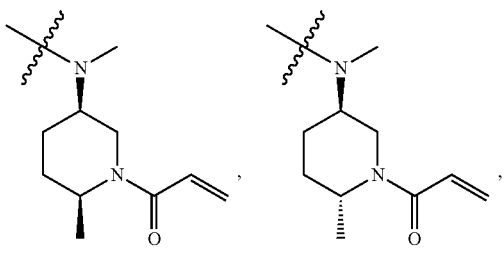
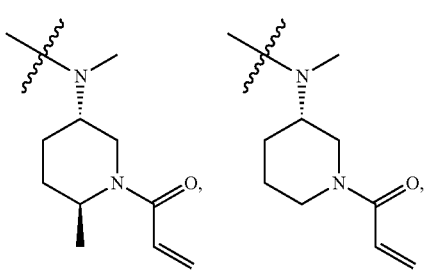
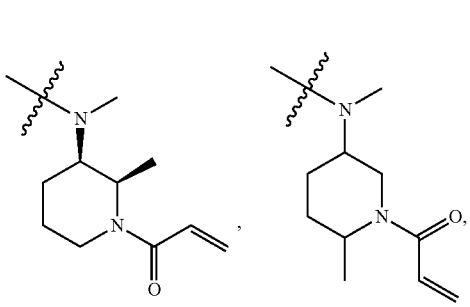
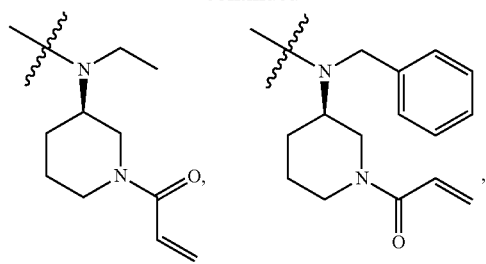
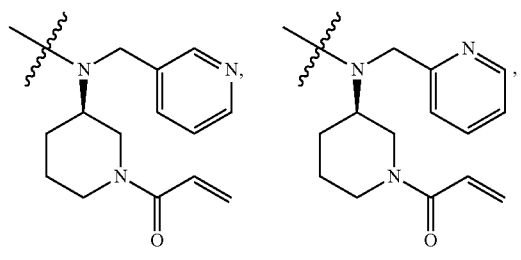
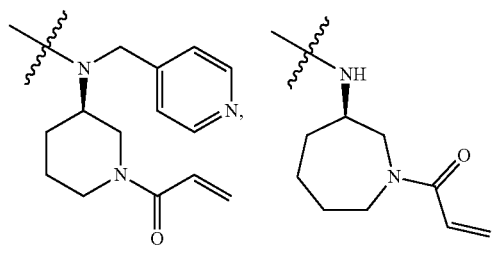
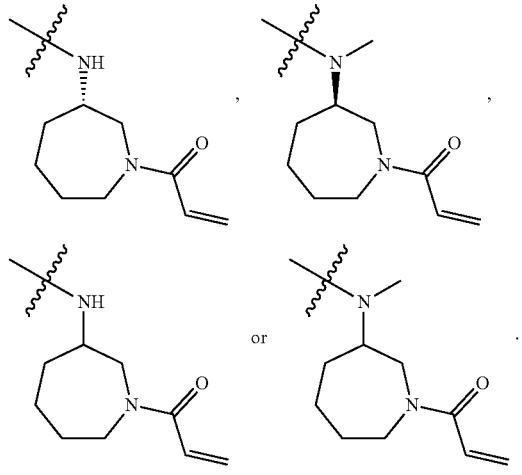
In another preferred embodiment, the formula (B) is selected from:
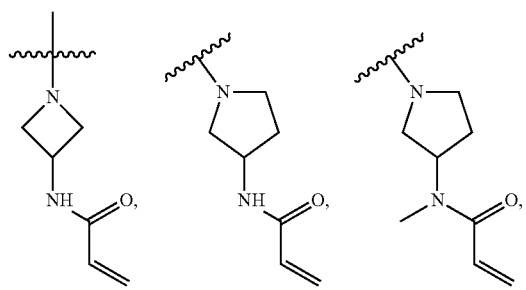

-continued

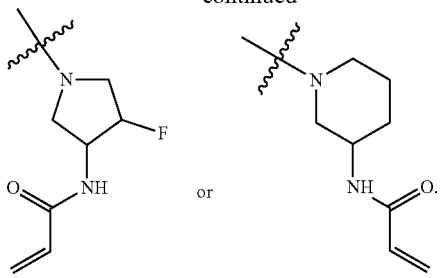

In another preferred embodiment, the formula (C) is selected from:

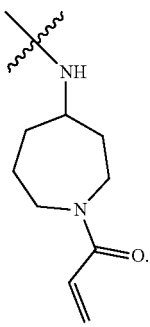 [SMILES: *NC1CCCN(C(=O)C=C)CC1]

In the second aspect of the present disclosure there is provided a compound of formula (II), or a pharmaceutically acceptable salt, stereoisomer, solvate or prodrug thereof:

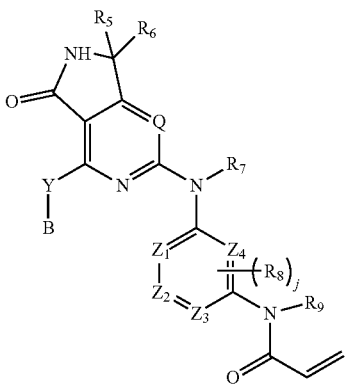

(II)

wherein Y is a bond, $NR_{a1}$, S, SO, $SO_2$ or O; wherein $R_{a1}$ is hydrogen, hydroxy or $C_{1-8}$ alkyl (preferably $C_{1-6}$ alkyl, more preferably $C_{1-3}$ alkyl);

B is $C_{6-10}$ aryl (preferably phenyl), a 4- to 7-membered saturated or unsaturated monoheterocyclic ring, a 5- to 6-membered monocyclic heteroaryl ring, or an 8- to 10-membered bicyclic heteroaryl ring;

Q is N or $CR_{b1}$; wherein $R_{b1}$ is hydrogen, halogen (preferably fluoro, chloro, bromo), cyano, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) or $C_{3-8}$ cycloalkoxy (preferably $C_{3-6}$ cycloalkoxy);

three of $Z_1$, $Z_2$, $Z_3$ and $Z_4$ are CH, and one of them is N; or $Z_1$, $Z_2$, $Z_3$ and $Z_4$ are CH;

$R_5$ and $R_6$ are each independently hydrogen, halogen (preferably fluoro, chloro, bromo), $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), $C_{1-8}$ alkoxy (preferably $C_{1-6}$ alkoxy, more preferably $C_{1-3}$ alkoxy), $C_{3-8}$ cycloalkyl (preferably $C_{3-6}$ cycloalkyl) or $C_{3-8}$ cycloalkoxy (preferably $C_{3-6}$ cycloalkoxy);

$R_7$ and $R_9$ are each independently hydrogen, $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl) or $C_{3-8}$ cycloalkyl (preferably $C_{3-6}$ cycloalkyl);

$R_8$ is hydrogen, halogen, cyano, $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl) or $C_{3-8}$ cycloalkyl (preferably $C_{3-6}$ cycloalkyl) or $NR_{a0}R_{b0}$; wherein $R_{a0}$ and $R_{b0}$ are each independently hydrogen, acetyl, $C_{1-8}$ alkyl (preferably $C_{1-6}$ alkyl, more preferably $C_{1-3}$ alkyl), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl);

j is 0, 1, 2, 3 or 4;

the alkyl, cycloalkyl, alkoxy, cycloalkoxy, aryl, saturated or unsaturated monoheterocyclic ring, monocyclic heteroaryl ring, or bicyclic heteroaryl ring is unsubstituted or substituted with 1, 2 or 3 substituents selected from the group consisting of: halogen, hydroxymethyl, hydroxyethyl, hydroxy, carboxy, $-O(CH_2)_pOC_{1-8}$ alkyl, $-O(CH_2)_pOH$, $-(CH_2)_pOC_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), $NR_{a0}R_{b0}$, $-C(O)OC_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), $-SO_2C_{1-8}$ alkyl (preferably $-SO_2C_{1-6}$ alkyl, more preferably $-SO_2C_{1-3}$ alkyl), $C_{6-10}$ aryl (preferably phenyl), 5- to 6-membered monocyclic heteroaryl or $-Y-L$; wherein Y is $(CH_2)_q$ or C(O); L is a 4- to 6-membered saturated monoheterocyclic ring or a 5- to 6-membered monocyclic heteroaryl ring; q is 1, 2 or 3; $R_{a0}$ and $R_{b0}$ are each independently hydrogen, acetyl, $C_{1-8}$ alkyl (preferably $C_{1-6}$ alkyl, more preferably $C_{1-3}$ alkyl), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl).

In another preferred embodiment, Y is a bond or $NR_{a1}$; wherein $R_{a1}$ is hydrogen or $C_{1-3}$ alkyl.

In another preferred embodiment, B is phenyl or a pyrazole ring.

In another preferred embodiment, Y is a bond; B is a 5- to 6-membered monocyclic heteroaryl ring; and the 5- to 6-membered monocyclic heteroaryl ring is optionally substituted with 1, 2 or 3 substituents selected from the group A1.

In another preferred embodiment, Y is a bond; B is a structure selected from the group B2.

In another preferred embodiment, Y is a bond; B is a pyrazole ring; the pyrazole ring is optionally substituted with 1, 2 or 3 substituents selected from the group A1.

In another preferred embodiment, Y is $NR_{a1}$; wherein $R_{a1}$ is hydrogen or $C_{1-3}$ alkyl; B is phenyl or a 5- to 6-membered monocyclic heteroaryl ring; the B is optionally substituted with 1, 2 or 3 substituents selected from the group A1, and the optional substitution means that the hydrogen on the ring atoms (including carbon atoms and N atoms) is replaced by a substituent.

In another preferred embodiment, Y is $NR_{a1}$; wherein $R_{a1}$ is hydrogen or $C_{1-3}$ alkyl; B is phenyl or a pyrazole ring; the phenyl or the pyrazole ring is optionally substituted with 1, 2 or 3 substituents selected from the group A1.

In another preferred embodiment, Y is $NR_{a1}$; wherein $R_{a1}$ is hydrogen or $C_{1-3}$ alkyl; B is a structure selected from the group B1.

In another preferred embodiment, $R_7$ and $R_9$ are each independently hydrogen, $C_{1-3}$ alkyl, halogenated $C_{1-3}$ alkyl or $C_{3-6}$ cycloalkyl.

In another preferred embodiment, the substituents of the group A1 are halogen, $-O(CH_2)_pOC_{1-8}$ alkyl, $-O(CH_2)_pOH$, $-(CH_2)_pOC_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), hydroxymethyl, hydroxyethyl, hydroxy, carboxy, $NR_{a0}R_{b0}$, $-C(O)OC_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), $-SO_2C_{1-8}$ alkyl (preferably $-SO_2C_{1-6}$ alkyl, more preferably $-SO_2C_{1-3}$ alkyl), $C_{6-10}$ aryl (preferably phenyl), 5- to 6-membered monocyclic heteroaryl or $-Y-L$; wherein Y is $(CH_2)_q$ or $C(O)$; L is a 4- to 6-membered saturated monoheterocyclic ring; and p and q are each independently 1, 2 or 3; $R_{a0}$ and $R_{b0}$ are each independently hydrogen, acetyl, $C_{1-8}$ alkyl (preferably $C_{1-6}$ alkyl, more preferably $C_{1-3}$ alkyl), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl).

In another preferred embodiment, the 4- to 6-membered saturated monoheterocycle in the substituents of the group A1 is selected from the group consisting of azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide and tetrahydropyran.

In another preferred embodiment, the 4- to 6-membered saturated monoheterocyclic ring in the substituents of the group A1 is unsubstituted or substituted with 1, 2 or 3 substituents selected from the group consisting of halogen, hydroxy, $C_{1-3}$ alkyl, O=, $NR_{a0}R_{b0}$, hydroxymethyl, hydroxyethyl, hydroxypropyl, carboxyl, $-C(O)OC_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, a pyrazine ring; wherein $R_{a0}$ and $R_{b0}$ are each independently hydrogen or $C_{1-3}$ alkyl.

In another preferred embodiment, the substituents of the group A1 are fluoro, chloro, bromo, hydroxymethyl, hydroxyethyl, hydroxy, carboxy, $-O(CH_2)_pOC_{1-3}$ alkyl, $-O(CH_2)_pOH$, $-(CH_2)_pOC_{1-3}$ alkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, methyl, ethyl, n-propyl, isopropyl, cyclopropyl, monochloroethyl, dichloromethyl, 1,2-dichloroethyl, monobromoethyl, monofluoromethyl, difluoromethyl, trifluoromethyl, monofluoroethyl, difluoroethyl, trifluoroethyl, monochlorocyclopropyl, dichlorocyclopropyl, trichlorocyclopropyl, monofluorocyclopropyl, difluorocyclopropyl, trifluorocyclopropyl, $NR_{a0}R_{b0}$, $-C(O)OC1-3$ alkyl, acetyl, methoxy, ethoxy, propoxy, isopropoxy, trifluoromethoxy, trifluoroethoxy, monofluoromethoxy, monofluoroethoxy, difluoromethoxy, difluoroethoxy, phenyl, pyridyl or $-Y-L$; wherein Y is $(CH_2)_q$ or $C(O)$; L is azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydrogenpyran; p is 1, 2 or 3; q is 1; $R_{a0}$ and $R_{b0}$ are each independently hydrogen, acetyl, methyl, ethyl, n-propyl, isopropyl, or, methoxy-substituted $C_{1-3}$ alkyl.

In another preferred embodiment, the structures of the group B1 are:

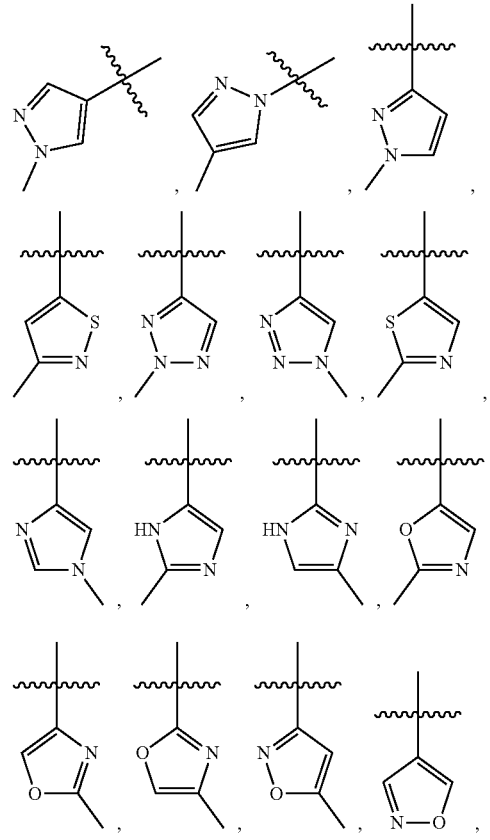

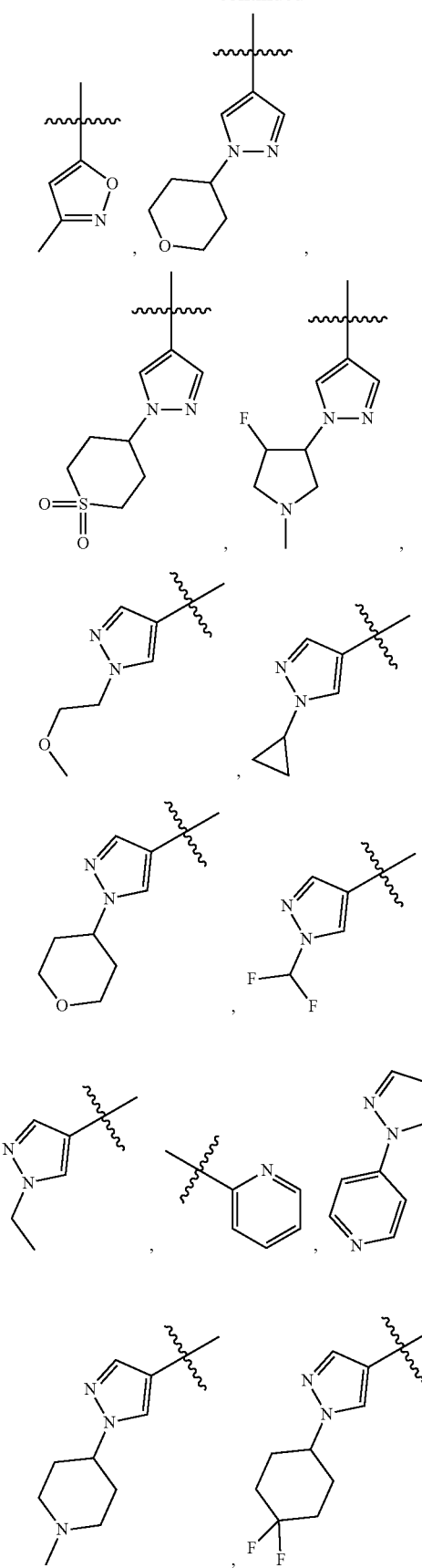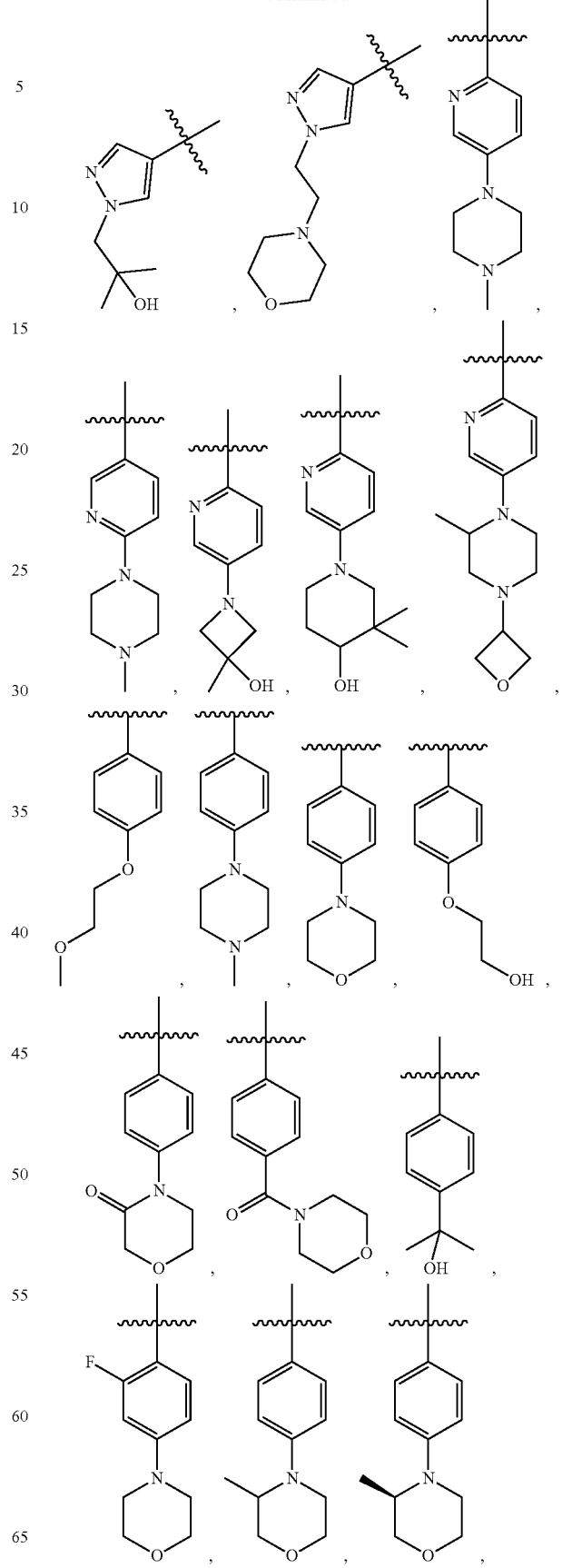

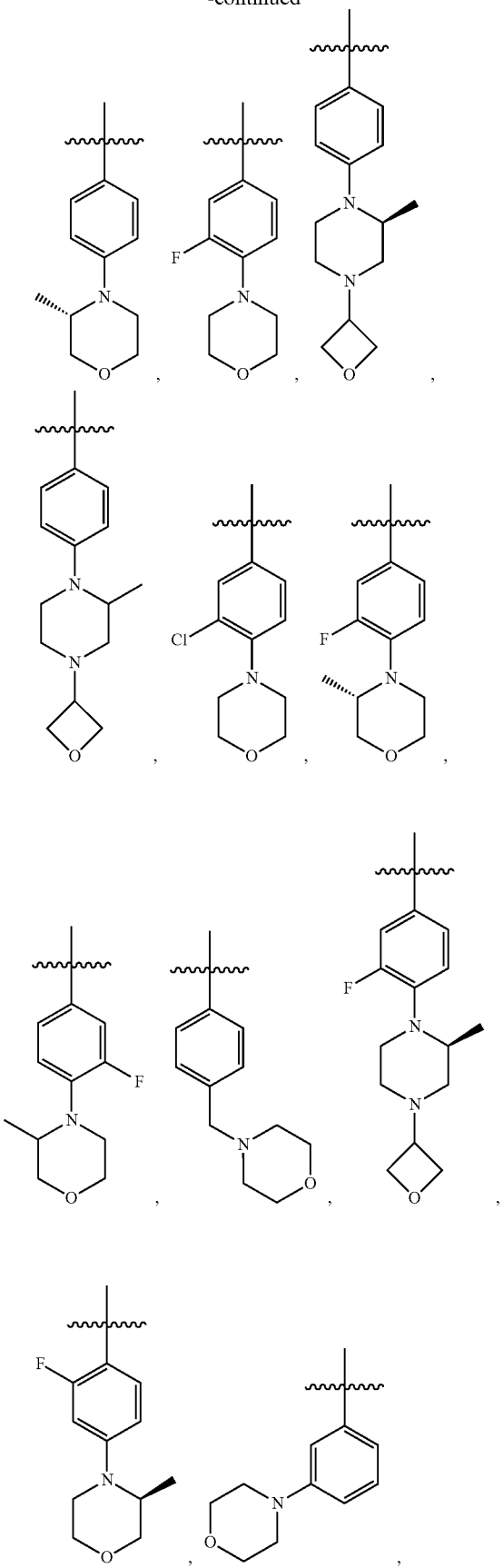
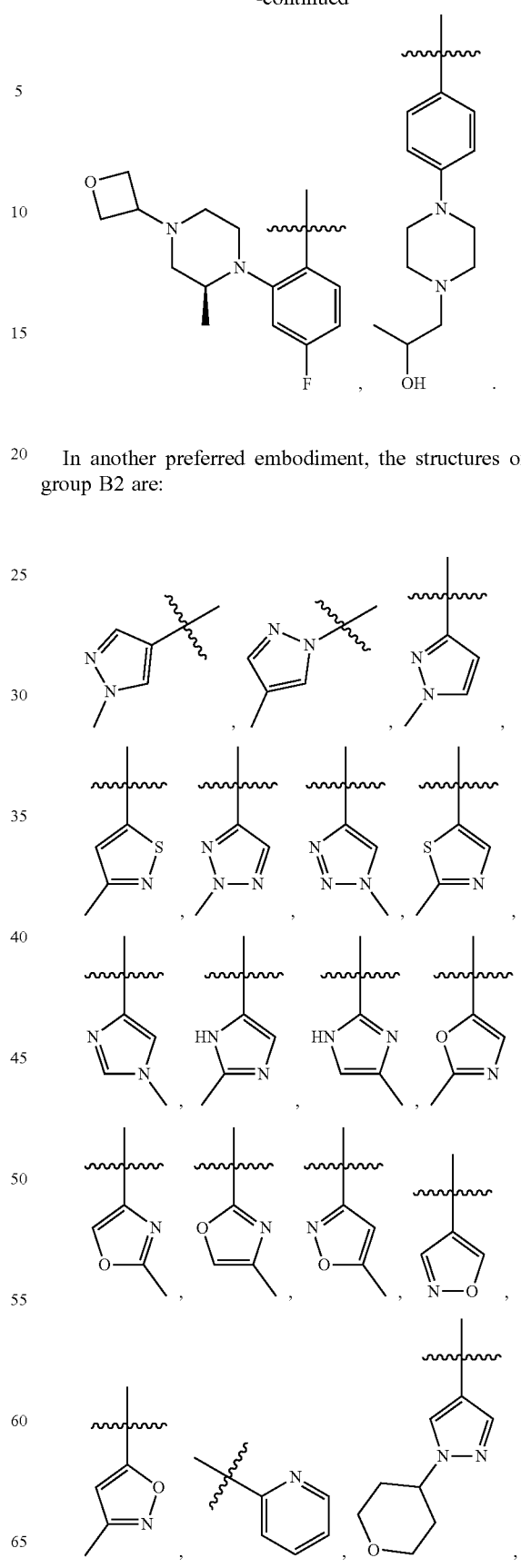
In another preferred embodiment, the structures of the group B2 are:

-continued
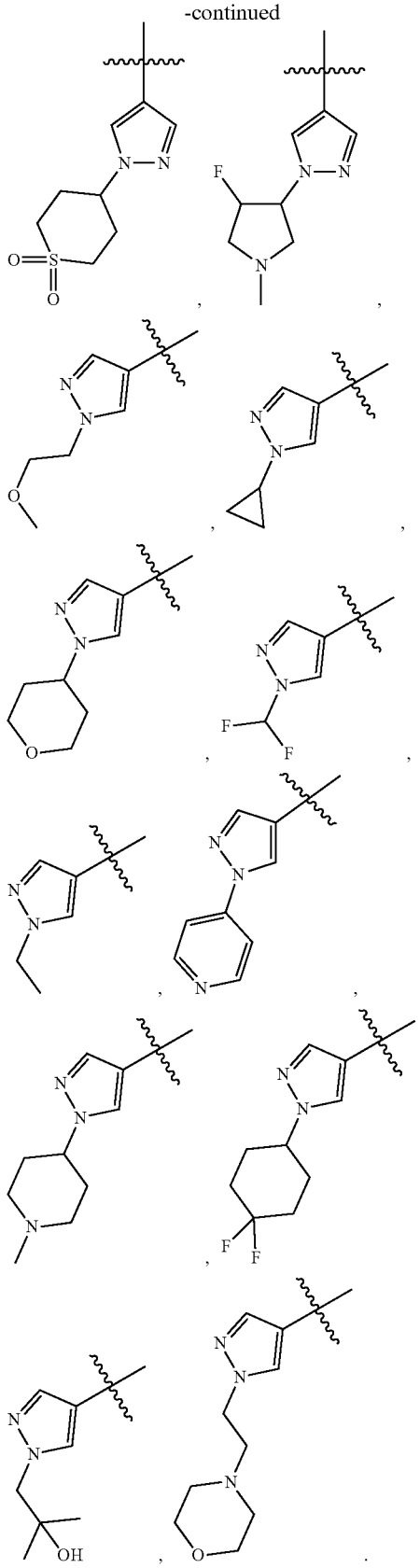
In another preferred embodiment, the compound of formula (I) is a structure selected from the group D1.
In another preferred embodiment, the structure of the group D1 is;
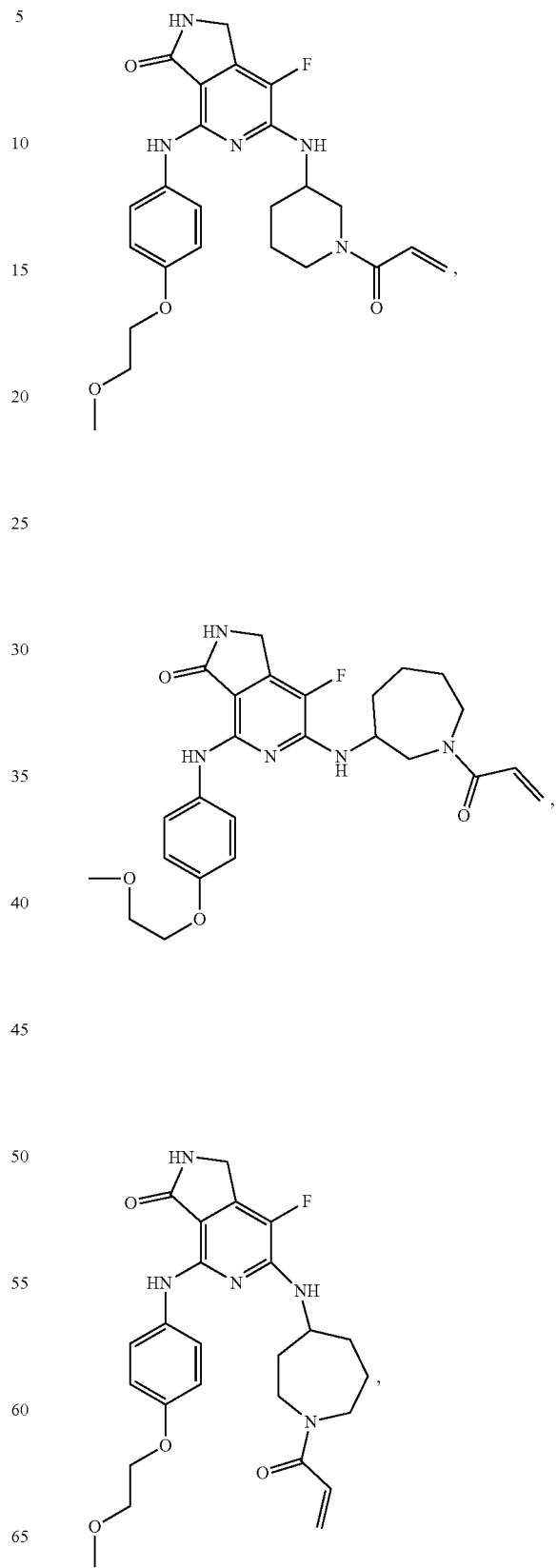

23
-continued
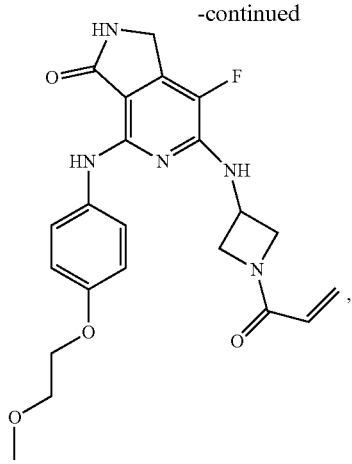
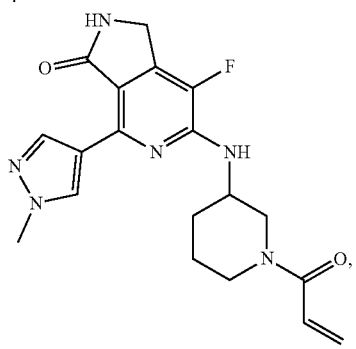
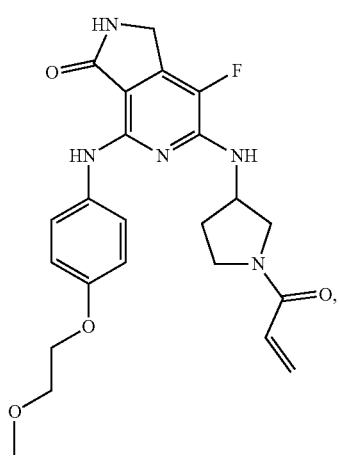
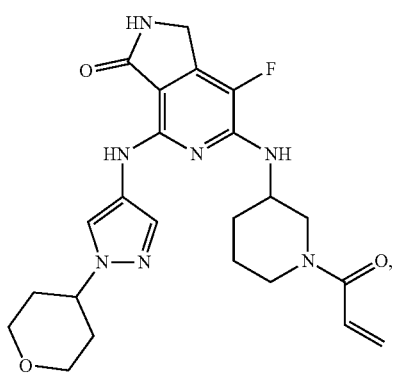
24
-continued
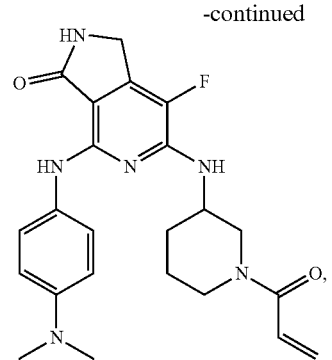
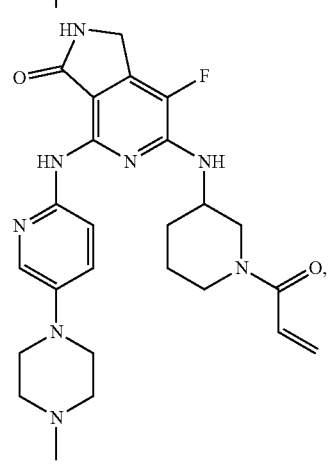
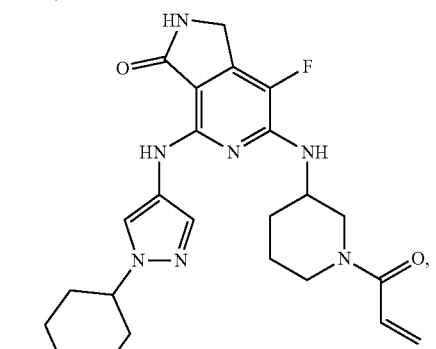
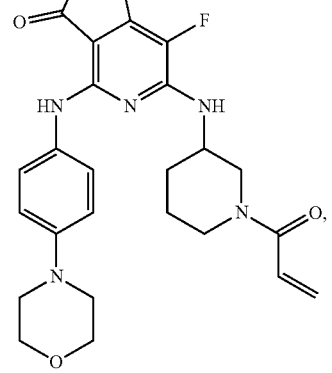

25
-continued
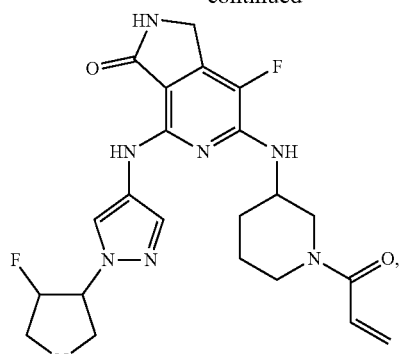
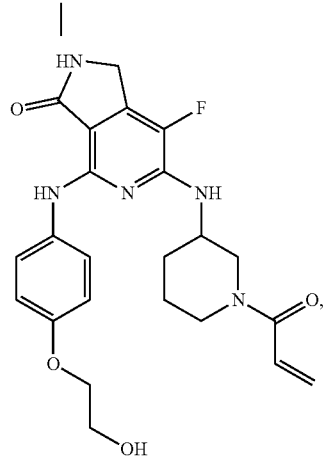
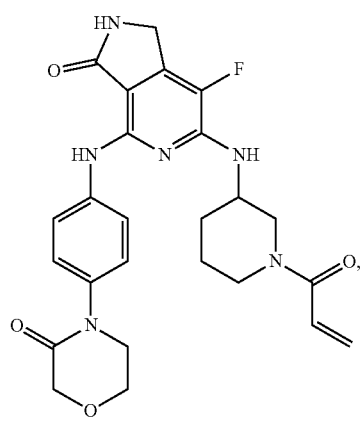
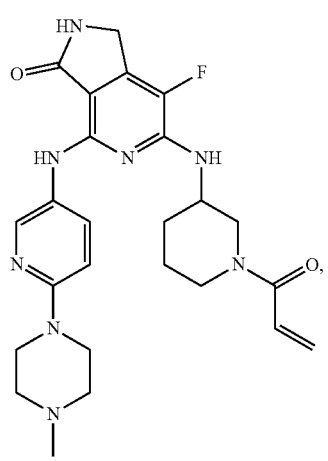
26
-continued
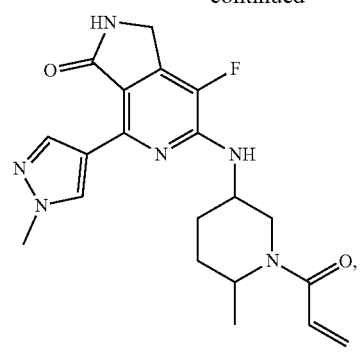
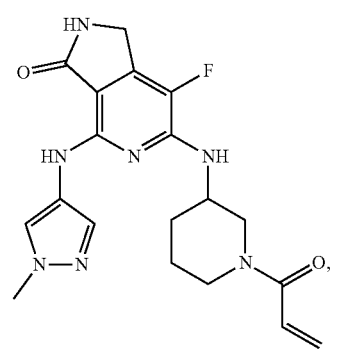
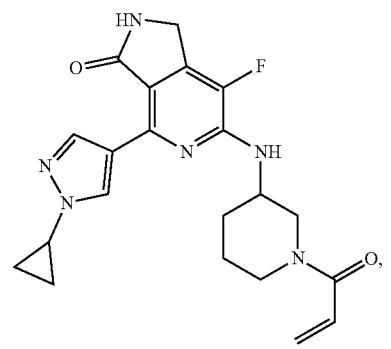
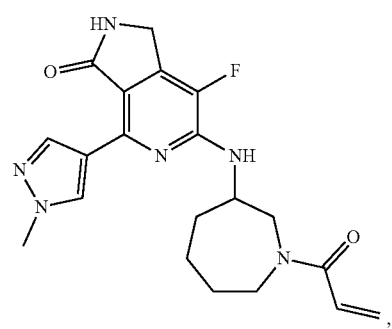

27
-continued
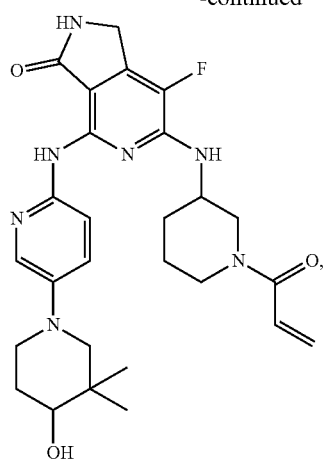
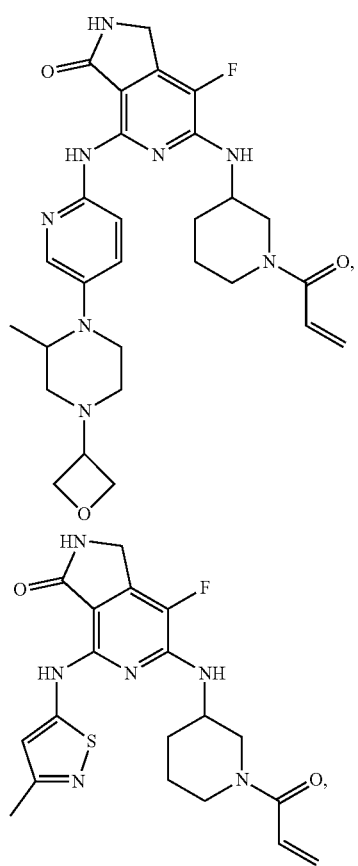
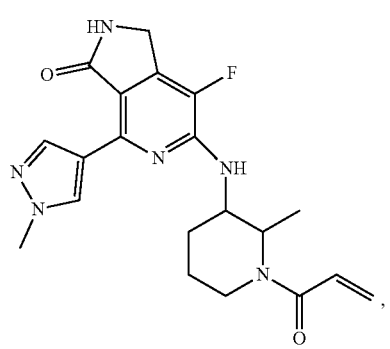
28
-continued
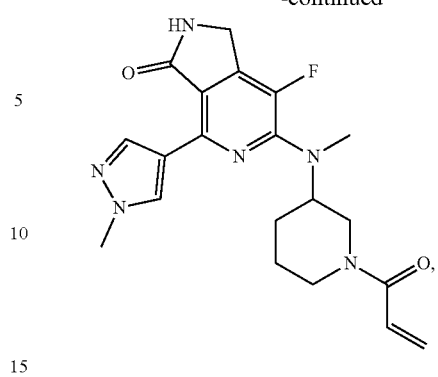
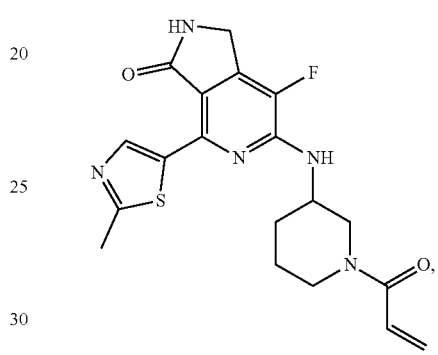
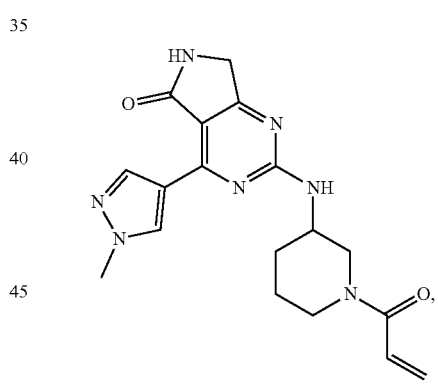
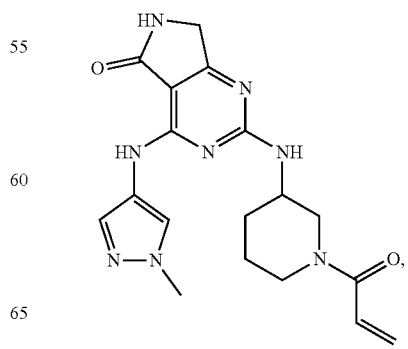

29
-continued
30
-continued
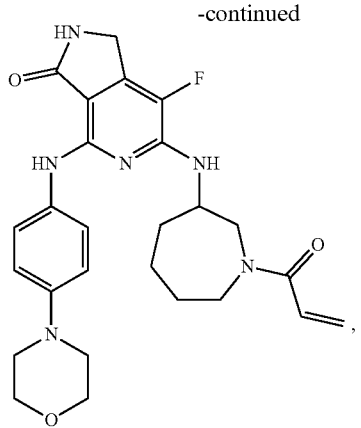
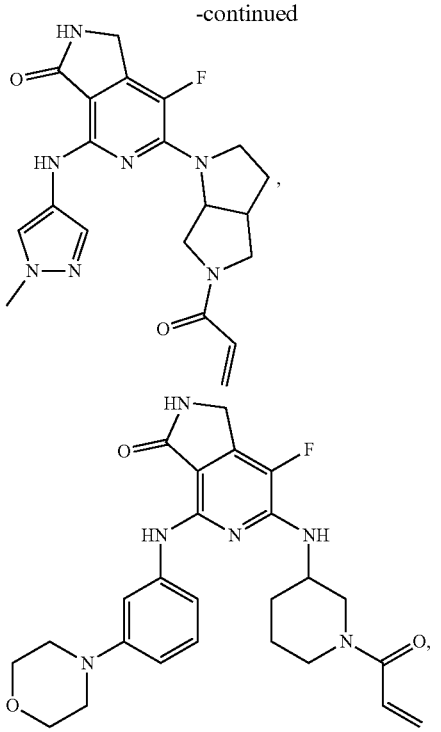

31
-continued
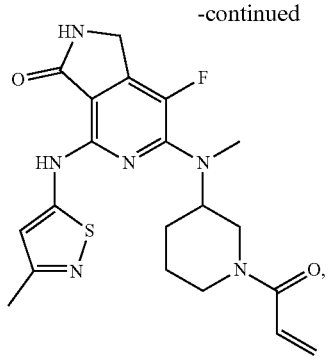
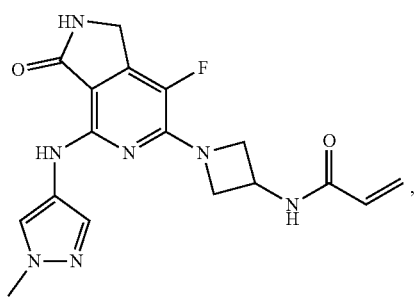
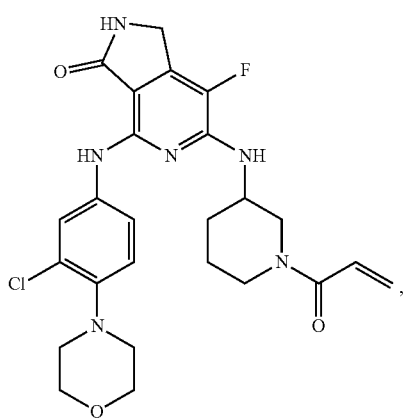
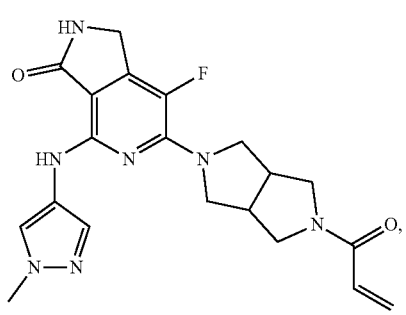
32
-continued
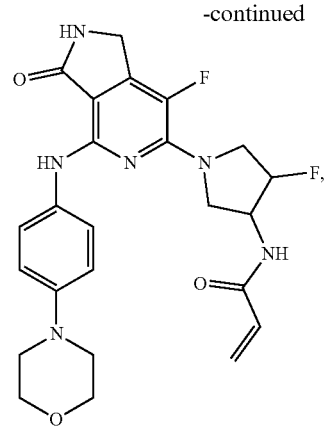
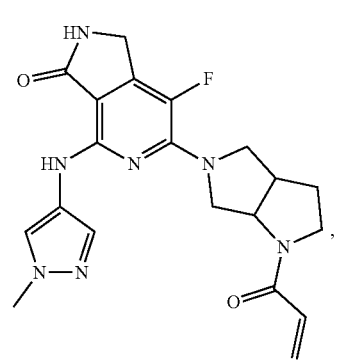
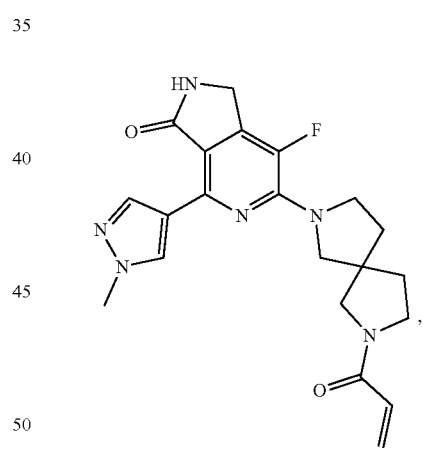
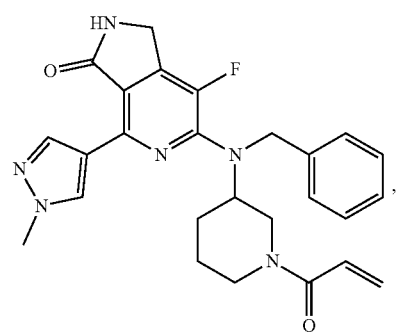

33
-continued
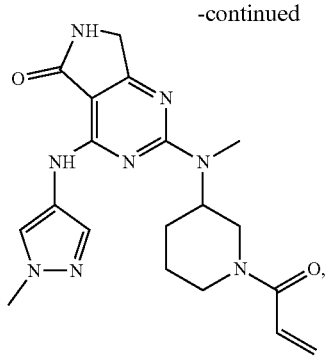
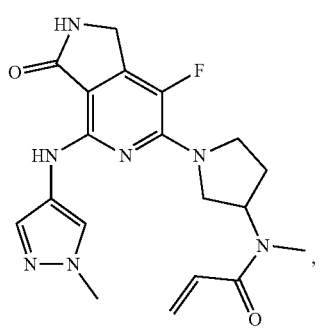
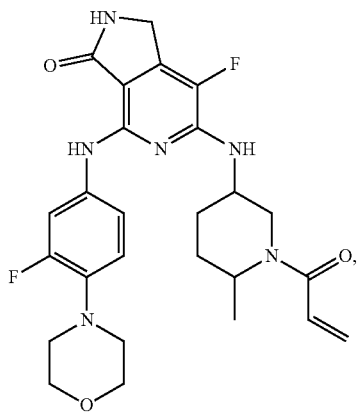
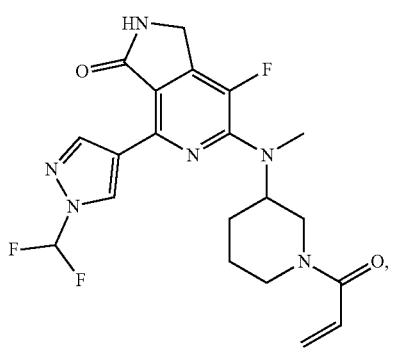
34
-continued
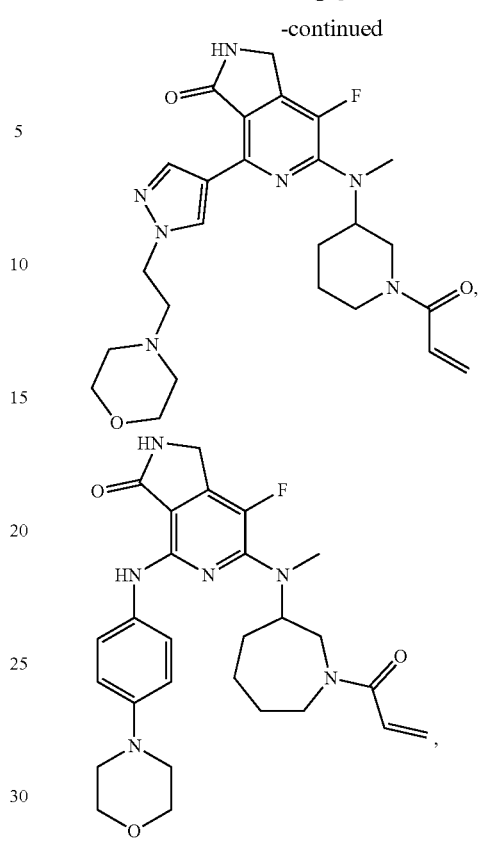
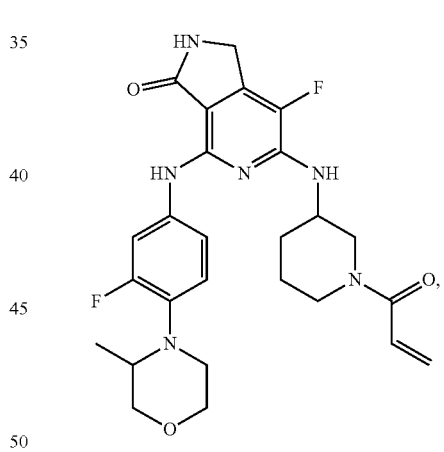
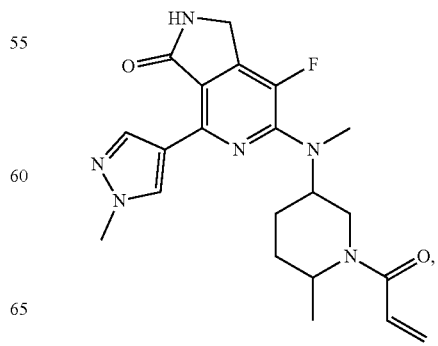

-continued
35
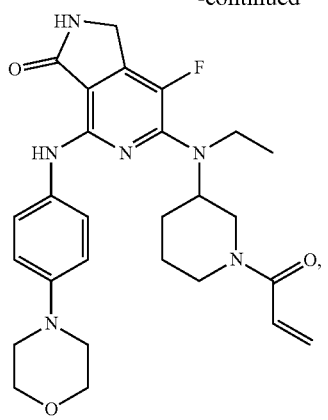
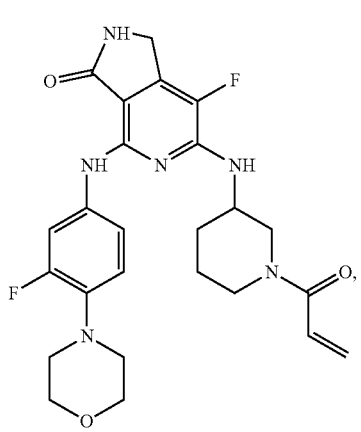
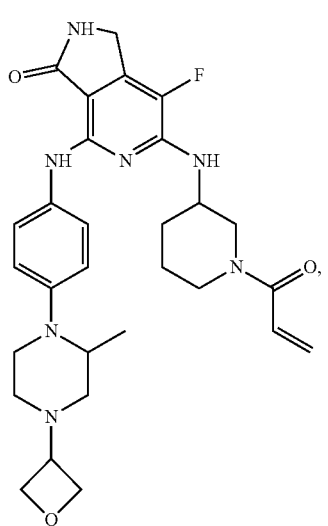
-continued
36
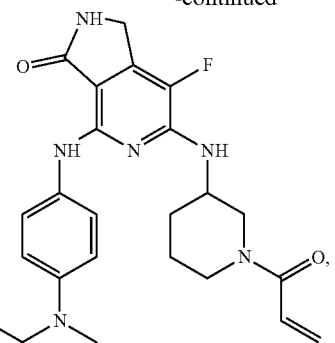
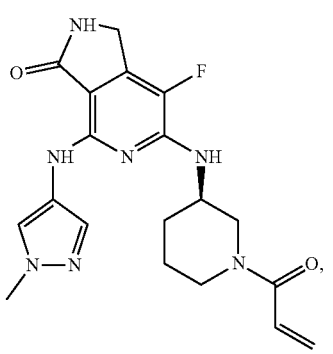

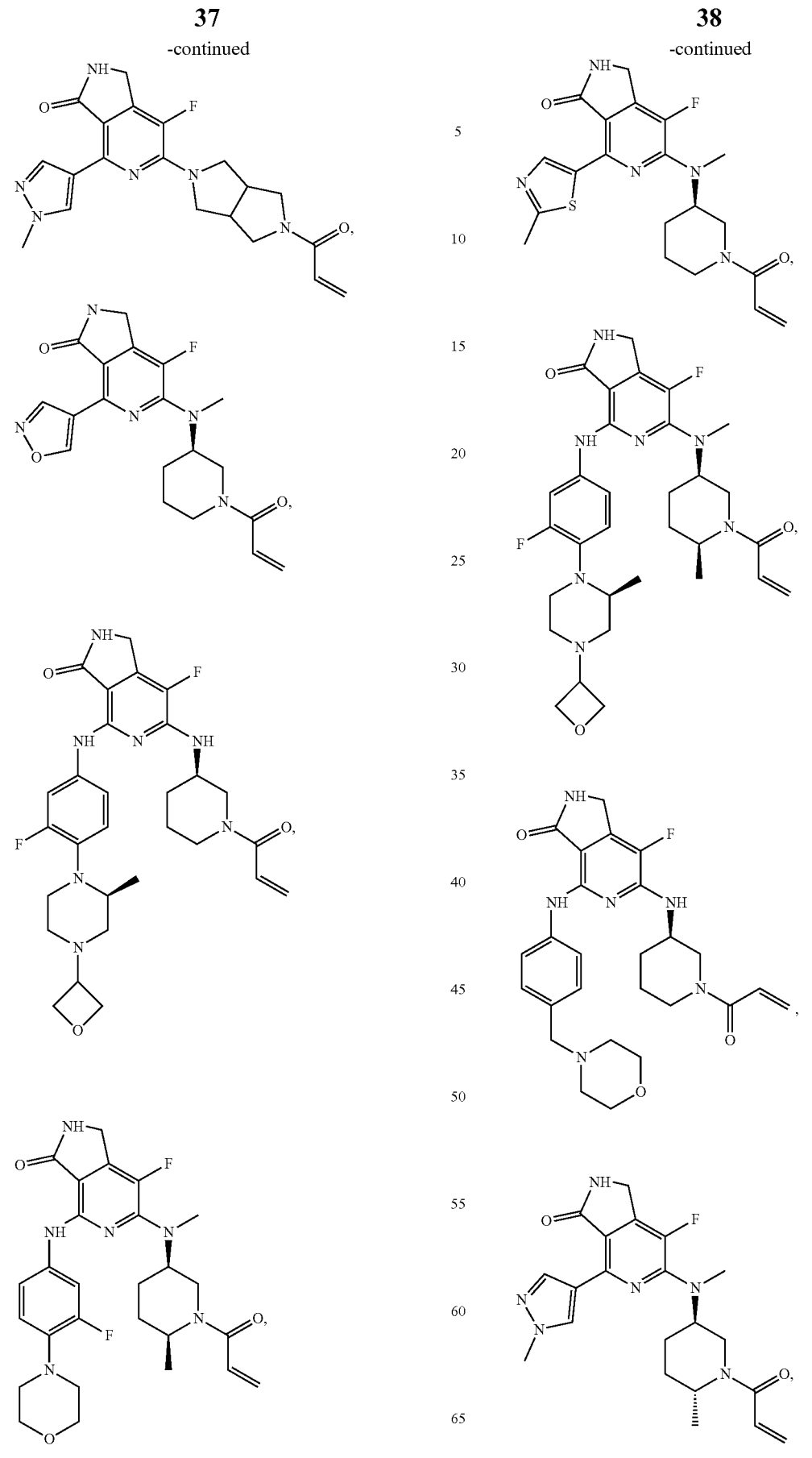

37
-continued

38
-continued

39
-continued
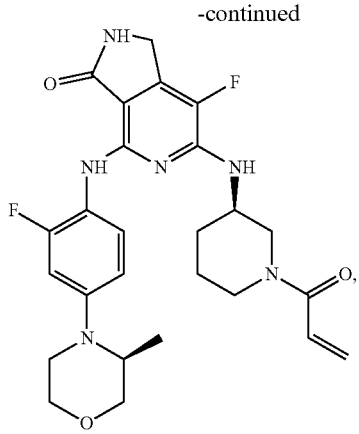
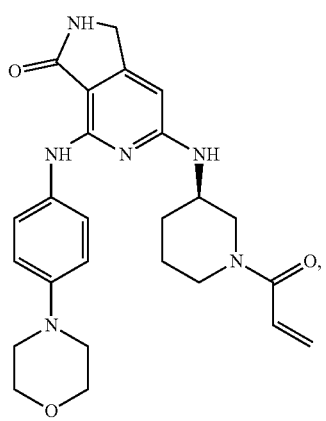
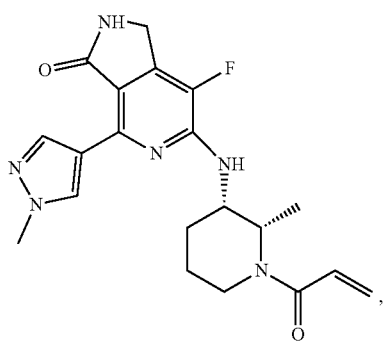
40
-continued
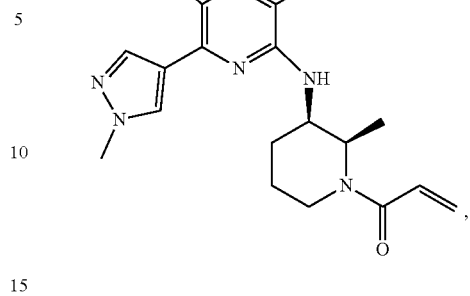
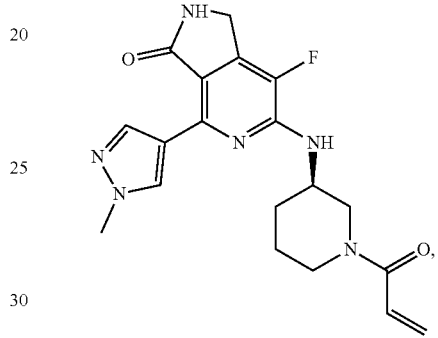

-continued
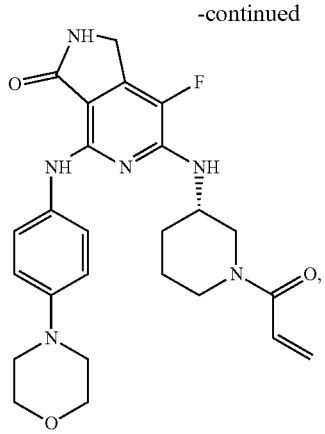
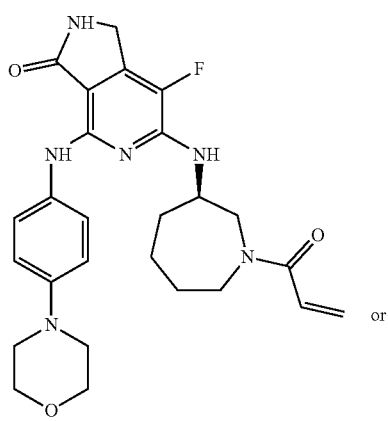
or
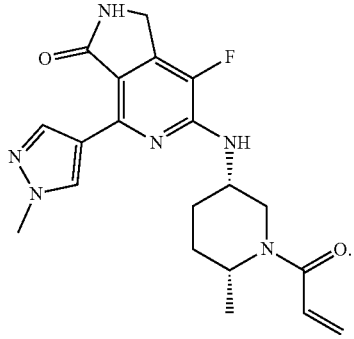
In another preferred embodiment, the compound of formula (II) is a structure selected from the group D2.
In another preferred embodiment, the structure of the group D2 is:
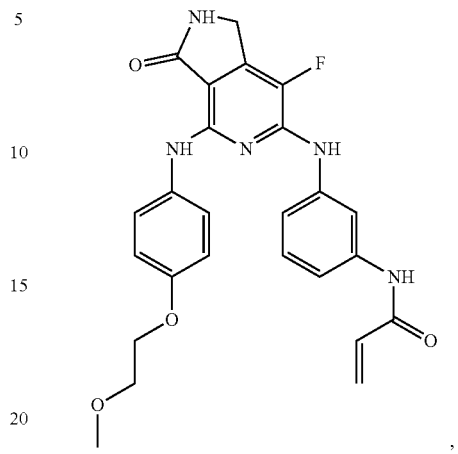
,
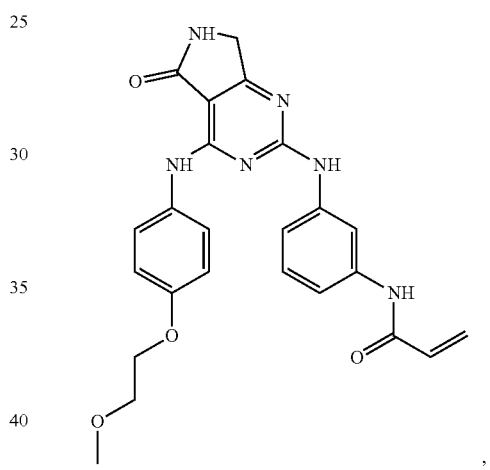
,
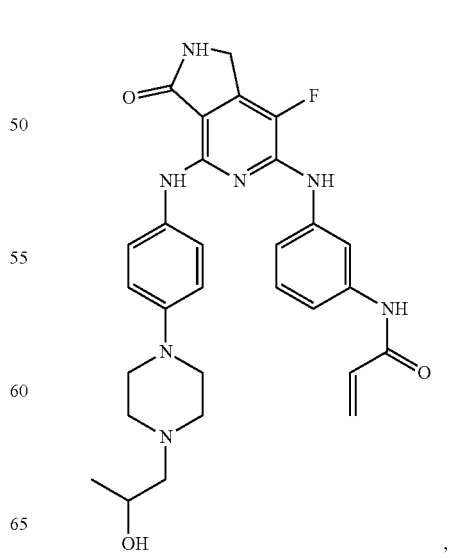
, -continued
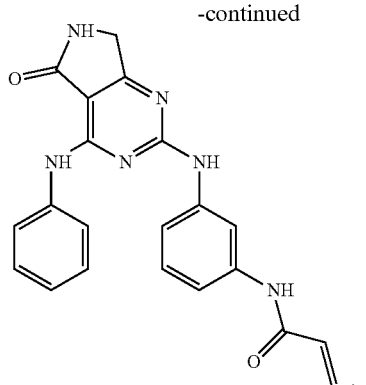
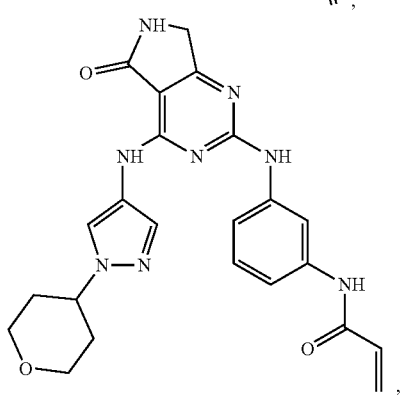
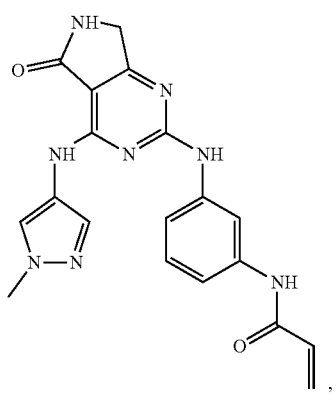
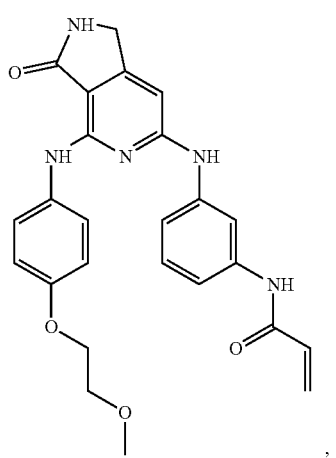
-continued
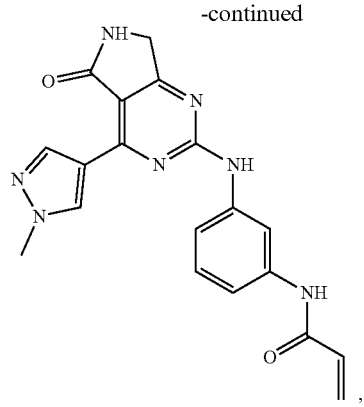
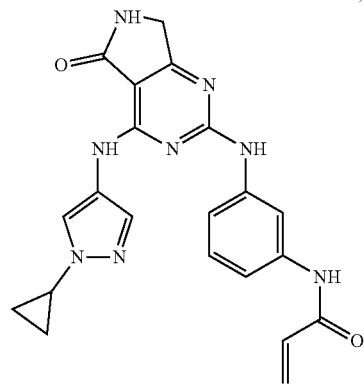
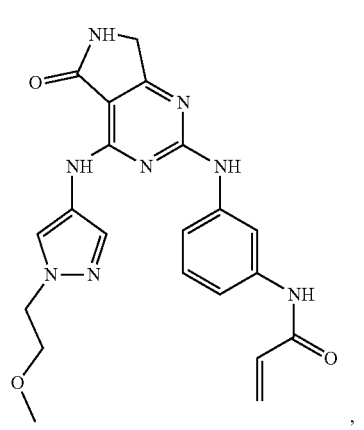
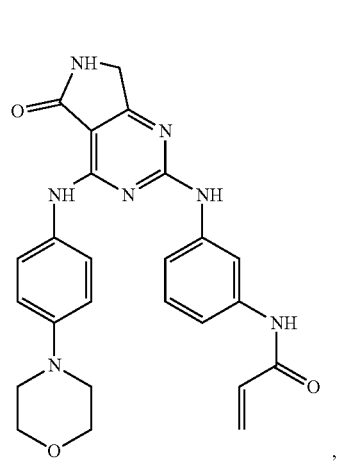

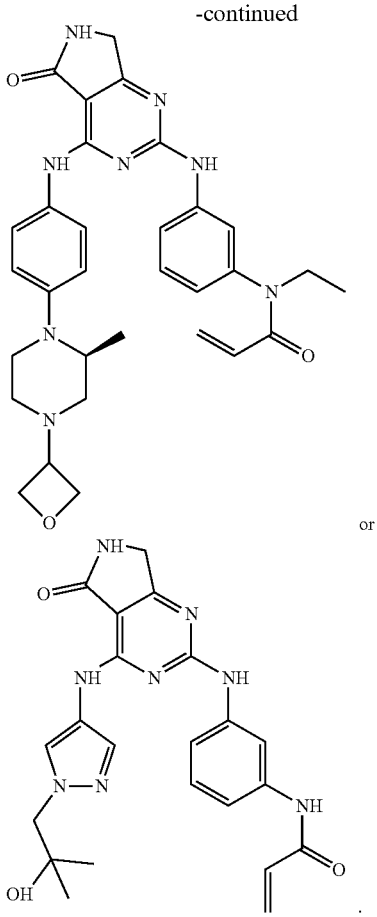

or

In the third aspect of the present disclosure there is provided a pharmaceutical composition comprising the compound of the first or second aspect of the present disclosure, or a pharmaceutically acceptable salt, solvate, stereoisomer or prodrug thereof; and a pharmaceutically acceptable carrier or excipient.

In the fourth aspect of the present disclosure there is provided a use of the compound of the first or second aspect of the present disclosure, or a pharmaceutically acceptable salt, solvate, stereoisomer or prodrug thereof or the pharmaceutical composition of the third aspect of the present disclosure, in the preparation of a kinase inhibitor drug.

In another preferred embodiment, the drug is used as a BTK inhibitor.

In the fifth aspect of the present disclosure there is provided a use of the compound of the first or second aspect of the present disclosure, or a pharmaceutically acceptable salt, solvate, stereoisomer or prodrug thereof or the pharmaceutical composition of the third aspect of the present disclosure, in the preparation of a drug used in the treatment of B cells-mediated diseases.

In the sixth aspect of the present disclosure there is provided a method for the treatment of B cells-mediated diseases, comprising administering the compound of the first or second aspect of the present disclosure, or a pharmaceutically acceptable salt, solvate, stereoisomer or prodrug thereof, or the pharmaceutical composition of the third aspect of the present disclosure, in a therapeutically effective amount to a patient in need thereof.

In the seventh aspect of the present disclosure there is provided a method for the treatment of B cells-mediated diseases, comprising administering the compound of the first or second aspect of the present disclosure, or a pharmaceutically acceptable salt, solvate, stereoisomer or prodrug thereof in a therapeutically effective amount and another therapeutically effective agent to a patient in need thereof.

In another preferred embodiment, the B cell-mediated disease is selected from the group consisting of a neoplastic disease, a proliferative disease, an allergic disease, an auto-immune disease, or an inflammatory disease.

In another preferred embodiment, the B cell-mediated disease is selected from the group consisting of solid tumor, acute lymphocytic leukemia, chronic lymphocytic leukemia, acute myeloid leukemia, chronic myelogenous leukemia, rheumatoid arthritis, psoriatic arthritis, osteoarthritis, systemic lupus erythematosus, psoriasis, rheumatoid spine inflammation and gouty arthritis.

In another preferred embodiment, the B cell-mediated disease is solid tumor.

In another preferred embodiment, the solid tumor is at least one of lymphoma, soft tissue sarcoma, lymphocytic lymphoma, mantle cell lymphoma, melanoma and multiple myeloma.

It is to be understood that within the scope of the present disclosure, the various technical features of the present disclosure and the various technical features specifically described hereinafter (as in the embodiments) may be combined with each other to form a new or preferred technical solution. Due to space limitations, we will not repeat them here.

DETAILED DESCRIPTION OF THE EMBODIMENTS

The inventors have conducted extensive and in-depth research, and unexpectedly discovered that the 4,6,7-trisubstituted 1,2-dihydropyrrolo[3,4-c]pyridin/pyrimidin-3-one derivatives as disclosed herein have a high inhibitory activity against enzymes such as BTK WT, and the like, and cells such as pBTK Y223, TNFα, and the like. Therefore, this series of compounds are expected to be developed into a drug for treating tumors. On this basis, the inventors completed the present disclosure.

Definition of Terms

As used herein, "alkyl" refers to a straight or branched saturated aliphatic hydrocarbyl. $C_{1-8}$ alkyl is an alkyl containing 1 to 8 carbon atoms, preferably $C_{1-6}$ alkyl or $C_{1-3}$ alkyl whose definition is similar. Non-limiting examples of the alkyl include methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof.

As used herein, "cycloalkyl" refers to a saturated or partially unsaturated monocyclic cyclic hydrocarbyl. "$C_{3-8}$ cycloalkyl" refers to a cyclic hydrocarbyl containing 3 to 8 carbon atoms, which is preferably $C_{3-6}$ cycloalkyl whose definition is similar. Non-limiting examples of cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclopentyl, cyclohexenyl.

As used herein, "spiroheterocycle" refers to a polycyclic hydrocarbon in which single rings share one atom (spiro atom), wherein one or two ring atoms are selected from heteroatoms such as nitrogen, oxygen, or $S(O)_n$ (wherein n is an integer from 0 to 2), and the remaining ring atoms are carbon atoms. These may contain one or more double bonds, but none of the rings have a completely conjugated π-electron system. According to the number of rings, the spiroheterocycles are divided into bicyclic spiroheterocycles or polycyclic spiroheterocycles, and wherein bicyclic spiroheterocycles are preferred. 4-membered/5-membered, 5-membered/5-membered, or 5-membered/6-membered bicyclic spiroheterocycle are more preferred. For example:

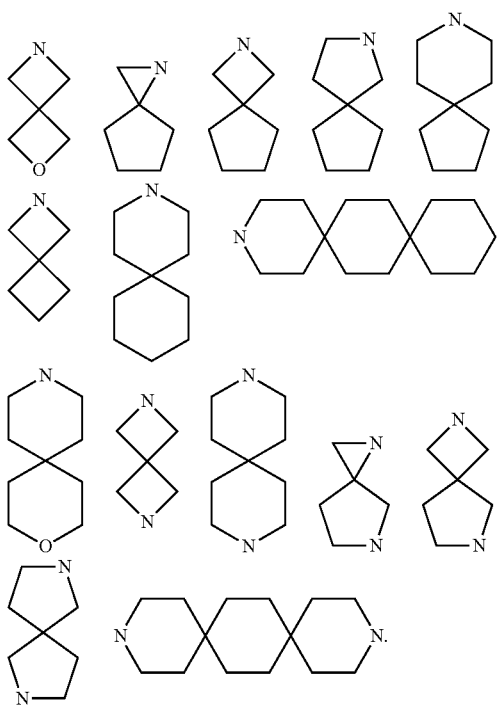

As used herein, "bridged heterocyclic ring" refers to a polycyclic group which shares two or more carbon atoms, wherein one or two ring atoms are selected from heteroatoms such as nitrogen, oxygen, or $S(O)_n$ (wherein n is an integer from 0 to 2), and the remaining ring atoms are carbon atoms. These bridged heterocyclic rings may contain one or more double bonds, but none of the rings have a completely conjugated π-electron system. Bicyclic bridged heterocyclic rings or tricyclic bridged heterocyclic ring are preferred. For example:

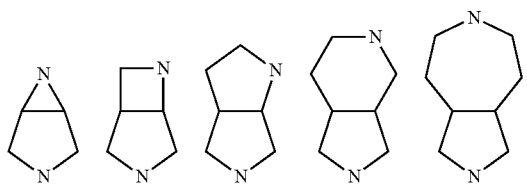

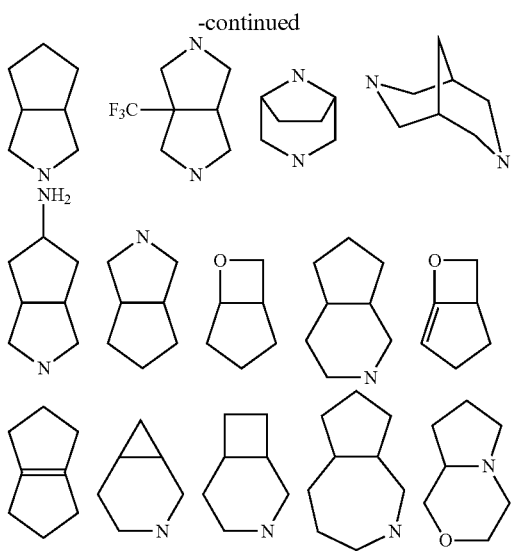

As used herein, "$C_{1-8}$ alkoxy" refers to —O—($C_{1-8}$ alkyl), in which the alkyl is defined as above. $C_{1-6}$ alkoxy is preferred, and $C_{1-3}$ alkoxy is more preferred. Non-limiting examples include methoxy, ethoxy, propoxy, isopropoxy, butoxy, tert-butoxy, isobutoxy, pentoxy and the like.

As used herein, "$C_{3-8}$ cycloalkoxy" refers to —O—($C_{3-8}$ cycloalkyl), in which the cycloalkyl is defined as above. $C_{3-6}$ cycloalkoxy is preferred. Non-limiting examples include cyclopropyloxy, cyclobutyloxy, cyclopentyloxy, cyclohexyloxy and the like.

As used herein, "$C_{6-10}$ aryl" refers to a full-carbon monocyclic ring or fused polycyclic rings having a conjugated i-electron system (i.e., rings that share adjacent carbon atom pairs), and is an aryl containing 6 to 10 carbon atoms; wherein phenyl and naphthyl are preferred, and phenyl is most preferred.

As used herein, "a bond" refers to a covalent bond through which two groups are attached.

As used herein, "halogen" refers to fluorine, chlorine, bromine or iodine.

As used herein, "halogenated" means that one or more (e.g., 1, 2, 3, 4, or 5) hydrogens in a group are substituted by halogen(s).

For example, "halogenated $C_{1-8}$ alkyl" means that the alkyl is substituted with one or more (e.g., 1, 2, 3, 4, or 5) halogens, in which the alkyl is defined as above. Halogenated $C_{1-6}$ alkyl is preferred, and halogenated $C_{1-3}$ alkyl is more preferred. Examples of halogenated $C_{1-8}$ alkyl include, but are not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

For example, "halogenated $C_{1-8}$ alkoxy" means that the alkoxy is substituted with one or more (e.g., 1, 2, 3, 4, or 5) halogens, in which the alkoxy is defined as above. Halogenated $C_{1-6}$ alkoxy is preferred, and halogenated $C_{1-3}$ alkoxy is more preferred. Examples of halogenated $C_{1-8}$ alkoxy include (but are not limited to) trifluoromethoxy, trifluoroethoxy, monofluoromethoxy, monofluoroethoxy, difluoromethoxy, difluoroethoxy and the like.

For another example, "halogenated $C_{3-8}$ cycloalkyl" means that the cycloalkyl is substituted with one or more (e.g., 1, 2, 3, 4, or 5) halogens, in which the cycloalkyl is defined as above. Halogenated $C_{3-6}$ cycloalkyl is preferred.

Examples of halogenated $C_{3-8}$ cycloalkyl include (but are not limited to) trifluorocyclopropyl, monofluorocyclopropyl, monofluorocyclohexyl, difluorocyclopropyl, difluorocyclohexyl and the like.

As used herein, "deuterated $C_{1-8}$ alkyl" means that the alkyl is substituted with one or more (e.g., 1, 2, 3, 4, or 5) deuterium atoms, wherein the alkyl group is defined as above. Deuterated $C_{1-6}$ alkyl is preferred, and deuterated $C_{1-3}$ alkyl is more preferred. Examples of deuterated $C_{1-8}$ alkyl include (but not limited to) mono-deuterated methyl, mono-deuterated ethyl, di-deuterated methyl, dideuterated ethyl, tri-deuterated methyl, tri-deuterated ethyl and the like.

As used herein, "amino" refers to —$NH_2$, "cyano" refers to —CN, "nitro" refers to $NO_2$, "benzyl" refers to —$CH_2$-phenyl, "oxo" refers to =O, "carboxyl" refers to —C(O)OH, "acetyl" refers to —$C(O)CH_3$, "hydroxymethyl" refers to —$CH_2OH$, "hydroxyethyl" refers to —$CH_2CH_2OH$, "hydroxy" refers to —OH, "thiol" refers to —SH, and the structure of "cyclopropylidene" is:

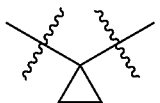

As used herein, "heteroaryl ring" and "heteroaryl" can be used interchangeably and refer to a group that has 5 to 10 ring atoms, preferably 5- or 6-membered monocyclic heteroaryl or 8- to 10-membered bicyclic heteroaryl which shares 6, 10 or 14 π electrons in the ring array and has 1 to 5 heteroatoms in addition to carbon atoms. "Heteroatom" refers to nitrogen, oxygen or sulfur.

As used herein, "4- to 7-membered saturated monoheterocyclic ring" means that 1, 2 or 3 carbon atoms in a 4- to 7-membered monocyclic ring are replaced by heteroatom(s) selected from nitrogen, oxygen or $S(O)_t$ (wherein t is an integer of 0 to 2), but the monocyclic ring does not include —O—O—, —O—S— or —S—S— ring moiety, and the remaining ring atoms are carbon; preferably 4- to 6-membered, more preferably 5- to 6-membered. Examples of 4- to 7-membered saturated monoheterocyclic ring include (but not limited to) propylene oxide, azetidine, oxetane, tetrahydrofuran, tetrahydrothiophene, tetrahydropyrrole, piperidine, pyrroline, oxazolidine, piperazine, dioxolane, dioxane, morpholine, thiomorpholine, thiomorpholine-1,1-dioxide, tetrahydropyran and the like.

As used herein, "5- to 6-membered monocyclic heteroaryl ring" means monoheteroaryl ring containing 5 to 6 ring atoms, for example, including (but not limited to) a thiophene ring, a N-alkylcyclopyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, a pyrazine ring and the like.

As used herein, "8- to 10-membered bicyclic heteroaryl ring" refers to a bicyclic heteroaryl ring containing 8 to 10 ring atoms, for example including (but not limited to) benzofuran, benzothiophene, indole, isoindole, quinoline, isoquinoline, indazole, benzothiazole, benzimidazole, quinazoline, quinoxaline, cinnoline and phthalazine.

As used herein, "substituted" means that one or more hydrogen atoms in a group, preferably 1 to 5 hydrogen atoms, are each independently substituted by the corresponding number of substituents, more preferably, 1 to 3 hydrogen atoms are each independently substituted by the corresponding number of substituents. It is obvious that substituents are only in their possible chemical positions, and those skilled in the art can, without any undue effort, determine (by experiment or theory) that it is possible or impossible. For example, an amino or hydroxyl with free hydrogen may be unstable when combined with a carbon atom having an unsaturated (such as olefinic) bond.

As used herein, any above-mentioned group may be substituted or unsubstituted. When the above-mentioned group is substituted, the substituent is preferably 1 to 5 (more preferably 1 to 3) of the following groups which is independently selected from the group consisting of halogen, —$O(CH_2)_pOC_{1-8}$ alkyl, —$O(CH_2)_pOH$, —$(CH_2)_pOC_{1-8}$ alkyl, 4- to 6-membered saturated monoheterocyclic ring, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), halogenated $C_{3-8}$ cycloalkyl (preferably halogenated $C_{3-6}$ cycloalkyl), hydroxy-substituted $C_{1-8}$ alkyl (preferably hydroxy-substituted $C_{1-6}$ alkyl, more preferably hydroxy-substituted $C_{1-3}$ alkyl), hydroxymethyl, hydroxyethyl, hydroxy, carboxy, $NR_{a0}R_{b0}$, —$C(O)OC_{1-6}$ alkyl, acetyl, $C_{1-8}$ alkoxy (preferably $C_{1-6}$ alkoxy, more preferably $C_{1-3}$ alkoxy), $C_{1-8}$ alkoxy-substituted $C_{1-8}$ alkyl (preferably $C_{1-6}$ alkoxy-substituted $C_{1-6}$ alkyl, more preferably $C_{1-3}$ alkoxy-substituted $C_{1-3}$ alkyl), halogenated $C_{1-8}$ alkoxy (preferably halogenated $C_{1-6}$ alkoxy, more preferably halogenated $C_{1-3}$ alkoxy), —$SO_2C_{1-8}$ alkyl (preferably —$SO_2C_{1-6}$ alkyl, more preferably —$SO_2C_{1-3}$ alkyl), $C_{6-10}$ aryl (preferably phenyl), 5- to 6-membered monocyclic heteroaryl or —Y-L; wherein Y is $(CH_2)_q$ or C(O); L is a 4- to 6-membered saturated monoheterocyclic ring or 5- or 6-membered monocyclic heteroaryl; and p and q are each independently 1, 2 or 3; $R_{a0}$ and $R_{b0}$ are each independently hydrogen, acetyl, $C_{1-8}$ alkyl (preferably $C_{1-6}$ alkyl, more preferably $C_{1-3}$ alkyl).

The above-mentioned various substituents of the present disclosure themselves can also be substituted with the groups described herein.

When 4- to 6-membered saturated single heterocycles described herein are substituted, the positions of the substituents may be at their possible chemical positions, and representative substitutions of the exemplary single heterocycles are shown below:

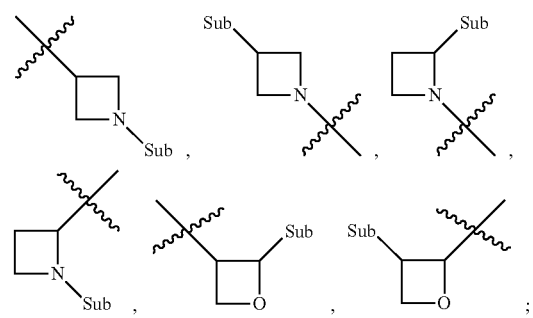

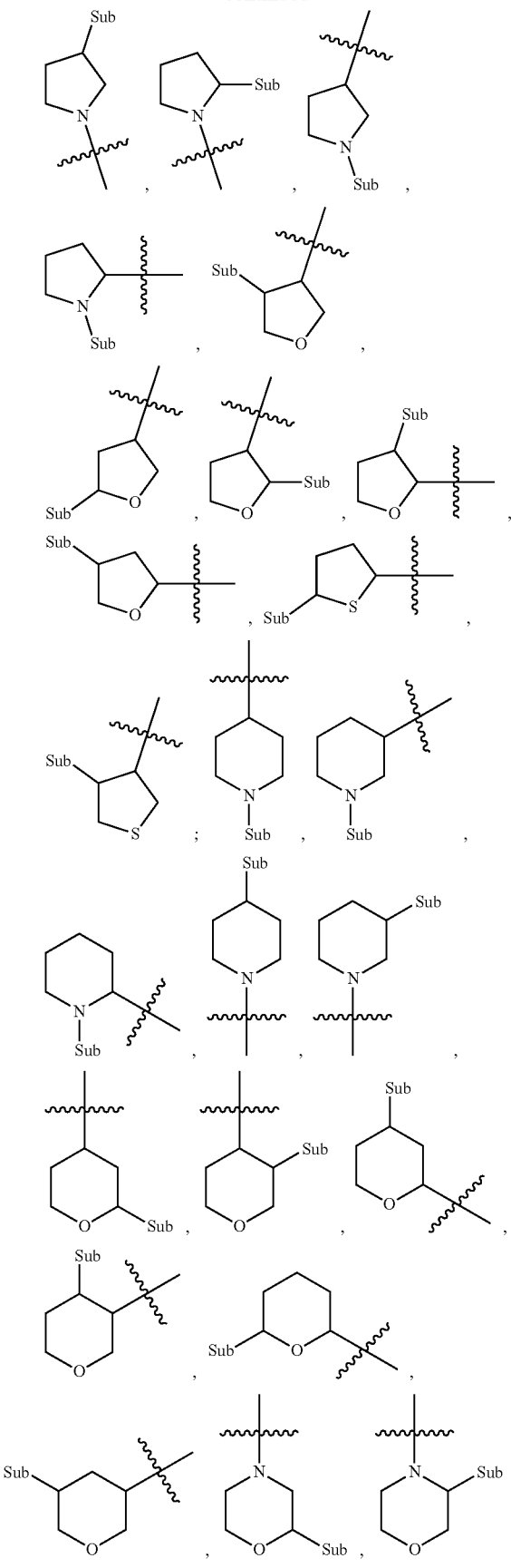

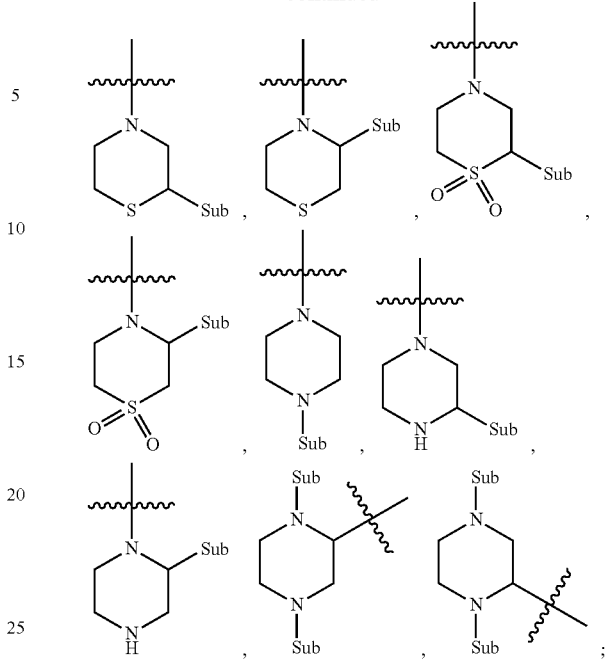

wherein "Sub" represents the various types of substituents described herein; "⌇" represents connections with other atoms.

When the 4- to 6-membered saturated single heterocycles described herein are substituents, they themselves may be unsubstituted or substituted with 1, 2 or 3 groups selected from the group consisting of halogen, hydroxy, $C_{1-3}$ alkyl, O=, $NR_{a0}R_{b0}$, hydroxymethyl, hydroxyethyl, carboxyl, —C(O)O$C_{1-3}$ alkyl, acetyl, halogenated $C_{1-3}$ alkyl, $C_{1-3}$ alkoxy, $C_{3-6}$ cycloalkyl, azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, a thiophene ring, a N-alkylpyrrole ring, a furan ring, a thiazole ring, an imidazole ring, an oxazole ring, a pyrrole ring, a pyrazole ring, a triazole ring, a tetrazole ring, an isoxazole ring, an oxadiazole ring, a thiadiazole ring, a pyridine ring, a pyridazine ring, a pyrimidine ring, and a pyrazine ring; wherein $R_{a0}$ and $R_{b0}$ are each independently hydrogen or $C_{1-3}$ alkyl.

The "pharmaceutically acceptable salt" includes pharmaceutically acceptable acid addition salts and pharmaceutically acceptable base addition salts.

"Pharmaceutically acceptable acid addition salt" means a salt formed with an inorganic or organic acid, with retaining the bioavailability of the free base without any other side effects.

"Pharmaceutically acceptable base addition salts", includes but not limited to salts of inorganic bases such as sodium, potassium, calcium and magnesium salts, and the like, and salts of organic bases such as ammonium salts, triethylamine salts, lysine salts, arginine salts and the like.

As mentioned herein, "solvate" refers to a complex of the compound of the present disclosure with a solvent. They either react in a solvent or precipitate or crystallize from the solvent. For example, a complex formed with water is referred to as a "hydrate". Solvates of the compound of formula (I) are within the scope of the present invention.

The compounds of formula (I) of the present disclosure may contain one or more chiral centers and exist in different optically active forms. When the compound contains one chiral center, the compound contains enantiomers. The present disclosure includes the two isomers and mixtures of the two isomers, such as racemic mixtures. Enantiomers can be resolved by methods known in the art, such as crystallization, chiral chromatography and the like. When the compound of formula (I) contains more than one chiral center, diastereomers may be present. The present disclosure includes resolved optically pure specific isomers as well as mixtures of diastereomers. Diastereomers can be resolved by methods known in the art, such as crystallization and preparative chromatography.

The present disclosure includes prodrugs of the above compounds. Prodrugs include those in which known amino protecting groups or carboxy protecting groups can be hydrolyzed under physiological conditions or released via an enzymatic reaction to give the parent compound. Specific prodrug preparation methods can be referred to (Saulnier, M. G.; Frennesson, D. B.; Deshpande, M. S.; Hansel, S. B. and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, M J Med. Chem. 2000, 43, 475.).

In general, the compound of the present disclosure, or a pharmaceutically acceptable salt thereof, or a solvate thereof, or a stereoisomer, or prodrug thereof, can be administered in a suitable dosage form with one or more pharmaceutically acceptable carriers. These dosage forms are suitable for oral, rectal, topical, intraoral, and other parenteral administration (e.g., subcutaneous, intramuscular, intravenous, etc.). For example, dosage forms suitable for oral administration include capsules, tablets, granules, syrups, and the like. The compound of the present disclosure contained in these preparations may be a solid powder or granule, a solution or suspension in an aqueous or non-aqueous liquid, a water-in-oil or oil-in-water emulsion or the like. The above dosage forms can be prepared from the active compound with one or more carriers or excipients via conventional pharmaceutical methods. The above carriers need to be compatible with the active compound or other excipients. For solid preparations, commonly used non-toxic carriers include, but not limited to, mannitol, lactose, starch, magnesium stearate, cellulose, glucose, sucrose, and the like. Carriers for liquid preparations include water, physiological saline, glucose aqueous solution, ethylene glycol, polyethylene glycol, and the like. The active compound can form a solution or suspension with the above carriers.

The compositions of the present disclosure are formulated, quantified, and administered in a manner consistent with medical practices. The "therapeutically effective amount" of a given compound will be determined by the factors such as the particular condition to be treated, the individual to be treated, the cause of the condition, the target of the drug, the mode of administration and the like.

As used herein, "therapeutically effective amount" refers to an amount of the compound of the present disclosure that will elicit the biological or medical response of a subject, for example, reduction or inhibition of an enzyme or a protein activity, or amelioration of a symptom, alleviation of a condition, slow or delay disease progression, or prevention of a disease, etc.

As used herein, "pharmaceutically acceptable carrier" refers to non-toxic, inert, solid or semi-solid substance or a liquid filler, a diluent, an encapsulating material or an auxiliary formulation or any type of excipient that is compatible with a patient which is preferably a mammal and more preferably a human. It is suitable for delivering active agent to a target without terminating the activity of the agent.

As used herein, "patient" refers to an animal, preferably a mammal, and more preferably a human. The term "mammal" refers to a warm-blooded vertebrate mammal, including, for example, cat, dog, rabbit, bear, fox, wolf, monkey, deer, rat, pig and human.

As used herein, "treating" refers to alleviating, delaying, attenuating, preventing, or maintaining an existing disease or disorder (eg, cancer). The treating also includes curing one or more symptoms of the disease or disorder, preventing its development or reducing it to some extent.

Preparation Method

The present disclosure provides preparation methods of compounds of formula (I), and the compounds of the present disclosure can be prepared by a variety of synthetic operations. Exemplary preparation methods of these compounds may include (but not limited to) the processes described below.

Preferably, the compounds of formula (I) can be prepared through the following schemes and exemplary methods described in embodiments, as well as the related publications available for those skilled in the art.

During the specific operations, the procedures of the methods can be extended or combined as desired in practice.

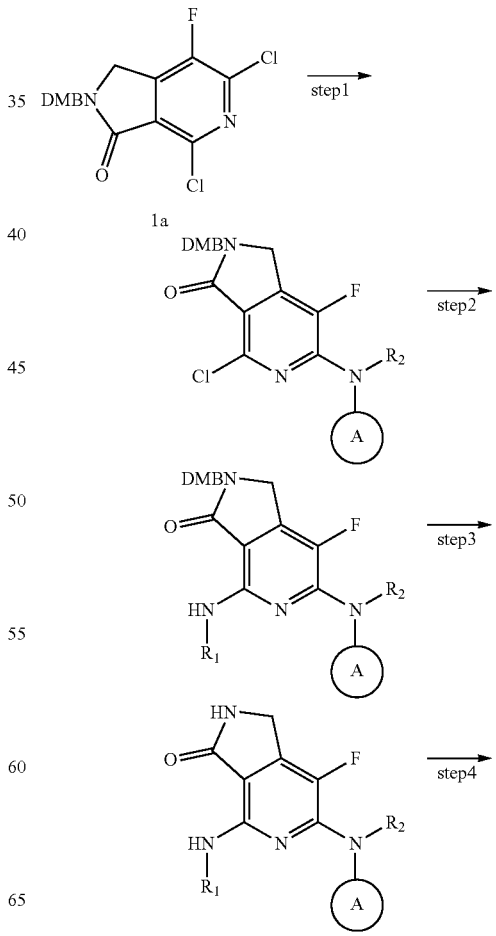

Scheme 1

-continued

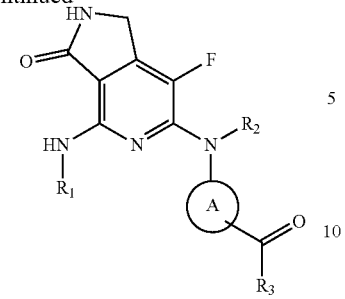

(I)

Step 1: Compound 1a is subjected to a nucleophilic substitution reaction with a corresponding amine (primary or secondary amine) under basic conditions.

Step 2: Chloride on the pyridine ring is subjected to a Buchwald coupling reaction with the corresponding amine under catalyzation of a palladium catalyst in basic conditions.

Step 3: The amine is deprotected under acidic conditions.

Step 4: The secondary amine on ring A is subjected to an amide condensation reaction with an acyl chloride under basic conditions.

Scheme 2

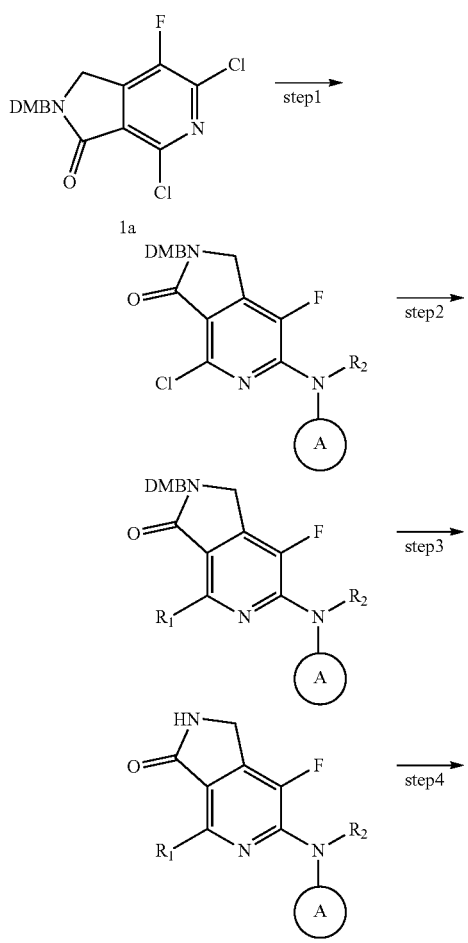

-continued

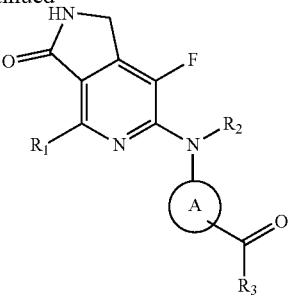

(I)

Step 1, Step 3, and Step 4 are the same as Step 1, Step 3, and Step 4 of Scheme 1.

Step 2: Chloride on the pyridine ring is subjected to a Suzuki coupling reaction with the corresponding boric acid under catalyzation of a palladium catalyst in basic conditions.

The reactions in the above various steps are conventional reactions known to those skilled in the art. Unless otherwise stated, the reagents and starting materials used in the synthetic routes are either commercially available or can be prepared according to the designed different compound structures by those skilled in the art by referring to known methods.

The main advantages of the present disclosure over the prior art include the following: A series of novel 4,6,7-trisubstituted 1,2-dihydropyrrolo[3,4-c]pyridin/pyrimidin-3-one derivatives are provided, and they have relatively high inhibitory activity against BTK WT enzyme and pBTK Y223 cell and the other cells and weak inhibitory activity against EGFR WT. They have obvious selective inhibition and can be used as a drug for treating tumors.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar with or equivalent to those described herein can be applied to the present invention.

As used herein, DMB refers to 2,4-dimethoxybenzyl, THF refers to tetrahydrofuran, EA refers to ethyl acetate, PE refers to petroleum ether, $Ac_2O$ refers to acetic anhydride, NBS refers to N-bromosuccinimide, DCM refers to dichloromethane, AIBN refers to azobisisobutyronitrile, Pd(dppf)$Cl_2$ refers to [1,1'-bis(diphenylphosphino)ferrocene]palladium dichloride, TFA refers to trifluoroacetic acid, TBSCl refers to tert-butyldimethylchlorosilane, NCS refers to N-chlorosuccinimide, DHP refers to dihydrotetrahydropyran, $LiAlH_4$ refers to lithium aluminum hydride, PMB refers to p-methoxybenzyl, LiHMDS refers to lithium bistrimethylsilylamide, $Pd_2(dba)_3$ refers to tris(dibenzylideneacetone)dipalladium, RuPhos refers to 2-dicyclohexylphos-2',6'-diisopropoxy-1,1'-biphenyl, DMAP refers to 4-dimethylaminopyridine, THP is tetrahydrotetrahydropyran, n-BuLi refers to n-butyllithium, TMsOTf refers to trimethylsilyl triflate, TEBAC refers to triethyl benzylammonium chloride, HATU refers to 2-(7-azobenzotriazole)-N,N,N',N'-tetramethyluronium hexafluorophosphate, DMF refers to dimethylformamide, DMSO refers to dimethylsulfoxide, DIPEA refers to N,N-diisopropylethylamine, BINAP refers to (2R,3S)-2,2'-bis diphenylphosphino-1,1'-binaphthyl, DIPA refers to diisopropylamine, NMP refers to alkylpyrrolidone, Xantphos refers to 9,9-dimethyl-4,5-bis(diphenylphosphino)xanthene.

As used herein, room temperature refers to about 20-25° C.

Preparation of Intermediate 1a

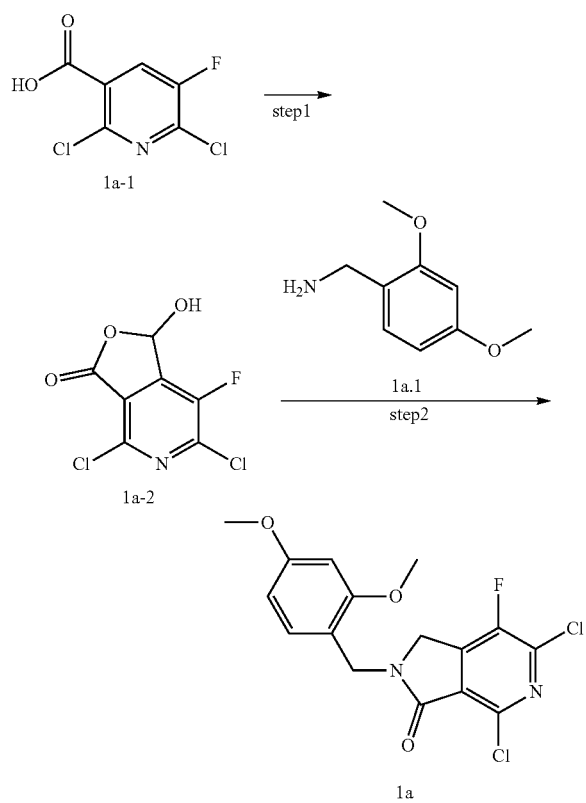

Step 1: A solution of compound 1a-1 (6.0 g, 30.0 mmol) in THF (80 mL) was added with n-BuLi (27 mL, 66 mmol) and DIPA (6.6 g, 66 mmol) at −78° C., and after stirring for 1 h, DMF (10 mL) was added, and then the mixture was warmed to room temperature and stirred for further 2 h. The reaction was followed by LC-MS until it was completed. The mixture was adjusted to pH 5-6 by adding HCl (2N) to the system, and extracted with EtOAc. The organic phase was washed with saturated brine, dried over anhydrous sodium sulfate and concentrated. The residue was purified by combiflash to give 6.8 g of compound 1a-2. MS m/z (ESI): 238 [M+H]+.

Step 2: Compound 1a-2 (6.8 g, 30.0 mmol) in 1,4-dioxane (80 mL) was added with compound 1a.1 (15 g, 90.0 mmol), acetate (2 mL) and NaBH(OAc)₃ (18.9 g, 90.0 mmol), and then the mixture was stirred at 50° C. overnight. The reaction was followed by LC-MS until it was completed. The mixture was evaporated to dryness under reduced pressure, washed with saturated brine and extracted with DCM. The organic phase was dried and concentrated. The residue was purified by combiflash to give 4.8 g of compound 1a. MS m/z (ESI): 371 [M+H]+.

Preparation of Intermediate 1b

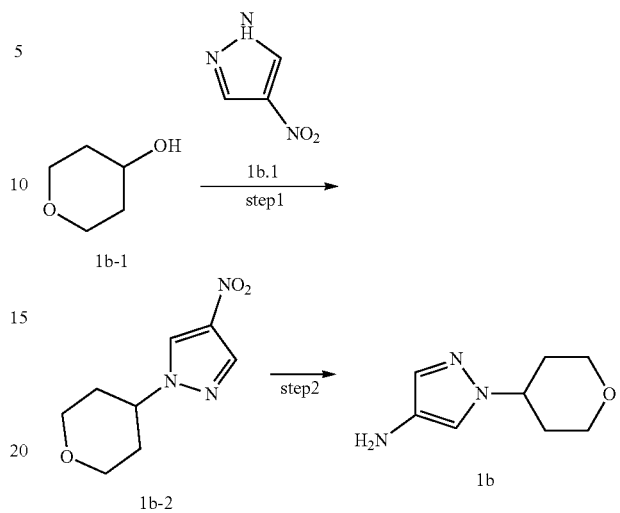

Step 1: A solution of compound 1b-1 (1.63 g, 16.0 mmol) and compound 1b.1 (1.8 g, 16.0 mmol) in THF (30 mL) was add with triphenylphosphine (5.03 g, 19.2 mmol), and then a solution of DIAD (4.2 g, 20.7 mmol) in tetrahydrofuran (20 mL) was added dropwise. The mixture was stirred at room temperature for 20 h. The reaction was followed by LC-MS until it was completed.

The mixture was concentrated and purified by combiflash to obtain 4.2 g of compound 1b-2. MS m/z (ESI):198 [M+H]+.

Step 2: A solution of compound 1b-2 (3.4 g, 17.2 mmol) in ethanol (50 mL) was added with a solution of iron powder (4.8 g, 86.3 mmol) and ammonium chloride (4.6 g, 86.3 mmol) in water (20 mL). The mixture was stirred at 90° C. for 2 h. The reaction was followed by LC-MS until it was completed. The reaction mixture was filtered, and the filtrate was concentrated to give compound 1b which was directly used for the next step. MS m/z (ESI): 168 [M+H]+.

Preparation of Intermediate 1c

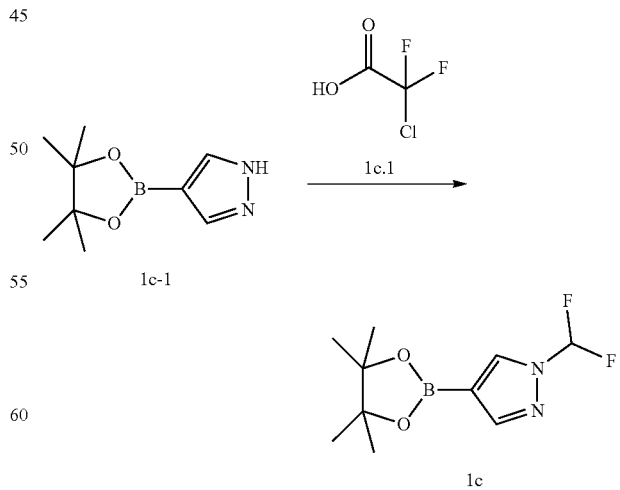

A solution of compound 1c-1 (500 mg, 2.58 mmol) in acetonitrile (15 mL) was added with compound 1c.1 (128 mg, 0.52 mmol) and 18-crown-6 (470 mg, 3.1 mmol). The mixture was stirred at 90° C. overnight. The reaction mixture was filtered, and the filtrate was evaporated to dryness to give 400 mg of yellow oily compound, which was compound 1c and used directly in the next step. MS m/z (ESI):244.0 [M+H]⁺.

Preparation of Intermediate 1d

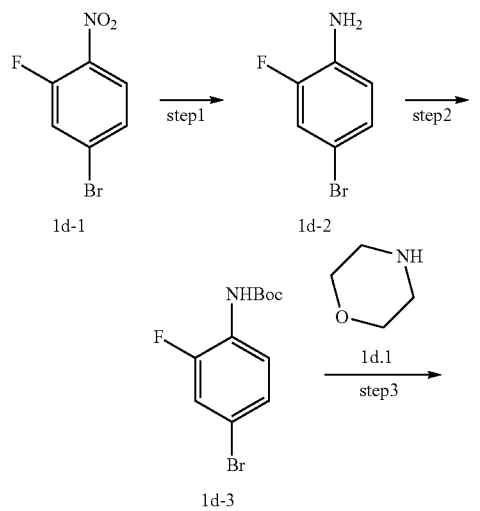

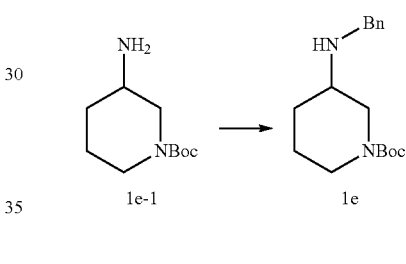

Step 1: The preparation method was the same as that for compound 1b, except that compound 1b-2 in the preparation of compound 1b was replaced with compound 1d-1. MS m/z (ESI): 191.9 [M+H]⁺.

Step 2: A solution of compound 1d-2 (1.5 g, 7.9 mmol) in ethyl acetate (50 mL) was added with (Boc)₂O (2.1 g, 9.5 mmol) and DIPEA. The mixture was stirred at room temperature for 3 h.

The reaction was followed by LC-MS until it was completed. The reaction mixture was concentrated to give compound 1d-3 which was used directly in the next step. MS m/z (ESI): 291 [M+H]⁺.

Step 3: Compound 1d-3 (1.5 g, 5.17 mmol), morpholine (470 mg, 5.39 mmol), Pd₂(dba)₃ (210 mg, 0.23 mmol), Xantphos (240 mg, 0.503 mmol), cesium carbonate (3.38 g, 10.37 mmol) and 1,4-dioxane (20 mL) were added to a 100 mL three-necked flask, the solution was reacted at 110° C. for 3 h. The reaction was followed by LC-MS until it was completed. The reaction solution was cooled to room temperature, concentrated and purified by combiflash (n-hexane containing 0-20% EA) to obtain the compound 1d-4. MS m/z (ESI): 297 [M+H]⁺.

Step 4: The preparation method was the same as that for compound 2-3, except that compound 2-2 in the preparation of compound 2-3 was replaced with compound 1d-4. MS m/z (ESI): 197 [M+H]⁺.

Preparation of Intermediate 1e

A solution of compound 1e-1 (2 g, 10.0 mmol), benzaldehyde (1.59 g, 15 mmol) and acetic acid (10 mL) in THF (50 mL) was stirred for 1 h, and then NaBH₃CN (1.89 g, 30 mmol) was added portionwise. The mixture was stirred for another 1 h at room temperature. The reaction was followed by LC-MS until it was completed. The reaction solution was washed with saturated sodium bicarbonate solution, and extracted with DCM. The organic layer was dried and concentrated. The residue was purified by combiflash to give oily compound 1e. MS m/z (ESI): 291 [M+H]⁺.

Example 2 Preparation of 6-(1-acryloylpiperidin-3-ylamino)-7-fluoro-4-(4-(2-methoxyethoxy) phenylamino)-1H-pyrrolo[3,4-c]pyridine-3 (2H)-one
(G-2)

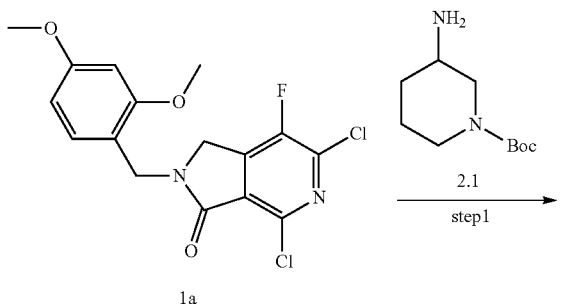

-continued

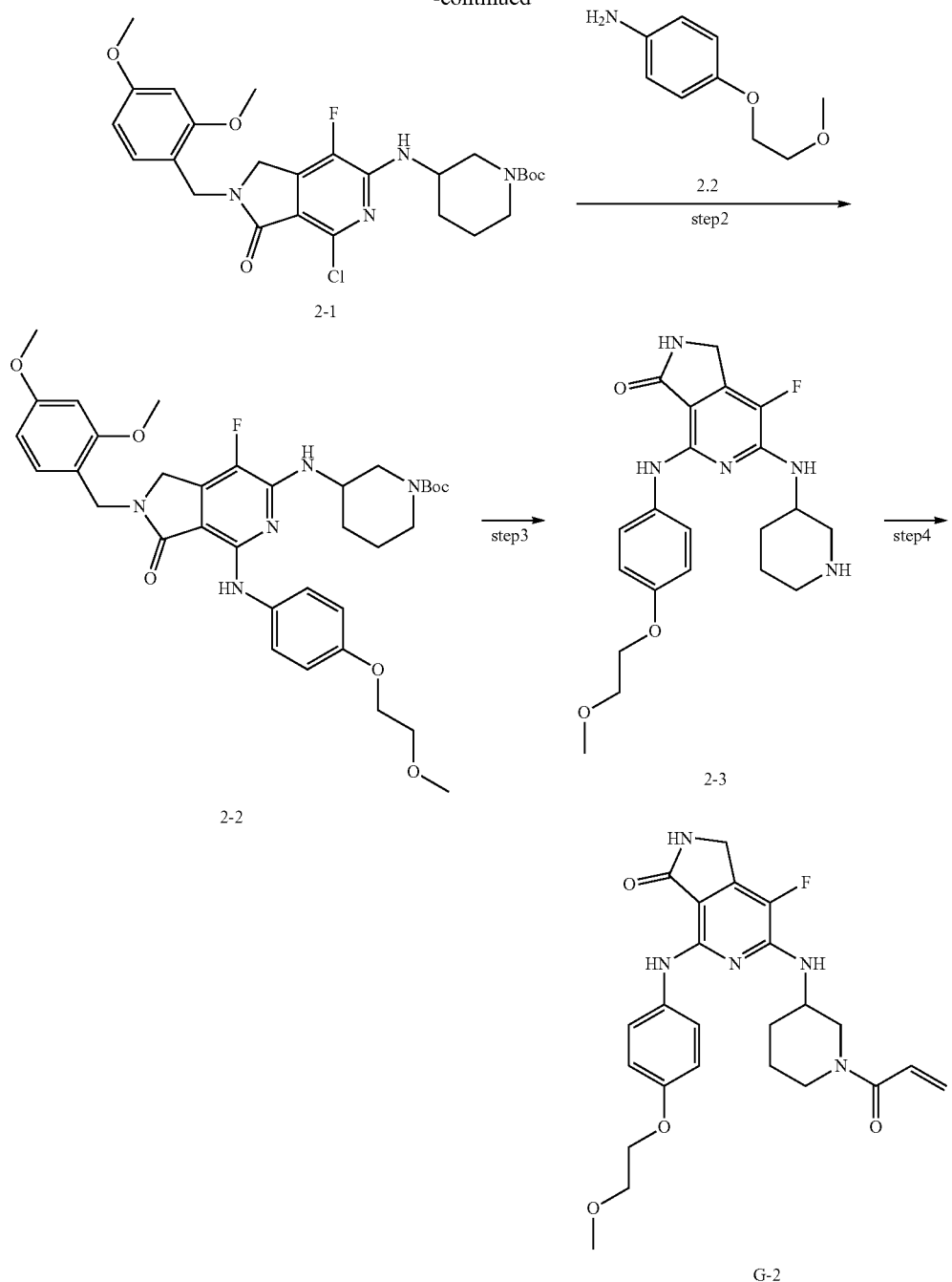

Step 1: A solution of compound 1a (740 mg, 2 mmol) in NMP (10 mL) was added with compound 2.1 (600 mg, 3 mmol) and DIPEA (780 mg, 6 mmol). The mixture was subjected to microwave reaction at 180° C. for 30 min under an argon atmosphere. The reaction was followed by LC-MS until it was completed. The reaction mixture was cooled to room temperature, diluted with DCM, and washed with water and saturated brine. The organic layer was dried and concentrated. The residue was purified by combiflash to give 300 mg of compound 2-1. MS m/z (ESI): 535 [M+H]$^+$.

Step 2: A solution of compound 2-1 (250 mg, 0.5 mmol), compound 2.2 (102 mg, 0.6 mmol), Pd$_2$(dba)$_3$ (45 mg, 0.05 mmol), Xantphos (54 mg, 0.1 mmol), and cesium carbonate (326 mg, 1 mmol) in 1,4-dioxane (15 mL) was subjected to microwave reaction at 160° C. for 50 min under an argon atmosphere. The reaction was followed by LC-MS until it was completed. The reaction mixture was cooled to room temperature, diluted with EA, and washed with water and saturated brine. The organic layer was dried and concentrated. The residue was purified by combiflash to give 270 mg of compound 2-2. MS m/z (ESI): 666 [M+H]$^+$.

Step 3: A solution of compound 2-2 (270 mg, 0.4 mmol) in TFA (5 mL) was subjected to microwave reaction at 110° C. for 20 min. The reaction was followed by LC-MS until it was completed. The reaction mixture was washed with saturated brine, and the mixture was adjusted to pH 7-8 with saturated sodium bicarbonate solution and extracted with DCM. The organic phase was dried and concentrated to give 124 mg of compound 2-3 which was used directly in the next step. MS m/z (ESI): 416 [M+H]+.

Step 4: A solution of compound 2-3 (83 mg, 0.2 mmol) in DCM (10 mL) was separately added with acryloyl chloride (18 mg, 0.2 mmol) and DIPEA (80 mg, 0.6 mmol) under an argon atmosphere. The mixture was stirred at room temperature for 2 h. The reaction was followed by LC-MS until it was completed. The reaction mixture was washed with saturated brine and extracted with DCM. The organic layer was dried and concentrated. The residue was purified to give compound G-2. MS m/z (ESI): 470.2 [M+H]+. $^1$H NMR (400 MHz, DMSO-d6) δ 8.54 (s, 1H), 7.73 (s, 1H), 7.48 (d, J=7.6 Hz, 2H), 6.81 (d, J=8.5 Hz, 2H), 6.60 (s, 1H), 6.44 (s, 1H), 6.00 (d, J=16.9 Hz, 1H), 5.52 (s, 1H), 4.31 (s, 2H), 4.05 (m, 4H), 3.62 (s, 2H), 3.31 (s, 2H), 2.00 (s, 2H), 1.77 (s, 1H), 1.69 (s, 1H), 1.46 (s, 1H).

Example 3 Preparation of 6-(1-acryloylazacycloheptane-3-ylamino)-7-fluoro-4-(4-(2-methoxyethoxy)phenylamino)-1H-pyrrolo[3,4-c]pyridine-3(2H)-one (G-3)

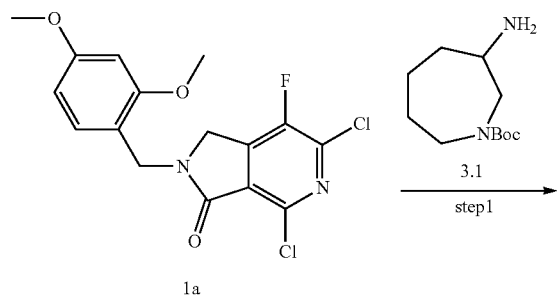

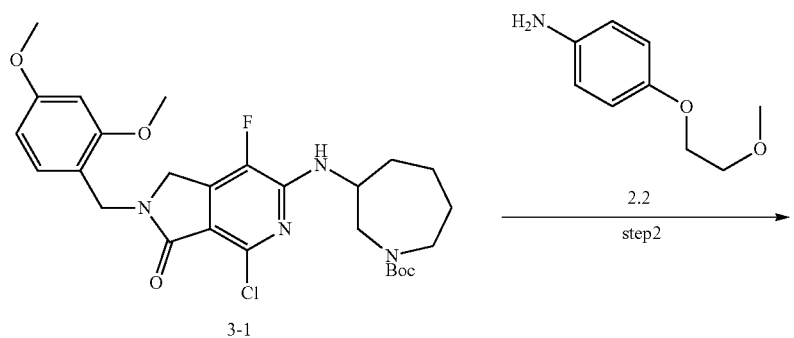

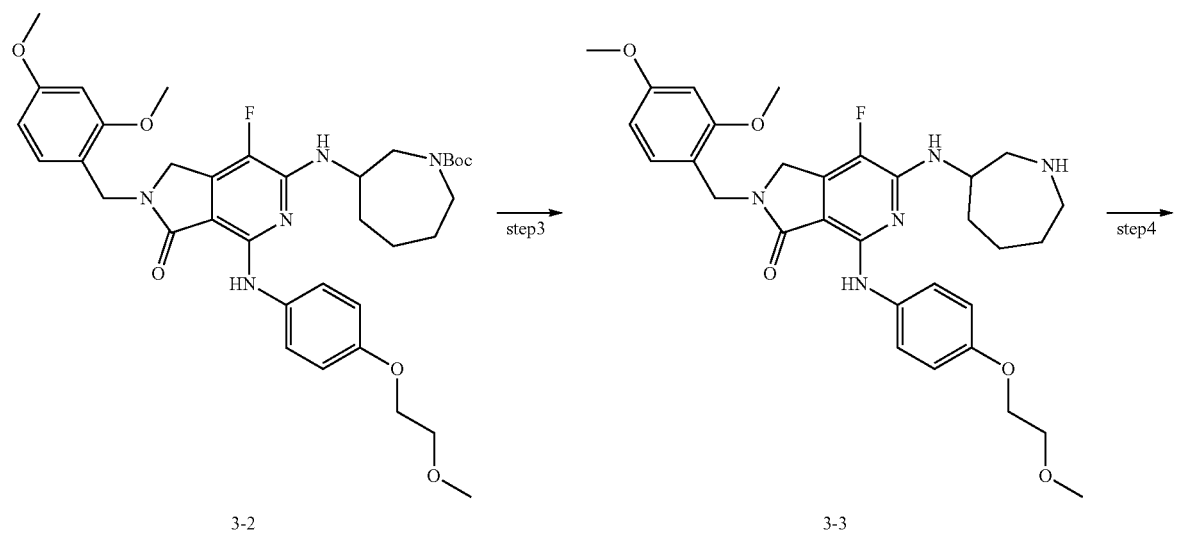

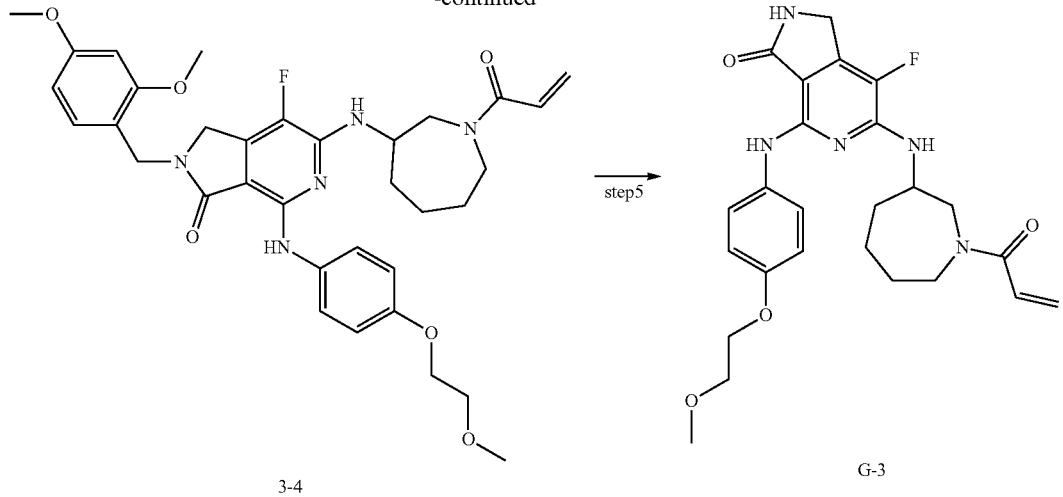

3-4

→ step5

G-3

Step 1: The preparation method was the same as that for compound 2-1, except that compound 2.1 in the preparation of compound 2-1 was replaced with compound 3.1. MS m/z (ESI): 549.3 [M+H]⁺.

Step 2: The preparation method was the same as that for compound 2-2, except that compound 2-1 in the preparation of compound 2-2 was replaced with compound 3-1. MS m/z (ESI): 680.5 [M+H]⁺.

Step 3: A solution of compound 3-2 (83 mg, 0.001 mmol) in DCM (5 mL) was added with TFA (2 mL). The mixture was stirred at room temperature for 1 h. The reaction was followed by LC-MS until it was completed. Most of TFA was removed under reduced pressure, and the pH of the mixture was adjusted to 7-8 by adding saturated sodium bicarbonate solution, and the mixture was extracted with DCM. The organic layers are combined, dried and concentrated to give compound 3-3 which was used directly in the next step. MS m/z (ESI): 580.3 [M+H]⁺.

Step 4: The preparation method was the same as that for compound G-2, except that compound 2-3 in the preparation of compound G-2 was replaced with compound 3-3. MS m/z (ESI): 634.4 [M+H]⁺.

Step 5: A solution of compound 3-4 (70 mg, 0.11 mmol) in TFA (3 mL) was added with Et₃SiH (0.2 mL). The mixture was heated to 80° C. and stirred for 2 h. The reaction was followed by LC-MS until it was completed. Most of TFA was removed under reduced pressure, and the pH of the mixture was adjusted to 7-8 by adding saturated sodium bicarbonate solution, and the mixture was extracted with ethyl acetate. The organic layers were combined, dried and concentrated. The residue was purified by Prep-HPLC to give 4.5 mg of compound G-3. MS m/z (ESI): 484 [M+H]⁺.
¹H NMR (400 MHz, DMSO-d6): δ 8.60 (s, 1H), 8.15 (d, J=12 Hz, 1H), 7.60 (d, J=8.8 Hz, 1H), 7.54 (d, J=8.8 Hz, 1H), 6.60-7.05 (m, 4H), 6.21 (dd, J₁=2.4 Hz, J₂=16.4 Hz, 0.5H), 6.08 (dd, J₁=2.4 Hz, J₂=16.4 Hz, 0.5H), 5.73 (dd, J₁=2.4 Hz, J₂=10.4 Hz, 0.5H), 5.44 (dd, J₁=2.4 Hz, J₂=10.4 Hz, 0.5H), 4.20-4.40 (m, 3H), 3.78-4.05 (m, 4H), 3.41-3.67 (m, 4H), 3.30 (s, 3H), 1.18-2.02 (m, 6H).

Example 7 Preparation of 6-(1-acryloylpiperidin-3-ylamino)-7-fluoro-4-(1-methyl-1H-pyrazole-4-yl)-1H-pyrrolo[3,4-c]pyridine-3(2H)-one (G-7)

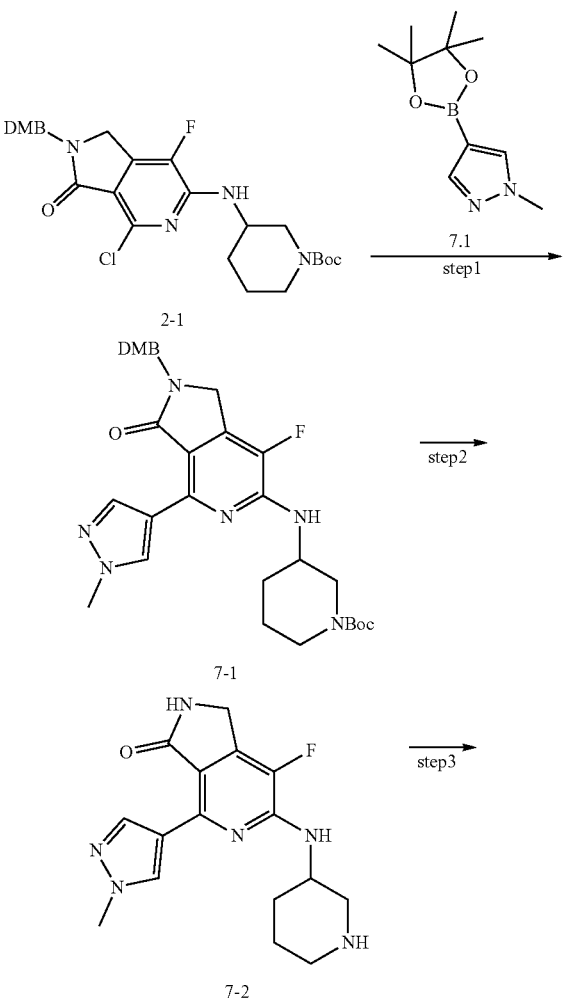

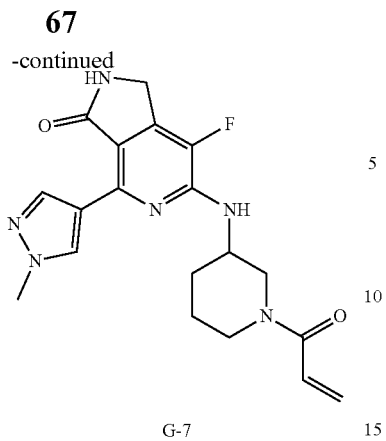

G-7

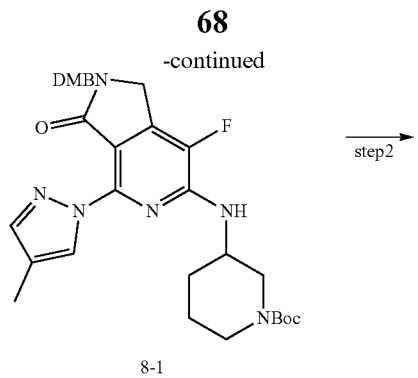

8-1

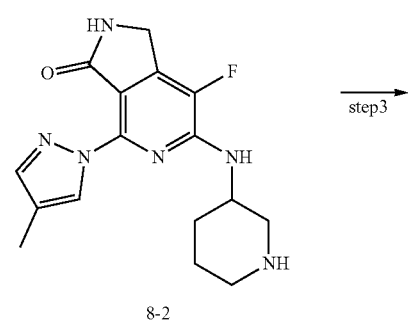

8-2

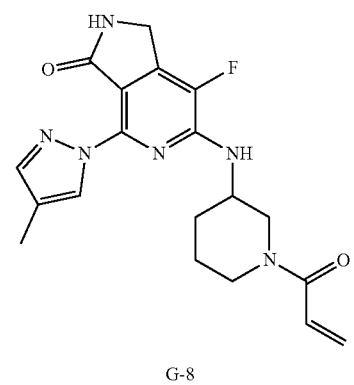

G-8

Step 1: A solution of compound 2-1 (150 mg, 0.3 mmol), compound 7.1 (150 mg, 0.5 mmol), Pd(dppf)Cl$_2$ (25 mg, 0.03 mmol), potassium carbonate (130 mg, 0.9 mmol) in a mixture of 1,4-dioxane (10 mL) and water (1 mL) was subjected to microwave reaction at 130° C. for 30 min under an argon atmosphere. The reaction was followed by LC-MS until it was completed. The solvent was evaporated to dryness under reduced pressure. The residue was purified by combiflash to give 140 mg of compound 7-1. MS m/z (ESI): 581 [M+H]$^+$.

Step 2: A solution of compound 7-1 (140 mg, 0.2 mmol) in TFA (3 mL) was stirred at 80° C. for 3 h. The reaction was followed by LC-MS until it was completed. The reaction mixture was adjusted to pH 7 by adding saturated sodium bicarbonate solution, extracted with DCM and washed with saturated brine. The organic phase was dried and concentrated to give 100 mg of compound 7-2. MS m/z (ESI): 331 [M+H]+.

Step 3: The preparation method was the same as that for compound G-2, except that compound 2-3 in the preparation of compound G-2 was replaced with compound 7-2. The residue was purified by Prep-HPLC to give compound G-7. MS m/z (ESI): 385 [M+H]$^+$. $^1$H NMR (400 MHz, DMSO-d$_6$) δ 8.80 (d, J=59.2 Hz, 1H), 8.30 (dd, J=44.8, 35.1 Hz, 2H), 7.00 (s, 1H), 6.73 (d, J=81.8 Hz, 1H), 6.11 (t, J=18.1 Hz, 1H), 5.59 (dd, J=70.2, 10.0 Hz, 1H), 4.84 (d, J=9.8 Hz, 1H), 4.32 (s, 1H), 4.27-4.06 (m, 1H), 4.01 (s, 1H), 3.84 (s, 2H), 3.01 (s, 1H), 2.75 (s, 1H), 1.97 (s, 1H), 1.75 (s, 2H), 1.48 (s, 1H).

Example 8 Preparation of 6-(1-acryloylpiperidin-3-ylamino)-7-fluoro-4-(4-methyl-1H-pyrazole-1-yl)-1H-pyrrolo[3,4-c]pyridine-3(2H)-one (G-8)

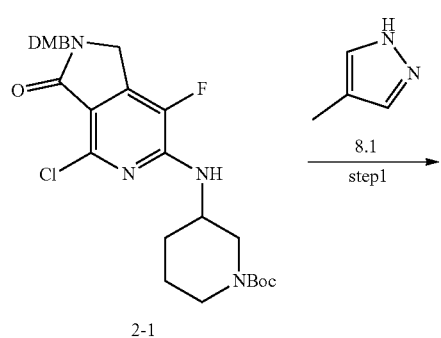

Step 1: The preparation method was the same as that for compound 2-2, except that compound 2.2 in the preparation of compound 2-2 was replaced with compound 8.1. MS m/z (ESI): 581 [M+H]$^+$.

Step 2: The preparation method was the same as that for compound 2-3, except that compound 2-2 in the preparation of compound 2-3 was replaced with compound 8-1. MS m/z (ESI): 331 [M+H]$^+$.

Step 3: The preparation method was the same as that for compound G-2, except that compound 2-3 in the preparation of compound G-2 was replaced with compound 8-2. MS m/z (ESI): 385.2 [M+H]$^+$. $^1$H NMR (400 MHz, DMSO-d$_6$) δ 8.47-8.18 (m, 2H), 7.52-7.47 (m, 1H), 7.36-7.31 (m, 1H), 7.09-6.73 (m, 2H), 6.09-6.01 (m, 1H), 5.66-5.49 (m, 1H), 4.43-4.32 (m, 2H), 3.93-3.90 (m, 1H), 3.79-3.72 (m, 1H), 3.03-2.84 (m, 1H), 2.70-2.64 (m, 1H), 2.75-2.61 (m, 1H), 2.05 (s, 3H), 1.96-1.94 (m, 1H), 1.76-1.73 (m, 1H), 1.44-1.35 (m, 1H).

Example 26 Preparation of 6-(1-acryloyl-6-methylpiperidin-3-ylamino)-7-fluoro-4-(1-methyl-1H-pyrazole-4-yl)-1H-pyrrolo[3,4-c]pyridine-3(2H)-one (G-26)

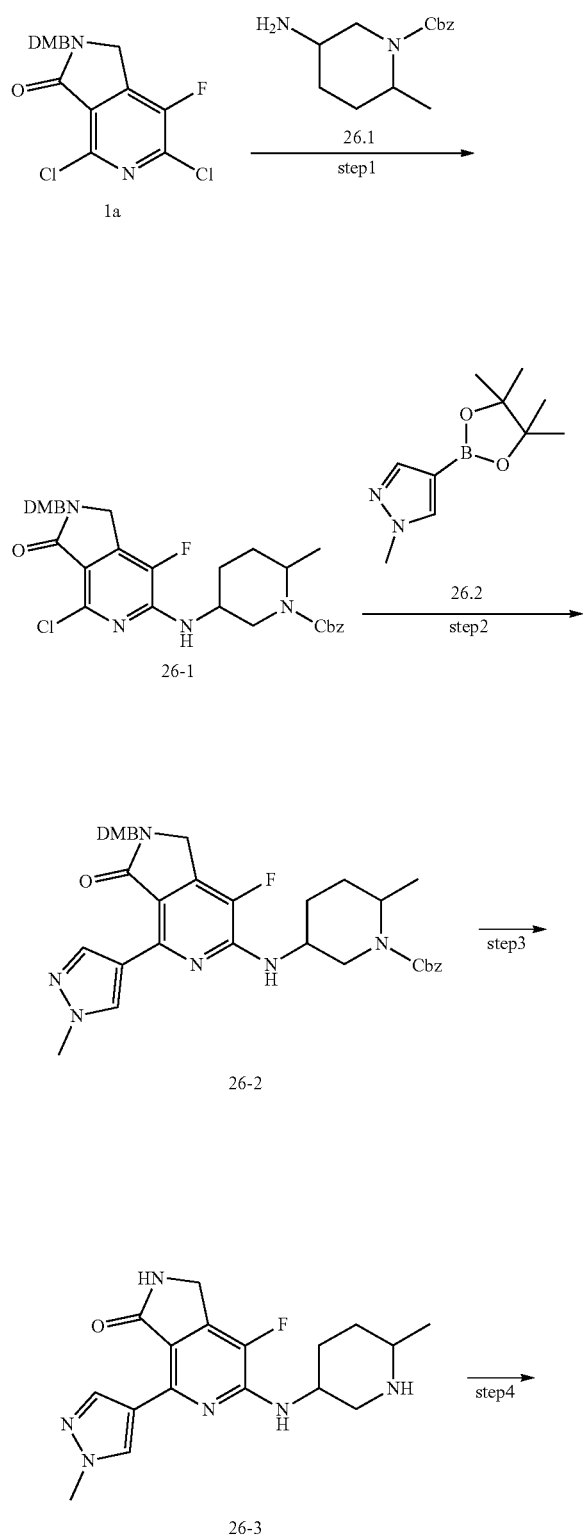

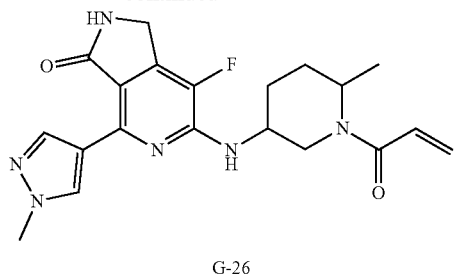

G-26

Step 1: The preparation method was the same as that for compound 2-1, except that compound 2.1 in the preparation of compound 2-1 was replaced with compound 26.1. MS m/z (ESI): 583.3 [M+H]+.

Step 2: The preparation method was the same as that for compound 7-1, except that compound 2-1 in the preparation of compound 7-1 was replaced with compound 26-1. MS m/z (ESI): 629.3 [M+H]+.

Step 3: A solution of compound 26-2 (100 mg, 0.159 mmol) in HBr/HOAc (4 mL) was stirred at 40° C. for 1 h. The reaction was followed by LC-MS until it was completed. The solvent was evaporated to dryness under reduced pressure. The residue was extracted with water and DCM. The aqueous layer was lyophilized to give 85 mg of compound 26-3 as a yellow solid. MS m/z (ESI): 345.2 [M+H]+.

Step 4: The preparation method was the same as that for compound G-2, except that compound 2-3 in the preparation of compound G-2 was replaced with compound 26-3. MS m/z (ESI): 399.3 [M+H]+. $^1$H NMR (400 MHz, DMSO-d6) δ 8.80 (d, J=39.8 Hz, 1H), 8.46-8.23 (m, 2H), 7.13-6.99 (m, 1H), 6.85 (dd, J=16.6, 10.2 Hz, 1H), 6.70 (dd, J=16.4, 10.6 Hz, 1H), 6.21-6.04 (m, 1H), 5.69 (d, J=10.1 Hz, 1H), 5.54 (d, J=10.3 Hz, 1H), 4.81 (d, J=11.8 Hz, 1H), 4.36 (s, 2H), 4.05 (d, J=10.1 Hz, 1H), 3.87 (s, 3H), 2.98 (t, J=12.7 Hz, 1H), 2.58 (t, J=11.8 Hz, 1H), 2.00-1.54 (m, 4H), 1.20 (dd, J=29.8, 6.6 Hz, 3H).

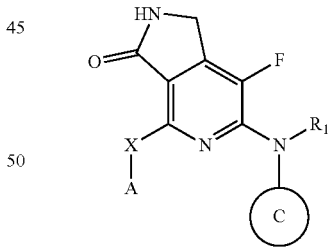

Compounds G-4, G-5, G-6, G-9 to G-25, G-27, and G-31 to G-42 were prepared by methods referring to those in example 2 or 3 with using intermediate 1a and different amines as starting materials.

Compounds G-44 to G-53, and G-55 to G-57 were prepared by methods referring to those in example 7 or 26 with using intermediate 1a or intermediate 2-1 and different boric acids as starting materials.

Compound G-69 was prepared by a method referring to that of example 60.

| Example No. | Compound No. | X | R₁ | A | C | MS [M + H]⁺ |
|---|---|---|---|---|---|---|
| 4 | G-4 | NH | H | 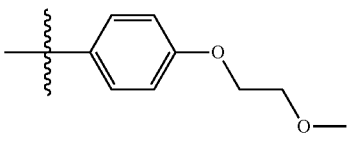 [SMILES: *c1ccc(OCCOC)cc1] | 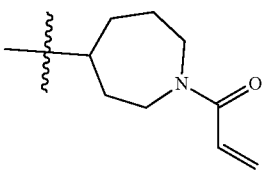 [SMILES: *C1CCCN(C(=O)C=C)CC1] | 484.2 |
| 5 | G-5 | NH | H | 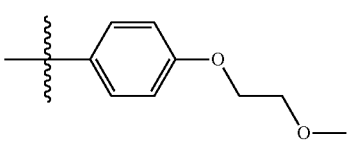 [SMILES: *c1ccc(OCCOC)cc1] | 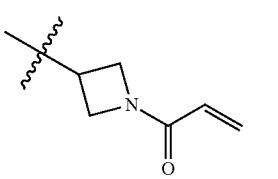 [SMILES: *C1CN(C(=O)C=C)C1] | 442.2 |
| 6 | G-6 | NH | H | 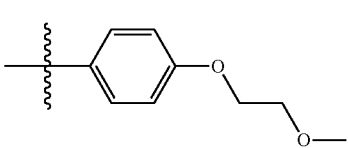 [SMILES: *c1ccc(OCCOC)cc1] | 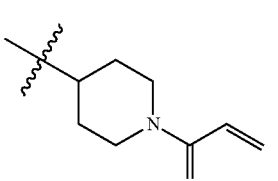 | 470.2 |
| 9 | G-9 | NH | H | 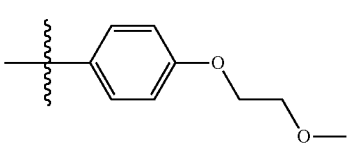 | 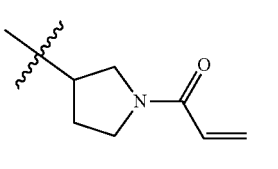 [SMILES: *C1CCN(C(=O)C=C)C1] | 456.2 |
| 10 | G-10 | NH | H | 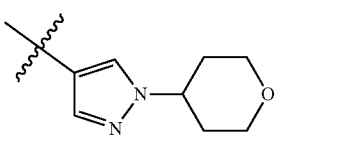 [SMILES: *c1cnn(C2CCOCC2)c1] | 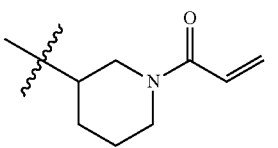 [SMILES: *C1CCCN(C(=O)C=C)C1] | 470.2 |
| 11 | G-11 | NH | H | 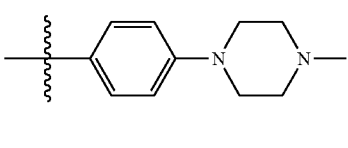 | 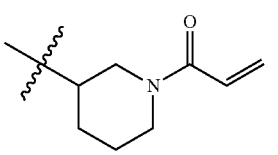 [SMILES: *C1CCCN(C(=O)C=C)C1] | 494.2 |
| 12 | G-12 | NH | H | 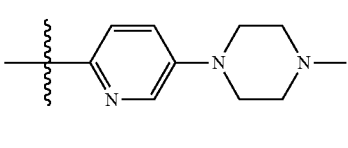 | 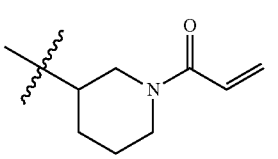 [SMILES: *C1CCCN(C(=O)C=C)C1] | 495.2 |
| 13 | G-13 | NH | H | 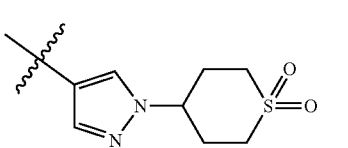 [SMILES: *c1cnn(C2CCS(=O)(=O)CC2)c1] | 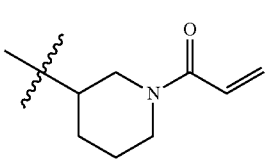 [SMILES: *C1CCCN(C(=O)C=C)C1] | 518.2 |
| 14 | G-14 | NH | H | 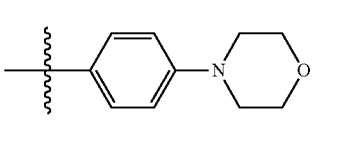 [SMILES: *c1ccc(N2CCOCC2)cc1] | 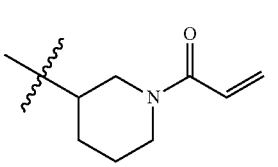 [SMILES: *C1CCCN(C(=O)C=C)C1] | 481.2 |

-continued
| Example No. | Compound No. | X | R₁ | A | C | MS [M + H]⁺ |
|---|---|---|---|---|---|---|
| 15 | G-15 | NH | H | 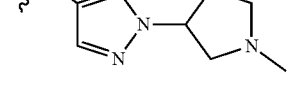 | 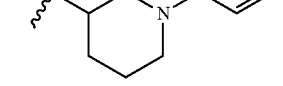 | 487.2 |
| 16 | G-16 | NH | H |  | 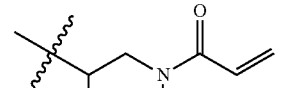 | 456.2 |
| 17 | G-17 | NH | H | 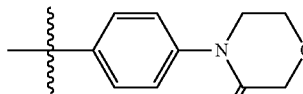 | 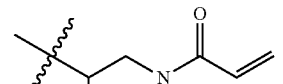 | 495.2 |
| 18 | G-18 | NH | H | 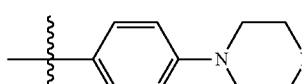 | 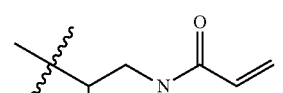 | 495.2 |
| 19 | G-19 | NH | H | 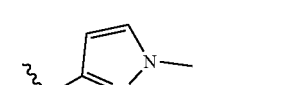 | 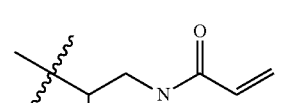 | 400.2 |
| 20 | G-20 | NH | H | 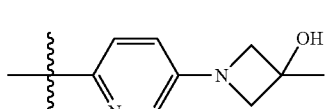 |  | 482.2 |
| 21 | G-21 | NH | H |  |  | 524.2 |
| 22 | G-22 | NH | H |  | 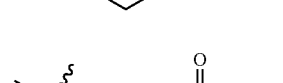 | 551.3 |
| 23 | G-23 | NH | H |  | 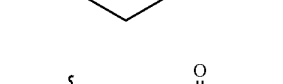 | 417.1 |

-continued

| Example No. | Compound No. | X | R₁ | A | C | MS [M + H]⁺ |
|---|---|---|---|---|---|---|
| 24 | G-24 | NH | H | 4-(morpholine-4-carbonyl)phenyl | 1-acryloylpiperidin-3-yl | 509.2 |
| 25 | G-25 | NH | H | 1-methyl-1H-pyrazol-4-yl | 1-acryloylpiperidin-3-yl | 400.2 |
| 27 | G-27 | NH | H | 4-morpholinophenyl | 1-acryloylazepan-3-yl | 495.2 |
| 28 | G-28 | NH | H | 4-morpholinophenyl | 1-acryloyl-6-methylpiperidin-3-yl | 495.2 |
| 29 | G-29 | NH | H | 4-morpholinophenyl | 1-acryloyl-6-methylpiperidin-3-yl (stereo) | 495.2 |
| 30 | G-30 | NH | H | 4-morpholinophenyl | 1-acryloylazepan-3-yl (stereo) | 495.2 |
| 31 | G-31 | NH | H | 3-fluoro-4-morpholinophenyl | 1-acryloylpiperidin-3-yl | 499.2 |
| 32 | G-32 | NH | H | 4-(3-methylmorpholino)phenyl | 1-acryloylpiperidin-3-yl | 495.2 |
| 33 | G-33 | NH | H | 2-fluoro-4-morpholinophenyl | 1-acryloylpiperidin-3-yl | 499.2 |

-continued

| Example No. | Compound No. | X | R₁ | A | C | MS [M + H]⁺ |
|---|---|---|---|---|---|---|
| 34 | G-34 | NH | H | 4-(2-methyl-4-(oxetan-3-yl)piperazin-1-yl)phenyl | 1-acryloylpiperidin-3-yl | 550.3 |
| 35 | G-35 | NH | H | 2-methyl-2H-1,2,3-triazol-4-yl | 1-acryloylpiperidin-3-yl | 401.2 |
| 36 | G-36 | NH | H | 1-methyl-1H-1,2,3-triazol-4-yl | 1-acryloylpiperidin-3-yl | 401.2 |
| 37 | G-37 | NH | H | 3-morpholinophenyl | 1-acryloylpiperidin-3-yl | 481.2 |
| 38 | G-38 | NH | H | 1-methyl-1H-pyrazol-4-yl | 1-acryloylpiperidin-3-yl | 400.2 |
| 39 | G-39 | NH | H | 3-chloro-4-morpholinophenyl | 1-acryloylpiperidin-3-yl | 515.2 |
| 40 | G-40 | NH | H | 4-morpholinophenyl | cyclohexane-3-carboxylate | 470.2 |
| 41 | G-41 | NH | H | 3-fluoro-4-morpholinophenyl | 1-acryloylpiperidin-3-yl | 513.2 |
| 42 | G-42 | NH | H | 3-fluoro-4-(3-methylmorpholino)phenyl | 1-acryloylpiperidin-3-yl | 513.2 |

-continued
| Example No. | Compound No. | X | R₁ | A | C | MS [M + H]⁺ |
|---|---|---|---|---|---|---|
| 43 | G-43 | a bond | H | 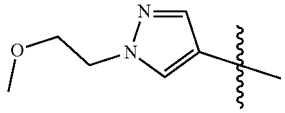 [SMILES: *c1cnn(CCOC)c1] | 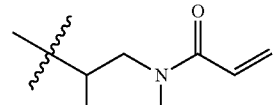 | 429.2 |
| 44 | G-44 | a bond | H | 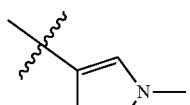 | 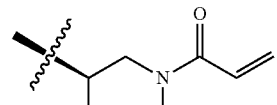 | 429.2 |
| 45 | G-45 | a bond | H | 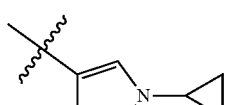 | 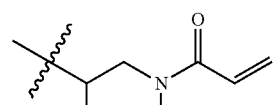 | 411.2 |
| 46 | G-46 | a bond | H | 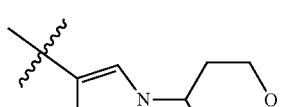 | 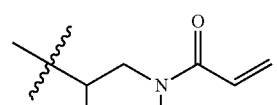 | 455.2 |
| 47 | G-47 | a bond | H | 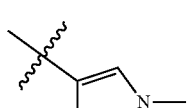 | 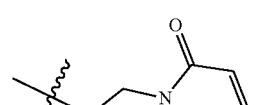 | 399.2 |
| 48 | G-48 | a bond | H |  | 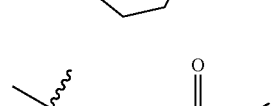 | 421.2 |
| 49 | G-49 | a bond | H | 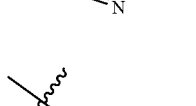 | 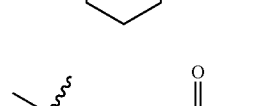 | 399.2 |
| 50 | G-50 | a bond | H |  | 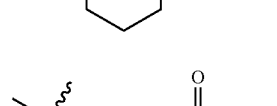 | 448.2 |
| 51 | G-51 | a bond | H | 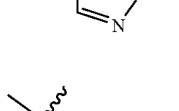 | 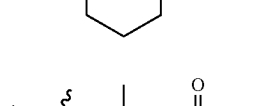 | 399.2 |

-continued

| Example No. | Compound No. | X | R₁ | A | C | MS [M + H]⁺ |
|---|---|---|---|---|---|---|
| 52 | G-52 | a bond | H | 4-(1-methylpiperidin-4-yl)pyrazol-1-yl | 1-acryloylpiperidin-3-yl | 468.2 |
| 53 | G-53 | a bond | H | 2-methylthiazol-5-yl | 1-acryloylpiperidin-3-yl | 402.1 |
| 54 | G-54 | a bond | H | 1-methylpyrazol-4-yl | (S)-1-acryloylpiperidin-3-yl | 385.1 |
| 55 | G-55 | a bond | H | pyridin-2-yl | 1-acryloylpiperidin-3-yl | 382.2 |
| 56 | G-56 | a bond | H | 1-methylpyrazol-4-yl | 2-aminocyclohexyl | 345.2 |
| 57 | G-57 | a bond | H | 4-(4,4-difluoropiperidin-1-yl)pyrazol-1-yl | 1-acryloylpiperidin-3-yl | 489.2 |
| 69 | G-69 | a bond | cyclopropylmethyl | 1-methylpyrazol-4-yl | 1-acryloylpiperidin-3-yl | 439.2 |

Example 58 Preparation of 2-(1-acryloylpiperidin-3-ylamino)-4-(1-methyl-1H-pyrazole-4-yl)-6,7-dihydrogen-5H-pyrrolo[3,4-d]pyrimidine-5(2H)-one (G-58)

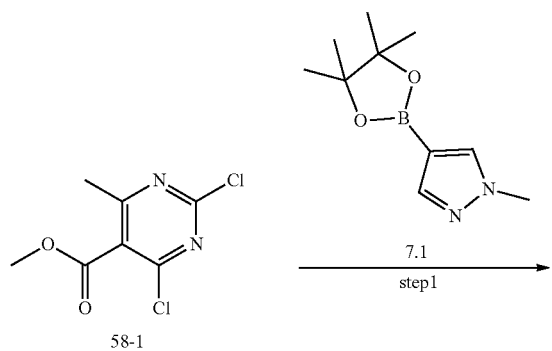

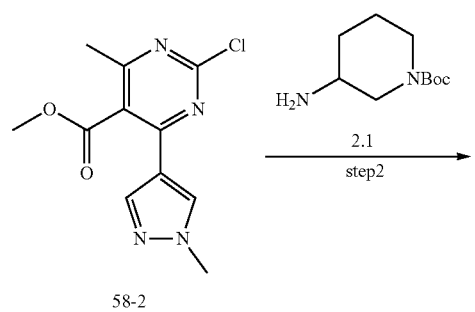

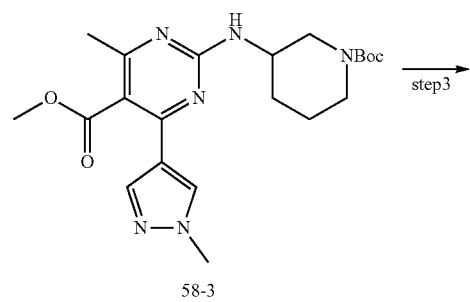

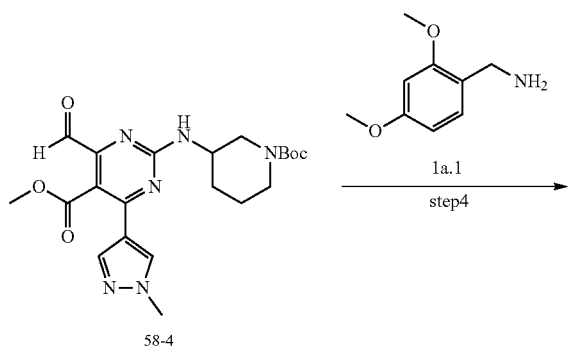

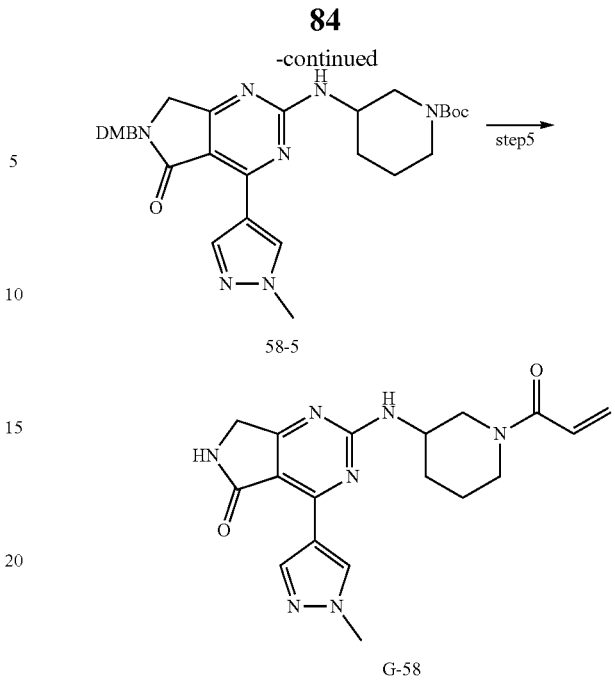

Step 1: The preparation method was the same as that for compound 7-1, except that compound 2-1 in the preparation of compound 7-1 was replaced with compound 58-1. MS m/z (ESI): 267.1 [M+H]$^+$.

Step 2: The preparation method was the same as that for compound 2-1, except that compound 1a in the preparation of compound 2-1 was replaced with compound 58-2. MS m/z (ESI): 431.2 [M+H]$^+$.

Step 3: A mixture of compound 58-3 (335 mg, 0.778 mmol), SeO$_2$ (460 mg, 4.146 mmol) and 1,4-dioxane (10 mL) was warmed at 100° C. overnight. The reaction was followed by LC-MS until it was completed. The reaction mixture was filtered and the solvent was removed under reduced pressure to give 600 mg of oily compound 58-4 which was used directly in the next step. MS m/z (ESI): 445.3 [M+H]$^+$.

Step 4: A mixture of 600 mg of crude product compound 58-4, compound 1a.1 (80 mg, 0.478 mmol), 10 mL of dichloromethane and 5 mL of methanol was stirred at room temperature for 1 h and then NaBH$_3$CN (100 mg, 1.591 mmol) was added. The mixture was stirred at room temperature for 30 min and then heated to 50° C. and stirred for further 4 h. The reaction was followed by LC-MS until it was completed. Water was added to the system, which was extracted with DCM. The organic layer was dried and concentrated. The residue was purified by Prep-HPLC to give yellow oily compound 58-5 (60 mg, 13.7% yield). MS m/z (ESI): 564.3 [M+H]$^+$.

Step 5: Compound 58-5 (146 mg, 0.26 mmol) was added to HCl/1,4-dioxane (4M, 2 mL), and the mixture was stirred at room temperature for 1 h, and concentrated to obtain a crude product. The crude product was added to DCM (20 mL) and triethylamine (105 mg, 1.04 mmol), a solution of acryloyl chloride (23.4 mg, 0.26 mmol) in DCM (8 mL) was slowly added to the mixture, stirred at room temperature for 2 h after the addition was completed. LC-MS was followed until the reaction was complete. The mixture was concentrated and purified by Prep-HPLC to obtain the compound G-58. MS m/z (ESI): 368.2 [M+H]$^+$. $^1$H NMR (400 MHz, DMSO-d$_6$) δ 8.97 (s, 1H), 8.45 (s, 1H), 7.77 (s, 1H), 7.19 (s, 1H), 6.66 (dd, J=16.8, 10.6 Hz, 1H), 6.04 (d, J=16.4 Hz, 1H), 5.57 (d, J=11.0 Hz, 1H), 4.26 (s, 1H), 4.15 (s, 2H), 3.89 (s, 4H), 2.00 (d, J=14.0 Hz, 1H), 1.79 (d, J=13.3 Hz, 1H), 1.66 (d, J=10.7 Hz, 1H), 1.48 (d, J=13.3 Hz, 1H), 1.24 (s, 1H).

Example 59 Preparation of 2-(1-acryloylpiperidin-3-ylamino)-4-(1-methyl-1H-pyrazole-4-yl amino)-6,7-dihydrogen-5H-pyrrolo[3,4-d]pyrimidine-5-one (G-59)

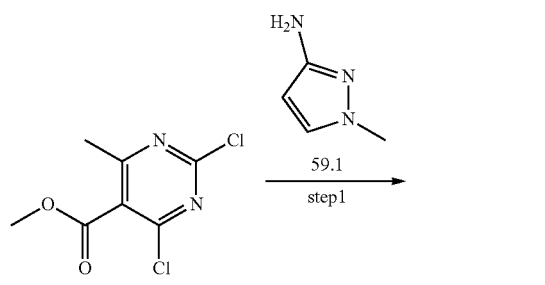

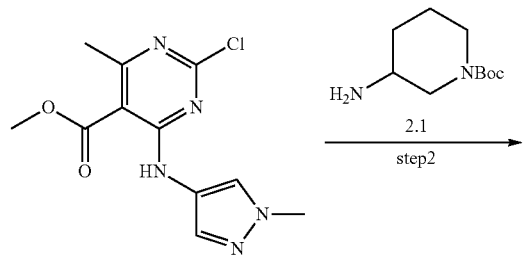

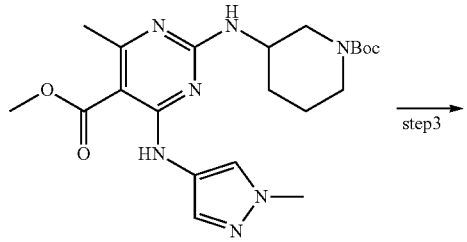

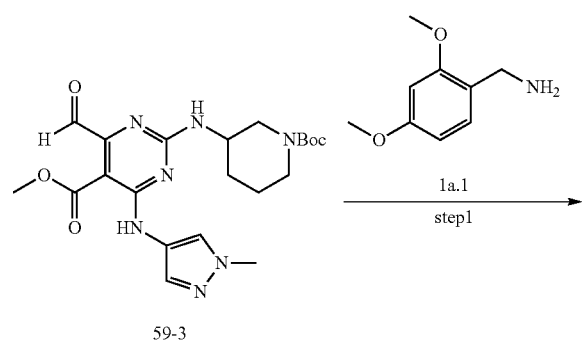

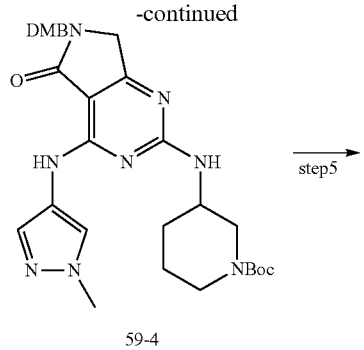

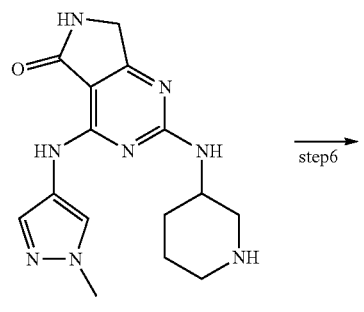

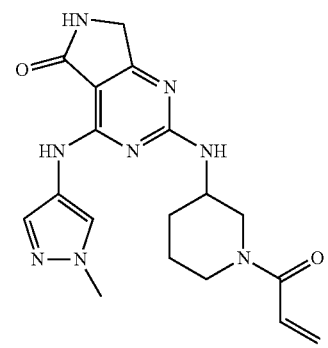

Step 1: The preparation method was the same as that for compound 2-1, except that compound 1a and compound 2.1 in the preparation of compound 2-1 were replaced with compound 58-1 and compound 59.1. MS m/z (ESI): 460.2 [M+H]⁺.

The steps 2 to 6 were the same as the steps 2 to 5 of Example G-58 (Steps 5 and 6 of Example 59 were combined in Example 58 into a one-step reaction, i.e. step 5). Finally the residue was purified by Prep-HPLC to give a white solid compound G-59 (90 mg, 65.2% yield). MS m/z (ESI): 383.2 [M+H]⁺. ¹H NMR (400 MHz, DMSO-d6) δ 8.69-8.44 (m, 1H), 8.32-8.02 (m, 1H), 8.07-7.91 (m, 1H), 7.86-7.40 (m, 2H), 6.94-6.38 (m, 1H), 6.22-5.92 (m, 1H), 5.79-5.34 (m, 1H), 4.53 (dd, J=69.7, 10.3 Hz, 0.5H), 4.22-3.65 (m, 7.5H), 3.17-2.97 (m, 1H), 2.97-2.54 (m, 1H), 1.98 (s, 1H), 1.79 (s, 1H), 1.70-1.35 (m, 2H).

Example 60 Preparation of 6-((1-acryloylpiperidin-3-yl)(methyl)amino)-7-fluoro-4-(1-methyl-1H-pyrazole-4-yl)-1H-pyrrolo[3,4-c]pyridine-3 (2H)-one (G-60)

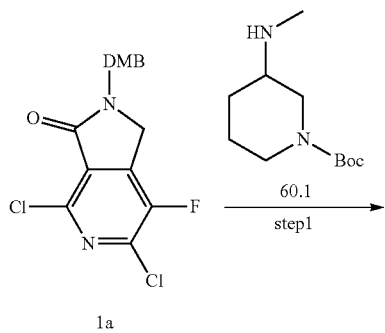

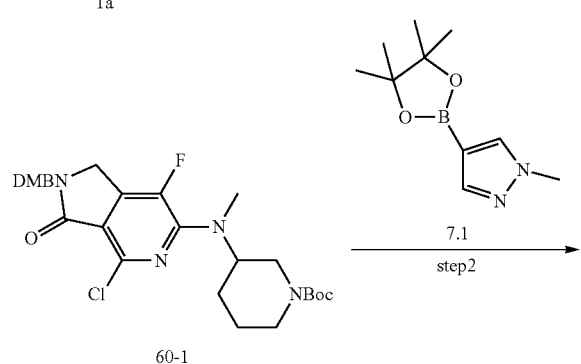

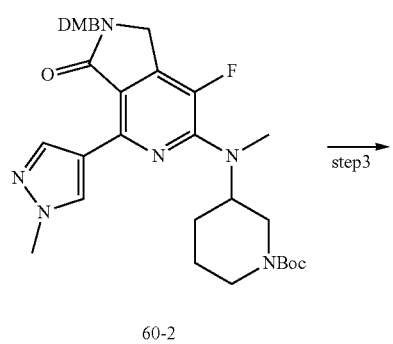

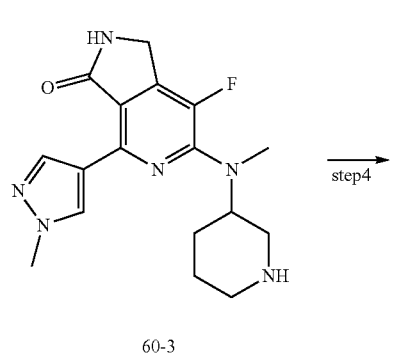

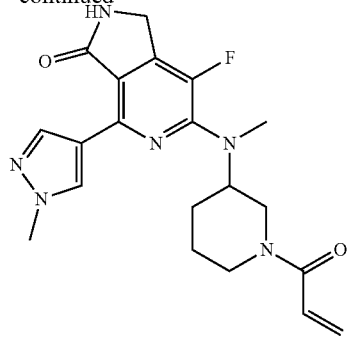

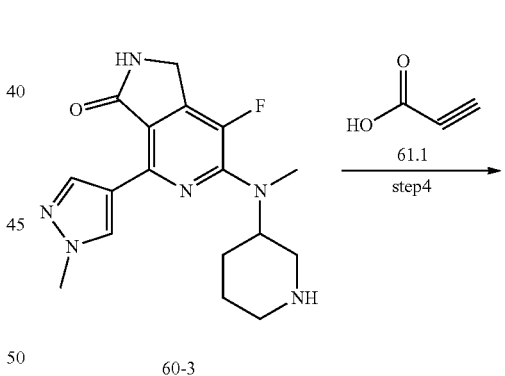

Step 1: The preparation method was the same as that for compound 2-1, except that compound 1a and compound 2.1 in the preparation of the compound 2-1 were replaced with compound 58-1 and compound 60.1. MS m/z (ESI): 460.2 [M+H]$^+$.

The method of steps 2 to 4 were the same as steps 1 to 3 of example G-7. Finally the residue was purified by Prep-HPLC to give a white solid compound G-60 (35 mg, 18.3% yield). MS m/z (ESI): 399.2 [M+H]$^+$. $^1$H NMR (400 MHz, DMSO-d6) δ 8.79-8.72 (m, 1H), 8.44-8.13 (m, 2H), 6.90-6.66 (m, 1H), 6.20-6.02 (m, 1H), 5.68-5.55 (m, 1H), 4.63-4.41 (m, 1H), 4.34 (s, 2H), 4.18-4.05 (m, 2H), 3.84 (s, 3H), 3.13-2.88 (m, 4H), 2.88-2.51 (m, 1H), 2.00-1.71 (m, 3H), 1.45 (d, J=12.0 Hz, 1H).

Example 61 Preparation of 7-fluoro-6-(methyl(1-acryloylpiperidin-3-yl)amino)-4-(1-methyl-1H-pyrazole-4-yl)-1H-pyrrolo[3,4-c]pyridine-3(2H)-one (G-61)

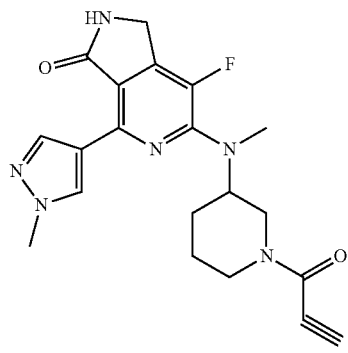

A solution of compound 61.1 (25 mg, 0.35 mmol) in MeCN (10 mL) was added with compound 60-3 (100 mg, 0.29 mmol), HATU (168 mg, 0.44 mmol) and DIPEA (75 mg, 0.58 mmol). The mixture was stirred at room temperature for 2 h. The reaction was followed by LC-MS until it was completed. Most of the solvent was removed under reduced pressure and then the residue was purified by Prep-HPLC to give yellow solid compound G-61 (2.58 mg, 2.2% yield). MS m/z (ESI): 397.1 [M+H]$^+$. $^1$H NMR (400 MHz, DMSO-d$_6$):δ 8.76 (s, 1H), 8.37-8.27 (m, 2H), 4.55-4.50 (m, 1H), 4.41-4.20 (m, 4H), 4.09-4.04 (m, 0.5H), 3.85 (s, 3H), 3.39-3.36 (m, 0.5H), 3.14-3.10 (m, 0.5H), 3.05-3.03 (m, 3H), 2.88-2.86 (m, 0.5H), 2.63-2.60 (m, 0.5H), 2.04-1.84 (m, 3H), 1.45-1.41 (m, 1H).

Example 62 Preparation of 7-fluoro-6-(methyl(1-acryloylpiperidin-3-yl)amino)-4-(1-methyl-1H-pyrazole-4-yl)-1H-pyrrolo[3,4-c]pyridine-3 (2H)-one (G-62)

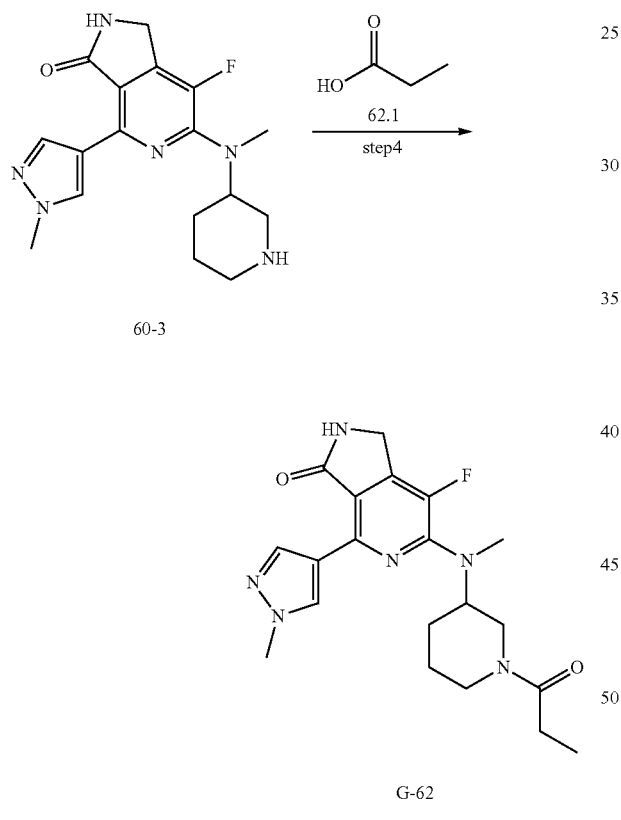

The preparation method was the same as that for the compound G-61, except that the compound 61.1 in the preparation of the compound G-61 was replaced with the compound 62.1. MS m/z (ESI): 401.2 [M+H]$^+$. 1H NMR (400 MHz, DMSO-d$_6$):δ 8.82-8.78 (m, 1H), 8.39-8.21 (m, 2H), 4.65-4.62 (d, J=12 Hz, 0.5H), 4.42-4.40 (d, J=8 Hz, 0.5H), 4.41 (s, 2H), 4.24-4.22 (m, 0.5H), 3.88-3.84 (m, 0.5H), 3.88-3.84 (m, 4H), 3.26-3.25 (m, 0.5H), 3.08 (m, 3H), 2.98-2.96 (m, 0.5H), 2.72-2.70 (m, 1H), 2.39-2.26 (m, 2H), 1.91-1.76 (m, 3H), 1.51-1.35 (m, 1H), 1.05-0.91 (m, 3H).

Example 63 Preparation of 6-((1-acryloylpiperidin-3-yl)(methyl)amino)-4-(1-(difluoro methyl)-1H-pyrazole-4-yl)-7-fluoro-1H-pyrrolo[3,4-c]pyridine-3 (2H)-one (G-63)

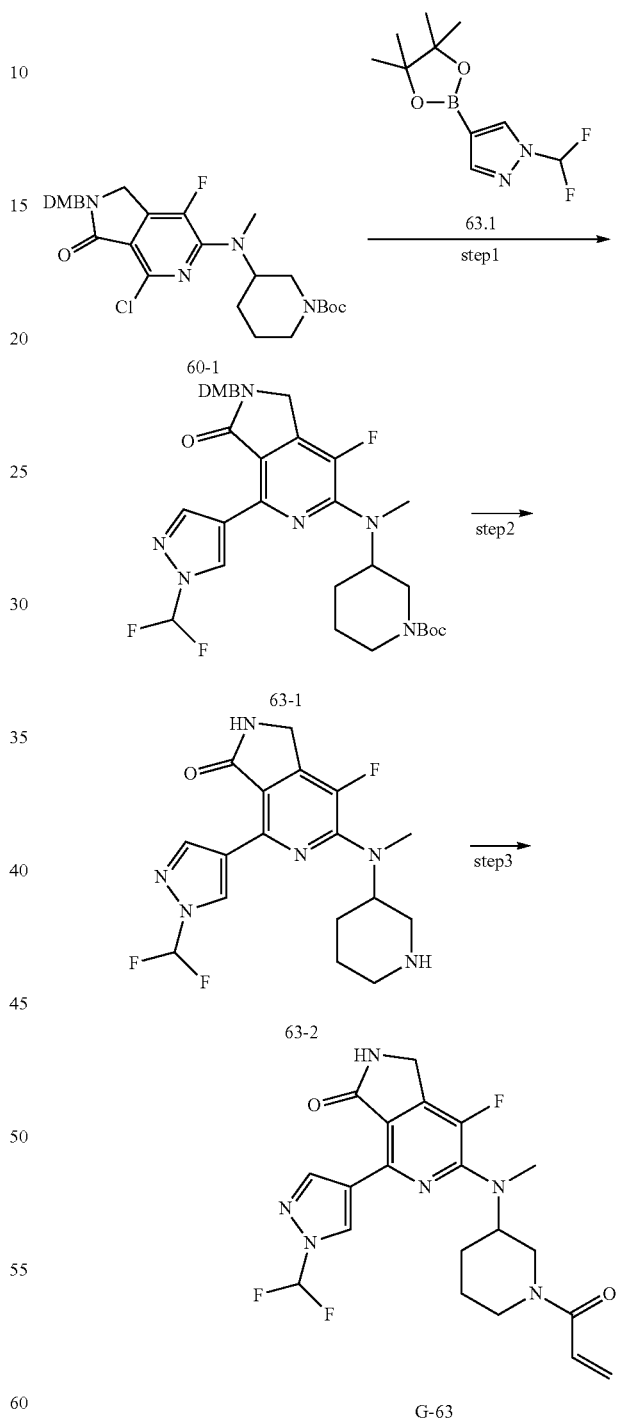

Steps 1 to 3 of compound G-63 were the same as steps 2 to 4 of example 60. Finally the residue was purified by Prep-HPLC to give compound G-63. MS m/z (ESI): 435.2 [M+H]$^+$. $^1$H NMR (400 MHz, DMSO-d$_6$) δ 9.33 (d, J=31.5 Hz, 1H), 8.51 (t, J=36.0 Hz, 2H), 7.82 (t, J=35.8 Hz, 1H), 6.92-6.69 (m, 1H), 6.22-6.05 (m, 1H), 5.71-5.47 (m, 1H), 4.64 (d, J=12.1 Hz, 1H), 4.37 (m, 2H), 4.07 (m, 2H), 3.08 (s, 3H), 2.99 (m, 1H), 2.82 (t, J=11.4 Hz, 1H), 2.00-1.74 (m, 3H), 1.46 (d, J=13.1 Hz, 1H).

Example 64 Preparation of 6-((1-acryloylpiperidin-3-yl)(methyl)amino)-7-fluoro-4-(1-(2-morpholinethyl)-1H-pyrazole-4-yl)-1H-pyrrolo[3,4-c]pyridine-3(2H)-one (G-64)

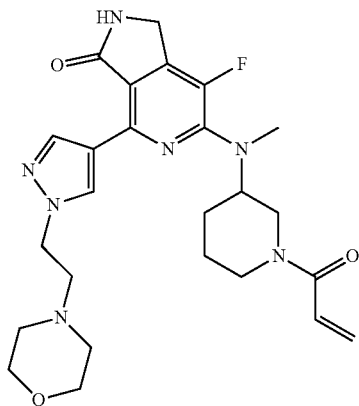

G-64

The preparation method for compound G-64 was the same as that for compound G-63. MS m/z (ESI): 498.3[M+H]⁺.
¹H NMR (400 MHz, DMSO-d₆) δ 8.81 (s, 1H), 8.29 (s, 1H), 7.98 (s, 1H), 6.71 (dd, J=16.8, 10.3 Hz, 1H), 6.06 (d, J=17.5 Hz, 1H), 5.59 (d, J=10.6 Hz, 1H), 4.32 (s, 2H), 4.20 (m, 4H), 3.53 (d, J=4.5 Hz, 4H), 3.09 (d, J=3.2 Hz, 3H), 2.96-2.91 (m, 3H), 2.74 (t, J=6.4 Hz, 2H), 2.41 (m, 4H), 1.88 (m, 3H), 1.51 (m, 1H).

Example 65 Preparation of 6-((1-acryloyl-6-methylpiperidin-3-yl)(methyl)amino)-7-fluoro-4-(1-methyl-1H-pyrazole-4-yl)-1H-pyrrolo[3,4-c]pyridine-3(2H)-one (G-65)

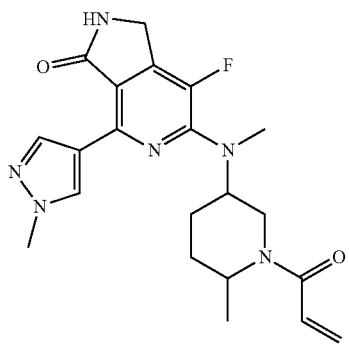

G-65

The preparation method for compound G-65 was the same as that for compound G-60. MS m/z (ESI): 413.2[M+H]⁺.
1H NMR (400 MHz, DMSO-d₆): δ 8.77-8.72 (d, J=20 Hz, 1H), 8.36 (m, 1H), 8.31 (s, 0.5H), 8.18 (s, 0.5H), 6.85-6.78 (m, 1H), 6.04-6.03 (m, 1H), 5.67-5.53 (m, 1H), 4.78-4.76 (m, 0.5H), 4.53-4.51 (m, 0.5H), 4.33 (s, 2H), 4.20-4.16 (m, 0.5H), 4.06-4.03 (m, 0.5H), 3.83 (s, 3H), 3.27 (m, 1H), 3.09 (s, 3H), 2.89-2.86 (m, 1H), 2.08-2.05 (m, 1H), 1.71-1.67 (m, 3H), 1.25-1.15 (m, 3H).

Example 66 Preparation of 6-((1-acryloylpiperidin-3-yl)(methyl)amino)-7-fluoro-4-(2-methyl thiazole-5-yl)-1H-pyrrolo[3,4-c]pyridine-3(2H)-one (G-66)

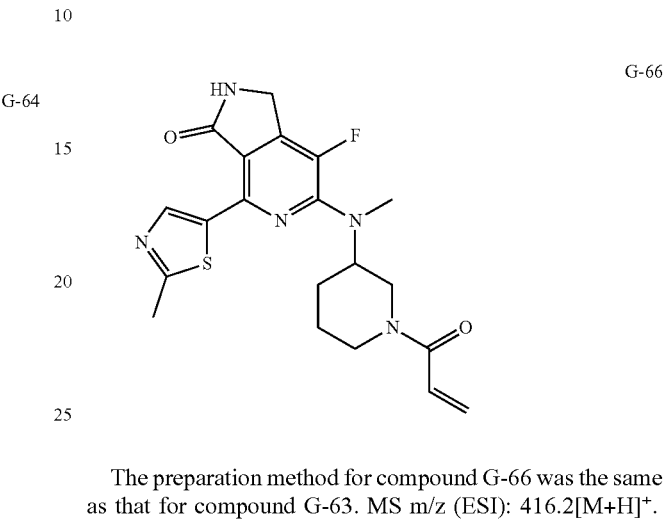

G-66

The preparation method for compound G-66 was the same as that for compound G-63. MS m/z (ESI): 416.2[M+H]⁺.

Example 67 Preparation of 6-((1-acryloylpiperidin-3-yl)(methyl)amino)-7-fluoro-4-(1-(2-hydroxy-2-methylpropyl)-1H-pyrazole-4-yl)-1H-pyrrolo[3,4-c]pyridine-3 (2H)-one (G-67)

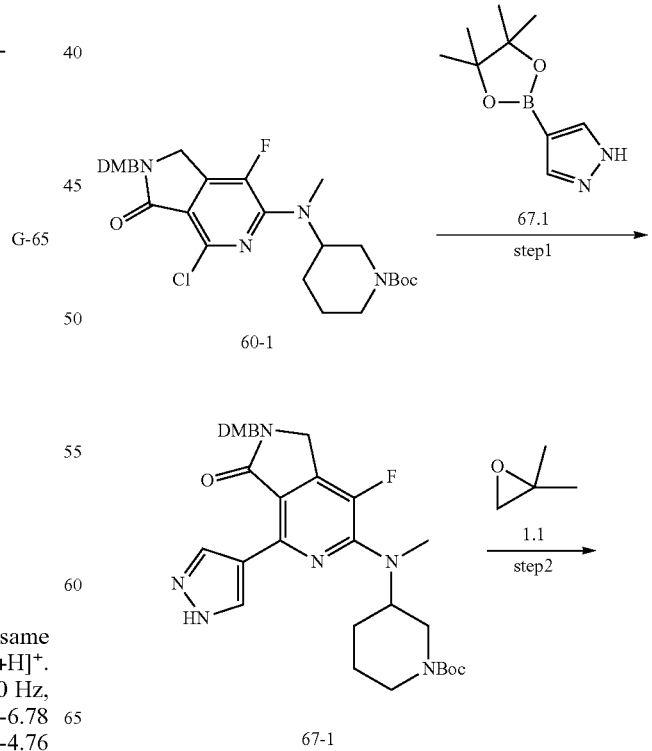

67-1

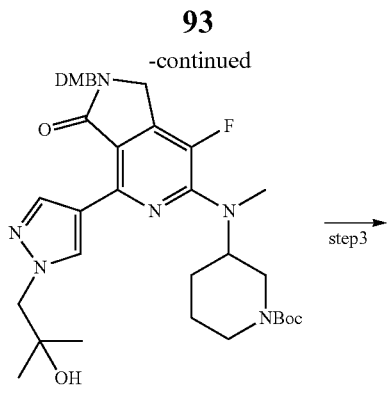

67-2

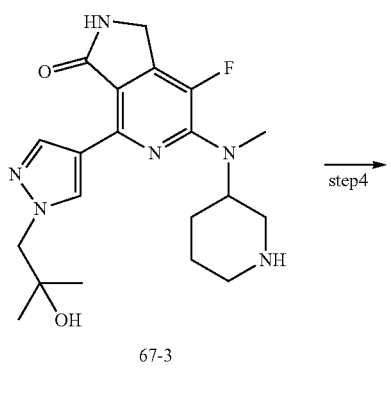

67-3

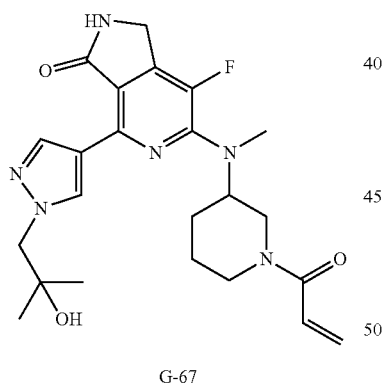

G-67

Step 1: The preparation method was the same as that for compound 7-1, except that compound 2-1 and compound 7.1 in the preparation of compound 7-1 were replaced with compound 60-1 and compound 67.1. MS m/z (ESI): 581 [M+H]⁺.

Step 2: A solution of compound 67-1 (5.8 g, 10.0 mmol), compound 1.1 (7.2 g, 100.0 mmol), and cesium carbonate (3.26 g, 10.0 mmol) in CH₃CN (30 mL) was sealed at 100° C. for overnight reaction. LC-MS was followed until the reaction was complete. The reaction solution was cooled to room temperature, filtered and concentrated, and purified by silica gel column chromatography to obtain compound 67-2. MS m/z (ESI): 652[M+H]⁺.

Steps 3 and 4 were the same as steps 3 and 4 of example 60. Finally the residue was purified by Prep-HPLC to give 5 mg of compound G-67 as a solid. MS m/z (ESI): 457[M+H]⁺. ¹H NMR (400 MHz, DMSO-d6) δ 8.89-8.85 (m, 1H), 8.39 (s, 1H), 8.35-8.19 (m, 1H), 6.86 (dd, J=16.6, 10.6 Hz, 0.5H), 6.76 (dd, J=16.6, 10.3 Hz, 0.5H), 6.13 (t, J=15.7 Hz, 1H), 5.70 (d, J=12.4 Hz, 0.5H), 5.58 (d, J=10.4 Hz, 0.5H), 4.71 (d, J=6.7 Hz, 1H), 4.64 (d, J=11.3 Hz, 0.5H), 4.46 (d, J=12.9 Hz, 0.5H), 4.36 (s, 2H), 4.22-4.10 (m, 2H), 4.03 (s, 2H), 3.09 (s, 3H), 3.02 (t, J=12.8 Hz, 0.5H), 2.87 (t, J=11.5 Hz, 0.5H), 2.65-2.56 (m, 1H), 1.93-1.81 (m, 3H), 1.52-1.38 (m, 1H), 1.08 (s, 6H).

Example 68 Preparation of 6-((1-acryloylpiperidin-3-yl)(ethyl)amino)-7-fluoro-4-(1-methyl-1H-pyrazole-4-yl)-1H-pyrrolo[3,4-c]pyridine-3 (2H)-one (G-68)

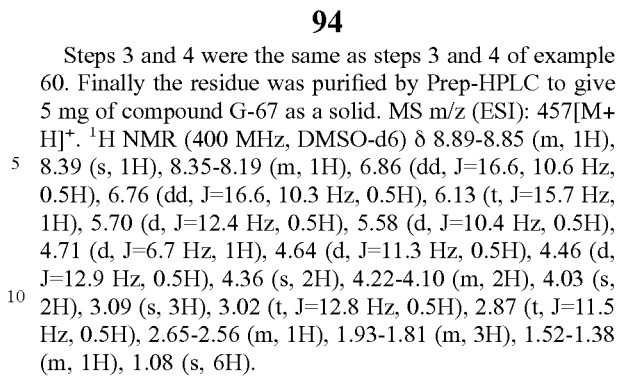

G-68

The preparation method for compound G-68 was the same as that for compound G-60. MS m/z (ESI): 413.2[M+H]⁺. ¹H NMR (400 MHz, DMSO-d₆) δ 8.71 (s, 1H), 8.24 (s, 1H), 8.01 (s, 1H), 6.67 (dd, J=16.7, 10.5 Hz, 1H), 6.09 (d, J=16.9 Hz, 1H), 5.58 (d, J=10.4 Hz, 1H), 4.32 (s, 2H), 4.23 (d, J=12.6 Hz, 3H), 3.85 (s, 3H), 3.41 (q, J=7.0 Hz, 2H), 3.19 (t, J=11.6 Hz, 1H), 3.01 (s, 1H), 1.98-1.87 (m, 1H), 1.82 (d, J=10.3 Hz, 2H), 1.71-1.59 (m, 1H), 1.14 (t, J=7.0 Hz, 3H).

Example 70 Preparation of 6-((1-acryloylpiperidin-3-yl)(methyl)amino)-7-fluoro-4-(1-methyl-1H-pyrazole-4-ylamino)-1H-pyrrolo[3,4-c]pyridine-3(2H)-one (G-70)

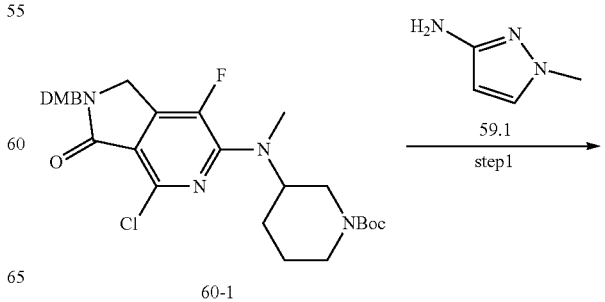

60-1

-continued

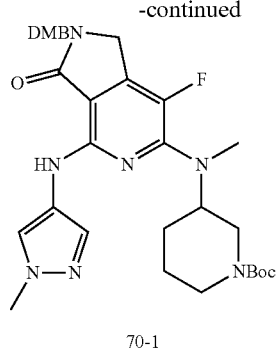

70-1 step2

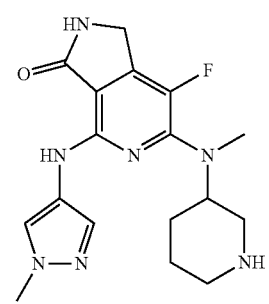

70-2 step3

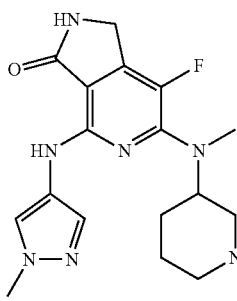

G-70

Step 1: The preparation method for compound 70-1 was the same as that for compound 2-2, except that compound 2-1 and compound 2.2 in the preparation for compound 2-2 were replaced with compound 60-1 and compound 59.1. MS m/z (ESI): 610[M+H]+.

Steps 2 and 3 were the same as steps 3 and 4 of example 60. Finally the residue was purified by Prep-HPLC to give compound G-70 (7 mg, yield 20%). MS m/z (ESI): 414.2 [M+H]+. $^1$H NMR (400 MHz, DMSO-d$_6$) δ 8.31-8.21 (m, 1H), 8.18 (s, 1H), 7.86-7.76 (m, 1H), 7.52 (d, J=3.7 Hz, 1H), 6.79 (ddd, J=28.5, 16.5, 10.3 Hz, 1H), 6.65-6.55 (m, 1H), 6.14-5.92 (m, 2H), 5.66 (s, 1H), 5.55-5.45 (m, 1H), 4.51-4.40 (m, 1H), 4.32 (d, J=6.9 Hz, 2H), 4.05 (dd, J=37.3, 13.7 Hz, 3H), 3.70 (d, J=4.2 Hz, 3H), 3.05-2.91 (m, 3H), 2.87 (d, J=15.2 Hz, 1H), 1.74 (dd, J=65.5, 13.3 Hz, 4H), 1.43 (s, 1H).

Example 71 Preparation of 6-((1-acryloylpiperidin-3-yl)(methyl)amino)-7-fluoro-4-(4-morpholin)-1H-pyrrolo[3,4-c]pyridine-3 (2H)-one (G-71)

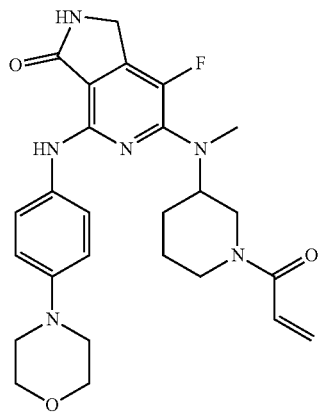

G-71

The preparation method for compound G-71 was the same as that for compound G-70. MS m/z (ESI): 495.2[M+H]+.

Example 72 Preparation of 6-((1-acryloylpiperidin-3-yl)(methyl)amino)-7-fluoro-4-(3-methyl isothiazole-5-ylamino)-1H-pyrrolo[3,4-c]pyridine-3(2H)-one (G-72)

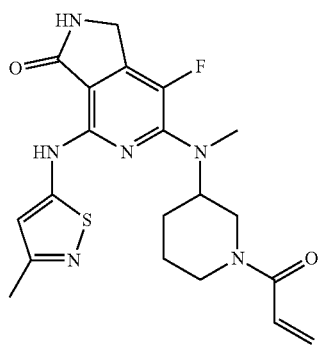

G-72

The preparation method for compound G-72 was the same as that for compound G-70. MS m/z (ESI): 431.2[M+H]+. 1H NMR (400 MHz, DMSO-d$_6$): δ 9.78 (s, 1H), 8.37 (s, 1H), 6.90 (s, 1H), 6.83-6.68 (m, 1H), 6.07-6.00 (m, 1H), 5.65-5.55 (m, 1H), 4.44-4.43 (m, 1H), 4.38 (s, 2H), 4.27-4.20 (m, 1H), 4.05-4.01 (m, 1H), 3.39-3.36 (m, 0.5H), 3.11 (s, 3H), 2.95-2.88 (m, 1H), 2.48-2.46 (m, 0.5H), 2.23 (s, 3H), 1.91-1.82 (m, 3H), 1.49-1.40 (m, 1H).

Example 73 Preparation of 6-((1-acryloylazacyclo-heptan-3-yl)(methyl)amino)-7-fluoro-4-(4-morpholin)-1H-pyrrolo[3,4-c]pyridine-3(2H)-one (G-73)
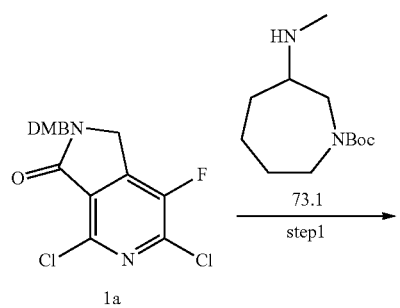
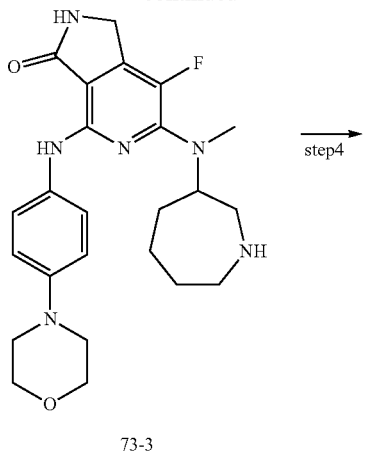
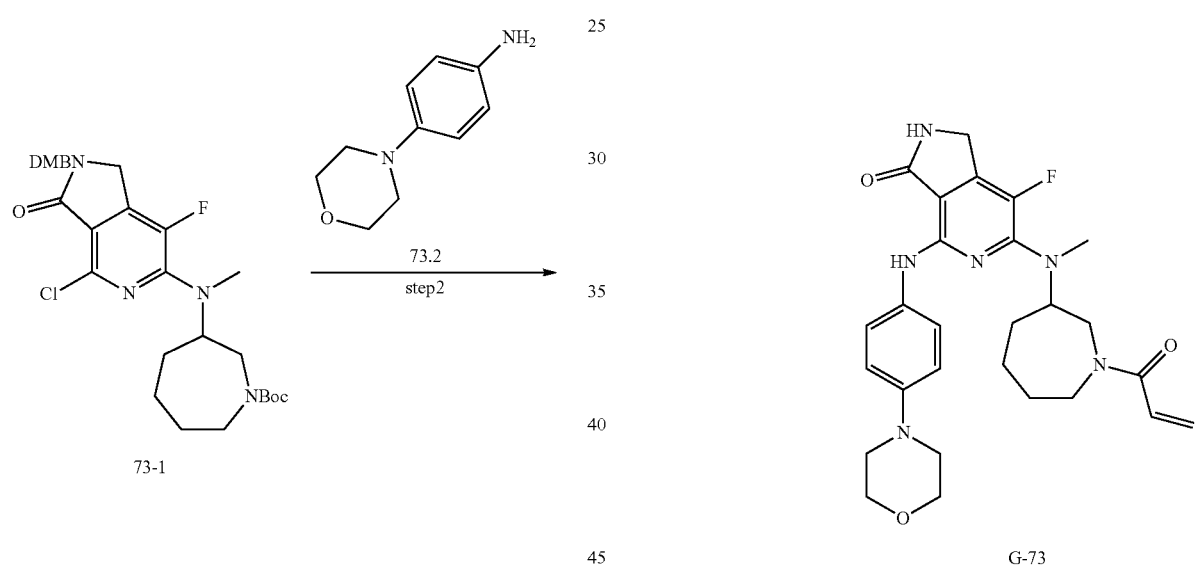
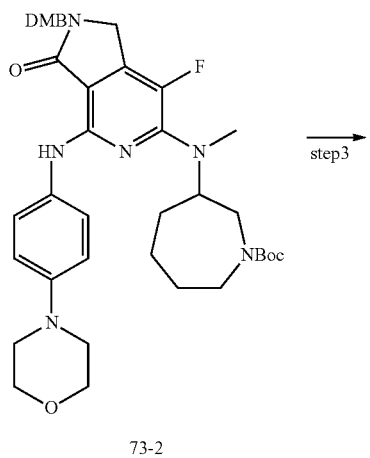
Step 1 to Step 4 of the preparation of compound G-73 were the same as those for compound G-2. MS m/z (ESI): 509.3[M+H]$^+$. $^1$H NMR (400 MHz, DMSO-d$_6$) δ 8.41 (d, J=5.3 Hz, 1H), 8.21 (d, J=6.4 Hz, 1H), 7.44 (dd, J=19.2, 9.0 Hz, 2H), 6.88-6.77 (m, 2H), 6.76-6.57 (m, 1H), 6.16-6.01 (m, 1H), 5.67 (dd, J=10.4, 2.4 Hz, 0.5H), 5.51 (dd, J=10.4, 2.4 Hz, 0.5H), 4.47-4.37 (m, 1H), 4.32 (s, 2H), 3.92-3.65 (m, 5H), 3.60-3.38 (m, 2H), 3.27-3.15 (m, 1H), 2.99-2.96 (m, 7H), 1.90-1.63 (m, 4H), 1.61-1.52 (m, 1H), 1.27-1.16 (m, 1H).

Example 74 Preparation of 6-((1-acryloylpiperidin-3-yl)(ethyl)amino)-7-fluoro-4-(4-morpholin)-1H-pyrrolo[3,4-c]pyridine-3(2H)-one (G-74)

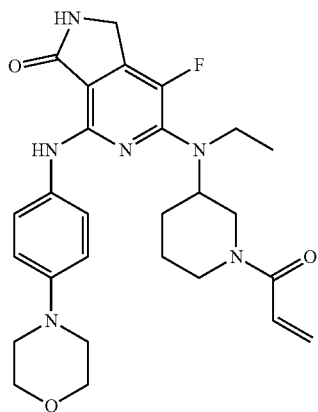

The preparation method for compound G-74 was the same as that for compound G-73. MS m/z (ESI): 509.3[M+H]⁺.
¹H NMR (400 MHz, DMSO-d₆) δ 8.44-8.37 (m, 1H), 8.21 (s, 1H), 7.41-7.37 (m, 2H), 6.91-6.72 (m, 2.5H), 6.66-6.49 (m, 0.5H), 6.11 (d, J=17.3 Hz, 0.5H), 5.96 (d, J=17.3 Hz, 0.5H), 5.68 (d, J=10.9 Hz, 0.5H), 5.47 (d, J=10.9 Hz, 0.5H), 4.52-4.24 (m, 4H), 3.99 (dd, J=34.1, 12.4 Hz, 1H), 3.69 (s, 4H), 3.50 (s, 3H), 2.96 (s, 4H), 2.83 (t, J=11.6 Hz, 1H), 1.80 (s, 3H), 1.37 (s, 1H), 1.13 (t, J=6.8 Hz, 3H).

Example 75 Preparation of 2-((1-acryloylpiperidin-3-yl)(methyl)amino)-4-(1-methyl-1H-pyrazole-4-yl amino)-6,7-dihydrogen-5H-pyrrolo[3,4-d]pyrimidine-5-one (G-75)

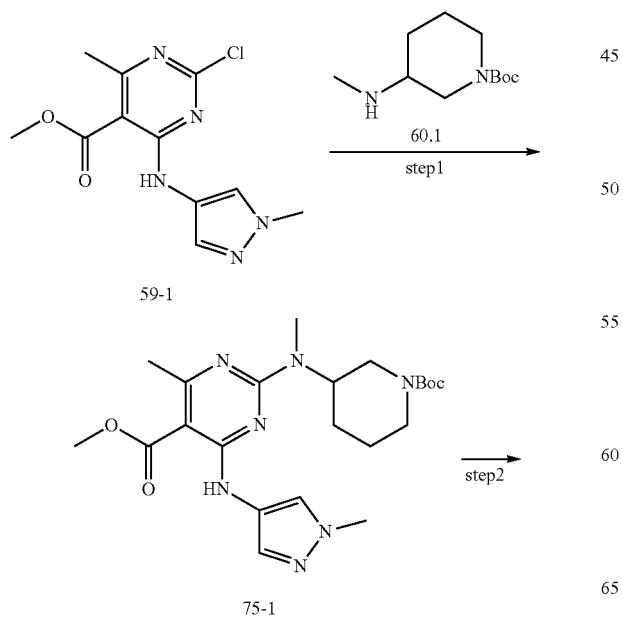

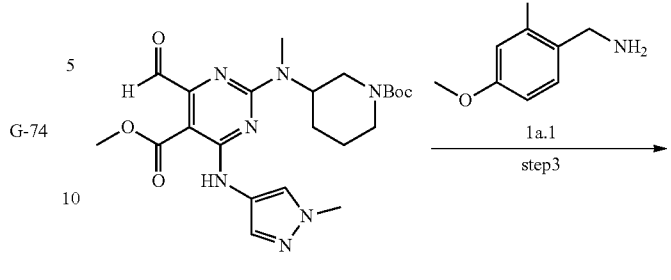

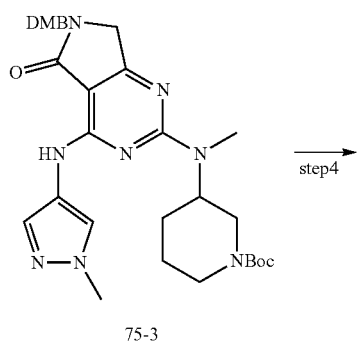

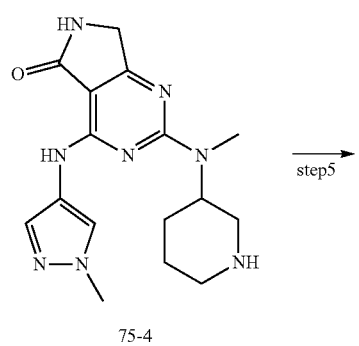

Step 1 to Step 5 of the preparation for compound G-75 were the same as Step 2 to Step 6 of the preparation for compound G-59. MS m/z (ESI): 397.2[M+H]⁺.

Example 76 Preparation of Compound G-76
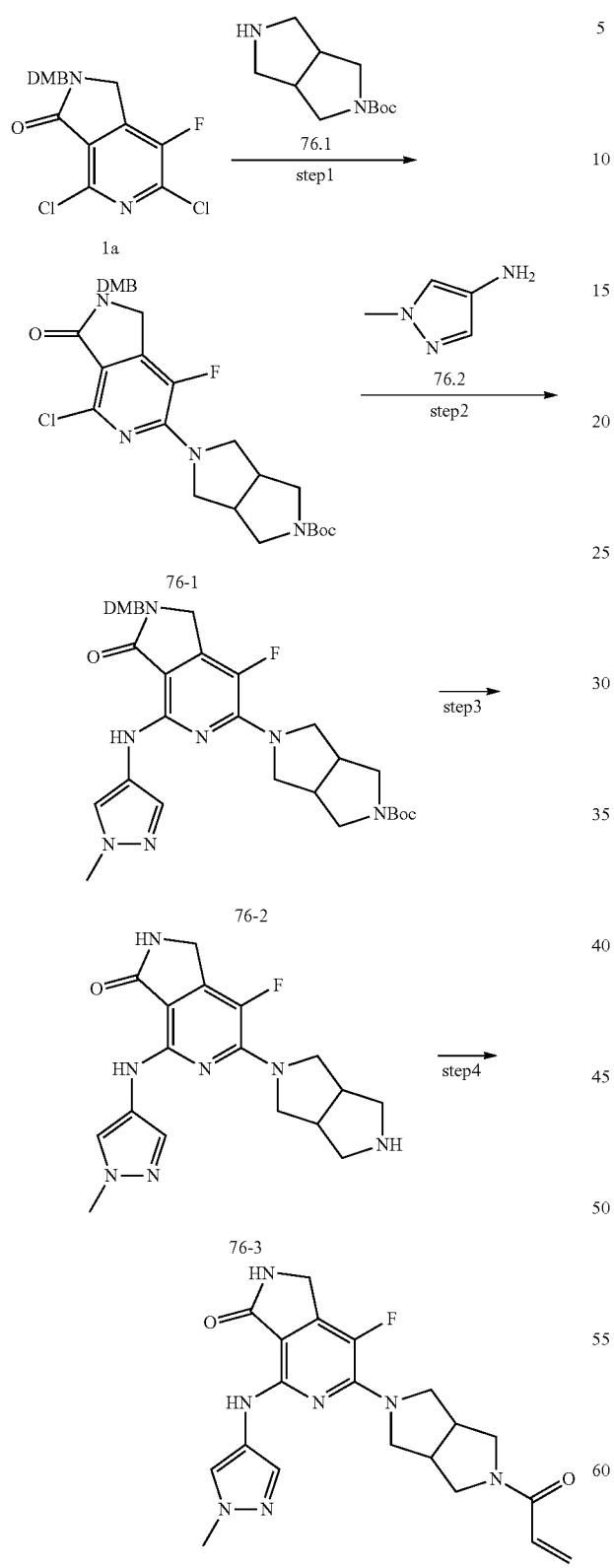
Step 1 to Step 4 of the preparation for compound G-76 were the same as Step 1 to Step 4 of the preparation for compound G-2. MS m/z (ESI): 412[M+H]+. 1H NMR (400 MHz, DMSO-d6) δ 8.27 (s, 1H), 8.07 (s, 1H), 7.87 (s, 1H), 7.60 (s, 1H), 6.54 (dd, J=16.8, 10.3 Hz, 1H), 6.09 (dd, J=16.8, 2.4 Hz, 1H), 5.63 (dd, J=10.3, 2.3 Hz, 1H), 4.29 (s, 2H), 3.93-3.85 (m, 2H), 3.81 (dd, J=10.7, 7.6 Hz, 1H), 3.76 (s, 3H), 3.66 (dd, J=12.6, 7.5 Hz, 1H), 3.57-3.51 (m, 3H), 3.35 (dd, J=12.8, 4.9 Hz, 1H), 3.08-3.02 (m, 1H), 2.98-2.92 (m, 1H).
Example 77 Preparation of Compound G-77
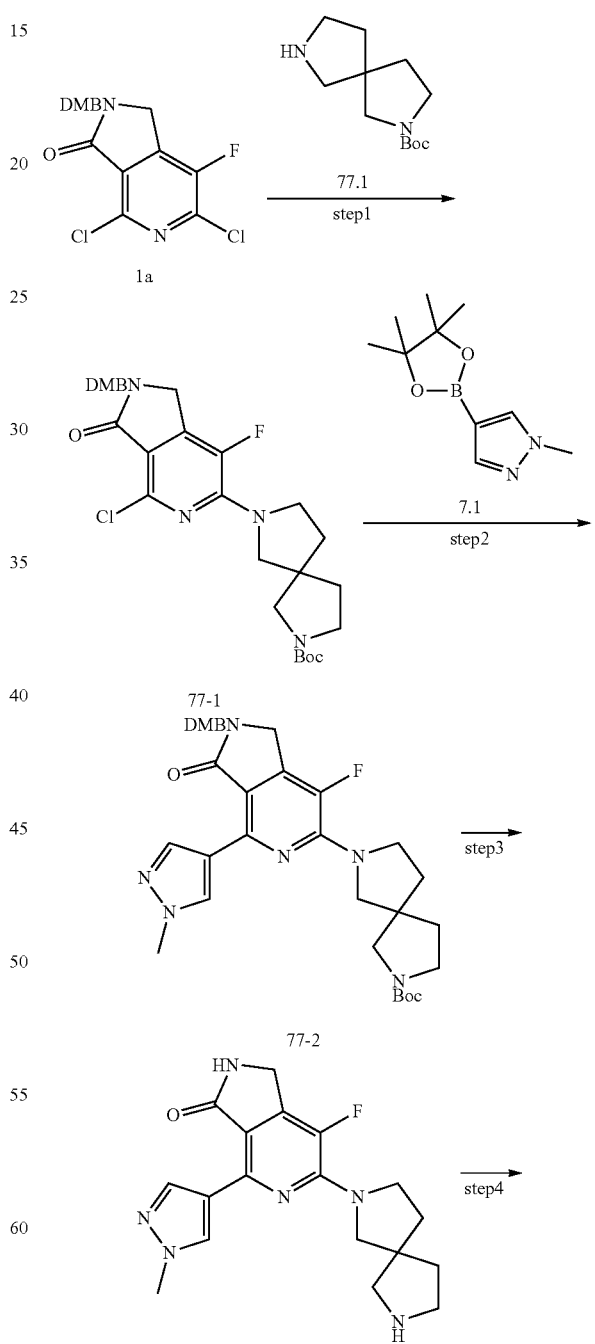

Example 79 Preparation of Compound G-79

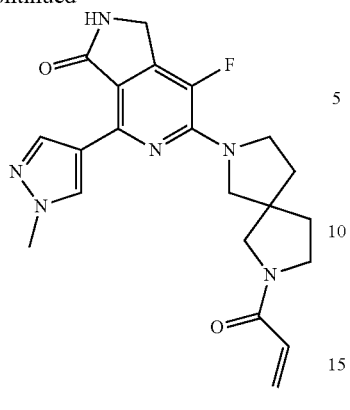

G-79

The preparation method for compound G-79 was the same as that for compound G-77. MS m/z (ESI): 411.2[M+H]$^+$. $^1$H NMR (400 MHz, DMSO-d$_6$): δ 8.93 (s, 0.5H), 8.78 (s, 0.5H), 8.50 (s, 0.5H), 8.34-8.24 (m, 1.5H), 6.84-6.78 (m, 0.5H), 6.45-6.41 (m, 0.5H), 6.18-6.12 (m, 1H), 5.69-5.47 (m, 1H), 4.80-4.76 (m, 1.5H), 4.32 (s, 2H), 4.23-4.20 (m, 1H), 4.02-3.98 (m, 0.5H), 4.00-3.96 (m, 4H), 3.67-3.52 (m, 2H), 2.79-2.63 (m, 0.5H), 2.13-1.6 (m, 4H).

Example 80 Preparation of Compound G-80

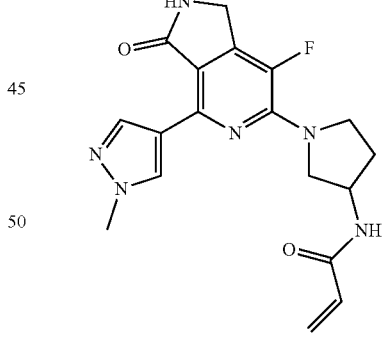

G-80

The preparation method for compound G-80 was the same as that for compound G-77. MS m/z (ESI): 371.2[M+H]$^+$. $^1$H NMR (400 MHz, DMSO-d$_6$) δ 8.79 (s, 1H), 8.42 (d, J=6.4 Hz, 1H), 8.31 (s, 2H), 6.27-6.20 (m, 1H), 6.16-6.09 (m, 1H), 5.61 (dd, J=9.9, 2.2 Hz, 1H), 4.42 (s, 1H), 4.36 (s, 2H), 3.88 (m, 4H), 3.79 (m, 2H), 3.60 (d, J=11.1 Hz, 1H), 2.20-2.14 (m, 1H), 1.92 (d, J=5.7 Hz, 1H).

---

G-77

The preparation method of Step 1 was the same as that for compound 2-1, except that compound 2.1 in the preparation of compound 2-1 was replaced with compound 77.1. MS m/z (ESI): 561[M+H]$^+$.

Step 2 to step 4 were the same as step 1 to step 3 for compound G-7. MS m/z (ESI): 411.3[M+H]$^+$. $^1$H NMR (400 MHz, DMSO-d$_6$) δ 8.79 (s, 1H), 8.31 (d, J=7.9 Hz, 2H), 6.59 (ddd, J=16.8, 13.7, 10.3 Hz, 1H), 6.14 (ddd, J=16.8, 6.4, 2.4 Hz, 1H), 5.66 (ddd, J=14.6, 10.3, 2.4 Hz, 1H), 4.34 (s, 2H), 3.88 (s, 3H), 3.84-3.74 (m, 2H), 3.72-3.42 (m, 6H), 2.06-1.86 (m, 4H).

Example 78 Preparation of N-(1-(7-fluoro-4-(1-methyl-1H-pyrazol-4-yl)-3-oxo-2,3-dihydro-1H-pyrrolo[3,4-c]pyridin-6-yl)piperidin-3-yl)acrylamide (G-78)

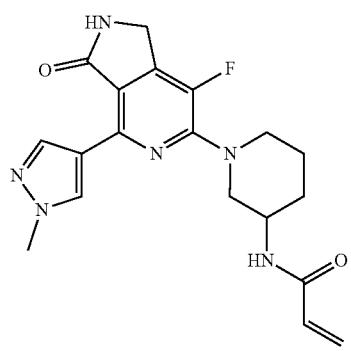

G-78

The preparation method for compound G-78 was the same as that for compound G-77. MS m/z (ESI): 385.2[M+H]$^+$. $^1$H NMR (400 MHz, DMSO-d6): δ 8.89 (s, 1H), 8.44 (s, 1H), 8.40 (s, 1H), 8.10-8.14 (m, 1H), 6.25 (dd, J$_1$=10.0 Hz, J$_2$=17.2 Hz, 1H), 6.12 (dd, J$_1$=2.0 Hz, J$_2$=17.2 Hz, 1H), 5.60 (dd, J$_1$=2.0 Hz, J$_2$=10.0 Hz, 1H), 4.37 (s, 2H), 4.12-4.20 (m, 1H), 3.90-4.01 (m, 2H), 3.89 (s, 3H), 3.15-3.28 (m, 1H), 2.95-3.06 (m, 1H), 1.76-1.96 (m, 2H), 1.48-1.63 (m, 2H).

Example 81 Preparation of Compound G-81

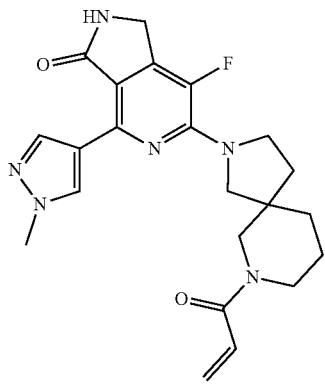

G-81

The preparation method for compound G-81 was the same as that for compound G-77. MS m/z (ESI): 425.2[M+H]⁺.
¹H NMR (400 MHz, DMSO-d6) δ 8.79 (s, 1H), 8.29 (s, 2H), 6.80 (ddd, J=39.1, 16.5, 10.8 Hz, 1H), 6.08 (d, J=16.0 Hz, 1H), 5.62 (dd, J=41.7, 11.1 Hz, 1H), 4.34 (s, 2H), 3.88 (s, 3H), 3.77 (s, 2H), 3.60 (d, J=5.6 Hz, 2H), 3.49 (d, J=3.7 Hz, 2H), 3.37 (d, J=12.4 Hz, 2H), 1.82 (s, 1H), 1.78-1.63 (m, 3H), 1.58 (s, 2H).

Example 82 Preparation of N-(1-(7-fluoro-4-(1-methyl-1H-pyrazol-4-ylamino)-3-oxo-2,3-dihydro-1H-pyrrolo[3,4-c]pyridin-6-yl)piperidin-3-yl)acrylamide (G-82)

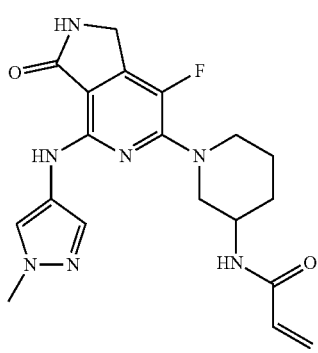

G-82

The preparation method for compound G-82 was the same as that for compound G-76. MS m/z (ESI): 400.2[M+H]⁺.
¹H NMR (400 MHz, DMSO-d₆) δ 8.30 (s, 1H), 8.24 (s, 1H), 8.14 (d, J=7.6 Hz, 1H), 7.89 (d, J=0.7 Hz, 1H), 7.53 (d, J=0.7 Hz, 1H), 6.23 (dd, J=17.1, 10.1 Hz, 1H), 6.07 (dd, J=17.1, 2.3 Hz, 1H), 5.57 (dd, J=10.1, 2.3 Hz, 1H), 4.32 (s, 2H), 4.14 (dd, J=12.6, 3.9 Hz, 1H), 3.95-3.79 (m, 2H), 3.73 (s, 3H), 3.15-3.04 (m, 1H), 2.91 (dd, J=12.6, 9.5 Hz, 1H), 1.90 (dd, J=12.6, 4.2 Hz, 1H), 1.84-1.75 (m, 1H), 1.58 (d, J=11.4 Hz, 1H), 1.48 (ddd, J=21.1, 12.2, 8.8 Hz, 2H).

Example 83 Preparation of N-(1-(7-fluoro-4-(1-methyl-1H-pyrazol-4-ylamino)-3-oxo-2,3-dihydro-1H-pyrrolo[3,4-c]pyridin-6,yl) pyrrolidin-3-yl)acrylamide (G-83)

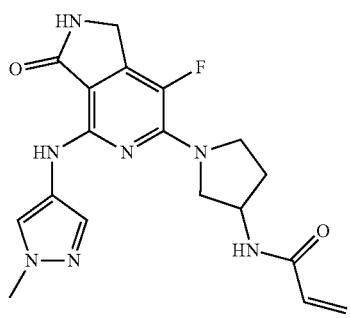

G-83

The preparation method for compound G-83 was the same as that for compound G-76. MS m/z (ESI): 386.2[M+H]⁺.
¹H NMR (400 MHz, DMSO-d₆) δ 8.38 (d, J=6.5 Hz, 1H), 8.28 (s, 1H), 8.09 (s, 1H), 7.88 (d, J=0.7 Hz, 1H), 7.62 (d, J=0.7 Hz, 1H), 6.20 (dd, J=17.1, 10.0 Hz, 1H), 6.08 (dd, J=17.1, 2.4 Hz, 1H), 5.56 (dd, J=9.9, 2.4 Hz, 1H), 4.41-4.33 (m, 1H), 4.30 (s, 2H), 3.76 (s, 4H), 3.58-3.50 (m, 1H), 2.13 (dt, J=13.8, 6.9 Hz, 1H), 3.26 (s, 1H), 1.89 (dq, J=12.1, 6.2 Hz, 1H).

Example 84 Preparation of Compound G-84

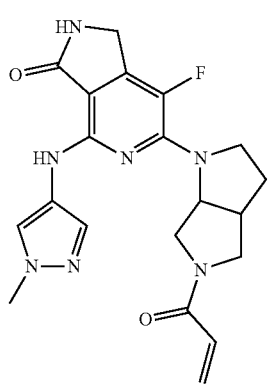

G-84

The preparation method for compound G-84 was the same as that for compound G-76. MS m/z (ESI): 412.2[M+H]⁺.
¹H NMR (400 MHz, DMSO-d6) δ 8.29 (d, J=10.1 Hz, 1H), 8.12 (s, 1H), 7.86 (d, J=1.9 Hz, 1H), 7.58 (d, J=9.8 Hz, 1H), 6.48 (m, 1H), 6.05 (m, 1H), 5.59 (m, 1H), 4.67 (d, J=30.3 Hz, 1H), 4.38-4.27 (m, 2H), 3.86-3.70 (m, 5H), 3.69-3.44 (m, 3H), 3.36 (m, 1H), 3.15-2.92 (m, 1H), 2.12-1.97 (m, 1H), 1.92-1.73 (m, 1H).

Example 85 Preparation of N-(1-(7-fluoro-4-(1-methyl-1H-pyrazol-4-ylamino)-3-oxo-2,3-dihydro-1H-pyrrolo[3,4-c]pyridin-6-yl)azetidin-3-yl)acrylamide (G-85)

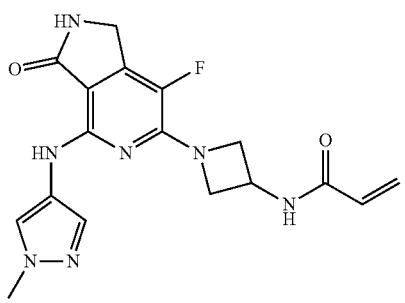

G-85

The preparation method for compound G-85 was the same as that for compound G-76. MS m/z (ESI): 372.2[M+H]⁺. ¹H NMR (400 MHz, DMSO-d₆) δ 8.77 (d, J=7.1 Hz, 1H), 8.37 (s, 1H), 8.14 (s, 1H), 7.91 (s, 1H), 7.59 (s, 1H), 6.14 (qd, J=17.1, 6.1 Hz, 2H), 5.62 (dd, J=9.7, 2.5 Hz, 1H), 4.70 (dd, J=12.9, 5.6 Hz, 1H), 4.45 (t, J=7.5 Hz, 2H), 4.32 (s, 2H), 4.07-3.93 (m, 2H), 3.76 (s, 3H).

Example 86 Preparation of N-(4-fluoro-1-(7-fluoro-4-(4-morpholin)-3-oxo-2,3-dihydro-1H-pyrrolo[3,4-c]pyridin-6-yl)pyrrolidine pyridine-3-yl)acrylamide (G-86)

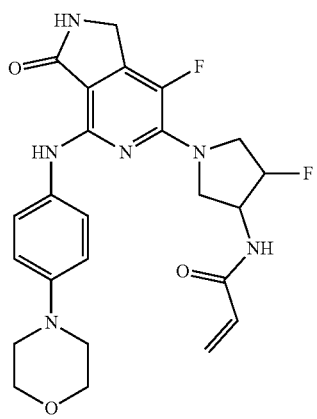

G-86

The preparation method for compound G-86 was the same as that for compound G-76. MS m/z (ESI): 485.2[M+H]⁺. ¹H NMR (400 MHz, DMSO-d₆) δ 8.53 (s, 1H), 8.44 (d, J=6.6 Hz, 2H), 8.21 (s, 1H), 7.55 (d, J=9.0 Hz, 2H), 6.89 (d, J=9.1 Hz, 2H), 6.15-6.12 (m, 1H), 5.61 (m, 1H), 5.19 (s, 0.5H), 5.07 (s, 0.5H), 4.50-4.40 (m, 1H), 4.35 (s, 2H), 4.02-3.64 (m, 9H), 3.05-2.96 (m, 4H).

Example 87 Preparation of Compound G-87

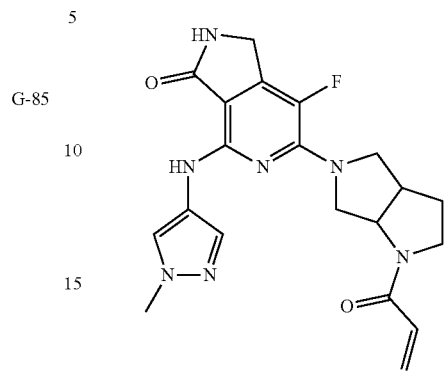

G-87

The preparation method for compound G-87 was the same as that for compound G-76. MS m/z (ESI): 412.2[M+H]⁺. ¹H NMR (400 MHz, DMSO-d6) δ 8.27 (s, 1H), 8.07 (s, 1H), 7.87 (s, 1H), 7.60 (s, 1H), 6.54 (dd, J=16.8, 10.3 Hz, 1H), 6.09 (dd, J=16.8, 2.4 Hz, 1H), 5.63 (dd, J=10.3, 2.4 Hz, 1H), 4.29 (s, 2H), 3.92-3.87 (m, 2H), 3.81 (dd, J=10.7, 7.6 Hz, 1H), 3.76 (s, 3H), 3.66 (dd, J=12.8, 7.6 Hz, 1H), 3.57-3.51 (m, 3H), 3.35 (dd, J=12.8, 5.0 Hz, 1H), 3.07-3.02 (m, 1H), 2.97-2.92 (m, 1H).

Example 88 Preparation of N-(1-(7-fluoro-4-(1-methyl-1H-pyrazol-4-ylamino)-3-oxo-2,3-dihydro-1H-pyrrolo[3,4-c]pyridin-6-yl)pyrrolidine-3-yl)-N-methyl acrylamide (G-88)

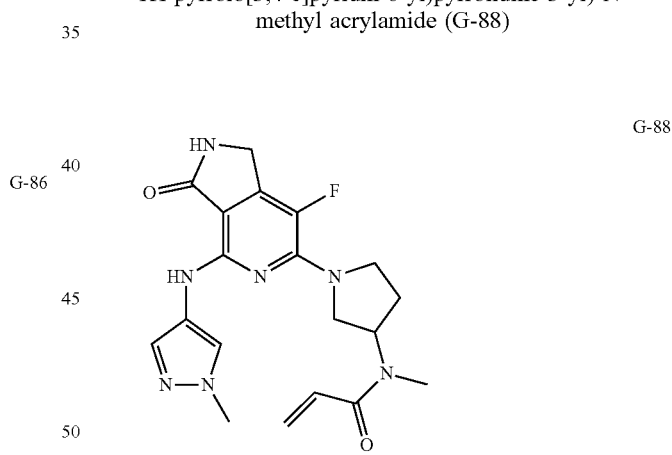

G-88

The preparation method for compound G-88 was the same as that for compound G-76. MS m/z (ESI): 400.2[M+H]⁺. ¹H NMR (400 MHz, DMSO-d₆) δ 8.28 (s, 1H), 8.08 (s, 1H), 7.86 (s, 1H), 7.61 (s, 1H), 6.88-6.73 (m, 1H), 6.10 (d, J=17.0 Hz, 1H), 5.66 (d, J=10.6 Hz, 1H), 5.09 (s, 1H), 4.79 (s, 1H), 4.30 (s, 2H), 3.86-3.79 (m, 2H), 3.75 (s, 3H), 3.70-3.51 (m, 2H), 2.97-2.81 (m, 2H), 2.10 (s, 2H).

Example 89 to Example 102

Compound G-89 to G-102 could be prepared according to the methods of the above examples, wherein the stereoisomers are synthesized by using chiral amines as raw materials.

| No. | Structure | ¹HNMR or MS |
|---|---|---|
| Example 89 | G-89 | ¹H NMR (400 MHz, DMSO-d₆) δ 8.76 (s, 1H), 8.27 (d, J = 3.2 Hz, 2H), 6.54 (dd, J = 16.8, 10.3 Hz, 1H), 6.09 (dd, J = 16.8, 2.4 Hz, 1H), 5.63 (dd, J = 10.3, 2.4 Hz, 1H), 4.31 (s, 2H), 3.94-3.87 (m, 2H), 3.84 (s, 3H), 3.83-3.77 (m, 1H), 3.65 (dd, J = 12.7, 7.6 Hz, 1H), 3.60-3.50 (m, 3H), 3.35 (dd, J = 12.7, 4.9 Hz, 1H), 3.04 (dd, J = 12.2, 4.9 Hz, 1H), 2.95 (dd, J = 12.1, 5.0 Hz, 1H).<br>MS: 397.1 [M + H]⁺ |
| Example 90 | G-90 | ¹H NMR (400 MHz, DMSO-d₆): δ 9.93 (s, 1H), 9.38 (s, 1H), 8.56 (s, 1H), 6.86-6.79 (m, 1H), 6.13-6.10 (m, 1H), 5.68-5.55 (m, 1H), 4.67 (d, J = 8 Hz, 1H), 4.39 (s, 2H), 4.04-4.02 (m, 1H), 3.75-3.55 (m, 1H), 3.23 (s, 3H), 3.03-2.97 (m, 1H), 2.80-2.76 (m, 1H), 1.95-1.71 (m, 3H), 1.46-1.20 (m, 1H).<br>MS(ESI) 386.2 [M + H]⁺ |
| Example 91 | G-91 | ¹H NMR (400 MHz, DMSO-d6) δ 8.78 (d, J = 11.6 Hz, 1H), 8.20 (s, 1H), 7.74 (dd, J = 25.8, 14.1 Hz, 1H), 7.18 (d, J = 26.6 Hz, 1H), 7.09 (d, J = 7.3 Hz, 1H), 7.03 (t, J = 9.0 Hz, 1H), 6.89-6.80 (m, 0.5H), 6.59-6.51 (m, 0.5H), 6.11 (d, J = 15.9 Hz, 0.5H), 5.96 (d, J = 16.7 Hz, 0.5H), 5.70 (d, J = 10.8 Hz, 0.5H), 5.38 (d, J = 10.6 Hz, 0.5H), 4.55 (dd, J = 10.9, 6.5 Hz, 2H), 4.45 (dt, J = 14.3, 6.1 Hz, 2H), 4.38 (s, 2H), 4.1-3.89 (m, 2H), 3.43 (dd, J = 12.7, 6.2 Hz, 1H), 3.27 (d, J = 12.6 Hz, 2H), 3.15-2.95 (m, 2H), 2.90-2.63 (m, 3H), 2.57 (d, J = 9.6 Hz, 1H), 2.27 (d, J = 8.6 Hz, 1H), 2.07 (s, 1H), 2.00-1.91 (m, 1H), 1.82 (d, J = 13.4 Hz, 1H), 1.62 (s, 1H), 1.45 (s, 1H), 0.84 (d, J = 6.2 Hz, 3H).<br>M⁺ = 568.2 [M + 1]⁺. |

| No. | Structure | ¹HNMR or MS |
|---|---|---|
| Example 92 | 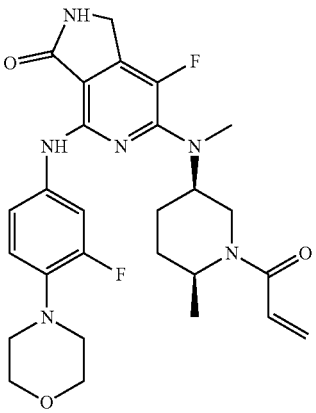<br>G-92 | ¹H NMR (400 MHz, DMSO-d₆) δ 8.60 (s, 1H), 7.99 (s, 1H), 7.57 (d, J = 15.0 Hz, 1H), 7.20 (d, J = 7.8 Hz, 1H), 6.93 (t, J = 9.1 Hz, 1H), 6.65 (s, 1H), 5.99 (d, J = 14.6 Hz, 1H), 5.56 (s, 1H), 4.36 (s, 2H), 4.20 (s, 1H), 3.74 (s, 4H), 3.16-3.02 (m, 6H), 2.96 (s, 4H), 2.09 (s, 1H), 1.74 (s, 3H), 1.23 (d, J = 6.2 Hz, 3H).<br>MS: 527.3 [M + H]⁺ |
| Example 94 | 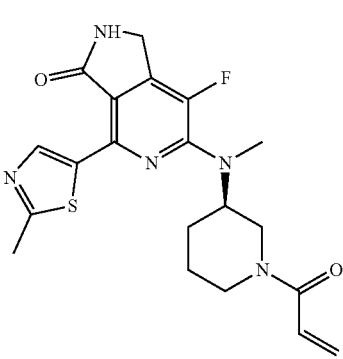<br>G-94 | ¹H NMR (400 MHz, DMSO-d₆): δ 9.22 (s, 1H), 8.52 (s, 1H), 6.85-6.72 (m, 1H), 6.10-6.06 (m, 1H), 5.66-5.58 (m, 1H), 4.45-4.42 (m, 1H), 4.37 (s, 2H), 4.08-4.01 (m, 2H), 3.05 (s, 3H), 3.03-2.89 (m, 1H), 2.60 (s, 3H), 1.99-1.79 (m, 4H), 1.46-1.40 (m, 1H).<br>MS(ESI) 416.1 [M + H]⁺ |
| Example 95 | 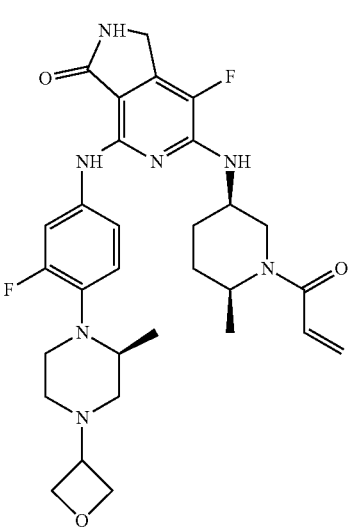<br>G-95 | ¹H NMR (400 MHz, DMSO-d6) δ 8.78 (d, J = 14.4 Hz, 1H), 8.22 (s, 1H), 7.75 (dd, J = 32.4, 14.7 Hz, 1H), 7.23-7.09 (m, 2H), 7.02 (t, J = 9.1 Hz, 1H), 6.89-6.79 (m, 0.5H), 6.61-6.52 (m, 0.5H), 6.10 (d, J = 16.2 Hz, 0.5H), 5.94 (d, J = 18.5 Hz, 0.5H), 5.68 (d, J = 8.8 Hz, 0.5H), 5.40 (d, J = 8.8 Hz, 0.5H), 4.79 (brs, 1H), 4.55 (dd, J = 10.9, 6.4 Hz, 2H), 4.50-4.41 (m, 2H), 4.38 (s, 2H), 3.94-3.82 (m, 2H), 3.42 (dt, J = 12.3, 6.2 Hz, 1H), 3.25 (s, 1H), 3.12-2.91 (m, 2H), 2.80-2.65 (m, 2H), 2.57 (d, J = 10.6 Hz, 1H), 2.25 (s, 1H), 1.98-1.81 (m, 3H), 1.68 (s, 2H), 1.26-1.10 (m, 3H), 0.83 (d, J = 5.9 Hz, 3H).<br>M⁺ = 582.3[M + 1]⁺. |

-continued

| No. | Structure | ¹HNMR or MS |
|---|---|---|
| Example 96 | 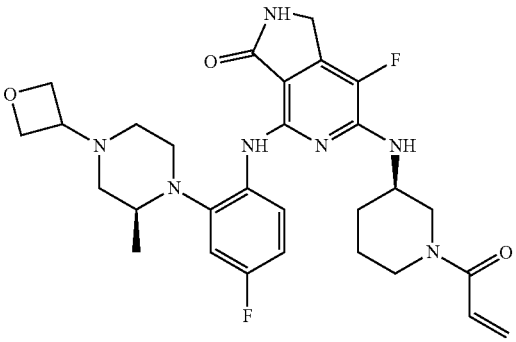<br>G-96 | ¹H NMR (400 MHz, DMSO-d6) δ 9.97 (s, 1H), 8.57 (s, 1H), 8.46 (s, 1H), 8.03 (s, 1H), 7.13 (d, J = 6.8 Hz, 1H), 6.95 (d, J = 7.4 Hz, 1H), 6.9-6.78 (m, 0.5H), 6.76 (t, J = 8.6 Hz, 1H), 6.49-6.43 (m, 0.5H), 6.09 (d, J = 15.4 Hz, 0.5H), 5.94 (s, 0.5H), 5.70 (s, 0.5H), 5.32 (s, 0.5H), 4.54 (dd, J = 11.6, 6.3 Hz, 2H), 4.45 (t, J = 6.2 Hz, 2H), 4.2 (s, 2H), 4.02-3.86 (m, 3H), 3.44-3.40 (m, 1H), 3.15-3.02 (m, 2H), 2.79-2.67 (m, 4H), 2.61 (d, J = 19.8 Hz, 2H), 2.02 (s, 2H), 1.78 (s, 1H), 1.64 (s, 1H), 1.47 (s, 1H), 0.69 (s, 3H).<br>M⁺ = 568.2 [M + 1]⁺. |
| Example 97 | 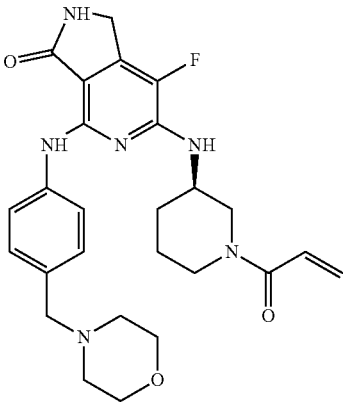<br>G-97 | ¹H NMR (400 MHz, DMSO-d₆) δ 8.75 (d, J = 13.2 Hz, 1H), 8.18 (s, 2H), 7.55 (s, 2H), 7.12 (m, 1H), 7.01 (d, J = 7.7 Hz, 1H), 6.85 (dd, J = 15.9, 10.3 Hz, 0.5H), 6.52 (dd, J = 16.1, 10.5 Hz, 0.5H), 6.14 (d, J = 16.6 Hz, 0.5H), 5.95 (d, J = 16.0 Hz, 0.5H), 5.70 (d, J = 10.1 Hz, 0.5H), 5.35 (d, J = 10.7 Hz, 0.5H), 4.51 (d, J = 9.3 Hz, 0.5H), 4.34 (s, 2H), 4.21 (d, J = 12.4 Hz, 0.5H), 4.06-3.91 (m, 2H), 3.56-3.49 (m, 4H), 3.32 (m, 2H), 3.04 (m, 1H), 2.68 (m, 1H), 2.28 (s, 4H), 2.00 (m, 1H), 1.79 (m, 1H), 1.62 (m, 1H), 1.40 (m, 1H).<br>MS: 495.2 [M + H]⁺ |
| Example 98 | 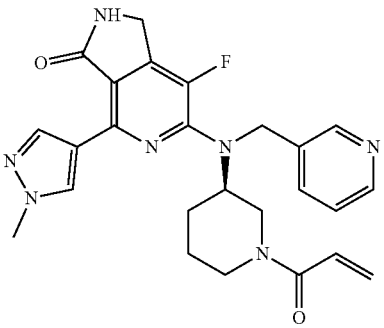<br>G-98 | MS(ESI) 476.2 [M + H]⁺ |
| Example 99 | 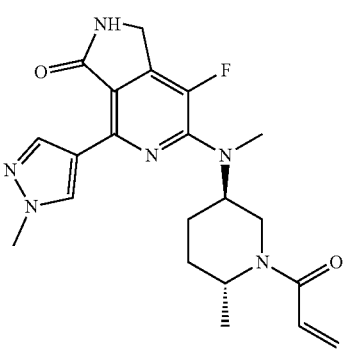<br>G-99 | ¹H NMR (400 MHz, DMSO-d₆): δ 8.78 (s, 1H), 8.36 (s, 1H), 8.27 (s, 1H), 6.76-6.69 (m, 1H), 6.13-6.08 (m, 1H), 5.64-5.61 (m, 1H), 4.68-4.67 (m, 1H), 4.33 (s, 2H), 4.24-4.17 (m, 2H), 3.86 (s, 3H), 3.48-3.44 (m, 1H), 2.94 (s, 3H), 1.92-1.86 (m, 2H), 1.62-1.59 (m, 1H), 1.46-1.37 (m, 1H), 1.15-1.13 (d, J = 5.6Hz, 3H).<br>MS(ESI) 413.3 [M + H]⁺ |

-continued

| No. | Structure | ¹HNMR or MS |
|---|---|---|
| Example 100 | 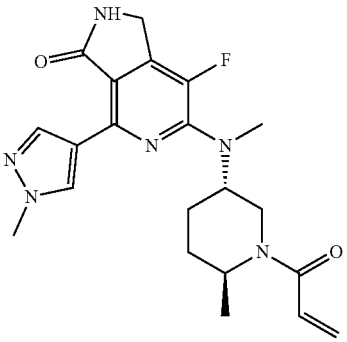<br>G-100 | ¹H NMR (400 MHz, DMSO-d₆): δ 8.78 (s, 1H), 8.36 (s, 1H), 8.27 (s, 1H), 6.76-6.70 (m, 1H), 6.12-6.08 (m, 1H), 5.64-5.61 (m, 1H), 4.70-4.67 (m, 1H), 4.33 (s, 2H), 4.26-4.16 (m, 2H), 3.86 (s, 3H), 3.48-3.44 (m, 1H), 2.94 (d, J = 4Hz, 3H), 1.94-1.86 (m, 2H), 1.62-1.56 (m, 1H), 1.37-1.30 (m, 1H), 1.15-1.13 (d, J = 5.6Hz, 3H). MS(ESI) 413.3 [M + H]⁺ |
| Example 101 | 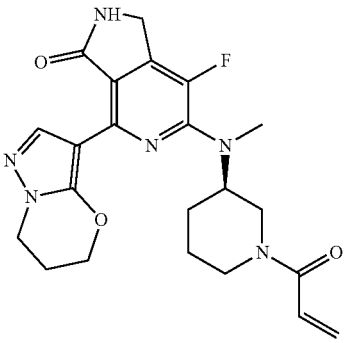<br>G-101 | ¹H NMR (400 MHz, DMSO-d₆) δ 8.40 (s, 1H), 7.81 (s, 1H), 6.66 (dd, J = 16.7, 10.6 Hz, 1H), 6.02 (d, J = 16.9 Hz, 1H), 5.52 (d, J = 9.3 Hz, 1H), 4.51 (s, 1H), 4.37-4.11 (m, 6H), 4.06 (t, J = 6.1 Hz, 2H), 3.09 (d, J = 3.9 Hz, 3H), 2.78 (s, 2H), 2.23-2.10 (m, 2H), 1.94-1.78 (m, 3H), 1.48 (s, 1H). MS: 441.2 [M + H]⁺ |
| Example 102 | 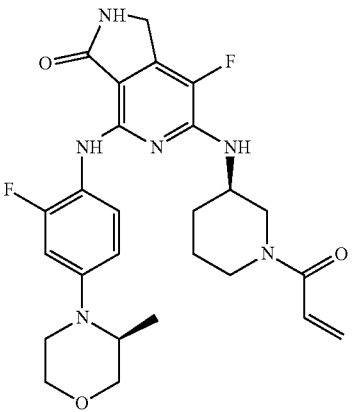<br>G-102 | ¹H NMR (400 MHz, DMSO-d6) δ 8.62 (s, 1H), 8.26-8.09 (m, 2H), 7.06-6.95 (m, 1H), 6.92-6.78 (m, 1.5H), 6.54-6.49 (m, 1.5H), 6.16 (d, J = 17.0 Hz, 0.5H), 5.99 (d, J = 16.7 Hz, 0.5H), 5.72 (d, J = 9.6 Hz, 0.5H), 5.43 (d, J = 10.3 Hz, 0.5H), 4.55 (d, J = 11.0 Hz, 0.5H), 4.37 (s, 2H), 4.17 (d, J = 12.7 Hz, 0.5H), 3.99 (t, J = 13.3 Hz, 1H), 3.87 (d, J = 11.3 Hz, 2H), 3.75-3.66 (m, 2H), 3.65-3.59 (m, 1H), 3.54 (td, J = 11.0, 3.1 Hz, 1H), 3.16-2.98 (m, 2H), 2.93 (dd, J = 16.8, 6.1 Hz, 1H), 2.80 (s, 0.5H), 2.68 (dd, J = 13.0, 9.3 Hz, 0.5H), 1.99 (s, 1H), 1.84-1.75 (m, 1H), 1.66 (d, J = 11.4 Hz, 1H), 1.48-1.36 (m, 1H), 0.95 (d, J = 6.7 Hz, 3H). M⁺ = 513.3 [M + 1]⁺. |
| Example 103 | 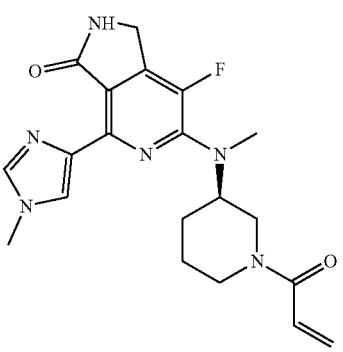<br>G-103 | MS(ESI) 399.2 [M + H]⁺ |

| No. | Structure | ¹HNMR or MS |
|---|---|---|
| Example 105 | 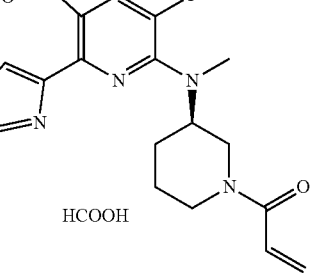<br>G-105 | MS(ESI) 399.2 [M + H]⁺ |
| Example 106 | 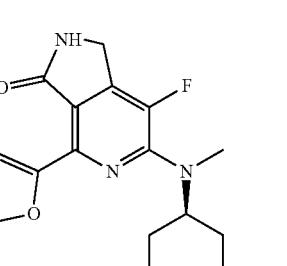<br>G-106 | MS(ESI) 400.2 [M + H]⁺ |
| Example 107 | 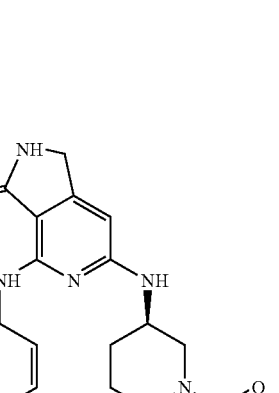<br>G-107 | MS(ESI) 463.2 [M + H]⁺ |

| No. | Structure | ¹HNMR or MS |
|---|---|---|
| Example 108 | G-108 | ¹H NMR (400 MHz, DMSO-d$_6$) δ 8.58 (d, J = 3.8 Hz, 1H), 8.14 (d, J = 13.5 Hz, 1H), 7.61-7.44 (m, 2H), 6.99 (t, J = 9.1 Hz, 1H), 6.91-6.84 (m, 2.5H), 6.84-6.76 (m, 0.5H), 6.69 (dd, J = 16.6, 10.4 Hz, 1H), 6.28-6.17 (m, 1H), 6.16-6.04 (m, 1H), 5.74 (dd, J = 10.3, 2.5 Hz, 0.5H), 5.44 (dd, J = 10.3, 2.6 Hz, 0.5H), 4.39-4.32 (m, 3H), 3.89-2.81 (m, 1H), 3.77-3.69 (m, 4H), 3.63 (s, 1H), 3.56-3.44 (m, 1H), 3.18 (dd, J = 13.9, 7.4 Hz, 1H), 3.05-2.95 (m, 4H), 1.80-1.91 (m, 0.5), 1.79 (d, J = 11.3 Hz, 3H), 1.65-1.46 (m, 1.5H), 1.37 (s, 1H).<br>MS: 495.3 [M + H]⁺ |
| Example 109 | G-109 | ¹H NMR (400 MHz, T = 80° C., DMSO-d6): δ 8.75 (s, 1H), 8.36 (s, 1H), 7.87 (s, 1H), 6.69 (dd, J$_1$ = 10.4 Hz, J$_2$ = 16.8 Hz, 1H), 6.57 (brs, 1H), 6.09 (dd, J$_1$ = 2.0 Hz, J$_2$ = 16.8 Hz, 1H), 5.59 (dd, J$_1$ = 2.0 Hz, J$_2$ = 10.4 Hz, 1H), 5.01-5.27 (m, 1H), 4.33 (s, 2H), 3.99-4.16 (m, 2H), 3.85 (s, 3H), 1.84-1.99 (m, 1H), 1.70-1.82 (m, 2H), 1.44-1.60 (m, 1H), 1.07 (d, J = 7.2 Hz, 3H). |
| Example 110 | G-110 | ¹H NMR (400 MHz, DMSO-d6): δ 8.92 (s, 0.6H), 8.73 (s, 0.4H), 8.49 (s, 0.6H), 8.20-8.32 (m, 1.4H), 7.02-7.21 (m, 1H), 6.60-6.90 (m, 1H), 6.10-6.20 (m, 1H), 5.50-5.73 (m, 2H), 4.62-4.71 (m, 0.6H), 4.36 (s, 2H), 4.07-4.18 (m, 0.4H), 3.78-4.01 (m, 4H), 1.41-2.03 (m, 4H), 0.93-1.29 (m, 3H). |
| Example 111 | G-111 | ¹H NMR (400 MHz, DMSO-d$_6$) δ 8.87 (s, 0.5H), 8.72 (s, 0.5H), 8.43 (s, 0.5H), 8.26 (s, 1H), 8.24 (s, 1H), 7.04-6.91 (m, 1H), 6.83 (m, 0.5H), 6.63 (m, 0.5H), 6.11 (t, J = 17.7 Hz, 2H), 5.67 (d, J = 11.4 Hz, 0.5H), 5.50 (d, J = 10.5 Hz, 0.5H), 4.83 (d, J = 10.8 Hz, 0.5H), 4.33 (s, 2H), 4.20 (d, J = 12.6 Hz, 0.5H), 4.10 (d, J = 12.8 Hz, 0.5H), 3.99 (m, 1H), 3.85 (m, 0.5H), 3.84 (s, 3H), 3.26 (s, 0.5H), 3.02 (t, J = 11.4 Hz, 1H), 2.76 (t, J = 11.3 Hz, 0.5H), 2.51 (m, 0.5H), 1.97 (m, 1H), 1.72 (m, 2H), 1.48 (m, 1H).<br>MS: 385.3 [M + H]⁺ |

-continued

| No. | Structure | ¹HNMR or MS |
|---|---|---|
| Example 112 | G-112 | ¹H NMR (400 MHz, T = 80° C., DMSO-d6): δ 8.72 (s, 1H), 8.28 (s, 1H), 7.98 (s, 1H), 6.72 (dd, J₁ = 10.8 Hz, J₂ = 16.0 Hz, 1H), 6.07 (dd, J₁ = 2.4 Hz, J₂ = 16.0 Hz, 1H), 5.60 (d, J = 10.8 Hz, 1H), 4.33 (s, 2H), 4.13-4.25 (m, 2H), 3.86 (s, 3H), 3.10 (d, J = 3.6 Hz, 3H), 2.75-2.94 (m, 3H), 1.79-1.99 (m, 3H), 1.45-1.58 (m, 1H). |
| Example 113 | G-113 | ¹H NMR (400 MHz, DMSO-d6): δ 8.72-8.85 (m, 1H), 8.18-8.42 (m, 2H), 6.69-6.91 (m, 1H), 6.07-6.20 (m, 1H), 5.55-5.74 (m, 1H), 4.41-4.71 (m, 1H), 4.36 (s, 2H), 4.01-4.28 (m, 3H), 3.87 (s, 3H), 3.06-3.12 (m, 3H), 2.80-3.06 (m, 2H), 1.77-2.01 (m, 3H), 1.41-1.55 (m, 1H). |
| Example 114 | G-114 | ¹H NMR (400 MHz, DMSO-d₆): δ 8.58-8.54 (d, J = 16 Hz, 1H), 8.16-8.14 (m, 1H), 7.52-7.50 (m, 2H), 7.00-6.80 (m, 3.5H), 6.55-6.53 (m, 0.5H), 6.20-6.16 (d, J = 6 Hz, 0.5H), 6.02-6.00 (d, J = 6 Hz, 0.5H), 5.74-5.72 (m, 0.5H), 5.44-5.42 (m, 0.5H), 4.58-4.54 (m, 0.5H), 4.36 (s, 2H), 4.25-4.23 (m, 0.5H), 4.10-4.03 (m, 2H), 3.73-3.71 (m, 4H), 3.05-3.03 (m, 0.5H), 3.00-2.98 (m, 4H), 2.88-2.86 (m, 0.5H), 2.68-2.66 (m, 1H), 2.01-1.99 (m, 1H) 1.80-1.78 (m, 1H), 1.68-1.66 (m, 1H), 1.48-1.45 (m, 1H). MS(ESI) 481.3 [M + H]⁺ |
| Example 115 | G-115 | ¹H NMR (400 MHz, DMSO-d₆) δ 8.80 (d, J = 39.8 Hz, 1H), 8.46-8.23 (m, 2H), 7.13-6.99 (m, 1H), 6.85 (dd, J = 16.6, 10.2 Hz, 1H), 6.70 (dd, J = 16.4, 10.6 Hz, 1H), 6.21-6.04 (m, 1H), 5.69 (d, J = 10.1 Hz, 1H), 5.54 (d, J = 10.3 Hz, 1H), 4.81 (d, J = 11.8 Hz, 1H), 4.36 (s, 2H), 4.05 (d, J = 10.1 Hz, 1H), 3.87 (s, 3H), 2.98 (t, J = 12.7 Hz, 1H), 2.58 (t, J = 11.8 Hz, 1H), 2.00-1.54 (m, 4H), 1.20 (dd, J = 29.8, 6.6 Hz, 3H). MS: 399.3 [M + H]⁺. |

| Compound | ¹H NMR or MS |
|---|---|
| G-4 | ¹H NMR (400 MHz, T = 80° C., DMSO-d6): δ 8.58 (s, 1H), 7.70 (s, 1H), 7.52 (d, J = 8.8 Hz, 2H), 6.90 (d, J = 8.4 Hz, 1H), 6.71 (dd, J₁ = 10.4 Hz, J₂ = 16.8 Hz, 1H), 6.48 (brs, 1H), 6.10 (dd, J₁ = 2.4 Hz, J₂ = 16.8 Hz, 1H), 5.62 (dd, J₁ = 2.4 Hz, J₂ = 10.4 Hz, 1H), 4.30 (s, 2H), 3.98-4.10 (m, 3H), 3.60-3.75 (m, 4H), 3.42-3.54 (m, 2H), 3.33 (s, 3H), 2.05-2.15 (m, 1H), 1.76-2.00 (m, 3H), 1.54-1.74 (m, 2H). |
| G-5 | ¹H NMR (400 MHz, DMSO-d6): δ 8.65 (s, 1H), 8.21 (s, 1H), 7.70 (d, J = 6.0 Hz, 1H), 7.55 (d, J = 8.8 Hz, 1H), 6.93 (d, J = 8.8 Hz, 1H), 6.34 (dd, J₁ = 10.0 Hz, J₂ = 16.8 Hz, 1H), 6.11 (dd, J₁ = 2.0 Hz, J₂ = 16.8 Hz, 1H), 5.67 (dd, J₁ = 2.0 Hz, J2 = 10.0 Hz, 1H), 4.64-4.72 (m, 1H), 4.50-4.57 (m, 1H), 4.38 (s, 2H), 4.21-4.28 (m, 1H), 4.12-4.19 (m, 1H), 4.03-4.08 (m, 2H), 3.94-4.00 (m, 1H), 3.61-3.67 (m, 2H), 3.33 (s, 3H). |
| G-6 | ¹H NMR (400 MHz, DMSO-d₆) δ 8.80 (d, J = 59.2 Hz, 1H), 8.30 (dd, J = 44.8, 35.1 Hz, 2H), 7.00 (s, 1H), 6.73 (d, J = 81.8 Hz, 1H), 6.11 (t, J = 18.1 Hz, 1H), 5.59 (dd, J = 70.2, 10.0 Hz, 1H), 4.84 (d, J = 9.8 Hz, 1H), 4.32 (s, 1H), 4.27-4.06 (m, 1H), 4.01 (s, 1H), 3.84 (s, 2H), 3.01 (s, 1H), 2.75 (s, 1H), 1.97 (s, 1H), 1.75 (s, 2H), 1.48 (s, 1H). MS: 470.2 [M + H]+ |
| G-9 | ¹H NMR (400 MHz, DMSO-d₆) δ 8.59 (d, J = 7.1 Hz, 1H), 8.16 (s, 1H), 7.55 (t, J = 8.9 Hz, 2H), 7.28 (dd, J = 18.0, 5.7 Hz, 1H), 6.85 (dd, J = 9.0, 5.1 Hz, 2H), 6.64-6.44 (m, 1H), 6.10 (ddd, J = 16.9, 5.3, 2.5 Hz, 1H), 5.63 (ddd, J = 15.1, 10.3, 2.4 Hz, 1H), 4.46 (ddd, J = 16.2, 11.2, 5.7 Hz, 1H), 4.33 (s, 2H), 4.00 (dd, J = 9.0, 4.0 Hz, 2H), 3.89 (dd, J = 10.5, 6.4 Hz, 1H), 3.70-3.45 (m, 5H), 3.27 (d, J = 3.9 Hz, 3H), 2.23-1.99 (m, 2H). MS: 456.2 [M + H]+ |
| G-10 | ¹H NMR (400 MHz, DMSO-d₆) δ 8.34 (d, J = 8.8 Hz, 1H), 8.05 (s, 1H), 7.95 (d, J = 19.3 Hz, 1H), 7.53 (d, J = 25.8 Hz, 1H), 6.97-6.81 (m, 1.5H), 6.52-6.45 (m, 0.5H), 6.11 (d, J = 14.7 Hz, 0.5H), 5.95 (d, J = 16.4 Hz, 0.5H), 5.70 (d, J = 10.5 Hz, 0.5H), 5.41 (d, J = 10.3 Hz, 0.5H), 4.57 (d, J = 10.4 Hz, 0.5H), 4.32 (s, 2H), 4.27-4.09 (m, 1.5H), 4.01-3.83 (m, 4H), 3.45-3.31 (m, 2H), 3.10-2.88 (m, 1H), 2.74-2.52 (m, 1H), 2.00-1.97 (m, 1H), 1.93-1.72 (m, 4H), 1.69-1.61 (m, 1H), 1.48-1.35 (m, 1H). MS: 470.3 [M + H]⁺ |
| G-11 | ¹H NMR (400 MHz, DMSO-d6) δ 8.59-8.44 (m, 1H), 8.17 (s, 1H), 8.10 (d, J = 7.7 Hz, 1H), 7.44 (t, J = 8.8 Hz, 2H), 7.02-6.71 (m, 3H), 6.48 (dd, J = 16.6, 10.5 Hz, 0.5H), 6.14 (d, J = 16.4 Hz, 0.5H), 5.96 (d, J = 16.7 Hz, 0.5H), 5.69 (d, J = 10.3 Hz, 0.5H), 5.44 (dd, J = 57.8, 9.4 Hz, 1H), 4.52 (d, J = 11.1 Hz, 0.5H), 4.32 (s, 2H), 4.16 (d, J = 13.0 Hz, 0.5H), 4.05-3.77 (m, 2H), 3.13-3.02 (m, 0.5H), 3.04-2.87 (m, 4H), 2.82-2.69 (m, 0.5H), 2.69-2.59 (m, 0.5H), 2.46-2.30 (m, 4.5H), 2.24 (s, 3H), 1.97 (s, 1H), 1.77 (d, J = 13.2 Hz, 1H), 1.62 (d, J = 7.5 Hz, 1H), 1.40 (d, J = 9.5 Hz, 1H).<br>M⁺ = 494.4[M + 1]⁺. |
| G-12 | ¹H NMR (400 MHz, DMSO-d₆) δ 9.06 (m, 1H), 8.15-7.95 (m, 2H), 7.90 (s, 1H), 7.20 (d, J = 8.8 Hz, 1H), 7.04 (s, 1H), 6.86 (m, 0.5H), 6.59-6.50 (m, 0.5H), 6.14 (d, J = 15.6 Hz, 0.5H), 5.98 (d, J = 16.1 Hz, 0.5H), 5.70 (d, J = 10.4 Hz, 0.5H), 5.38 (d, J = 9.4 Hz, 0.5H), 4.58 (d, J = 11.9 Hz, 0.5H), 4.34 (s, 2H), 4.17 (s, 0.5H), 3.99 (m, 2H), 3.10 (m, 0.5H), 3.01 (s, 5H), 2.78 (s, 0.5H), 2.64 (t, J = 11.3 Hz, 1H), 2.45-2.36 (m, 4H), 2.18 (s, 3H), 2.01 (s, 1H), 1.78 (d, J = 13.3 Hz, 1H), 1.71-1.59 (m, 1H), 1.47 (d, J = 11.5 Hz, 1H). MS: 495.3 [M + H]⁺ |
| G-13 | ¹H NMR (400 MHz, DMSO-d₆): δ 8.43 (s, 0.6H), 8.39 (s, 0.4H), 8.10 (s, 1H), 8.01 (s, 0.6H), 7.96 (s, 0.4H), 7.66 (s, 0.4H), 7.60 (s, 0.6H), 6.86-7.04 (m, 1.5H), 6.44-6.56 (m, 0.5H), 6.12 (d, J = 17.2 Hz, 0.6H), 5.98 (d, J = 17.2 Hz, 0.4H), 5.72 (d, J = 10.0 Hz, 0.6H), 5.44 (d, J = 10.0 Hz, 0.4H), 4.54-4.62 (m, 1H), 4.38-4.48 (m, 1H), 4.35 (s, 2H), 4.17-4.27 (m, 1H), 3.90-4.10 (m, 2H), 2.95-3.22 (m, 3H), 2.58-2.83 (m, 2H), 2.18-2.40 (m, 4H), 1.97-2.07 (m, 1H), 1.45-1.88 (m, 3H). |
| G-14 | ¹H NMR (400 MHz, DMSO-d₆): δ 8.54-8.51 (d, J = 12 Hz, 1H), 8.40 (s, 1H), 8.09 (s, 1H), 7.49-7.45 (m, 2H), 6.95-6.90 (m, 1H), 6.82-6.80 (m, 0.5H), 6.79-6.76 (d, J = 8 Hz, 2H), 6.50-6.47 (m, 0.5H), 6.16-6.11 (m, 0.5H), 5.99-5.95 (m, 0.5H), 5.70-5.68 (J, d = 11 Hz, 0.5H), 5.40-5.38 (J, d = 11 Hz, 0.5H), 4.50-4.46 (m, 1H), 4.42-4.38 (m, 0.5H), 4.32 (s, 2H), 4.19-4.16 (m, 0.5H), 3.94-3.85 (m, 2H), 3.69 (t, J = 4 Hz, 4H), 3.06-2.99 (m, 1H), 2.96-2.94 (m, 1H), 1.95-1.87 (m, 1H), 1.79-1.75 (m, 1H), 1.65-1.61 (m, 1H), 1.43-1.38 (m, 1H). MS (ESI)481.3 [M + H]+ |
| G-15 | ¹H NMR (400 MHz, DMSO-d6): δ 8.38-8.45 (m, 1H), 7.97-8.13 (m, 2H), 7.53-7.61 (m, 1H), 6.80-6.99 (m, 1.5H), 6.41-6.55 (m, 0.5H), 5.90-6.18 (m, 1H), 5.36-5.74 (m, 1H), 4.75-5.29 (m, 3H), 4.42-4.54 (m, 1H), 4.35 (s, 2H), 3.88-4.08 (m, 2H), 2.60-3.17 (m, 5H), 1.43-2.08 (m, 4H). |
| G-16 | ¹H NMR (400 MHz, DMSO-d₆): δ 8.54 (s, 1H), 8.10 (s, 1H), 7.53-7.46 (m, 2H), 6.95-6.90 (m, 1H), 6.89-6.82 (m, 0.5H), 6.76 (d, J = 9.2 Hz, 2H), 6.50-6.47 (m, 0.5H), 6.16-6.11 (m, 0.5H), 5.99-5.95 (m, 0.5H), 5.70-5.68 (J, d = 11 Hz, 0.5H), 5.40-5.38 (J, d = 11 Hz, 0.5H), 4.82-4.78 (m, 1H), 4.54-4.50 (d, J = 20 Hz, 0.5H), 4.32 (s, 2H), 4.19-4.16 (d, J = 20 Hz, 0.5H), 3.94-3.85 (m, 4H), 3.69-3.64 (m, 2H), 3.06-2.99 (m, 1H), 2.73-2.64 (m, 1H), 1.95-1.87 (m, 1H), 1.79-1.75 (m, 1H), 1.65-1.61 (m, 1H), 1.43-1.38 (m, 1H). MS (ESI)456.2 [M + H]⁺ |
| G-17 | ¹H NMR (400 MHz, DMSO-d6) δ 8.82 (d, J = 12.1 Hz, 1H), 8.21 (d, J = 4.8 Hz, 1H), 7.64 (t, J = 7.5 Hz, 2H), 7.18 (d, J = 8.8 Hz, 2H), 7.05 (d, J = 7.6 Hz, 1H), 6.84 (dd, J = 16.7, 10.7 Hz, 0.5H), 6.54 (dd, J = 16.7, 10.3 Hz, 0.5H), 6.12 (d, J = 15.7 Hz, 0.5H), 5.97 (d, J = 16.7 Hz, 0.5H), 5.68 (d, J = 10.9 Hz, 0.5H), 5.39 (d, J = 10.4 Hz, 0.5H), 4.52 (d, J = 10.6 Hz, 0.5H), 4.35 (s, 2H), 4.25-4.09 (m, 2.5H), 4.05-3.82 (m, 4H), 3.62 (t, J = 5.1 Hz, 2H), 3.15-2.96 (m, 1H), 2.80-2.62 (m, 1H), 2.00 (s, 1H), 1.78 (d, J = 13.5 Hz, 1H), 1.62 (s, 1H), 1.43 (s, 1H). M⁺ = 495.3[M + 1]⁺. |
| G-18 | ¹H NMR (400 MHz, DMSO-d₆): δ 9.10 (s, 0.5H), 9.04 (s, 0.5H), 8.17-8.14 (m, 1H), 8.10-8.06 (m, 1H), 7.91 (s, 1H), 7.22-7.20 (m, 1H), 7.08-7.05 (m, 1H), 7.08-7.05 (m, 0.5H), 6.85-6.82 (m, 0.5H), 6.56-6.52 (m, 0.5H), 6.18-6.16 (d, J = 12 Hz, 0.5H), 6.00-5.96 (d, J = 16 Hz, 0.5H), 5.71-5.68 (d, J = 12 Hz, 0.5H), 5.39-5.36 (d, J = 12 Hz, 0.5H), 4.60-4.57 (d, J = 12 Hz, 0.5H), 4.44 (s, 2H), 4.35-4.33 (m, 0.5H), 4.21-4.00 (m, 2H), 3.31 (m, 4H), 2.67-2.64 (m, 1H), 2.63-2.60 (m, 4H), 2.27 (s, 3H), 2.03-2.01 (m, 1H), 1.77-1.75 (m, 1H), 1.66-1.62 (m, 1H), 1.52-1.46 (m, 1H). MS (ESI)495.3 [M + H]+ |
| G-19 | ¹H NMR (400 MHz, T = 80° C., DMSO-d6): δ 8.78 (s, 1H), 7.75 (s, 1H), 7.40 (s, 1H), 6.55-6.60 (m, 1H), 6.42-6.54 (m, 2H), 6.01 (d, J = 16 Hz, 0.4H), 5.53 (d, J = 10.4 Hz, 1H), 4.32 (s, 2H), 3.90-4.18 (m, 3H), 3.70 (s, 3H), 3.07-3.19 (m, 2H), 1.97-2.09 (m, 1H), 1.60-1.86 (m, 2H), 1.38-1.54 (m, 1H). |
| G-20 | ¹H NMR (400 MHz, DMSO-d₆) δ 9.03 (d, J = 21.6 Hz, 1H), 8.30-7.98 (m, 2H), 7.50 (s, 1H), 7.06 (s, 1H), 6.91-6.85 (m, 1H), 6.78 (s, 0.5H), 6.59 (s, 0.5H), 6.19 (d, J = 16.5 Hz, 1H), 6.03 (d, J = 16.3 Hz, 1H), 5.76 (m 0.5H), 5.51 (s, 1H), 5.45 (s, 0.5H), 4.61 (s, 1H), 4.37 (s, 2H), 4.19 (m, |

| Compound | ¹H NMR or MS |
|---|---|
| | 0.5H), 4.02 (m, 2H), 3.73 (s, 2H), 3.56 (d, J = 6.3 Hz, 2H), 3.24-3.12 (m, 1H), 3.04 (m, 1H), 2.82 (m, 1H), 2.66 (m, 1H), 2.02 (m, 1H), 1.80 (m, 1H), 1.68 (m, 1H), 1.45 (m, 1H). MS: 482.2 [M + H]⁺ |
| G-21 | ¹H NMR (400 MHz, DMSO-d₆) δ 9.06 (d, J = 24.2 Hz, 1H), 8.26-8.01 (m, 1.5H), 7.89 (d, J = 9.1 Hz, 0.5H), 7.20 (d, J = 6.3 Hz, 0.5H), 7.08 (m, 1H), 6.95-6.88 (m, 0.5H), 6.64-6.51 (m, 0.5H), 6.19 (d, J = 17.5 Hz, 0.5H), 6.01 (d, J = 16.4 Hz, 0.5H), 5.73 (d, J = 12.3 Hz, 0.5H), 5.40 (d, J = 10.7 Hz, 0.5H), 4.75-4.63 (m, 2H), 4.37 (s, 2H), 4.25-3.88 (m, 3H), 4.09-3.76 (m, 2H), 3.28-3.21 (m, 2H), 3.08-3.01 (m, 2H), 2.75-2.58 (m, 2H), 2.46-2.41 (m, 1H), 2.07-1.93 (m, 2H), 1.93-1.48 (m, 6H), 0.92 (d, J = 3.8 Hz, 6H). MS: 524.2 [M + H]⁺ |
| G-22 | ¹H NMR (400 MHz, DMSO-d₆) δ 9.12 (m, 1H), 8.30-8.03 (m, 2H), 7.90 (s, 1H), 7.24 (s, 1H), 7.09 (s, 1H), 6.95-6.84 (m, 0.5H), 6.67-6.53 (m, 0.5H), 6.17 (d, J = 16.7 Hz, 0.5H), 6.02 (d, J = 13.5 Hz, 0.5H), 5.74 (d, J = 10.6 Hz, 0.5H), 5.48-5.35 (m, 0.5H), 4.63 (s, 0.5H), 4.57 (td, J = 6.4, 2.9 Hz, 2H), 4.48 (t, J = 6.0 Hz, 1H), 4.42 (t, J = 6.0 Hz, 1H), 4.38 (s, 2H), 4.23 (s, 0.5H), 4.13-3.88 (m, 2H), 3.71 (s, 1H), 3.43-3.38 (m, 1H), 3.19-2.89 (m, 3H), 2.81 (s, 0.5H), 2.63 (m, 1.5H), 2.42-2.24 (m, 2H), 2.16 (t, J = 8.5 Hz, 1H), 2.04 (s, 1H), 1.82 (d, J = 12.8 Hz, 1H), 1.70 (m, 1H), 1.50 (d, J = 12.7 Hz, 1H), 1.08-0.80 (m, 3H). MS:551.3 [M + H]⁺ |
| G-23 | ¹H NMR (400 MHz, DMSO-d₆): δ 9.85 (s, 1H), 8.29 (s, 1H), 7.28-7.26 (d, J = 4 Hz, 1H), 6.94 (s, 1H), 6.90-6.86 (m, 0.5H), 6.68-6.66 (m, 0.5H), 6.12-5.98 (m, 1H), 5.72-5.69 (d, J = 6 Hz, 0.5H), 5.53-5.51 (d, J = 4 Hz, 0.5H), 4.42 (s, 2H), 4.27-4.23 (m, 2H), 4.05-4.02 (m, 1H), 3.28-3.22 (m, 0.5H), 3.13-3.08 (m, 0.5H), 2.95-2.90 (m, 0.5H), 2.86-2.79 (m, 0.5H), 2.26 (s, 3H), 2.21-2.18 (m, 1H), 1.83-1.80 (m, 1H), 1.51-1.27 (m, 2H). MS (ESI)417.2 [M + H]⁺ |
| G-24 | ¹H NMR (400 MHz, DMSO-d₆): δ 8.92 (s, 1H), 8.23 (s, 1H), 7.70-7.66 (m, 2H), 7.28-7.26 (m, 2H), 7.12-7.10 (m, 1H), 6.88-6.84 (m, 0.5H), 6.51-6.47 (m, 0.5H), 5.70-5.68 (d, J = 6 Hz, 0.5H), 5.38-5.36 (d, J = 6 Hz, 0.5H), 4.58-4.56 (d, J = 6 Hz, 0.5H), 4.41 (s, 2H), 4.23-4.21 (d, J = 6 Hz, 0.5H), 4.05-3.98 (m, 2H), 3.57-3.55 (m, 4H), 3.50-3.44 (m, 4H), 3.02-3.00 (m, 1H), 2.70-2.64 (m, 1H), 2.03-1.99 (m, 1H), 1.78-1.76 (m, 1H), 1.70-1.65 (m, 1H), 1.45-1.41 (m, 1H). MS (ESI)509.3 [M + H]⁺ |
| G-25 | ¹H NMR (400 MHz, DMSO-d6) δ 8.30 (s, 1H), 7.86 (s, 1H), 7.70 (s, 1H), 7.48 (s, 1H), 6.64 (s, 1H), 6.46 (s, 1H), 6.04 (d, J = 17.4 Hz, 1H), 5.57 (s, 1H), 4.33 (s, 2H), 4.08-3.97 (m, 2H), 3.74 (s, 3H), 3.05-2.96 (m, 2H), 2.09-2.01 (m, 1H), 1.88-1.65 (m, 2H), 1.58-1.44 (m, 1H). M⁺ = 400.1[M + 1]⁺ |
| G-27 | ¹H NMR (400 MHz, DMSO-d₆) δ 8.58 (d, J = 3.8 Hz, 1H), 8.14 (d, J = 13.5 Hz, 1H), 7.61-7.44 (m, 2H), 6.99 (t, J = 9.1 Hz, 1H), 6.91-6.84 (m, 2.5H), 6.84-6.76 (m, 0.5H), 6.69 (dd, J = 16.6, 10.4 Hz, 1H), 6.28-617 (m, 1H), 6.16-6.04 (m, 1H), 5.74 (dd, J = 10.3, 2.5 Hz, 0.5H), 5.44 (dd, J = 10.3, 2.6 Hz, 0.5H), 4.39-4.32 (m, 3H), 3.89-2.81 (m, 1H), 3.77-3.69 (m, 4H), 3.63 (s, 1H), 3.56-3.44 (m, 1H), 3.18 (dd, J = 13.9, 7.4 Hz, 1H), 3.05-2.95 (m, 4H), 1.80-1.91 (m, 0.5), 1.79 (d, J = 11.3 Hz, 3H), 1.65-1.46 (m, 1.5H), 1.37 (s, 1H). MS: 495.3 [M + H]⁺ |
| G-28 | ¹H NMR (400 MHz, DMSO-d₆) δ 8.56 (d, J = 18.1 Hz, 1H), 8.14 (s, 1H), 7.50 (d, J = 7.5 Hz, 2H), 7.01 (d, J = 7.0 Hz, 1H), 6.93-6.73 (m, 1.5H), 6.54 (s, 0.5H), 6.23-5.93-5.87 (m, 1H), 5.73 (s, 0.5H), 5.43 (s, 0.5H), 4.80 (s, 0.5H), 4.58 (s, 0.5H), 4.36 (s, 2H), 3.85-3.80 (m, 4H), 3.28-3.22 (m, 2H), 2.98 (s, 3H), 2.67 (s, 1H), 2.59-2.50 (m, 4H), 1.75 (d, J = 61.6 Hz, 3H), 1.17 (d, J = 28.0 Hz, 2H). MS: 495.3 [M + H]⁺. |
| G-31 | ¹H NMR (400 MHz, DMSO-d₆) δ 8.65 (d, J = 2.6 Hz, 1H), 8.28-8.16 (m, 2H), 7.08-6.99 (m, 1H), 6.87 (d, J = 14.3 Hz, 1.5H), 6.58 (d, J = 9.1 Hz, 1.5H), 6.18-5.98 (m, 1H), 5.72 (d, J = 10.4 Hz, 0.5H), 5.42 (d, J = 10.6 Hz, 0.5H), 4.55 (d, J = 12.4 Hz, 0.5H), 4.37 (s, 2H), 4.17 (d, J = 12.6 Hz, 0.5H), 3.99 (s, 1H), 3.89 (s, 1H), 3.71 (t, J = 4.6 Hz, 4H), 3.03-2.98 (m, 5H), 2.66-2.85 (m, 1H), 2.00 (s, 1H), 1.79 (d, J = 13.5 Hz, 1H), 1.65 (d, J = 12.5 Hz, 1H), 1.43 (s, 1H). MS: 499.3 [M + H]⁺ |
| G-32 | ¹H NMR (400 MHz, DMSO-d₆) δ 8.53 (d, J = 18.5 Hz, 1H), 8.09 (s, 1H), 7.47 (s, 2H), 6.95 (s, 1H), 6.91-6.80 (m, 0.5H), 6.75 (d, J = 8.8 Hz, 2H), 6.57-6.50 (m, 0.5H), 6.13 (d, J = 17.5 Hz, 0.5H), 5.97 (d, J = 16.4 Hz, 0.5H), 5.69 (d, J = 11.3 Hz, 0.5H), 5.39 (d, J = 10.3 Hz, 0.5H), 4.52 (d, J = 13.3 Hz, 0.5H), 4.32 (s, 2H), 4.17 (d, J = 13.3 Hz, 0.5H), 4.04-3.84 (m, 2H), 3.83-3.67 (m, 2H), 3.57-3.52 (m, 3H), 3.07-2.86 (m, 3H), 2.76-2.61 (m, 1H), 1.99-1.94 (m, 1H), 1.80-1.75 (m, 1H), 1.66-1.60 (m, 1H), 1.45-1.35 (m, 1H), 0.87 (d, J = 6.0 Hz, 3H). MS: 495.3 [M + H]⁺ |
| G-33 | ¹H NMR (400 MHz, DMSO-d6) δ 8.73 (d, J = 7.1 Hz, 1H), 8.21 (s, 1H), 7.75 (dd, J = 29.9, 14.8 Hz, 1H), 7.25-7.10 (m, 2H), 6.91-6.82 (m, 1.5H), 6.53 (dd, J = 16.3, 10.4 Hz, 0.5H), 6.12 (d, J = 16.1 Hz, 0.5H), 5.96 (d, J = 16.1 Hz, 0.5H), 5.70 (d, J = 9.1 Hz, 0.5H), 5.38 (d, J = 9.3 Hz, 0.5H), 4.55-4.47 (m, 0.5H), 4.37 (s, 2H), 4.3-4.22 (m, 0.5H), 4.18-4.02 (m, 1H), 3.97-3.85 (m, 1H), 3.72 (t, J = 4.4 Hz, 4H), 3.12-3.00 (m, 1H), 2.90 (d, J = 2.8 Hz, 4H), 2.79-2.69 (m 1H), 2.08 (d, J = 10.9 Hz, 1H), 1.82 (d, J = 13.2 Hz, 1H), 1.69-1.52 (m, 1H), 1.51-1.39 (m, 1H). M⁺ = 499.3[M + 1]⁺. |
| G-34 | ¹H NMR (400 MHz, DMSO-d6) δ 8.57-8.51 (m, 1H), 8.13-8.11 (m, 1H), 7.48 (d, J = 8.9 Hz, 2H), 6.98 (d, J = 8.4 Hz, 1H), 6.88 (dd, J = 16.6, 10.6 Hz, 0.5H), 6.79 (d, J = 8.7 Hz, 2H), 6.58-6.51 (m, 0.5H), 6.17 (d, J = 16.7 Hz, 0.5H), 5.99 (d, J = 16.8 Hz, 0.5H), 5.73 (d, J = 11.9 Hz, 0.5H), 5.41 (d, J = 10.4 Hz, 0.5H), 4.56 (td, J = 6.5, 2.8 Hz, 2H), 4.48 (t, J = 6.0 Hz, 1H), 4.42 (t, J = 6.0 Hz, 1H), 4.35 (s, 2H), 4.20 (d, J = 11.8 Hz, 0.5H), 4.08-3.89 (m, 2.5H), 3.71 (d, J = 6.2 Hz, 1H), 3.40 (dd, J = 12.6, 6.2 Hz, 1H), 3.12-2.98 (m, 2H), 2.92 (t, J = 9.2 Hz, 1H), 2.83-2 .61 (m, 2H), 2.37 (s, 1H), 2.29 (t, J = 11.9 Hz, 1H), 2.12 (d, J = 8.4 Hz, 1H), 2.00 (s, 1H), 1.80 (d, J = 13.3 Hz, 1H), 1.74-1.59 (m, 1H), 1.42 (dd, J = 24.6, 11.8 Hz, 1H), 0.95 (d, J = 6.2 Hz, 3H). M⁺ = 550.3[M + 1]⁺. |
| G-35 | ¹H NMR (400 MHz, DMSO-d₆) δ 8.87 (s, 1H), 8.19 (s, 1H), 7.79 (d, J = 21.2 Hz, 1H), 7.05 (d, J = 7.1 Hz, 1H), 6.85-6.78 (m, 1H), 6.51-6.47 (m. 0.5H), 6.02 (dd, J = 50.3, 16.4 Hz, 1H), 5.65 (d, J = 9.4 Hz, 0.5H), 5.41 (d, J = 9.4 Hz, 0.5H), 4.45-4.36 (m, 2.5H), 4.17-4.14 (m, 0.5H), 4.02-3.89 (m, 5H), 3.17-2.96 (m, 1H), 2.81-2.73 (m, 1H), 2.01 (d, J = 10.1 Hz, 1H), 1.80-1.77 (m, 1H), 1.67-1.59 (m, 1H), 1.46-1.37 (m, 1H). MS: 401.2 [M + H]⁺ |

| Compound | ¹H NMR or MS |
|---|---|
| G-36 | ¹H NMR (400 MHz, DMSO-d₆) δ 8.87 (d, J = 22.7 Hz, 1H), 8.19 (s, 1H), 8.06 (s, 0.5H), 7.85 (s, 0.5H), 7.14-6.97 (m, 1H), 6.86 (dd, J = 16.7, 10.5 Hz, 0.5H), 6.45 (dd, J = 16.8, 10.4 Hz, 0.5H), 6.14 (dd, J = 16.7, 2.1 Hz, 0.5H), 5.99 (d, J = 16.6 Hz, 0.5H), 5.70 (dd, J = 10.5, 2.1 Hz, 0.5H), 5.32 (d, J = 10.8 Hz, 0.5H), 4.76 (d, J = 8.3 Hz, 1H), 4.36 (s, 2H), 4.22-3.97 (m, 2H), 3.93-3.88 (m, 3H), 3.09-2.90 (m, 1H), 2.84-2.69 (m, 0.5H), 2.47-2.41 (m, 0.5H), 2.02-1.93 (m, 1H), 1.79-1.68 (m, 2H), 1.56-1.49 (m, 1H). MS: 401.2 [M + H]⁺ |
| G-37 | ¹H NMR (400 MHz, DMSO-d₆) δ 8.78 (s, 1H), 8.17 (s, 1H), 7.27-6.75 (m, 5H), 6.59-6.34 (m, 1H), 6.08 (d, J = 16.9 Hz, 0.5H), 5.90 (d, J = 16.7 Hz, 0.5H), 5.66 (d, J = 10.6 Hz, 0.5H), 5.30 (d, J = 10.3 Hz, 0.5H), 4.49-4.15 (m, 3H), 4.02-3.93 (m, 2H), 3.72-3.54 (m, 4H), 3.41 (s, 1H), 3.01 (s, 4H), 2.76-2.66 (m, 1H), 2.04-1.97 (m, 1H), 1.79 (d, J = 13.6 Hz, 1H), 1.70-1.56 (m, 1H), 1.43-1.32 (m, 1H). MS: 481.2 [M + H]⁺ |
| G-38 | ¹H NMR (400 MHz, DMSO-d₆) δ 8.32 (d, J = 7.7 Hz, 1H), 8.04 (s, 1H), 7.86 (s, 0.5H), 7.75 (s, 0.5H), 7.47 (d, J = 32.0 Hz, 1H), 6.98-6.87 (m, 1H), 6.86-6.79 (m, 0.5H), 6.51-6.46 (m, 0.5H), 6.11 (dd, J = 16.8, 1.8 Hz, 0.5H), 5.97 (d, J = 16.1 Hz, 0.5H), 5.71-5.62 (m, 0.5H), 5.38 (d, J = 10.5 Hz, 0.5H), 4.62 (d, J = 9.5 Hz, 0.5H), 4.31 (s, 2H), 4.20 (d, J = 12.4 Hz, 0.5H), 4.07-3.87 (m, 2H), 3.66 (d, J = 5.4 Hz, 3H), 3.00 (m, 1H), 2.73 (t, J = 11.2 Hz, 0.5H), 2.61-2.52 (m, 0.5H), 1.98 (s, 1H), 1.78 (m, 1H), 1.65 (m, 1H), 1.46 (d, J = 12.3 Hz, 1H). MS: 400.1 [M + H]⁺ |
| G-39 | ¹H NMR (400 MHz, DMSO-d₆) δ 8.71 (s, 1H), 8.18 (s, 1H), 8.12 (s, 0.5H), 8.02 (s, 0.5H), 7.33 (d, J = 7.3 Hz, 0.5H), 7.23 (d, J = 7.2 Hz, 0.5H), 7.03 (M , 2H), 6.82 (m, 0.5H), 6.45 (m, 0.5H), 6.08 (d, J = 16.9 Hz, 0.5H), 5.90 (d, J = 16.4 Hz, 0.5H), 5.66 (d, J = 10.6 Hz, 0.5H), 5.31 (d, J = 10.8 Hz, 0.5H), 4.46 (d, J = 11.0 Hz, 0.5H), 4.34 (s, 2H), 4.23 (d, J = 13.0 Hz, 0.5H), 3.99 (m, 2H), 3.68 (m, 4H), 3.02 (m, 1H), 2.83 (m, 4H), 2.77-2.62 (m, 1H), 2.11-2.01 (m, 1H), 1.77-1.69 (m, , 1H), 1.66-1.41 (m, 2H). MS: 515.3 [M + H]⁺ |
| G-40 | ¹H NMR (400 MHz, DMSO-d₆) δ 8.54 (s, 1H), 8.04 (s, 1H), 7.55-7.53 (d, J = 8 Hz, 2H), 6.95-6.86 (m, 2H), 4.30 (s, 2H), 3.85-3.80 (m, 1H), 3.71-3.69 (m, 4H), 3.00-2.98 (m, 4H), 2.33-2.30 (m, 1H), 2.21-2.20 (m, 1H), 1.80-1.77 (m, 3H), 1.40-1.20 (m, 4H), MS (ESI)469.3 [M + H]⁺ |
| G-41 | ¹H NMR (400 MHz, DMSO-d₆) δ 8.70 (d, J = 8.1 Hz, 1H), 8.17 (s, 1H), 7.83-7.65 (m , 1H), 7.31-7.05 (m, 2H), 6.79-6.65 (m, 1H), 6.61-6.50 (m, 1H), 6.12-5.97 (dd, 1H), 4.79-4.46 (m, 1H), 4.41 (d, J = 10.4 Hz, 2H), 3.72-3.71 (m, 2H), 3.70 (s, 4H), 3.06-2.89 (m, 0.5H), 2.88 (m, 4H), 2.75-2.62 (m, 0.5H), 1.86-1.67 (m, 4H), 1.22-1.13 (m, 3H). MS: 513 [M + H]⁺ |
| G-42 | ¹H NMR (400 MHz, DMSO-d₆): δ 8.77-8.74 (d, J = 12 Hz, 1H), 8.18 (s, 1H), 7.78-7.66 (m, 1H), 7.12-7.00 (m, 3H), 6.85-6.79 (m, 0.5H), 6.55-6.49 (m, 0.5H), 6.11-6.07 (d, J = 16 Hz, 0.5H), 5.95-5.91 (d, J = 16 Hz, 0.5H), 5.68-5.66 (d, J = 12 Hz, 0.5H), 5.37-5.34 (d, J = 12 Hz, 0.5H), 4.48-4.45 (d, J = 12 Hz, 0.5H), 4.35 (s, 2H), 4.28-4.22 (d, J = 12 Hz, 0.5H), 4.00-3.89 (m, 2H), 3.62-3.54 (m, 3H), 3.07-2.91 (m, 4H), 2.66-2.64 (m, 2H), 2.08-2.04 (m, 1H), 1.79-1.77 (m, 1H), 1.63-1.59 (m, 1H), 1.45-1.42 (m, 1H). MS (ESI)513.2 [M + H]⁺ |
| G-43 | ¹H NMR (400 MHz, DMSO-d₆): δ 8.94 (s, 1H), 8.80 (s, 0.5H), 8.49 (s, 1H), 8.28 (s, 2H), 7.03-7.01 (m, 1H), 6.85-6.82 (m, 1H), 6.66-6.63 (m, 1H), 6.18-6.08 (m, 2H), 5.72 (d, J = 8 Hz, 1H), 5.54-5.51 (d, J = 6 Hz, 1H), 4.90-4.87 (d, J = 6 Hz, 1H), 4.36 (s, 2H), 4.21-4.19 (m, 2H), 3.91-3.88 (m, 1H), 3.753.70 (m, 1H), 3.23 (s, 3H), 3.06-3.02 (m, 2H), 2.82-2.78 (m, 1H), 2.03-2.00 (m, 1H), 1.52-1.48 (m, 3H), 1.30-1.25 (m, 1H). MS (ESI)429.2 [M + H]⁺ |
| G-44 | ¹H NMR (400 MHz, T = 80° C., DMSO-d6): δ 8.73 (s, 1H), 8.31 (s, 1H), 7.88 (s, 1H), 6.59-6.75 (m, 2H), 6.06 (d, J = 16.4 Hz, 1H), 5.57 (d, J = 10.4 Hz, 1H), 4.49-4.65 (m, 2H), 4.33 (s, 2H), 3.90-4.06 (m, 2H), 3.85 (s, 3H), 1.60-1.95 (m, 4H), 1.21 (d, J = 6.4 Hz, 3H). |
| G-45 | ¹H NMR (400 MHz, DMSO-d₆) δ 8.90 (s, 0.5H), 8.83 (s, 0.5H), 8.50 (s, 0.5H), 8.30 (d, J = 10.8 Hz, 1H), 8.22 (s, 0.5H), 7.03 (m, 1H), 6.87 (m, 0.5H), 6.66 (m, 0.5H), 6.25-6.07 (m, 1H), 5.76-5.68 (m, 0.5H), 5.53 (d, J = 10.7 Hz, 0.5H), 4.93 (d, J = 9.6 Hz, 1H), 4.36 (s, 2H), 4.23 (d, J = 12.7 Hz 0.5H), 4.13 (d, J = 12.9 Hz, 0.5H), 4.04 (d, J = 12.9 Hz, 0.5H), 3.87 (d, J = 5.9 Hz, 0.5H), 3.81-3.71 (m, 1H), 3.04 (m, 1H), 2.79 (t, J = 11.3 Hz, 0.5H), 2.44 (m, 0.5H), 1.99 (s, 1H), 1.76 (m, 2H), 1.50 (d, J = 12.4 Hz, 1H), 1.12-0.92 (m, 4H). MS: 411.2 [M + H]+ |
| G-46 | ¹H NMR (400 MHz, DMSO-d₆) δ 8.92 (s, 0.5H), 8.82 (s, 0.5H), 8.55 (s, 0.5H), 8.27-8.24 (m, 1.5H), 7.02-6.99 (m, 1H), 6.84 (dd, J = 16.5, 10.3 Hz, 0.5H), 6.62 (dd, J = 16.9, 10.3 Hz, 0.5H), 6.19 (d, J = 16.6 Hz, 0.5H), 6.06 (d, J = 16.7 Hz, 0.5H), 5.69 (d, J = 12.4 Hz, 0.5H), 5.46 (d, J = 11.2 Hz, 0.5H), 4.95 (d, J = 10.6 Hz, 0.5H), 4.46-4.28 (m, 2.5H), 4.24-3.97 (m, 2H), 3.93 (d, J = 11.9 Hz, 2H), 3.86-3.78 (m, 1H), 3.44 (td, J = 11.5, 3.4 Hz, 2H), 3.05-2.96 (m, 1H), 2.83-2.70 (m, 0.5H), 2.42-2.32 (m, 0.5H), 2.03-1.90 (m, 5H), 1.79-1.67 (m, 2H), 1.51-1.45 (m, 2H). MS: 455.3 [M + H]⁺ |
| G-47 | ¹H NMR (400 MHz, DMSO-d₆) δ 8.87 (s, 0.5H), 8.74 (s, 0.5H), 8.37-8.22 (m, 1H), 7.25-7.02 (m, 2H), 6.92-6.77 (m, 1H), 6.23-6.11 (m, 1H), 5.72 (dd, J = 10.3, 2.4 Hz, 0.5H), 5.41 (dd, J = 10.3, 2.5 Hz, 0.5H), 4.35 (d, J = 5.3 Hz, 2H), 4.10 (dd, J = 13.4, 5.7 Hz, 1H), 3.96-3.80 (m, 3H), 3.75-3.63 (m, 1H), 3.59-3.43 (m, 2H), 3.19-3.07 (m, 1H), 2.01-1.54 (m, 3H), 1.36-1.34 (m, 1H), 1.28-0.79 (m, 2H). MS: 399.3 [M + H]⁺ |
| G-48 | ¹H NMR (400 MHz, DMSO-d₆): δ 8.47 (s, 0.5H), 9.31 (s, 0.5H), 8.75 (s, 0.5H), 8.55 (s, 0.5H), 8.44 (s, 1H), 8.07-7.74 (m, 1H), 7.17 (m, 1H), 6.87-6.83 (m, 0.5H), 6.25-6.20 (m, 0.5H), 6.20-6.08 (m, 1H), 5.73-5.70 (m, 0.5H), 5.50-5.48 (m, 0.5H), 4.91-4.88 (m, 0.5H), 4.41 (s, 2H), 4.23-4.02 (m, 2H), 3.91 (s, 1H), 3.03-3.01 (m, 0.5H), 2.60-2.56 (m, 0.5H), 2.03-2.00 (m, 1H), 1.55-1.50 (m, 2H), 1.53-1.50 (m, 1H). MS (ESI)421.1 [M + H]⁺ |
| G-49 | ¹H NMR (400 MHz, DMSO-d₆): δ 68.93 (s, 0.5H), 8.79 (s, 0.5H), 8.50 (s, 0.5H), 8.29-8.27 (m, 1.5H), 7.04-7.00 (m, 1H), 6.90-6.84 (m, 0.5H), 6.68-6.63 (m, 0.5H), 5.72-5.69 (m, 0.5H), 5.53-5.51 (m, 0.5H), 4.92-4.89 (d, J = 6 Hz, 0.5H), 4.36 (s, 2H), 4.15-4.02 (m, 4H), 3-90-3.86 (m, 0.5H), 3.08-3.05 (m, 1H), 2.79-2.77 (m, 1H), 2.03-2.00 (m, 1H), 1.79-1.70 (m, 2H), 1.42-1.24 (m, 4H). MS (ESI)399.2 [M + H]⁺ |
| G-50 | ¹H NMR (400 MHz, DMSO-d₆) δ 9.58 (d, J = 20.2 Hz, 1H), 9.11 (s, 1H), 8.69-8.63 (m, 2H), 8.44 (d, J = 9.5 Hz, 1H), 8.12 (d, J = 6.1 Hz, 1.5H), 7.84 (d, J = 5.6 Hz, 0.5H), 7.21-7.16 (m, 1H), 6.96 (dd, J = 16.7, 10.5 Hz, 0.5H), 6.67 (dd, J = 16.6, 10.4 Hz, 0.5H), 6.32 (dd, J = 16.6, 2.1 |

-continued

| Compound | $^1$H NMR or MS |
|---|---|
| | Hz, 0.5H), 6.05 (d, J = 16.8 Hz, 0.5H), 5.84 (dd, J = 10.4, 2.1 Hz, 0.5H), 5.20 (d, J = 16.8 Hz, 0.5H), 4.42 (s, 2H), 4.29-4.02 (m, 1H), 3.92-3.84 (m, 1H), 3.06 (t, J = 12.4 Hz, 1.5H), 2.90-2.73 (m, 0.5H), 2.43-2.27 (m, 1H), 2.02 (d, J = 11.3 Hz, 1H), 1.89-1.68 (m, 2H), 1.64-1.44 (m, 1H). MS: 448.2 [M + H]$^+$ |
| G-51 | $^1$H NMR (400 MHz, T = 80° C., DMSO-d6): δ 8.75 (s, 1H), 8.36 (s, 1H), 7.87 (s, 1H), 6.69 (dd, J$_1$ = 10.4 Hz, J2 = 16.8 Hz, 1H), 6.57 (brs, 1H), 6.09 (dd, J$_1$ = 2.0 Hz, J$_2$ = 16.8 Hz, 1H), 5.59 (dd, J$_1$ = 2.0 Hz, J2 = 10.4 Hz, 1H), 5.01-5.27 (m, 1H), 4.33 (s, 2H), 3.99-4.16 (m, 2H), 3.85 (s, 3H), 1.84-1.99 (m, 1H), 1.70-1.82 (m, 2H), 1.44-1.60 (m, 1H), 1.07 (d, J = 7.2 Hz, 3H). |
| G-52 | $^1$H NMR (400 MHz, DMSO-d$_6$) δ 8.91 (s, 0.5H), 8.80 (s, 0.5H), 8.52 (s, 0.5H), 8.25-8.23 (m, 1.5H), 7.00-6.97 (m, 1H), 6.84 (dd, J = 16.6, 10.5 Hz, 0.5H), 6.62 (dd, J = 16.7, 10.3 Hz, 0.5H), 6.22 (d, J = 16.5 Hz, 0.5H), 6.06 (d, J = 16.1 Hz, 0.5H), 5.69 (d, J = 12.3 Hz, 0.5H), 5.47 (d, J = 9.2 Hz, 0.5H), 4.92 (d, J = 11.7 Hz, 1H), 4.33 (s, 2H), 4.24-3.96 (m, 3H), 3.88-3.79 (m, 1H), 3.09-2.94 (m, 1H), 2.81-2.78 (m, 2H), 2.17 (s, 3H), 2.08-1.89 (m, 7H), 1.79-1.67 (m, 2H), 1.51-1.42 (m, 1H). MS: 468.2 [M + H]$^+$ |
| G-53 | $^1$H NMR (400 MHz, DMSO-d$_6$): δ 9.22 (s, 1H), 8.44 (s, 1H), 7.25-7.22 (m, 1H), 6.85-6.83 (m, 0.5H), 6.65-6.63 (m, 0.5H), 6.10-6.05 (m, 1H), 5.66-5.64 (m, 0.5H), 5.55-5.52 (m, 0.5H), 4.37 (s, 2H), 4.08-4.07 (m, 0.5H), 4.06-4.04 (m, 0.5H), 3.95-3.88 (m, 1H), 3.09-3.06 (m, 1H), 2.82-2.78 (m, 1H), 2.58 (s, 3H), 2.01-1.98 (m, 1H), 1.77-1.72 (m, 2H), 1.43 (m, 1H). MS (ESI)402.1 [M + H]$^+$ |
| G-54 | $^1$H NMR (400 MHz, DMSO-d$_6$) δ 8.87 (s, 0.5H), 8.72 (s, 0.5H), 8.43 (s, 0.5H), 8.26 (s, 0.5H), 8.23 (s, 1H), 7.03-6.93 (m, 1H), 6.83 (m, 0.5H), 6.63 (m, 0.5H), 6.11 (m, 0.5H), 5.67 (d, J = 11.6 Hz, 0.5H), 5.50 (d, J = 10.5 Hz, 0.5H), 4.83 (d, J = 10.4 Hz, 1H), 4.33 (s, 2H), 4.25 (m, 1H), 4.20 (d, J = 12.7 Hz, 1H), 4.10 (m, 1H), 3.84 (s, 3H), 3.26 (s, 1H), 3.02 (t, J = 11.2 Hz, 1H), 2.76 (t, J = 12.1 Hz, 0.5H), 2.53 (s, 0.5H), 1.97 (s, 1H), 1.72 (m, 2H), 1.47 (m, 1H). MS: 385.3 [M + H]$^+$ |
| G-55 | $^1$H NMR (400 MHz, DMSO-d$_6$) δ 8.64-8.60 (m, 1H), 8.31-8.26 (m, 1H), 8.13 (s, 1H), 7.85-7.82 (m, 1H), 7.63-7.61 (m, 1H), 7.46-7.39 (m, 1H), 7.23-7.14 (m, 1H), 6.80-6.74 (m, 1H), 6.13-5.91 (m, 1H), 5.69-5.22 (m, 1H), 4.48-4.19 (m, 3.5H), 4.00-3.79 (m, 1.5 H), 3.06-2.60 (m, 2H), 1.97 (d, J = 9.4 Hz, 1H), 1.76-1.60 (m, 2H), 1.49-1.31 (m, 1H). |
| G-56 | $^1$H NMR (400 MHz, DMSO-d$_6$): δ 8.79-8.77 (d, J = 8 Hz, 1H), 8.27-8.25 (m, 2H), 6.42-6.40 (m, 1H), 4.35 (s, 2H), 4.12-4.10 (m, 1H), 3.17-3.16 (d, J = 4 Hz, 1H), 1.69-1.57 (m, 6H), 1.57-1.40 (m, 2H). |
| G-57 | $^1$H NMR (400 MHz, DMSO-d$_6$) δ 8.91 (s, 1H), 8.52 (s, 1H), 8.25 (d, J = 10.2 Hz, 1H), 6.97 (d, J = 8.1 Hz, 1H), 6.83 (dd, J = 16.6, 10.4 Hz, 1H), 6.11 (dd, J = 31.6, 16.6 Hz, 1H), 5.68 (d, J = 10.3 Hz, 1H), 4.91 (d, J = 11.8 Hz, 1H), 4.41 (s, 1H), 4.33 (s, 2H), 4.19 (d, J = 13.2 Hz, 1H), 4.04 (dd, J = 28.6, 13.5 Hz, 1H), 3.01 (q, J = 13.1, 11.9 Hz, 1H), 2.40 (d, J = 11.0 Hz, 1H), 2.14-1.93 (m, 8H), 1.82-1.62 (m, 2H), 1.47 (d, J = 12.5 Hz, 1H). MS: 489.3 [M + H]$^+$ |
| G-69 | $^1$H NMR (400 MHz, DMSO-d$_6$) δ 8.71 (s, 1H), 8.23 (s, 1H), 8.01 (s, 1H), 6.72 (dd, J = 16.7, 10.5 Hz, 1H), 6.07 (d, J = 16.5 Hz, 1H), 5.57 (d, J = 10.4 Hz, 1H), 4.41-4.15 (m, 4H), 4.15-4.03 (m, 1H), 3.85 (s, 3H), 3.40-3.13 (m, 3H), 3.00 (s, 1H), 2.05-1.93 (m, 1H), 1.84 (d, J = 11.3 Hz, 2H), 1.73-1.60 (m, 1H), 0.98 (s, 1H), 0.49 (d, J = 8.0 Hz, 2H), 0.29 (s, 2H). MS: 439.1 [M + H]$^+$. |

Bioassay

Test Example 1: Lantha Screening Kinase Reaction Experimental Method

The compound was predissolved in 100% DMSO. 10 mM drug stock solution was obtained by dissolution at room temperature and then serially diluted with 8 vol % DMSO solution to a final concentration of 10-0.005 μM. 2.5 μl of a solution of substance to be tested and 2.5 μl of kinase (Invitrogen PV3363) diluted with the reaction buffer were added into each well of 384-well plate (Corning 3676), and then the mixture of Fluososcei-PolyGT (Invitrogen PV3610) substrate and ATP (Invitrogen PV3227) diluted with 5 μl of the reaction buffer were added to initiate the reaction. Among the wells, the kinase in the blank well was replaced with a reaction buffer and the kinase well (Enzyme) was not added with any drug. After shaking at 25° C. for 60 minutes in the dark, 10 μl of Detection Solution (mixture of Invitrogen PV3528 and EDTA, which was diluted with TR-FRET dilution buffer, the working concentration of EDTA was 5 mM, the working concentration of Lanthascreening Tb PY20 antibody was 0.2 nM) was added and shaken at room temperature for 30 minutes. The plates were read on a VictorX5 fluorescent plate reader (PerkinElmer) and the light absorption at an excitation wavelength of 340 nm and emission wavelengths of 500 nm and 520 nm was measured.

The calculation method for the inhibition ratio (referring to the specification of Invitrogen, PV3363) was as follows:

Emission ratio (ER):Coumarin Emission (520 nm)/Fluorescein Emission (500 nm)     1.

The inhibition ratio (IR):(ER$_{kinase}$−ER$_{test\ compound}$)/(ER$_{kinase}$−ER$_{blank}$)×100%.     2.

The half-inhibitory concentration IC50 was calculated by fitting with XLFIT5.0 software (IDBS, UK). The results were show in table 1:

TABLE 1 the inhibition of compounds against BTK WT

| Compound | BTK WT IC50(nM) | Compound | BTK WT IC50(nM) | Compound | BTK WT IC50(nM) |
|---|---|---|---|---|---|
| G-2 | 3 | G-3 | 2 | G-4 | 7 |
| G-5 | 48 | G-7 | 35 | G-9 | 7 |
| G-10 | 3 | G-11 | 1 | G-12 | 21 |
| G-13 | 3 | G-14 | 3 | G-15 | 3 |
| G-16 | 2 | G-17 | 2 | G-18 | 41 |
| G-21 | 59 | G-22 | 66 | G-23 | 5 |
| G-24 | 5 | G-25 | 2 | G-26 | 27 |
| G-27 | 5 | G-28 | 5 | G-31 | 7 |
| G-32 | 5 | G-33 | 5 | G-34 | 5 |
| G-37 | 18 | G-38 | 2 | G-39 | 2 |
| G-41 | 2 | G-42 | 5 | G-44 | 77 |
| G-45 | 69 | G-47 | 75 | G-51 | 62 |
| G-53 | 51 | G-54 | 15 | G-58 | 80 |
| G-59 | 13 | G-60 | 9 | G-61 | 16 |
| G-63 | 25 | G-64 | 62 | G-65 | 7 |
| G-66 | 15 | G-70 | 5 | G-71 | 5 |
| G-72 | 5 | G-73 | 5 | G-74 | 7 |

TABLE 1-continued the inhibition of compounds against BTK WT

| Compound | BTK WT IC50(nM) | Compound | BTK WT IC50(nM) | Compound | BTK WT IC50(nM) |
|---|---|---|---|---|---|
| G-75 | 6 | G-76 | 0.8 | G-77 | 51 |
| G-84 | 89 | G-85 | 32 | G-86 | 1 |
| G-87 | 1 | G-88 | 17 | G-89 | 5 |
| G-91 | 5 | G-92 | 8 | G-94 | 20 |
| G-95 | 5 | G-97 | 5 | G-99 | 18 |
| G-102 | 5 | G-105 | 8 | G-107 | 5 |
| G-109 | 62 | G-111 | 69 | G-112 | 18 |
| G-113 | 5 | G-114 | 34 | | |

Test Example 2: Experimental Method for Detecting HTRF by Intracellular βBTK Y223 Phosphorylation The compound was predissolved in 100% DMSO. 10 mM drug stock solution was obtained by dissolution at room temperature and then serially diluted with 5 vol % DMSO solution to a final concentration of 3-0.0014 μM. Ramos cells were seeded into 96-well plates at a density of $4\times10^5$/well with 45 μl of 1640 medium containing 10% (V/V) FBS per well, and 5 μl of diluted solution of substance to be tested was added to each well, which was incubated for 1 hour at 37° C., 5% (V/V) $CO_2$. 10 μl of sodium pervanadate dilution (diluted with 1640 without serum) was added, and to the negative control wells was added 10 μl of serum-free medium, which was incubated at 25° C. for 30 minutes on a shaker. 20 μl of lysate (4× lysate: blocked mother liquor is 25:1) was added to each well and incubated for 30 minutes at 25° C. on a shaker. It was shaken on an oscillator at 800 rpm for 1 minute. 16 μl of cell lysate was added to a 384-well plate (Greiner 784075), and 4 μl of pre-mixed antibody solution (Phospho-BTK d2 antibody and Phospho-BTK Cryptate antibody diluted 20-fold with the test solution) was added, which was incubated at 25° C. overnight on a shaker. The plates were read on a VictorX5 fluorescent plate reader (PerkinElmer) and the light absorption at an excitation wavelength of 317 nm and emission wavelengths of 500 nm and 520 nm was measured (referring to the specification of 63ADK017PEH, Cisbio). The half-inhibitory concentration IC50 was calculated by fitting with XLFIT 5.0 software (IDBS, UK). The results were show in table 2:

TABLE 2

Inhibition activity of compounds against βBTK Y223 cell

| Compound | βBTK Y223 IC50(nM) | Compound | βBTK Y223 IC50(nM) | Compound | βBTK Y223 IC50(nM) |
|---|---|---|---|---|---|
| G-2 | 5 | G-3 | 11 | G-4 | 23 |
| G-5 | 59 | G-6 | 29 | G-7 | 11 |
| G-10 | 7 | G-11 | 2 | G-12 | 80 |
| G-13 | 45 | G-14 | 3 | G-15 | 5 |
| G-17 | 16 | G-25 | 2 | G-26 | 47 |
| G-27 | 11 | G-28 | 10 | G-31 | 11 |
| G-35 | 35 | G-37 | 12 | G-39 | 3 |
| G-41 | 3 | G-44 | 107 | G-45 | 109 |
| G-48 | 62 | G-51 | 80 | G-59 | 16 |
| G-60 | 24 | G-63 | 50 | G-71 | 3 |
| G-72 | 4 | G-76 | 2 | G-85 | 43 |
| G-86 | 5 | G-87 | 4 | G-88 | 56 |

It can be seen from tables 1 and 2 that the representative compounds of the present disclosure have high inhibitory activity against enzymes and cells.

Test Example 3: Wild Type EGFR Kinase Inhibition Test

All the following reagents used in z-lyte test are commercially available from Invitrogen.

The inhibitory effects of compounds to be tested on wild-type EGFR kinase (Invitrogen, PV3872) were measured by z-lyte methods.

The working concentration of each component in 10 μl wild-type EGFR kinase reaction system was: 10 μM ATP, 0.8 ng/μl wild-type EGFR kinase (Invitrogen, PV3872), 2 μM Tyr04 substrate (Invitrogen, PV3193). After the compounds to be tested were added, the final concentration of DMSO was 2%. 10 mM drug stock solutions dissolved at room temperature were gradiently diluted with 4% DMSO in water to a final concentrations of 10-0.005 μM. To each well were added 2.5 μl of a solution of the test compounds and 5 μl of a mixture of wild-type EGFR kinase and Tyr04 substrate diluted by a reaction buffer, and then 2.5 μl of ATP was added to initiate the reaction. Reaction buffer instead of ATP were added to C1 wells, no drugs were added to C2 wells, and the phosphorylated substrates were added to C3 wells according to the instruction. After shaking on a shaker at 25° C. for 60 minutes in the dark, 5 μl of Development Reagent B (Invitrogen, diluted with TR-FRET dilution buffer) was added, and reacted on a shaking table at room temperature for 60 min. The plates were read in a VictorX5 fluorescent microplate reader (PerkinElmer) and the light absorbance at an excitation wavelength of 405 nm and emission wavelengths of 450 nm and 520 nm was measured (For example, $C3_{520nm}$ represents the reading of C3 well at 520 nm).

The calculation method for the inhibition ratio (referring to the specification of Invitrogen, PV3363) was as follows:

$$ER = \text{Coumarin Emission(450 nm)/Fluorescein Emission(520 nm)} \quad\quad 1.$$

$$\text{Phosphorylation ratio} = (1 - ((ER \times C3_{520nm} - C3_{450nm})/((C1_{450nm} - C3_{450nm}) + ER \times (C3_{520nm} - C1_{520nm})))) \times 100\% \quad\quad 2.$$

$$\text{Inhibition ratio (IR)} = (1 - \text{phosphorylation ratio of the test compound}/\text{phosphorylation ratio of } C_2)) \times 100\% \quad\quad 3.$$

The half-inhibitory concentration $IC_{50}$ was calculated by fitting with XLFIT 5.0 software (IDBS, UK).

TABLE 3

Inhibition activity of compounds against to EGFR WT

| Compound | EGFR WT IC50(nM) | Compound | EGFR WT IC50(nM) | Compound | EGFR WT IC50(nM) |
|---|---|---|---|---|---|
| G-2 | 1618 | G-3 | 2289 | G-4 | 2374 |
| G-5 | 1908 | G-7 | 3949 | G-9 | 1009 |
| G-10 | 1743 | G-11 | 4250 | G-12 | 3852 |
| G-13 | 1601 | G-14 | 4132 | G-15 | 1216 |
| G-16 | 2746 | G-17 | 1504 | G-18 | 1602 |
| G-21 | 8308 | G-22 | 9011 | G-23 | 1795 |
| G-24 | 1786 | G-25 | 1094 | G-26 | 6694 |
| G-27 | 3690 | G-28 | 2297 | G-31 | 7932 |
| G-32 | 5341 | G-33 | 7171 | G-34 | 3169 |
| G-37 | 3856 | G-38 | 1293 | G-39 | 6309 |
| G-41 | 2276 | G-42 | 5192 | G-44 | >10000 |
| G-45 | 8302 | G-47 | >10000 | G-51 | 6817 |
| G-54 | >10000 | G-53 | 7445 | G-58 | >10000 |
| G-59 | 1016 | G-60 | >10000 | G-61 | 1002 |
| G-63 | >10000 | G-64 | >10000 | G-65 | >10000 |
| G-66 | >10000 | G-70 | >10000 | G-71 | 1588 |
| G-72 | 1663 | G-73 | 1564 | G-74 | 1372 |

TABLE 3-continued

Inhibition activity of compounds against to EGFR WT

| Compound | EGFR WT IC50(nM) | Compound | EGFR WT IC50(nM) | Compound | EGFR WT IC50(nM) |
|---|---|---|---|---|---|
| G-75 | 1631 | G-76 | 1365 | G-77 | >10000 |
| G-84 | >10000 | G-85 | 1124 | G-86 | 1185 |
| G-87 | 1478 | G-88 | 1051 | G-109 | 6817 |
| G-111 | >10000 | G-112 | >10000 | G-113 | 6166 |
| G-114 | 4132 | | | | |

It can be seen from table 3 that the representative compounds of the present disclosure have low inhibitory activity against wild-type EGFR kinase. Therefore, the exemplary compounds of the present disclosure had selective inhibitory activities against BTK WT kinase.

Test Example 4: In Vivo Test in Mice

Test Animals: ICR mice, weight 28-30 g, male, totally 12, purchased from SLAC Laboratory Animal Co., Ltd. Mice were fasting one night before administration and freely fed 4 hours after administration.

Administration and Blood collection: 6 mice were administered intragastrically (PO) in a administered dosage of 30 mg/kg and a administered volume of 10 mL/kg. One administration route was subjected with 6 mice, blood samples of three mice were collected at one time point, and blood samples of another three mice were collected at alternate time point alternately. Blood was collected at 8 time points of 0.083, 0.25, 0.5, 1, 2, 4, 8, 24 h after administration respectively.

Animals were manually controlled at the time of collection and approximately 80 μL of blood was collected from the mice fundus venous plexus into a tube containing K2EDTA. The collected blood sample was put on wet ice, centrifuged within 15 min (8000 rpm, 4 min at 4° C.), and then the plasma sample was taken and stored at minus 20° C. till analysis. The compounds were prepared on the day of the experiment.

Solvent excipient information: DMSO (brand: Sigma, batch number: SHBD2446V); 2-hydroxypropyl-3-cyclodextrin (brand: Sigma, batch number: BCBN8227V), acetic acid (brand: Sinopharm Group, batch number: 20150616), sodium acetate (Brand: GENERAL-REAGENT, batch number: P1246037).

Preparation of a 3 mg/mL PO dosing solution: the solvent was a solution of 5% DMSO and 95% PH4.5 (sodium acetate-acetate) in 20% of 2-hydroxypropyl-β-cyclodextrin. 6.47 mg of compound to be tested was weighed into a clean EP tube and then 0.108 ml DMSO was added, which was vortexed for 2-3 min, and then 2.049 ml of a solution of PH4.5 (sodium acetate-acetate) in 20% of 2-hydroxypropyl-β-cyclodextrin was added, which was vortexed for 1-2 min and treated by ultrasound for 1-2 min, then the solution was clear and transparent.

Analytical method: Plasma samples were analyzed by liquid chromatography-tandem mass spectrometry (Instrument type: Triple Quad™ 4000).

Preparation of the standard curve: preparing a standard curve of the test compound 1n the plasma matrix of ICR mice with a linear range of 1.00-3000 ng/mL, and preparing control samples at low, medium and high concentrations of 3 ng/mL, 500 ng/mL, and 2400 ng/mL respectively.

Treatment of biological samples: the frozen plasma samples were thawed on ice, and after the samples were thawed, they were vortexed on a vortex for 5 min. 20 μL of plasma sample was added to a 96-well plate, and 200 μL of acetonitrile (brand: Merck, Lot: 1854029643) containing an internal standard dexamethasone (Brand: NIFDC, Lot: 1N2V-DPGY, 2000 ng/mL) was added to precipitate protein, which were vortexed for 5 min, and then centrifuged at 3700 rpm and 4° C. for 15 min. The supernatant was extracted and twice centrifuged under the same conditions, and finally 2 μL of the supernatant solution was analyzed by LC-MS/MS. Some of the compounds of the present disclosure had the pharmacokinetic properties in mice in vivo in the same mode of administration shown in Table 4:

TABLE 4

Pharmacokinetic parameters of compounds in mice in vivo

| Compound No. | Tmax (hr) | Maximum blood concentration $C_{max}$ (ng/mL) | half-time $T_{1/2}$ (hr) | Area under curve AUC (hr * ng/mL) | Oral relative bio-availability F (%) |
|---|---|---|---|---|---|
| G-7 | 0.08 | 1833.3 | 1.55 | 1328 | 25.38 |
| G-14 | 0.08 | 1240.0 | 2.47 | 1072 | 13.7 |
| G-23 | 0.08 | 878.7 | 3.25 | 645 | 14 |
| G-26 | 0.08 | 2403.7 | 2.12 | 1288 | 13.12 |
| G-31 | 0.25 | 1237.0 | 1.72 | 1839 | 28.2 |
| G-32 | 0.50 | 837.7 | 1.21 | 1463 | 14.7 |
| G-33 | 0.08 | 964.0 | 1.19 | 1193 | 15.6 |
| G-34 | 0.08 | 1990.0 | 1.44 | 1869 | 28.6 |
| G-37 | 0.25 | 672.2 | 3.26 | 1723 | NA |
| G-39 | 0.08 | 1501.0 | 2.30 | 1182 | 15.2 |
| G-42 | 0.25 | 945.0 | 1.73 | 1266 | 12.3 |
| G-60 | 0.08 | 351.7 | 10.57 | 109 | 3 |
| G-71 | 0.08 | 532.7 | 11.32 | 606 | 7.4 |
| G-72 | 0.25 | 10.7 | 11.32 | 107 | NA |
| G-91 | 0.25 | 2910.0 | 4.70 | 3152 | 21.3 |
| G-111 | 0.08 | 3486.7 | 5.93 | 2179 | 79.72 |
| G-114 | 0.08 | 1240.0 | 2.47 | 1072 | 13.7 |

NA represents undetected.

It can be seen from table 4 that the exemplified compounds of the present disclosure have good pharmacological absorption, have significant pharmacological absorption effects, and exhibit good bioavailability. It has been found that when there is a substituent (such as methyl) on the nitrogen atom attached to the piperidine ring, the efficacy of the compound 1n mice is significantly lower than that of the compound when there is no substituent (such as compounds G-7 and G-60, compounds G-14 and G-71, compounds G-23 and G-72).

All publications mentioned herein are incorporated by reference as if each individual document is cited as a reference, as in the present application. It should also be understood that, after reading the above teachings of the present disclosure, those skilled in the art can make various changes or modifications, equivalents of which fall in the scope of claims as defined in the appended claims.

What is claimed is:

1. A compound of formula (I), or a pharmaceutically acceptable salt, stereoisomer, solvate or prodrug thereof:

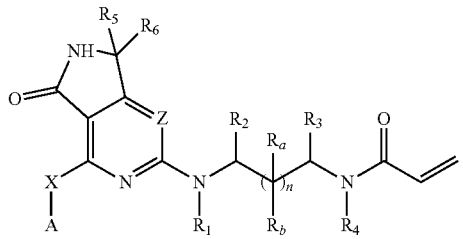

wherein X is a bond, $NR_{a1}$, S, SO, $SO_2$ or O; wherein $R_{a1}$ is hydrogen, hydroxy or $C_{1-8}$ alkyl;

A is $C_{6-10}$ aryl, a 4- to 7-membered saturated or unsaturated monoheterocyclic ring, a 5- to 6-membered monocyclic heteroaryl ring, or an 8- to 10-membered bicyclic heteroaryl ring;

Z is N or $CR_{b1}$; wherein $R_{b1}$ is hydrogen, halogen, cyano, $C_{1-8}$ alkyl, halogenated $C_{1-8}$ alkyl, $C_{1-8}$ alkoxy, $C_{3-8}$ cycloalkyl or $C_{3-8}$ cycloalkoxy;

$R_5$ and $R_6$ are each independently hydrogen, halogen, $C_{1-8}$ alkyl, halogenated $C_{1-8}$ alkyl, $C_{1-8}$ alkoxy, $C_{3-8}$ cycloalkyl or $C_{3-8}$ cycloalkoxy;

n is 0 or 1; wherein
(i) when n is 0, $R_1$ and $R_3$ are each independently hydrogen, halogen, hydroxy, alkoxy, or $C_{1-8}$ alkyl; $R_2$ and $R_4$ are bonded together to form a 4- to 7-membered saturated or unsaturated monoheterocyclic ring;
(ii) when n is 0, $R_2$ and $R_4$ are each independently hydrogen, halogen, hydroxy, alkoxy, or $C_{1-8}$ alkyl; $R_1$ and $R_3$ are bonded together to form a 4- to 7-membered saturated or unsaturated monoheterocyclic ring;
(iii) when n is 0, $R_2$ is hydrogen, halogen, or $C_{1-8}$ alkyl; $R_3$ is bonded with $R_1$ and $R_4$ to form a bridged heterocycle; or $R_3$ is hydrogen, halogen, or $C_{1-8}$ alkyl; $R_2$ is bonded with $R_1$ and $R_4$ to form a bridged heterocycle;
(iv) when n is 1, $R_2$ and $R_3$ are each independently hydrogen, halogen, hydroxy, alkoxy, or $C_{1-8}$ alkyl; $R_a$ and $R_1$ are bonded and $R_b$ and $R_4$ are bonded together to form a spiro heterocyclic ring;
(v) when n is 1, $R_2$, $R_3$ and $R_b$ are each independently hydrogen, halogen, hydroxy, alkoxy, or $C_{1-8}$ alkyl; $R_a$ is bonded with $R_1$ and $R_4$ respectively together to form a bridged heterocyclic ring;
(vi) when n is 1, $R_1$, $R_3$, $R_a$, $R_b$ are each independently hydrogen, halogen, hydroxy, alkoxy, or $C_{1-8}$ alkyl; $R_2$ and $R_4$ are bonded together to form a 5- to 7-membered saturated or unsaturated monoheterocyclic ring;

the alkyl, cycloalkyl, alkoxy, aryl, saturated or unsaturated monoheterocyclic ring, monocyclic heteroaryl ring, bicyclic heteroaryl ring, spiro heterocyclic ring, or bridged heterocyclic ring is unsubstituted or substituted with 1, 2 or 3 substituents selected from the group consisting of: hydroxymethyl, hydroxyethyl, hydroxy, carboxy, halogen, $-O(CH_2)_pOC_{1-8}$ alkyl, $-O(CH_2)_pOH$, $-(CH_2)_pOC_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, $NR_{a0}R_{b0}$, $-C(O)OC_{1-6}$ alkyl, acetyl, $C_{1-8}$ alkoxy, $C_{1-8}$ alkoxy-substituted $C_{1-8}$ alkyl, halogenated $C_{1-8}$ alkoxy, $-SO_2C_{1-8}$ alkyl, $C_{6-10}$ aryl, 5- to 6-membered monocyclic heteroaryl or $-Y-L$; wherein Y is $(CH_2)_q$ or C(O); L is a 4- to 6-membered saturated monoheterocyclic ring or a 5- to 6-membered monocyclic heteroaryl ring; and p and q are each independently 1, 2 or 3; $R_{a0}$ and $R_{b0}$ are each independently hydrogen, acetyl, $C_{1-8}$ alkyl, $C_{1-8}$ alkoxy-substituted $C_{1-8}$ alkyl.

2. The compound of claim 1, or a pharmaceutically acceptable salt, stereoisomer, solvate or prodrug thereof, wherein

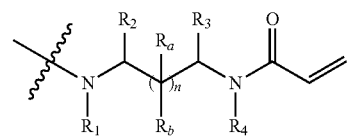

is a structure as shown in formula (A), (B) or (C):

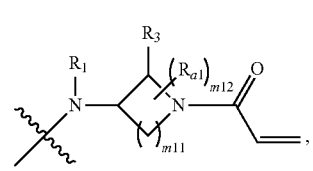

(A)

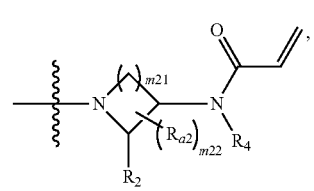

(B)

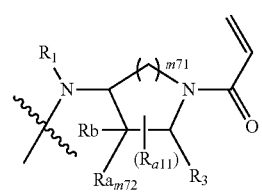

(C)

wherein, m11 and m21 are each independently 1, 2, 3 or 4; m71 is 1, 2 or 3;

m12 and m22 are each independently 0, 1, 2, 3 or 4; m72 is 0, 1, 2 or 3;

$R_{a1}$, $R_{a2}$, and $R_{a11}$ are each independently halogen, $C_{1-8}$ alkyl, halogenated $C_{1-8}$ alkyl, hydroxy-substituted $C_{1-8}$ alkyl, $C_{1-8}$ alkoxy, $C_{1-8}$ alkoxy-substituted $C_{1-8}$ alkyl, or $C_{3-8}$ cycloalkyl;

$R_1$, $R_2$, $R_3$, $R_4$, $R_a$ and $R_b$ are as defined in claim 1.

3. The compound of claim 1, or a pharmaceutically acceptable salt, stereoisomer, solvate or prodrug thereof, wherein

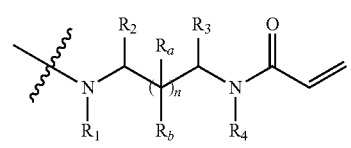

is a structure as shown in formula (D), (E) or (F):

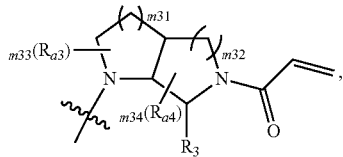

(D)

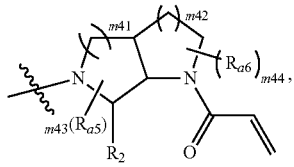

(E)

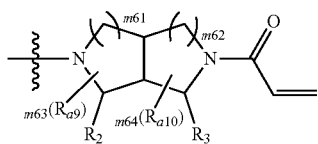

(F)

wherein, m31, m32, m41, m42, m61 and m62 are each independently 0, 1, 2, or 3;

m33, m34, m43, m44, m63 and m64 are each independently 0, 1, 2, or 3;

$R_{a3}$, $R_{a4}$, $R_{a5}$, $R_{a6}$, $R_{a9}$ and $R_{a10}$ are each independently halogen, $C_{1-8}$ alkyl, halogenated $C_{1-8}$ alkyl, hydroxy-substituted $C_{1-8}$ alkyl, $C_{1-8}$ alkoxy, $C_{1-8}$ alkoxy-substituted $C_{1-8}$ alkyl, or $C_{3-8}$ cycloalkyl;

$R_2$ and $R_3$ are as defined in claim 1.

4. The compound of claim 1, or a pharmaceutically acceptable salt, stereoisomer, solvate or prodrug thereof, wherein

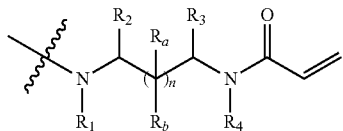

is a structure as shown in formula (G):

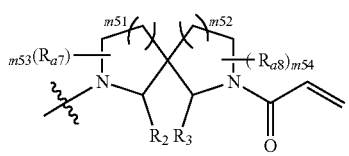

(G)

wherein, m51 and m52 are each independently 0, 1, 2, or 3;

m53 and m54 are each independently 0, 1, 2, 3 or 4;

$R_{a7}$ and $R_{a8}$ are each independently halogen, $C_{1-8}$ alkyl, halogenated $C_{1-8}$ alkyl, hydroxy-substituted $C_{1-8}$ alkyl, $C_{1-8}$ alkoxy, $C_{1-8}$ alkoxy-substituted $C_{1-8}$ alkyl, or $C_{3-8}$ cycloalkyl;

$R_2$ and $R_3$ are as defined in claim 1.

5. The compound of claim 1, or a pharmaceutically acceptable salt, stereoisomer, solvate or prodrug thereof, wherein X is a bond or $NR_{a1}$; wherein $R_{a1}$ is hydrogen or $C_{1-3}$ alkyl.

6. The compound of claim 1, or a pharmaceutically acceptable salt, stereoisomer, solvate or prodrug thereof, wherein A is $C_{6-10}$ aryl or a 5- to 6-membered monocyclic heteroaryl ring; A is optionally substituted with 1, 2 or 3 substituents selected from a group A1 consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxy, $NR_{a0}R_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (CH$_2$)$_q$ or C(O); L is a 4- to 6-membered saturated monoheterocyclic ring; and p and q are each independently 1, 2 or 3; $R_{a0}$ and $R_{b0}$ are each independently hydrogen, acetyl, $C_{1-8}$ alkyl, or $C_{1-8}$ alkoxy-substituted $C_{1-8}$ alkyl.

7. The compound of claim 1, or a pharmaceutically acceptable salt, stereoisomer, solvate or prodrug thereof, wherein X is NH; A is $C_{6-10}$ aryl or a 5- to 6-membered monocyclic heteroaryl ring; A is optionally substituted with 1, 2 or 3 substituents selected from a group A1 consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxy, $NR_{a0}R_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (CH$_2$)$_q$ or C(O); L is a 4- to 6-membered saturated monoheterocyclic ring; and p and q are each independently 1, 2 or 3; $R_{a0}$ and $R_{b0}$ are each independently hydrogen, acetyl, $C_{1-8}$ alkyl, or $C_{1-8}$ alkoxy-substituted $C_{1-8}$ alkyl.

8. The compound of claim 1, or a pharmaceutically acceptable salt, stereoisomer, solvate or prodrug thereof, wherein X is a bond; A is a 5- to 6-membered monocyclic heteroaryl ring; A is optionally substituted with 1, 2 or 3 substituents selected from a group A1 consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxy, $NR_{a0}R_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (CH$_2$)$_q$ or C(O); L is a 4- to 6-membered saturated monoheterocyclic ring; and p and q are each independently 1, 2 or 3; $R_{a0}$ and $R_{b0}$ are each independently hydrogen, acetyl, $C_{1-8}$ alkyl, or $C_{1-8}$ alkoxy-substituted $C_{1-8}$ alkyl.

9. The compound of claim 1, or a pharmaceutically acceptable salt, stereoisomer, solvate or prodrug thereof, wherein the 5- to 6-membered monocyclic heteroaryl ring is selected from:

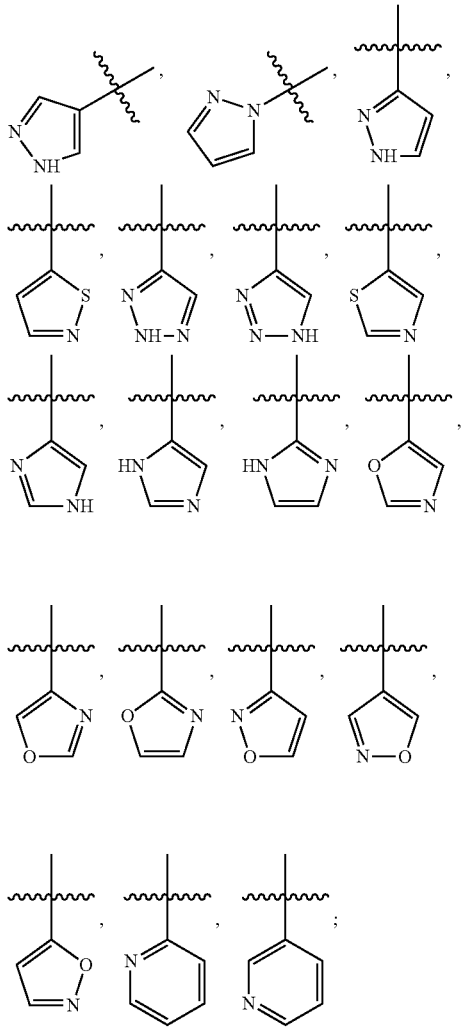

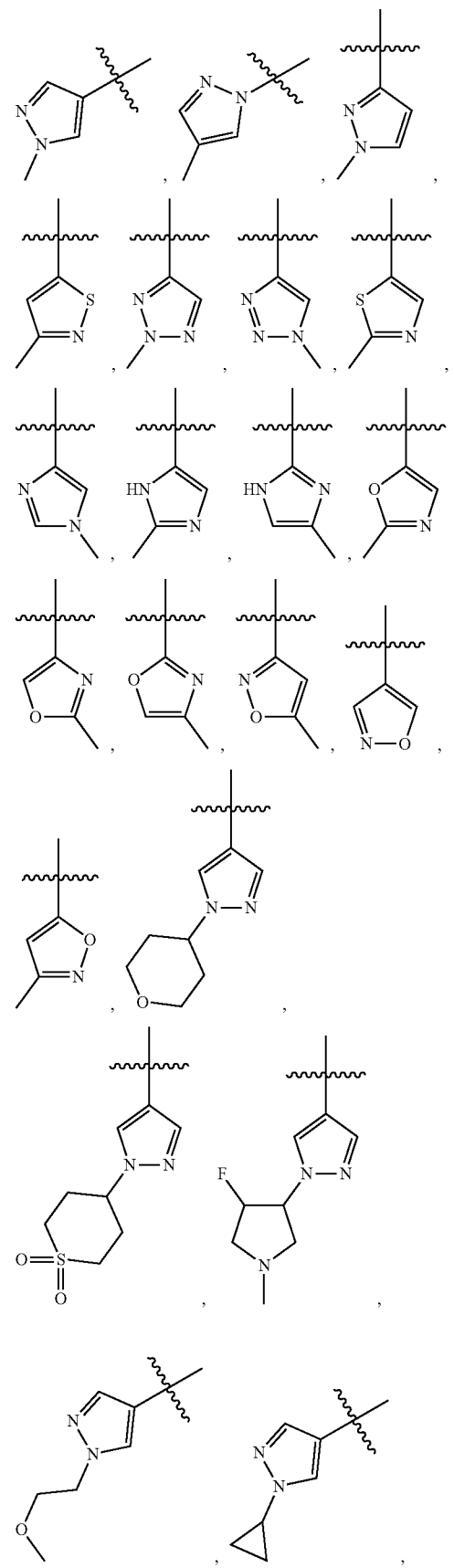

the 5- to 6-membered monocyclic heteroaryl ring is optionally substituted with 1, 2 or 3 substituents selected from a group A1 consisting of halogen, —O(CH$_2$)$_p$OC$_{1-8}$ alkyl, —O(CH$_2$)$_p$OH, —(CH$_2$)$_p$OC$_{1-8}$ alkyl, 4- to 6-membered saturated monoheterocyclic ring, C$_{1-8}$ alkyl, C$_{3-8}$ cycloalkyl, halogenated C$_{1-8}$ alkyl, halogenated C$_{3-8}$ cycloalkyl, hydroxy-substituted C$_{1-8}$ alkyl, hydroxymethyl, hydroxyethyl, hydroxy, carboxy, NR$_{a0}$R$_{b0}$, —C(O)OC$_{1-6}$ alkyl, acetyl, C$_{1-8}$ alkoxy, C$_{1-8}$ alkoxy-substituted C$_{1-8}$ alkyl, halogenated C$_{1-8}$ alkoxy, —SO$_2$C$_{1-8}$ alkyl, C$_{6-10}$ aryl, 5- to 6-membered monocyclic heteroaryl and —Y-L; wherein Y is (CH$_2$)$_q$ or C(O); L is a 4- to 6-membered saturated monoheterocyclic ring; and p and q are each independently 1, 2 or 3; R$_{a0}$ and R$_{b0}$ are each independently hydrogen, acetyl, C$_{1-8}$ alkyl, or C$_{1-8}$ alkoxy-substituted C$_{1-8}$ alkyl.

10. The compound of claim 1, or a pharmaceutically acceptable salt, stereoisomer, solvate or prodrug thereof, wherein X is NH; A is a structure selected from a group B1 consisting of:

141
-continued
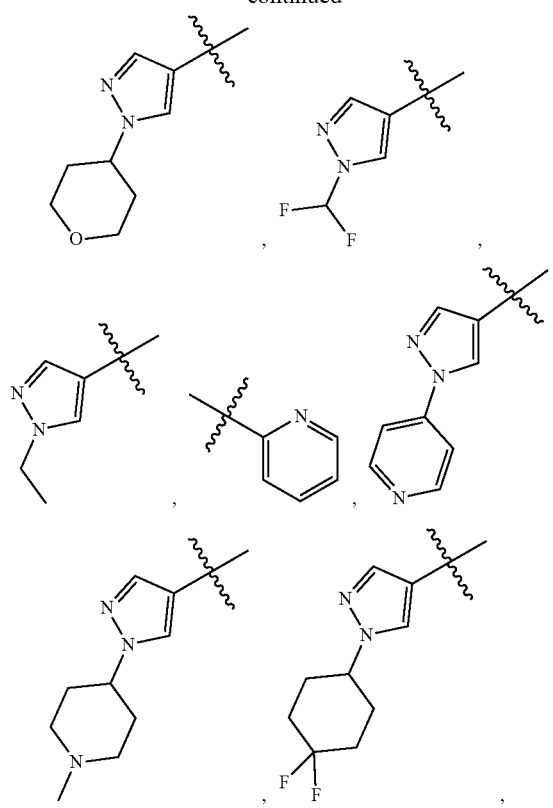
142
-continued
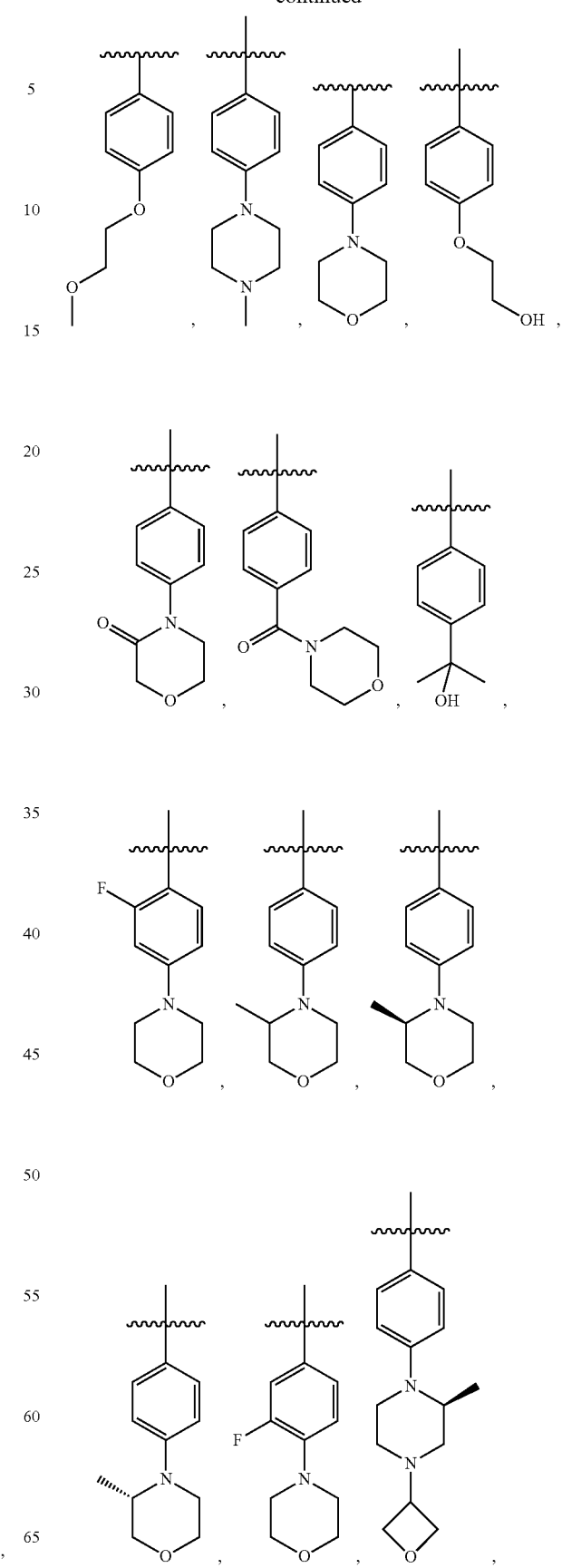

-continued
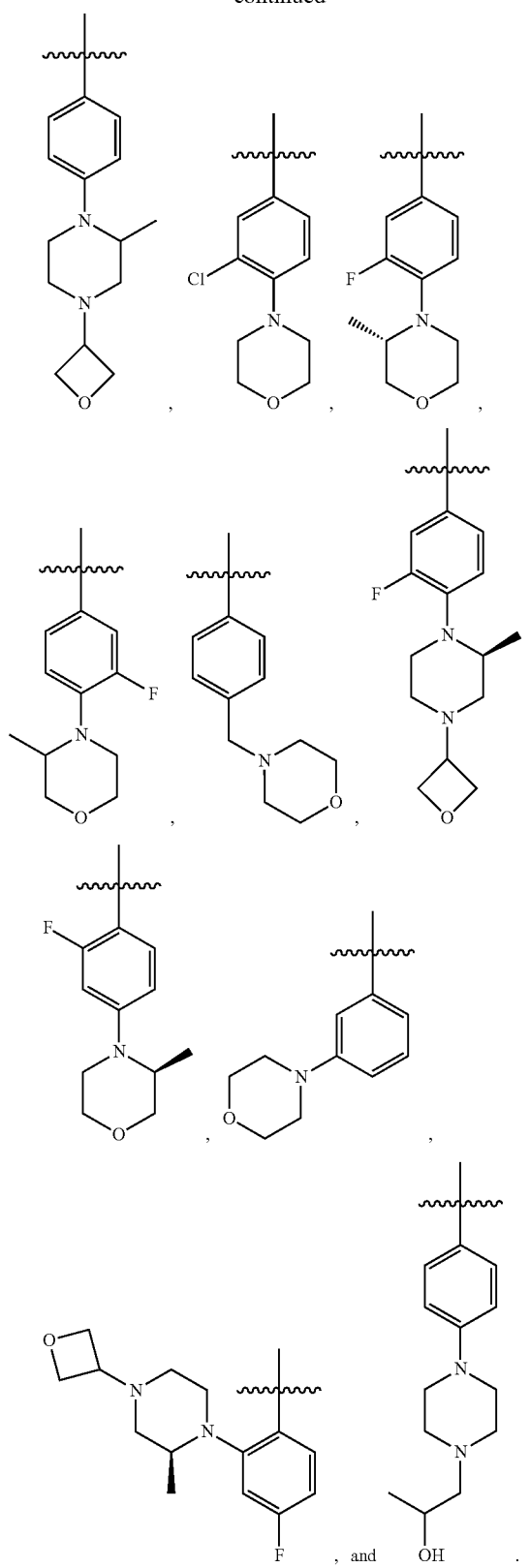
11. The compound of claim 1, or a pharmaceutically acceptable salt, stereoisomer, solvate or prodrug thereof,
wherein X is a bond; A is a structure selected from a group B1 or a group B2,
wherein the group B1 is consisting of:
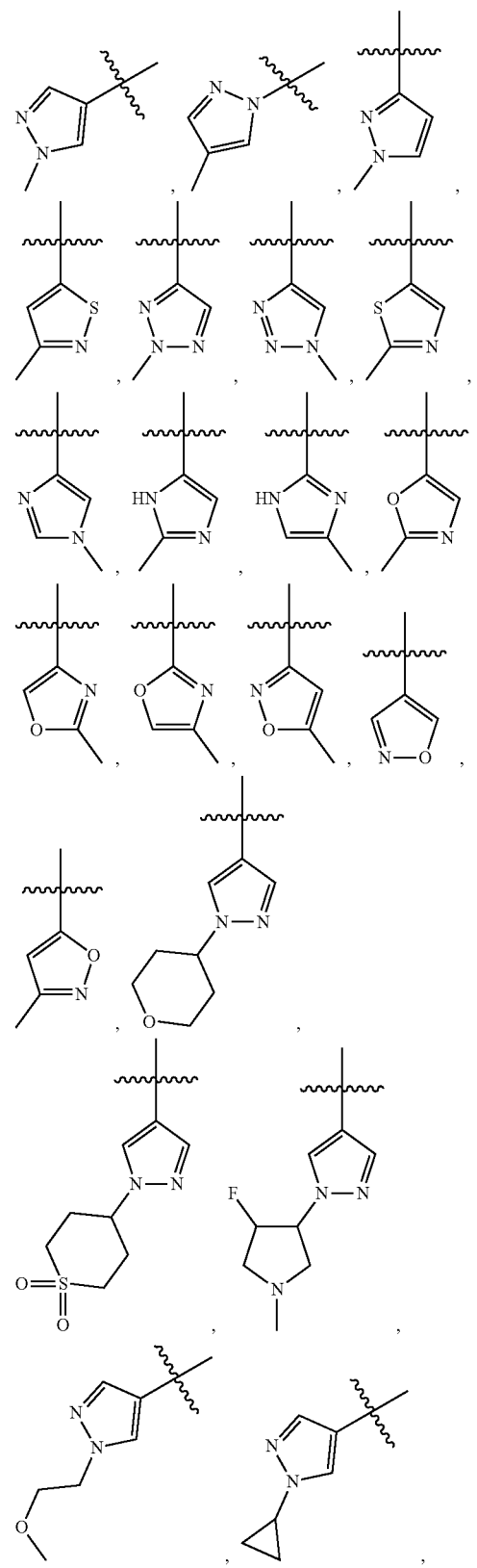

145
-continued
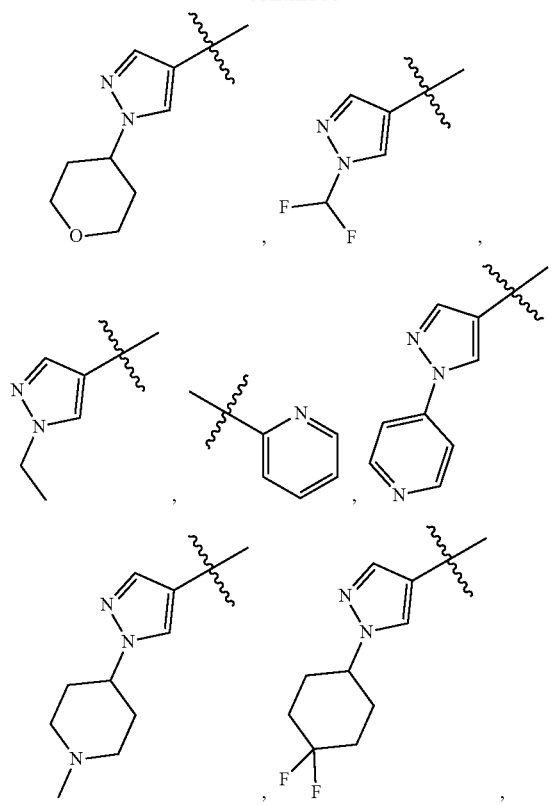
146
-continued
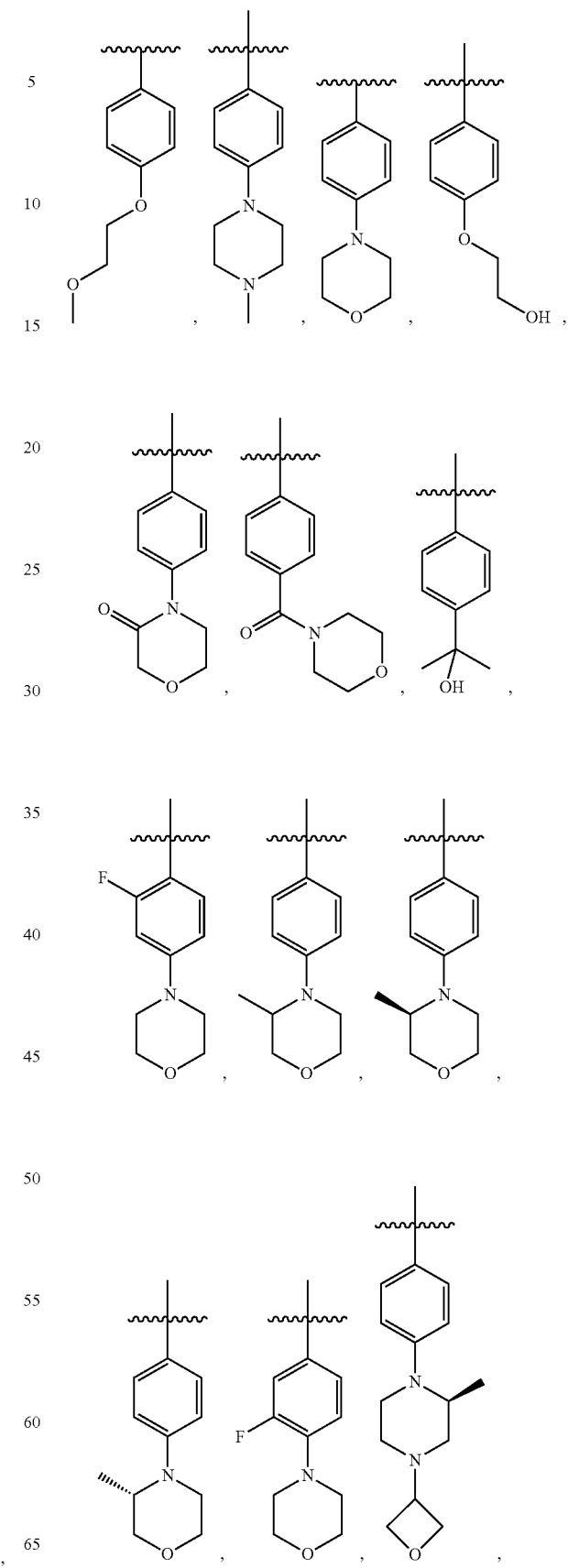

147
-continued
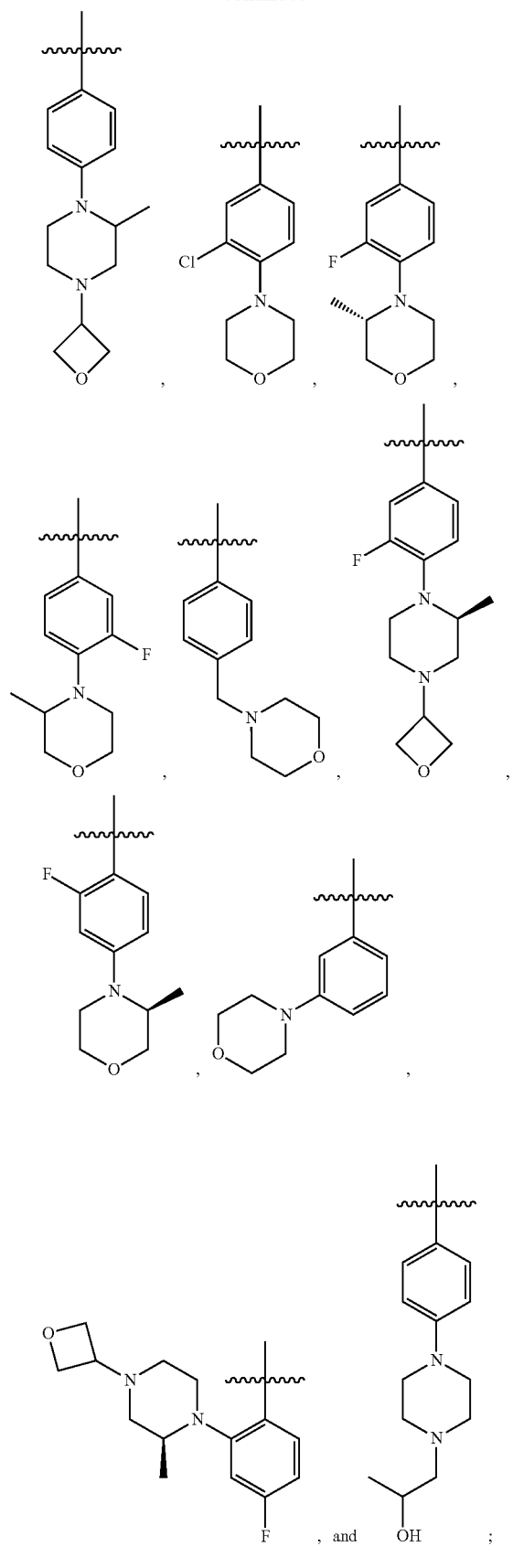
148
wherein the group B2 is consisting of:
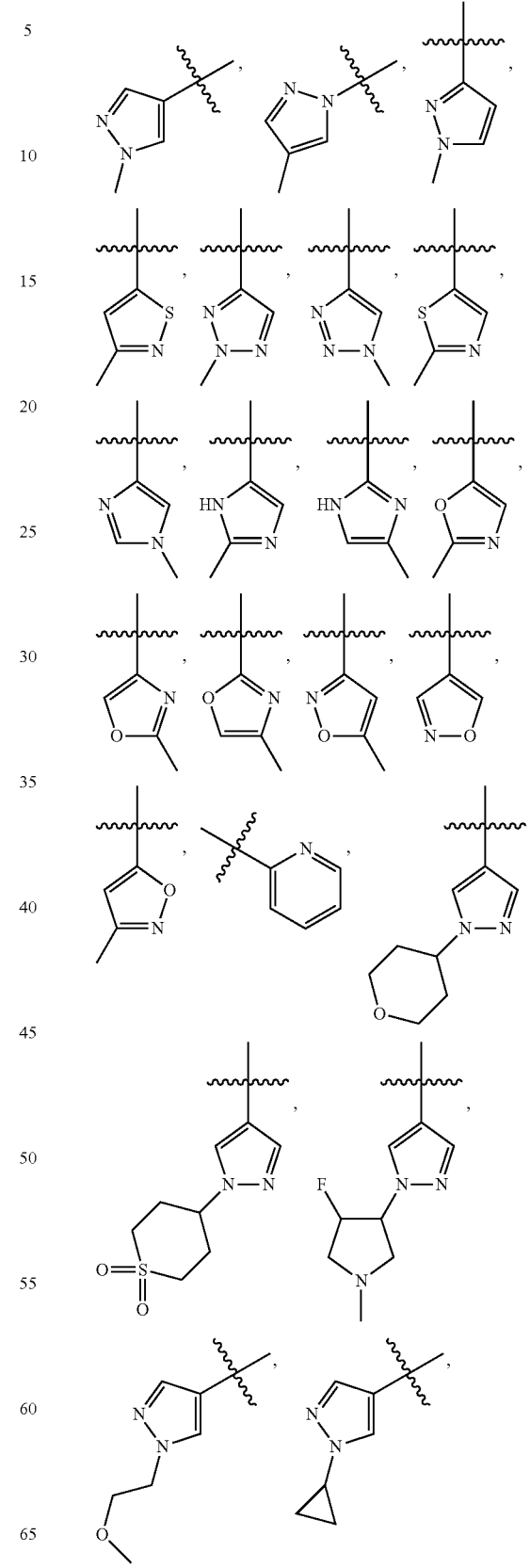

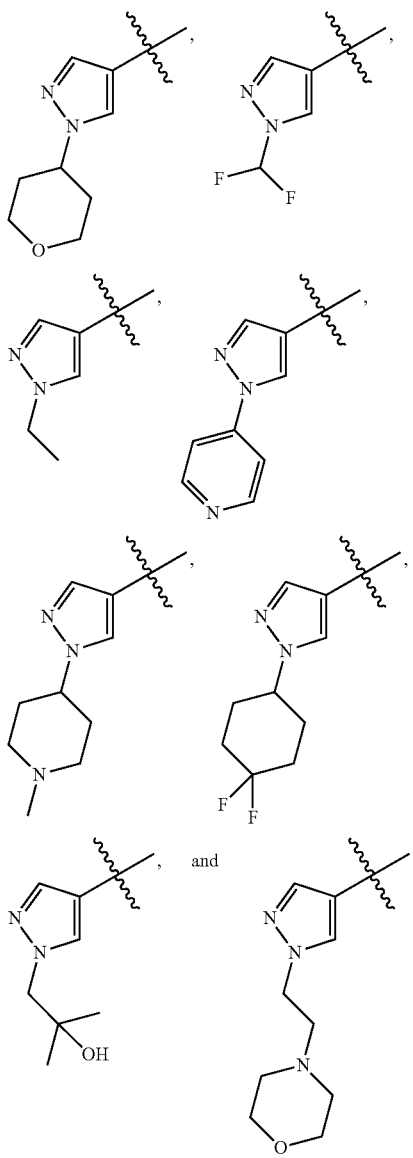

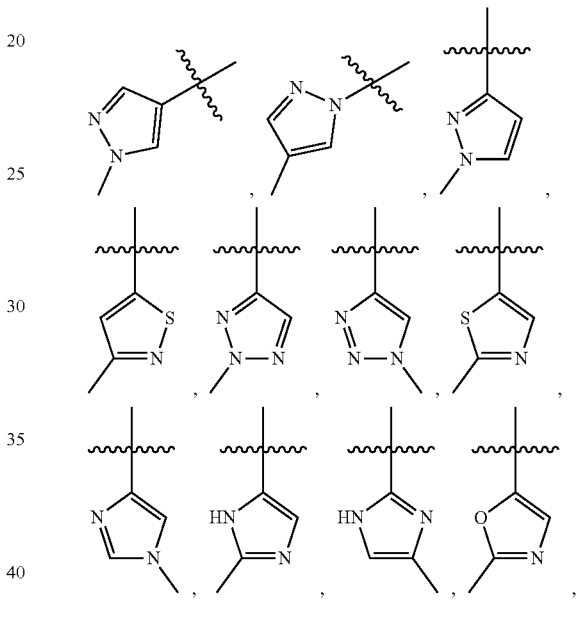

is a structure of formula (A); wherein the groups in the formula (A) are defined as in claim 2;

R₁ is hydrogen or C₁₋₈ alkyl.

13. The compound of claim 2, or a pharmaceutically acceptable salt, stereoisomer, solvate or prodrug thereof, wherein X is NH; A is a structure selected from a group B1 consisting of:

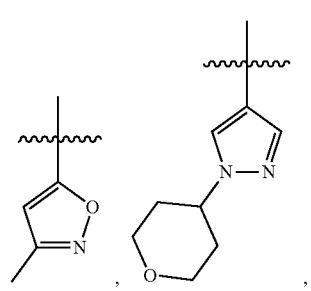

12. The compound of claim 2, or a pharmaceutically acceptable salt, stereoisomer, solvate or prodrug thereof, wherein X is NH; A is C₆₋₁₀ aryl or a 5- to 6-membered monocyclic heteroaryl ring; A is optionally substituted with 1, 2 or 3 substituents selected from a group A1 consisting of halogen, —O(CH₂)ₚOC₁₋₈ alkyl, —O(CH₂), OH, —(CH₂)ₚOC₁₋₈ alkyl, 4- to 6-membered saturated monoheterocyclic ring, C₁₋₈ alkyl, C₃₋₈ cycloalkyl, halogenated C₁₋₈ alkyl, halogenated C₃₋₈ cycloalkyl, hydroxy-substituted C₁₋₈ alkyl, hydroxymethyl, hydroxyethyl, hydroxy, carboxy, NRₐ₀Rᵦ₀, —C(O)OC₁₋₆ alkyl, acetyl, C₁₋₈ alkoxy, C₁₋₈ alkoxy-substituted C₁₋₈ alkyl, halogenated C₁₋₈ alkoxy, —SO₂C₁₋₈ alkyl, C₆₋₁₀ aryl, 5- to 6-membered monocyclic heteroaryl and —Y-L; wherein Y is (CH₂)_q or C(O); L is a 4- to 6-membered saturated monoheterocyclic ring; and p and q are each independently 1, 2 or 3; Rₐ₀ and Rᵦ₀ are each independently hydrogen, acetyl, C₁₋₈ alkyl, or C₁₋₈ alkoxy-substituted C₁₋₈ alkyl;

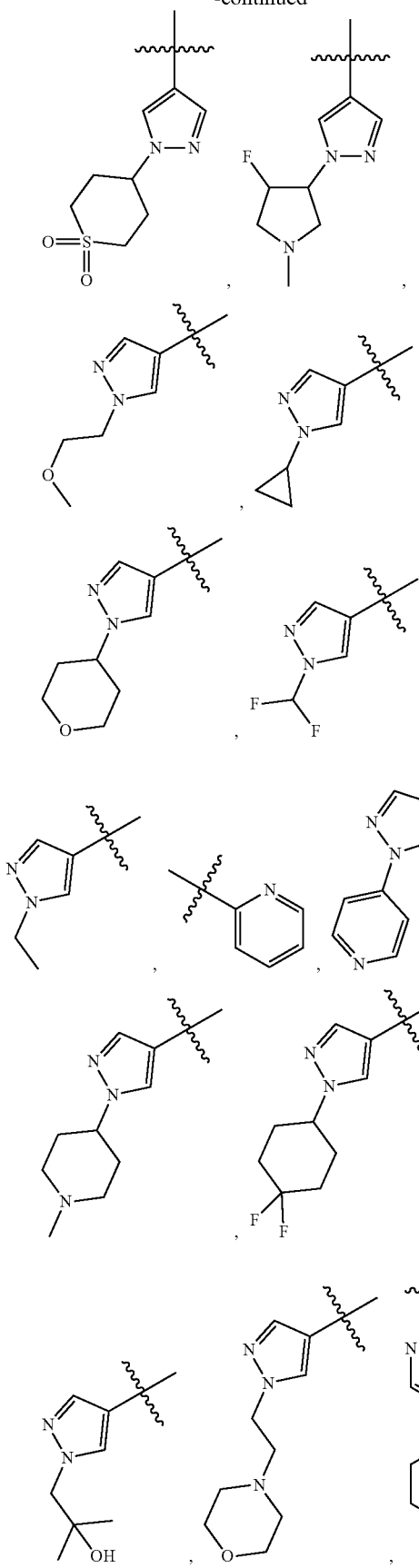
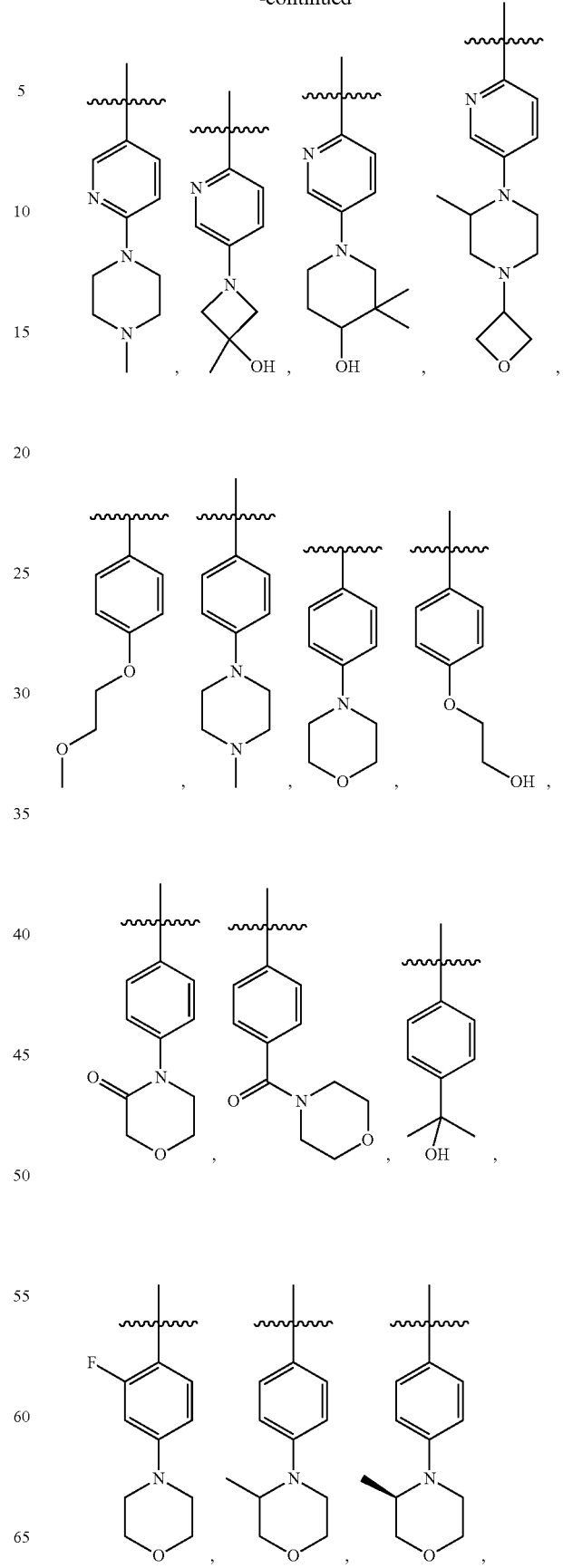

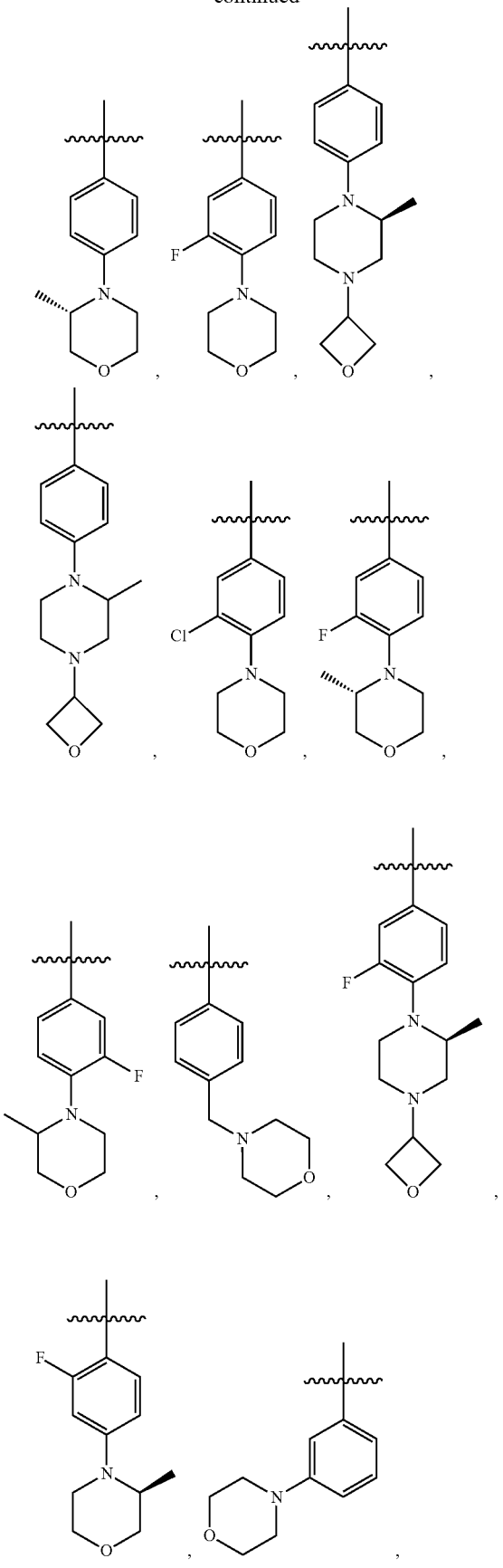

,

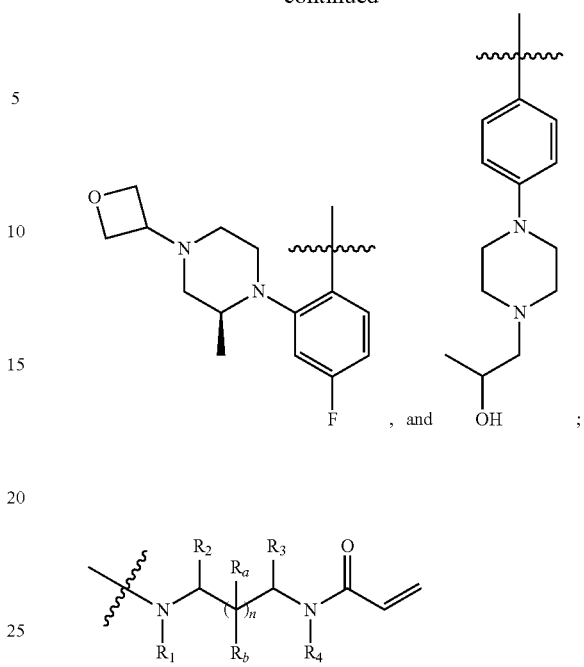

, and

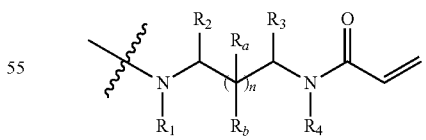

is a structure of formula (A); wherein the groups in the formula (A) are defined as in claim 2;

$R_1$ is hydrogen or $C_{1-8}$ alkyl.

14. The compound of claim 2, or a pharmaceutically acceptable salt, stereoisomer, solvate or prodrug thereof, wherein X is a bond; A is a 5- to 6-membered monocyclic heteroaryl ring; A is optionally substituted with 1, 2 or 3 substituents selected from a group A1 consisting of halogen, —O(CH$_2$)$_p$OC$_{1-8}$ alkyl, —O(CH$_2$), OH, —(CH$_2$)OC$_{1-8}$ alkyl, 4- to 6-membered saturated monoheterocyclic ring, $C_{1-8}$ alkyl, $C_{3-8}$ cycloalkyl, halogenated $C_{1-8}$ alkyl, halogenated $C_{3-8}$ cycloalkyl, hydroxy-substituted $C_{1-8}$ alkyl, hydroxymethyl, hydroxyethyl, hydroxy, carboxy, NR$_{a0}$R$_{b0}$, —C(O)OC$_{1-6}$ alkyl, acetyl, $C_{1-8}$ alkoxy, $C_{1-8}$ alkoxy-substituted $C_{1-8}$ alkyl, halogenated $C_{1-8}$ alkoxy, —SO$_2$C$_{1-8}$ alkyl, $C_{6-10}$ aryl, 5- to 6-membered monocyclic heteroaryl and —Y-L; wherein Y is (CH$_2$)$_q$ or C(O); L is a 4- to 6-membered saturated monoheterocyclic ring; and p and q are each independently 1, 2 or 3; R$_{a0}$ and R$_{b0}$ are each independently hydrogen, acetyl, $C_{1-8}$ alkyl, or $C_{1-8}$ alkoxy-substituted $C_{1-8}$ alkyl;

is a structure of formula (A); wherein the groups in the formula (A) are defined as in claim 2;

$R_1$ is hydrogen or $C_{1-8}$ alkyl.

15. The compound of claim 2, or a pharmaceutically acceptable salt, stereoisomer, solvate or prodrug thereof, wherein X is a bond; A is a structure selected from a group B1 or a group B2;

wherein the group B1 is consisting of:
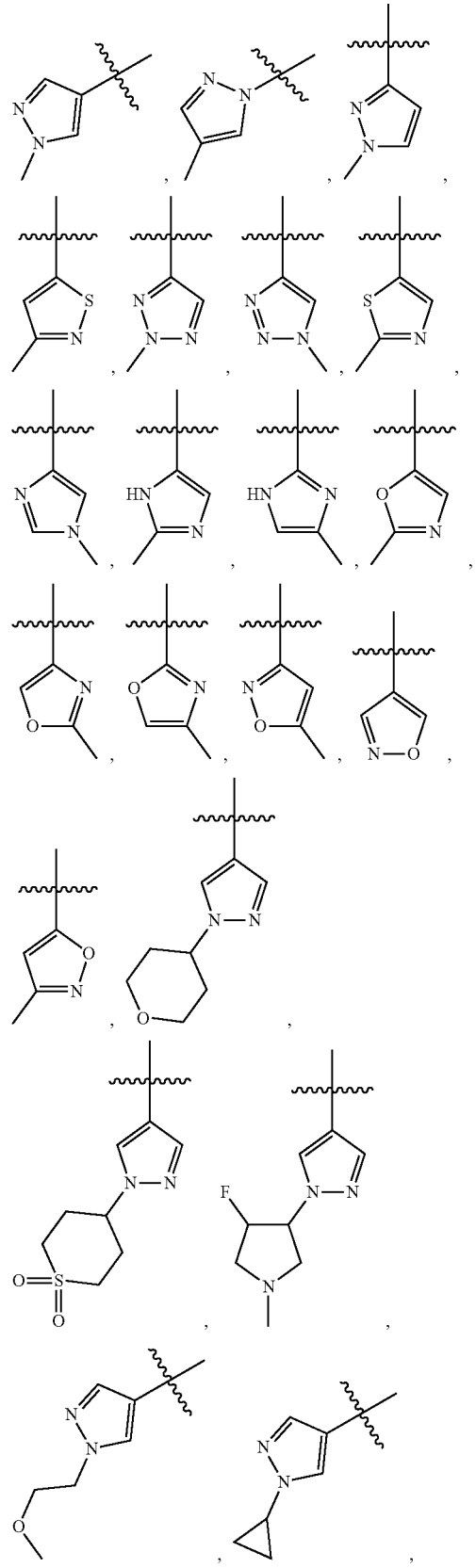
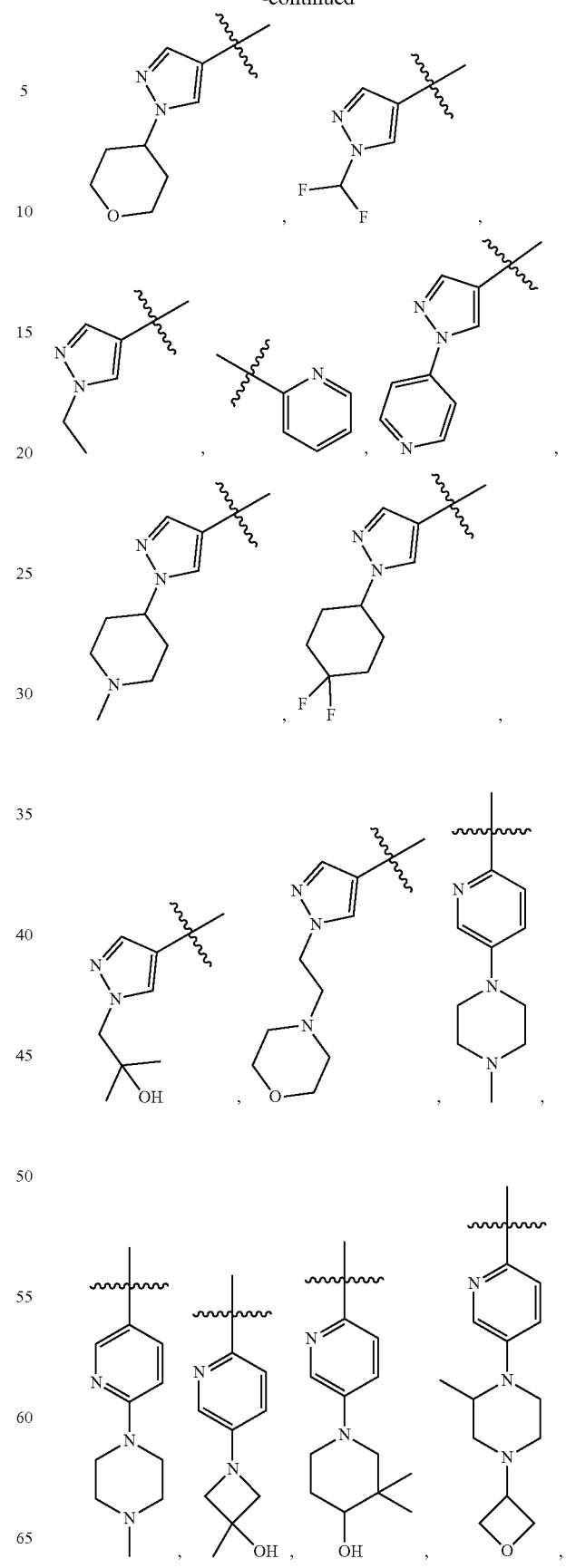

157
-continued
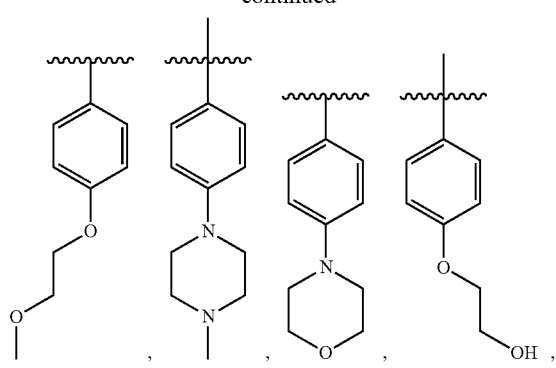
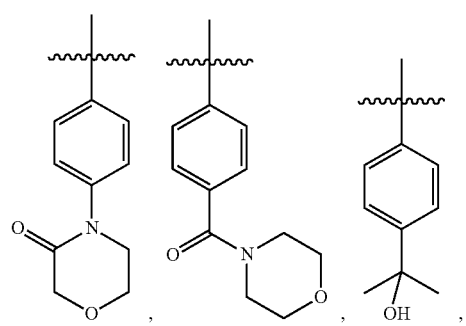
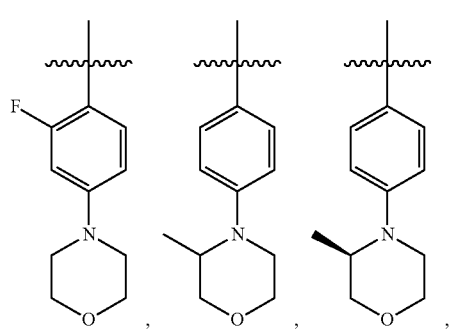
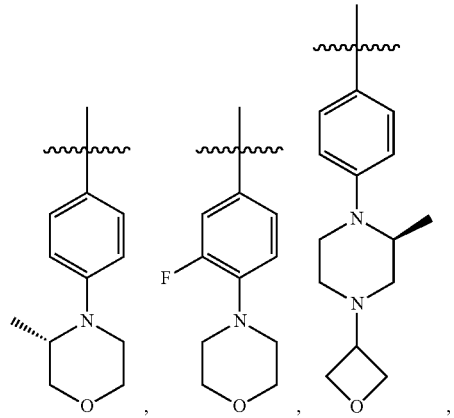
158
-continued
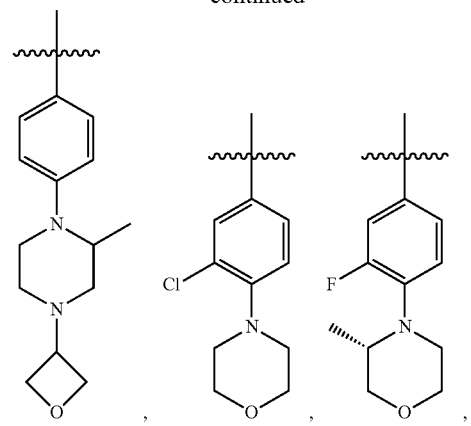
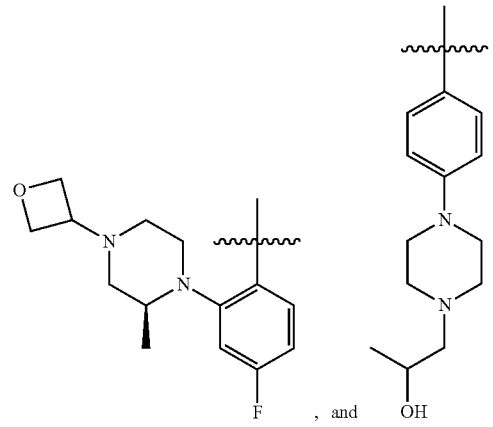

the group B2 is consisting of:
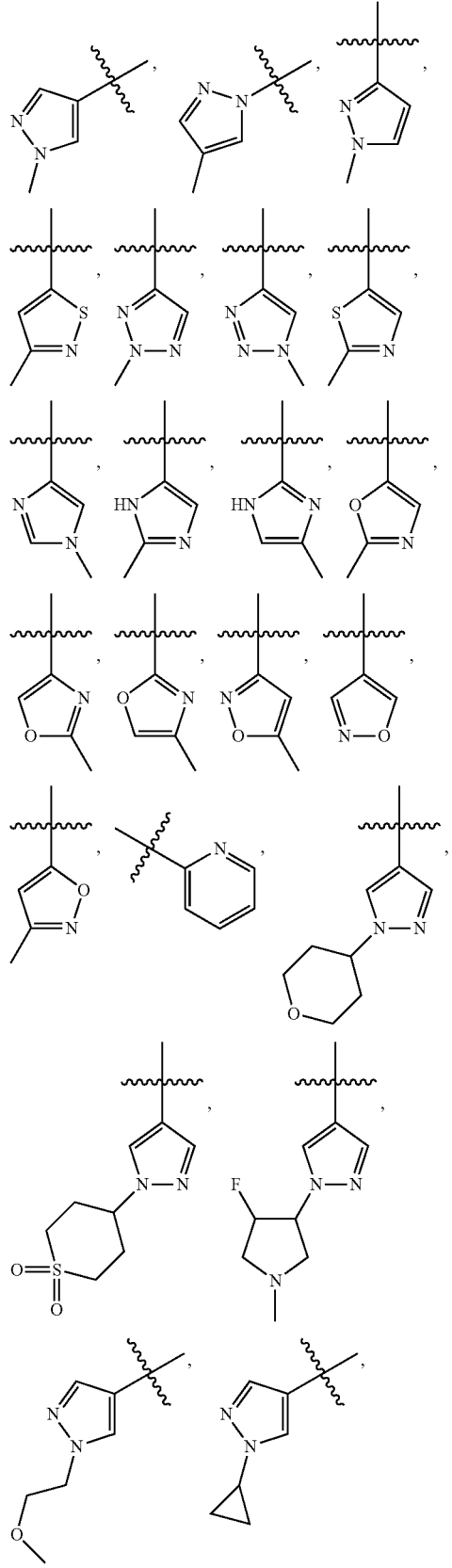
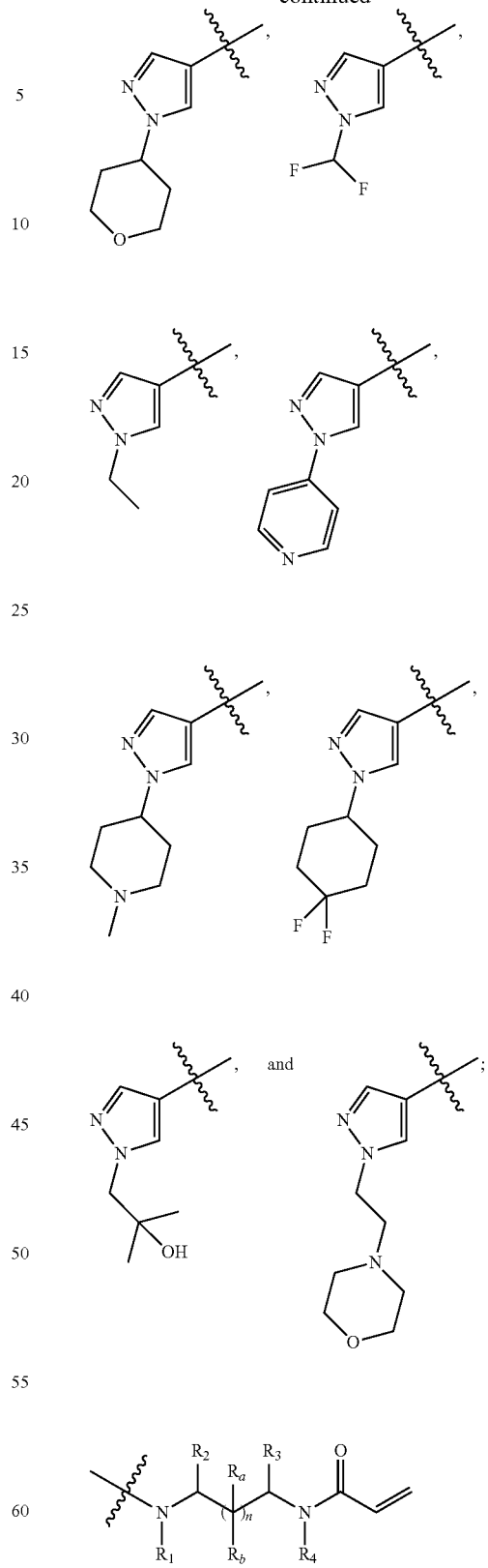
is a structure of formula (A); wherein the groups in the formula (A) are defined as in claim 2;
$R_1$ is hydrogen or $C_{1-8}$ alkyl.

16. The compound of claim 3, or a pharmaceutically acceptable salt, stereoisomer, solvate or prodrug thereof, wherein formula (D), (E), or (F) is selected from:
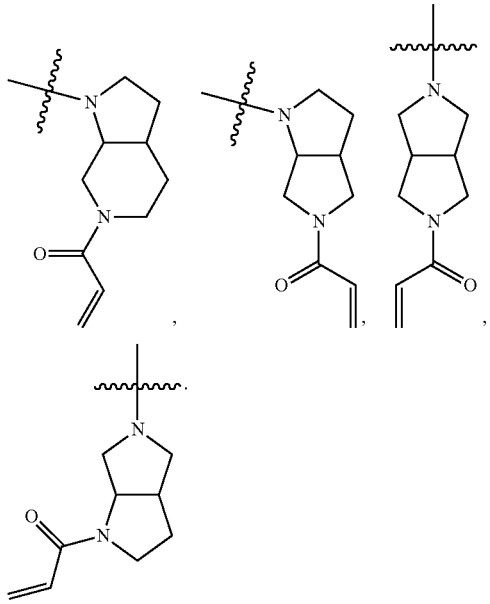
17. The compound of claim 2, or a pharmaceutically acceptable salt, stereoisomer, solvate or prodrug thereof, wherein the formula (A) is a structure selected from a group $C_1$ consisting of:
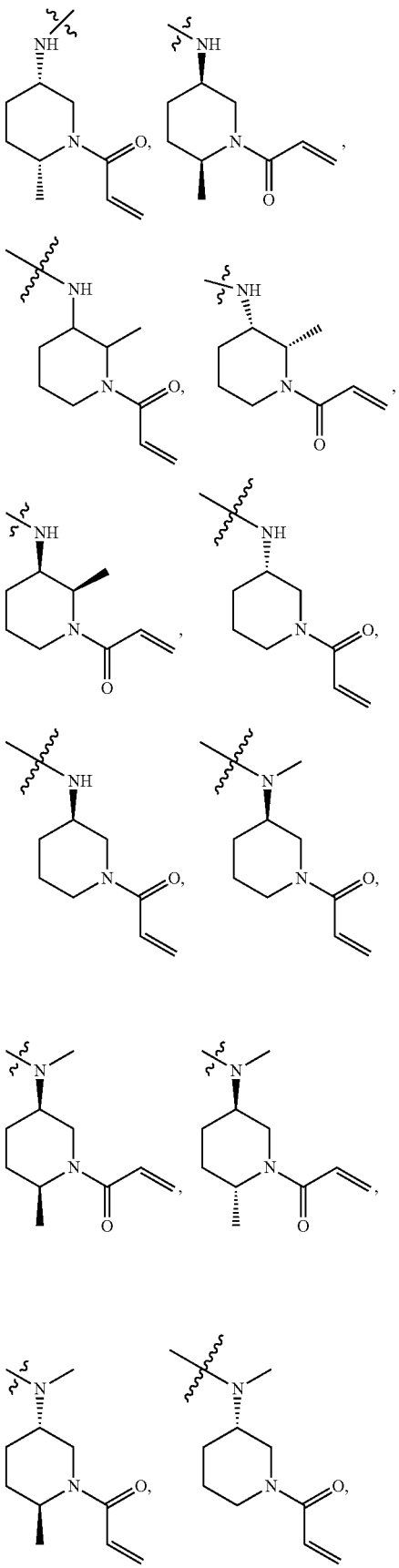

163
-continued
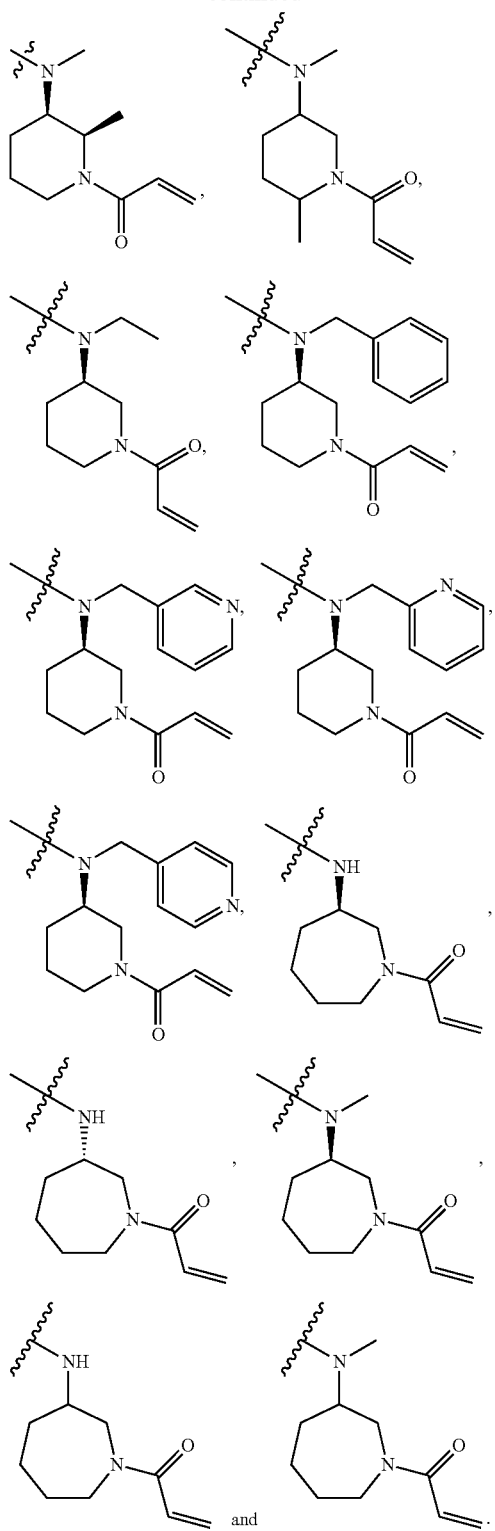
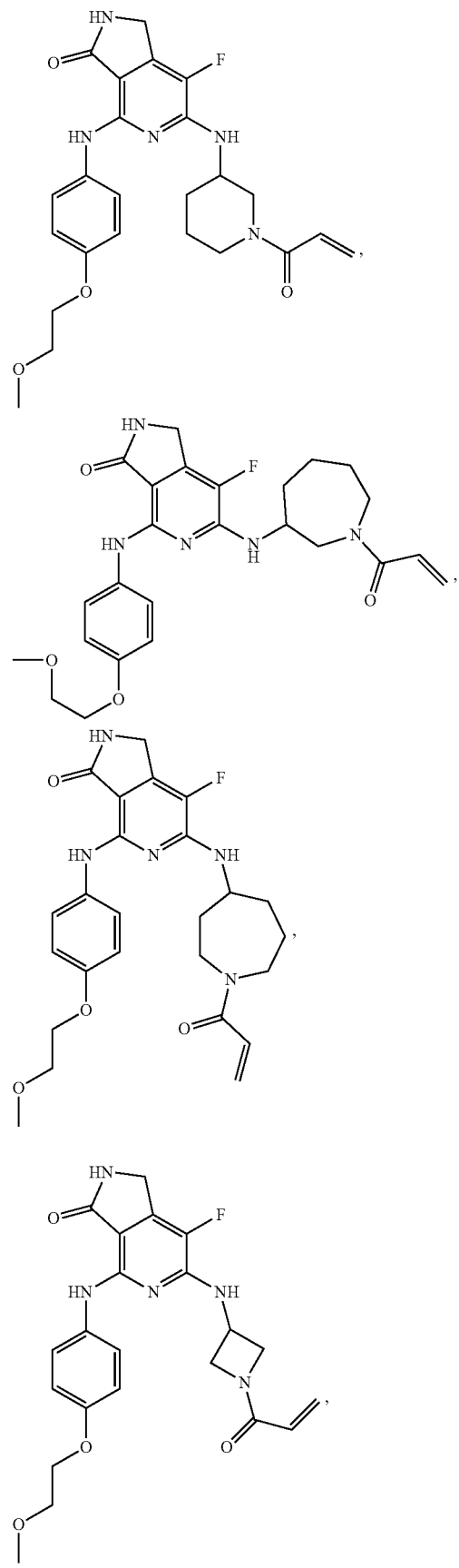
and.
18. The compound of claim 1, or a pharmaceutically acceptable salt, stereoisomer, solvate or prodrug thereof, wherein the compound of formula (I) is a structure selected from a group D1 consisting of:

165
-continued
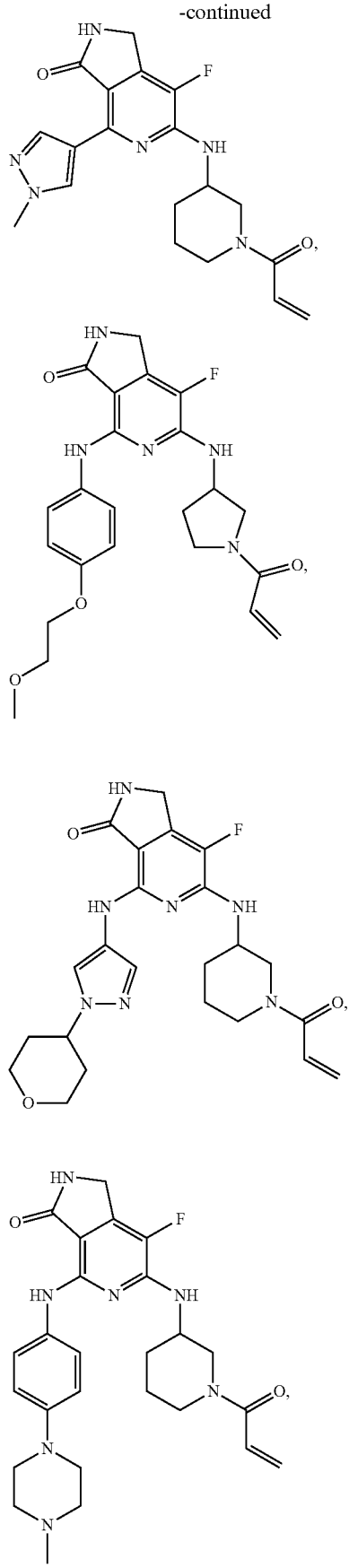
166
-continued
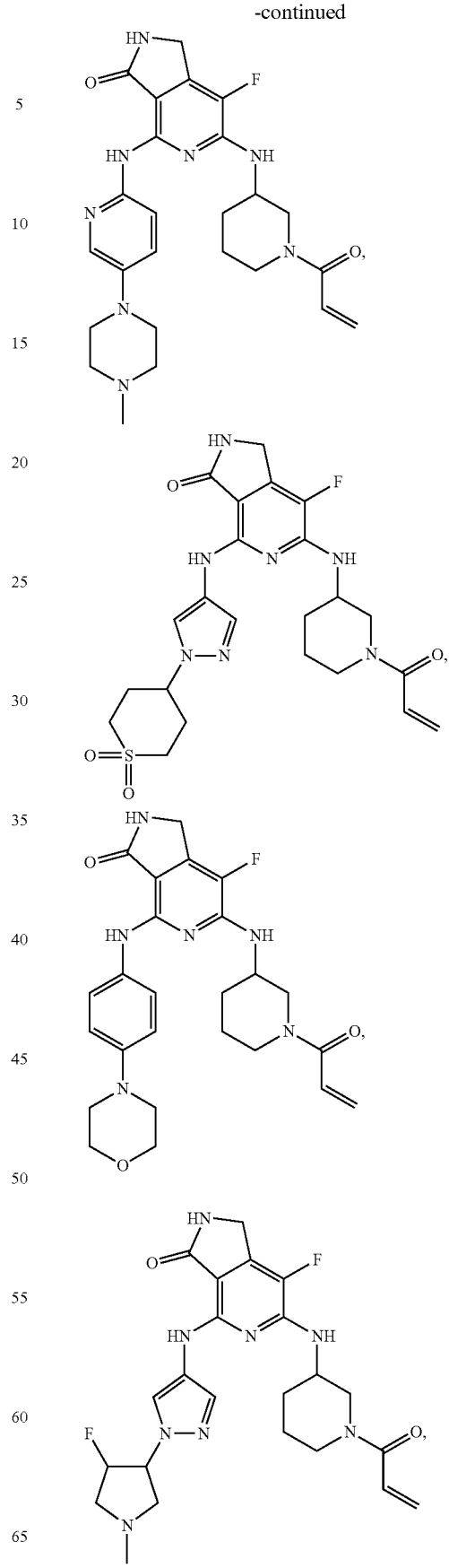

167
-continued
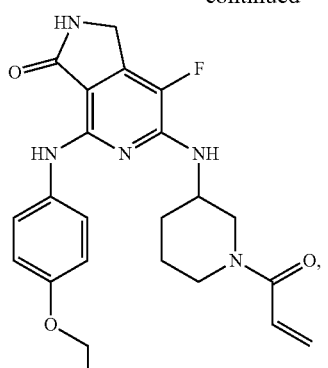
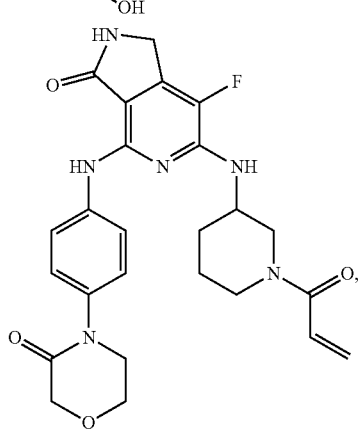
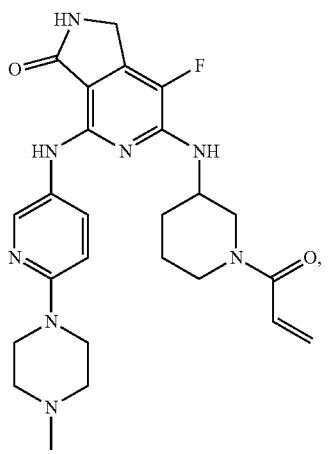
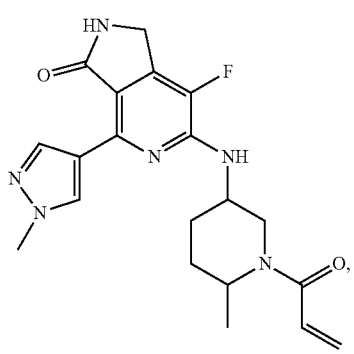
168
-continued
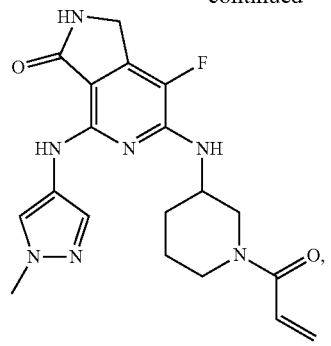
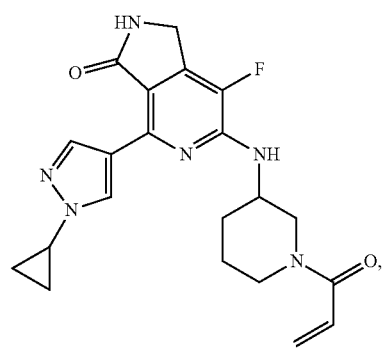
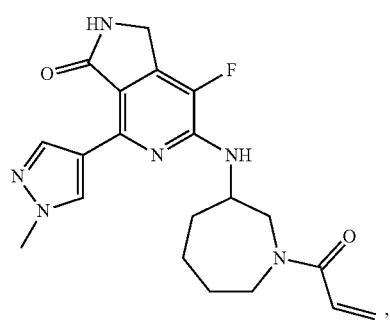
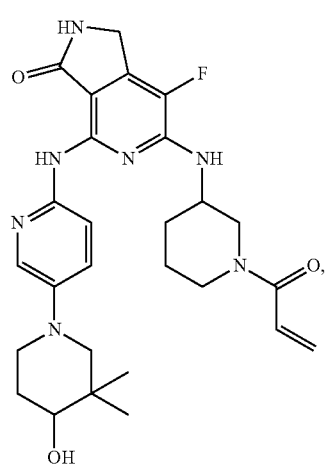

169
-continued
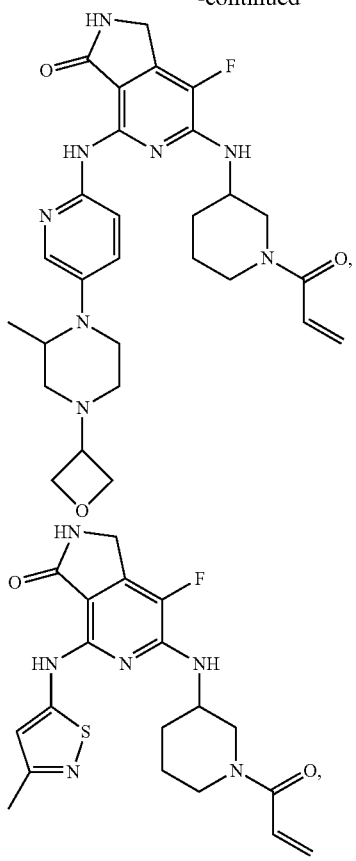
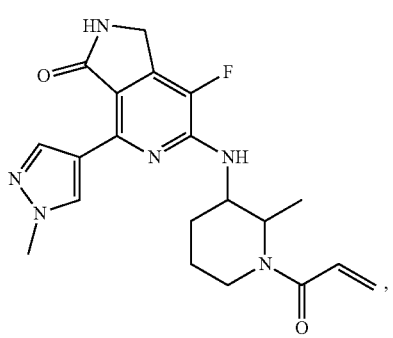
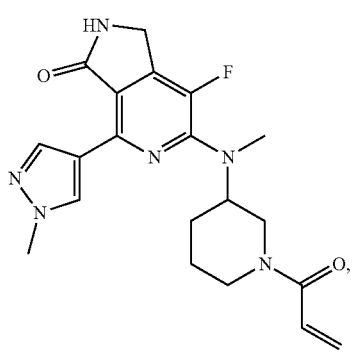
170
-continued
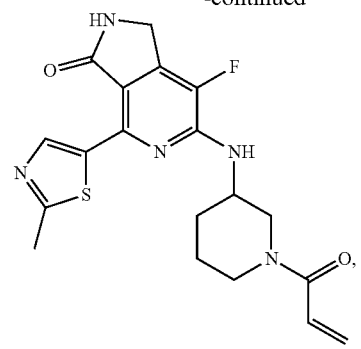
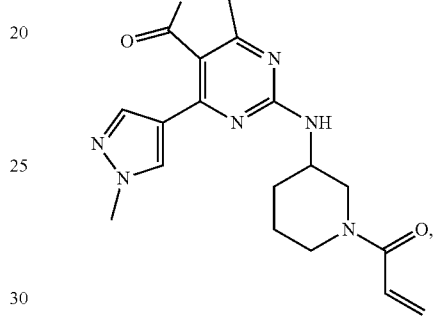
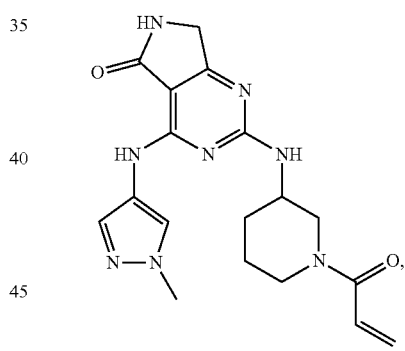
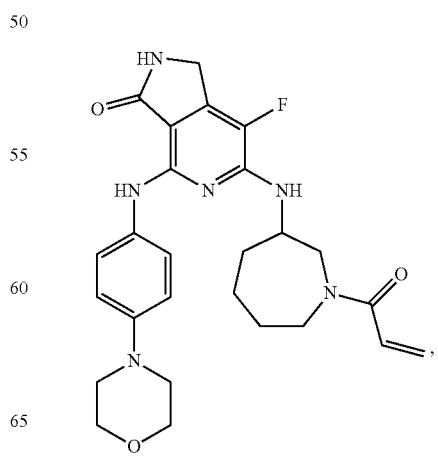

171
-continued
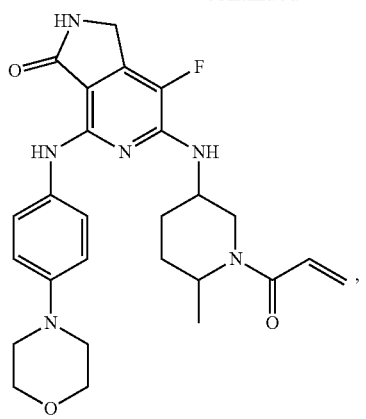
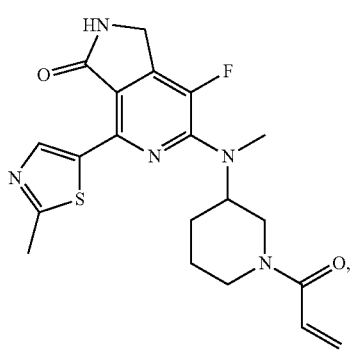
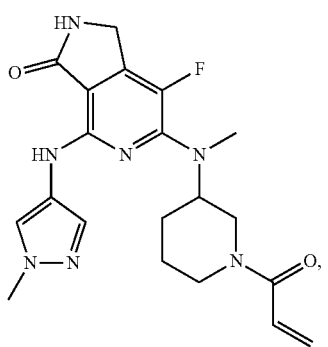
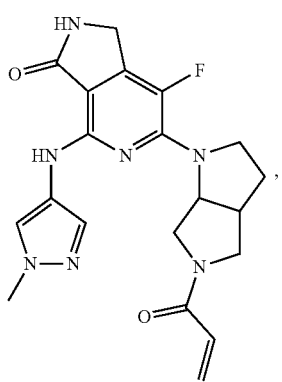
172
-continued
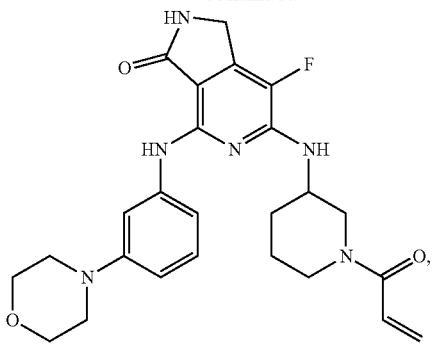
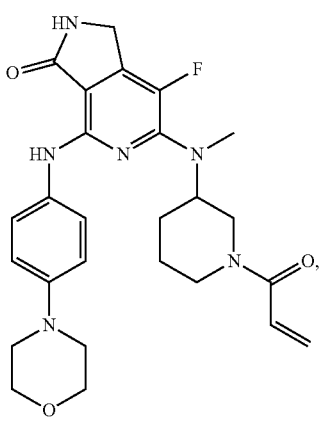
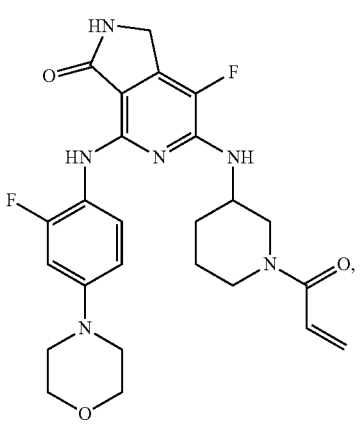
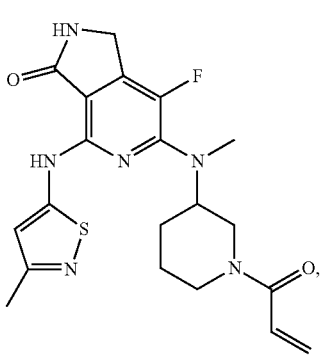

173
-continued
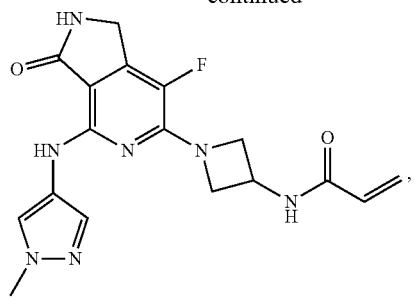
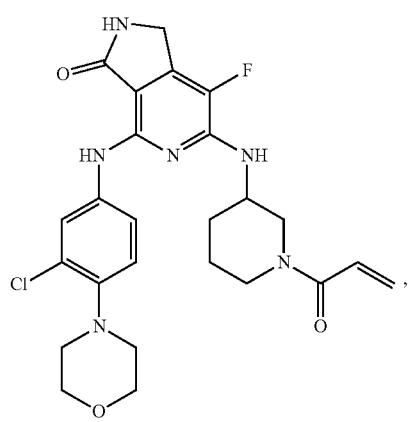
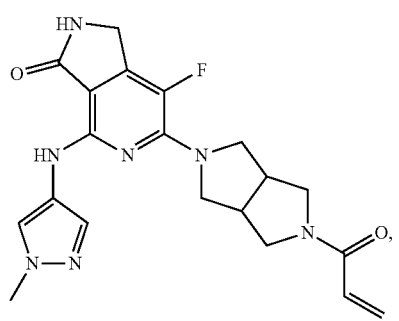
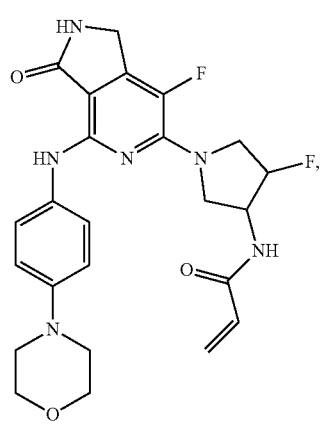
174
-continued
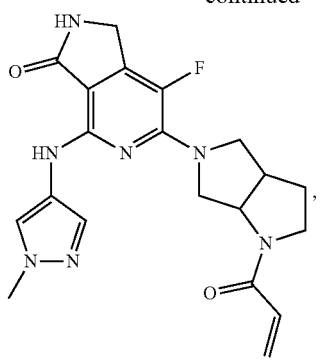
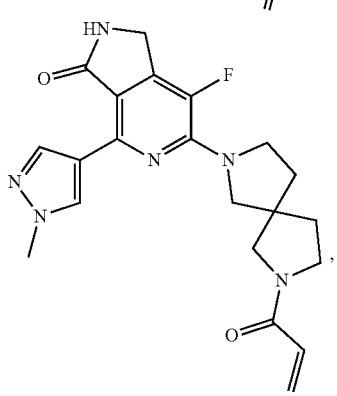
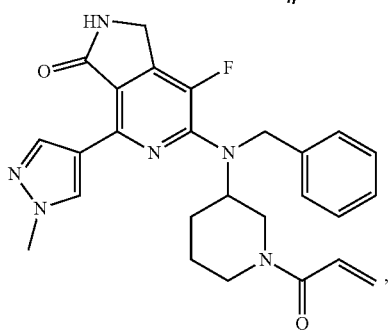
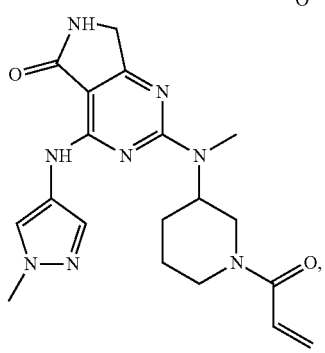
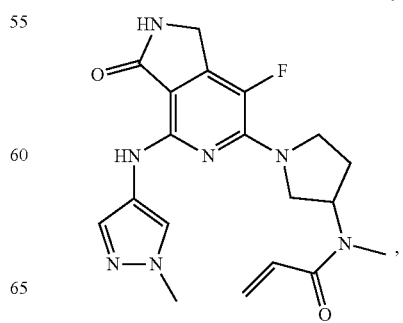

175
-continued
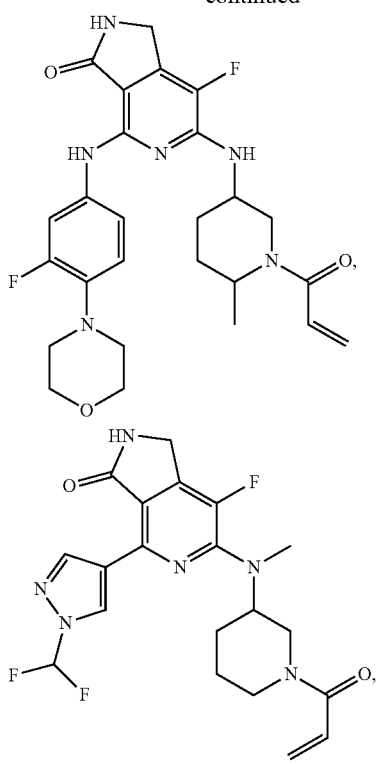
176
-continued
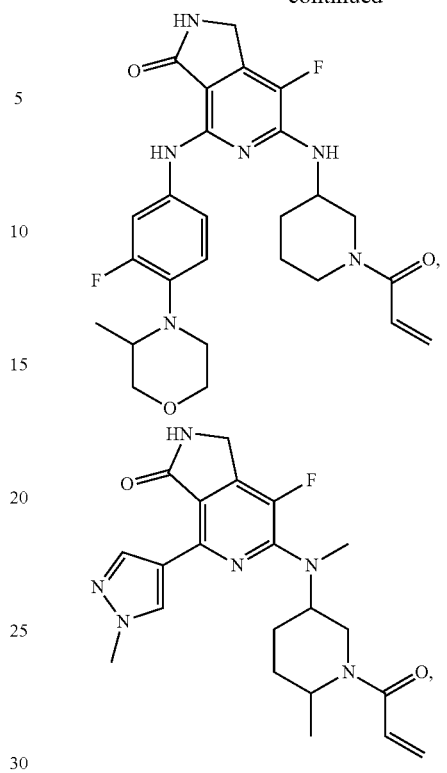
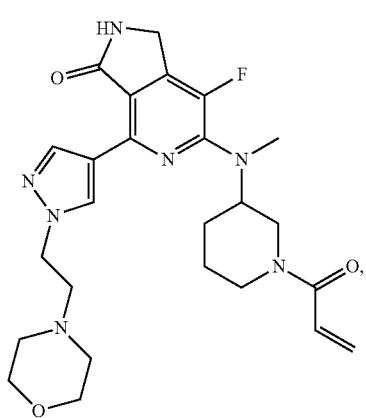
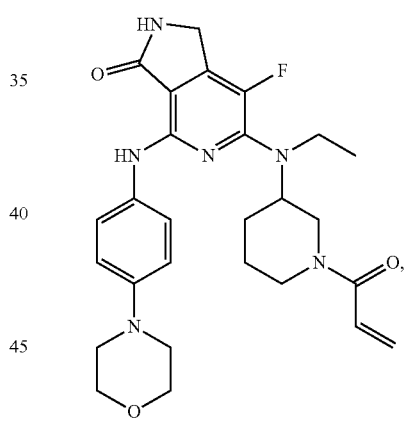
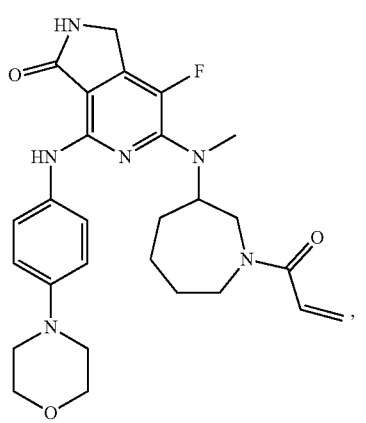
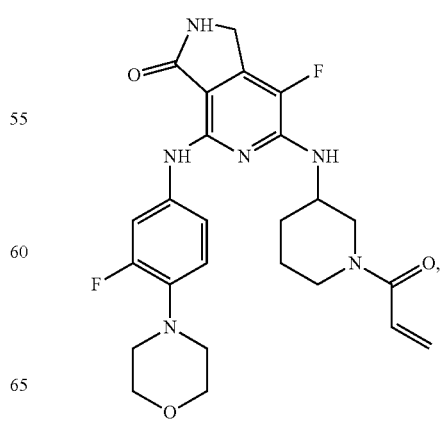

177
-continued
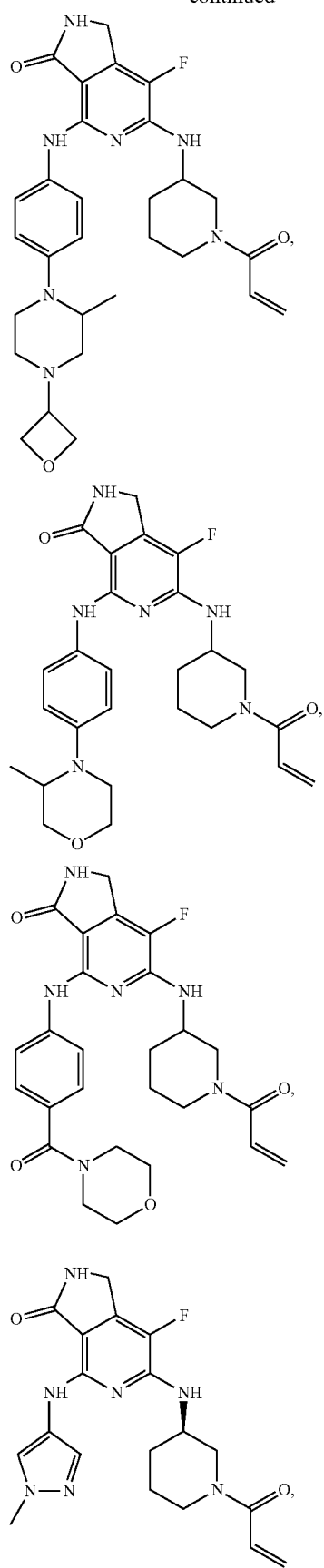
178
-continued
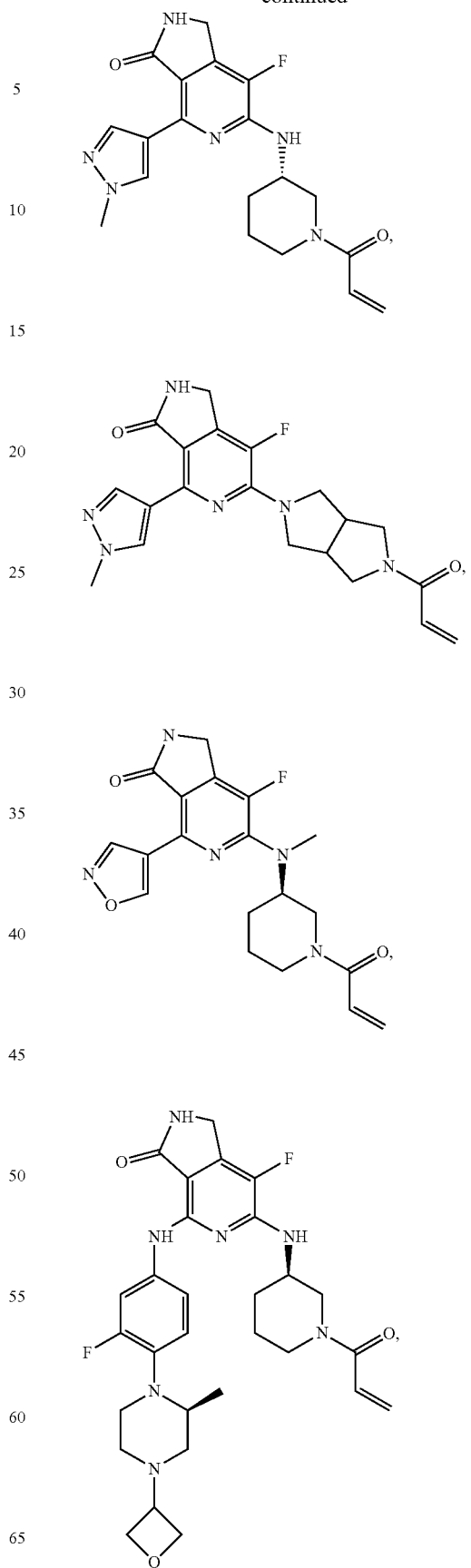

179
-continued
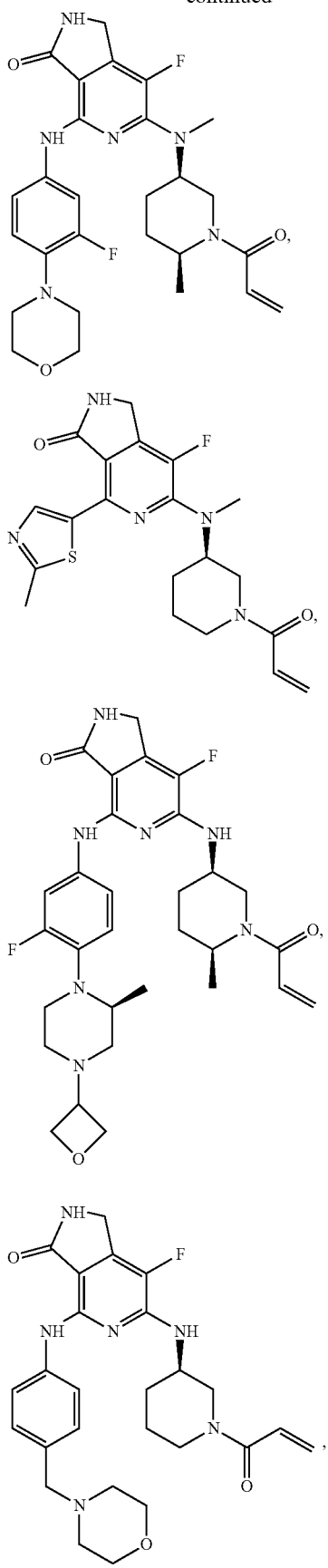
180
-continued
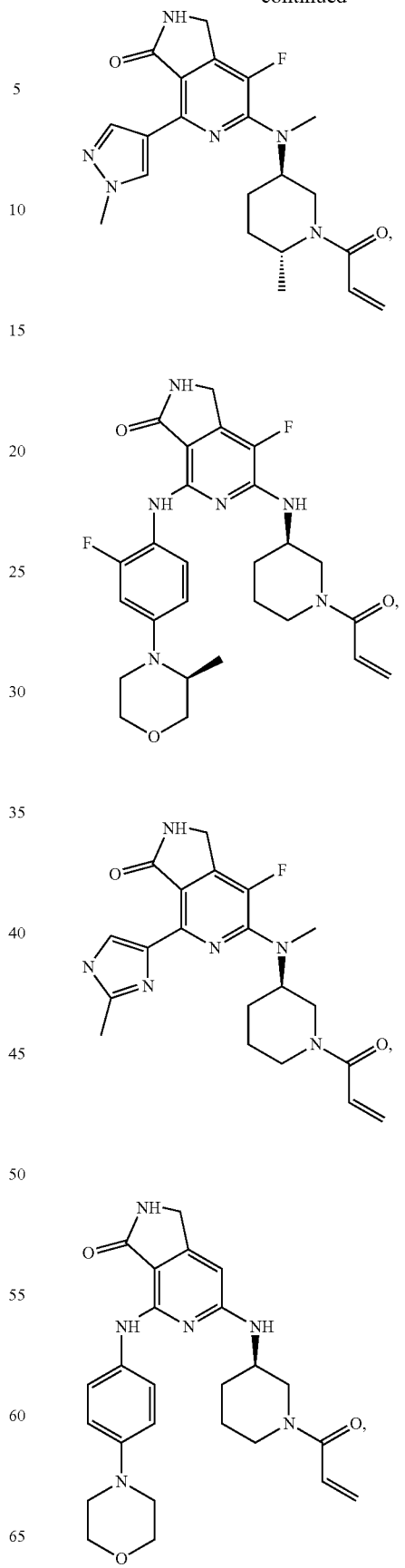

181
-continued
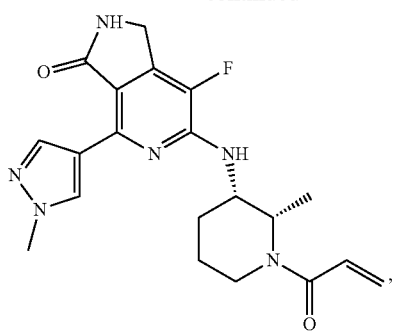
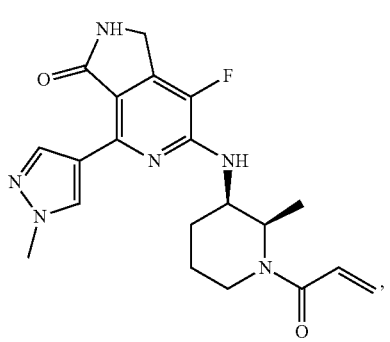
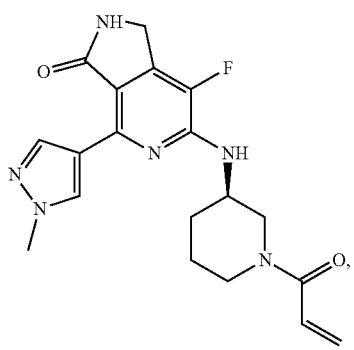
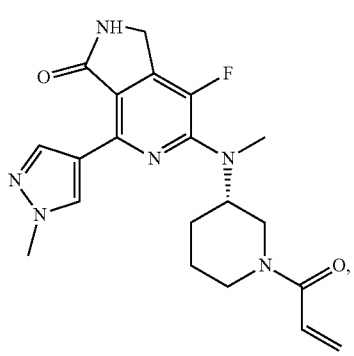
182
-continued
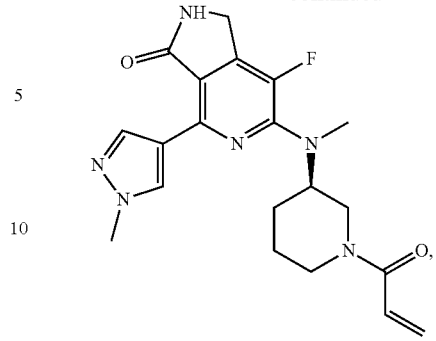
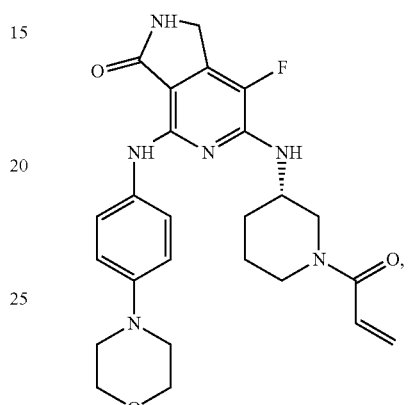
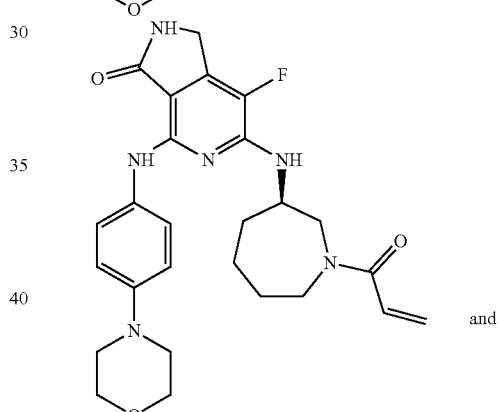
and
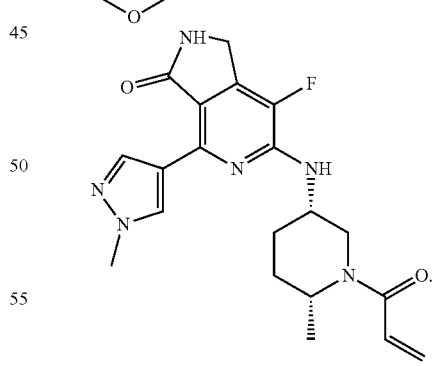
19. A pharmaceutical composition comprising the compound of claim 1 and a pharmaceutically acceptable carrier or excipient.
* * * * *